United States Patent
St. Goar et al.

(10) Patent No.: US 7,753,923 B2
(45) Date of Patent: Jul. 13, 2010

(54) LEAFLET SUTURING

(75) Inventors: Frederick G. St. Goar, Menlo Park, CA (US); James I-Lin Fann, Portola Valley, CA (US); Mark E. Deem, Mountain View, CA (US); Hanson S. Gifford, III, Woodside, CA (US); Martin S. Dieck, Cupertino, CA (US); Brian B. Martin, Boulder Creek, CA (US); Sylvia Wen-Chin Fan, San Francisco, CA (US); Eric A. Goldfarb, San Francisco, CA (US); Kent D. Dell, Redwood City, CA (US); Ferolyn T. Powell, San Francisco, CA (US)

(73) Assignee: Evalve, Inc., Menlo Park, CA (US)

( * ) Notice: Subject to any disclaimer, the term of this patent is extended or adjusted under 35 U.S.C. 154(b) by 132 days.

(21) Appl. No.: 10/927,263

(22) Filed: Aug. 25, 2004

(65) Prior Publication Data
US 2005/0021056 A1 Jan. 27, 2005

Related U.S. Application Data

(63) Continuation of application No. 10/638,022, filed on Aug. 7, 2003, which is a continuation of application No. 09/544,930, filed on Apr. 7, 2000, now Pat. No. 6,629,534.

(60) Provisional application No. 60/128,690, filed on Apr. 9, 1999.

(51) Int. Cl.
*A61B 17/10* (2006.01)
*A61B 17/04* (2006.01)

(52) U.S. Cl. ...................... 606/148; 606/139

(58) Field of Classification Search .............. 606/139, 606/144, 148, 149, 213, 142, 216, 151; 623/2.1, 623/2.11, 2.12
See application file for complete search history.

(56) References Cited

U.S. PATENT DOCUMENTS
2,097,018 A 10/1937 Chamberlain
(Continued)

FOREIGN PATENT DOCUMENTS
DE 3504292 7/1986
(Continued)

OTHER PUBLICATIONS
Abe et al., "De Vega's annuloplasty for acquired tricuspid disease: Early and late results in 110 patients" Ann. Thorac. Surg. (1989) 48:670-676.
(Continued)

*Primary Examiner*—Julian W Woo
*Assistant Examiner*—Melissa Ryckman
(74) *Attorney, Agent, or Firm*—Townsend and Townsend and Crew LLP; Jonathan Feuchtwang, Esq.

(57) ABSTRACT

The methods, devices, and systems are provided for performing endovascular repair of atrioventricular and other cardiac valves in the heart. Regurgitation of an atrioventricular valve, particularly a mitral valve, can be repaired by modifying a tissue structure selected from the valve leaflets, the valve annulus, the valve chordae, and the papillary muscles. These structures may be modified by suturing, stapling, snaring, or shortening, using interventional tools which are introduced to a heart chamber. Preferably, the tissue structures will be temporarily modified prior to permanent modification. For example, opposed valve leaflets may be temporarily grasped and held into position prior to permanent attachment.

8 Claims, 84 Drawing Sheets

U.S. PATENT DOCUMENTS

| | | |
|---|---|---|
| 2,108,206 A | 2/1938 | Meeker |
| 3,296,668 A | 1/1967 | Aiken |
| 3,378,010 A | 4/1968 | Codling et al. |
| 3,671,979 A | 6/1972 | Moulopoulos |
| 3,874,338 A | 4/1975 | King et al. |
| 3,874,388 A | 4/1975 | King et al. |
| 4,007,743 A | 2/1977 | Blake |
| 4,056,854 A | 11/1977 | Boretos et al. |
| 4,064,881 A | 12/1977 | Meredith |
| 4,112,951 A | 9/1978 | Hulka et al. |
| 4,235,238 A | 11/1980 | Ogiu et al. |
| 4,297,749 A | 11/1981 | Davis et al. |
| 4,425,908 A | 1/1984 | Simon |
| 4,484,579 A | 11/1984 | Meno et al. |
| 4,487,205 A | 12/1984 | Di Giovanni et al. |
| 4,498,476 A | 2/1985 | Cerwin et al. |
| 4,510,934 A | 4/1985 | Batra et al. |
| 4,578,061 A | 3/1986 | Lemelson |
| 4,686,965 A | 8/1987 | Bonnet et al. |
| 4,777,951 A | 10/1988 | Cribier et al. |
| 4,809,695 A | 3/1989 | Gwathmey et al. |
| 4,917,089 A | 4/1990 | Sideris |
| 4,944,295 A | 7/1990 | Gwathmey et al. |
| 4,969,890 A | 11/1990 | Sugita et al. |
| 4,994,077 A | 2/1991 | Dobben |
| 5,015,249 A | 5/1991 | Nakao et al. |
| 5,019,096 A | 5/1991 | Fox, Jr. et al. |
| 5,042,707 A | 8/1991 | Taheri |
| 5,047,041 A | 9/1991 | Samuels |
| 5,049,153 A | 9/1991 | Nakao et al. |
| 5,061,277 A | 10/1991 | Carpentier et al. |
| 5,069,679 A | 12/1991 | Taheri |
| 5,108,368 A | 4/1992 | Hammerslag et al. |
| 5,125,758 A | 6/1992 | DeWan |
| 5,171,252 A | 12/1992 | Friedland |
| 5,171,259 A | 12/1992 | Inoue |
| 5,190,554 A | 3/1993 | Coddington et al. |
| 5,195,968 A | 3/1993 | Lundquist et al. |
| 5,209,756 A | 5/1993 | Seedhom et al. |
| 5,226,429 A | 7/1993 | Kuzmak |
| 5,226,911 A | 7/1993 | Chee et al. |
| 5,234,437 A | 8/1993 | Sepetka |
| 5,250,071 A | 10/1993 | Palermo |
| 5,251,611 A | 10/1993 | Zehel et al. |
| 5,254,130 A | 10/1993 | Poncet et al. |
| 5,261,916 A | 11/1993 | Engelson |
| 5,275,578 A | 1/1994 | Adams |
| 5,282,845 A | 2/1994 | Bush et al. |
| 5,304,131 A | 4/1994 | Paskar |
| 5,306,283 A | 4/1994 | Conners |
| 5,306,286 A | 4/1994 | Stack et al. |
| 5,312,415 A | 5/1994 | Palermo |
| 5,314,424 A | 5/1994 | Nicholas |
| 5,318,525 A | 6/1994 | West et al. |
| 5,320,632 A * | 6/1994 | Heidmueller ................ 606/144 |
| 5,325,845 A | 7/1994 | Adair |
| 5,330,442 A | 7/1994 | Green et al. |
| 5,332,402 A | 7/1994 | Teitelbaum |
| 5,350,397 A | 9/1994 | Palermo et al. |
| 5,350,399 A | 9/1994 | Erlebacher et al. |
| 5,359,994 A | 11/1994 | Krauter |
| 5,368,564 A | 11/1994 | Savage |
| 5,368,601 A | 11/1994 | Sauer et al. |
| 5,383,886 A | 1/1995 | Kensey et al. |
| 5,403,312 A | 4/1995 | Yates et al. |
| 5,403,326 A | 4/1995 | Harrison et al. |
| 5,411,552 A | 5/1995 | Andersen et al. |
| 5,417,699 A | 5/1995 | Klein et al. |
| 5,417,700 A | 5/1995 | Egan |
| 5,423,857 A | 6/1995 | Rosenman et al. |
| 5,423,858 A | 6/1995 | Bolanos et al. |
| 5,423,882 A | 6/1995 | Jackman et al. |
| 5,431,666 A | 7/1995 | Sauer et al. |
| 5,437,551 A | 8/1995 | Chalifoux |
| 5,437,681 A | 8/1995 | Meade et al. |
| 5,447,966 A | 9/1995 | Hermes et al. |
| 5,450,860 A | 9/1995 | O'Connor |
| 5,456,400 A | 10/1995 | Shichman et al. |
| 5,456,684 A | 10/1995 | Schmidt et al. |
| 5,462,527 A | 10/1995 | Stevens-Wright et al. |
| 5,472,044 A | 12/1995 | Hall et al. |
| 5,476,470 A | 12/1995 | Fitzgibbons, Jr. |
| 5,477,856 A | 12/1995 | Lundquist |
| 5,478,309 A | 12/1995 | Sweezer et al. |
| 5,478,353 A | 12/1995 | Yoon |
| 5,487,746 A | 1/1996 | Yu et al. |
| 5,507,725 A | 4/1996 | Savage et al. |
| 5,507,757 A | 4/1996 | Sauer et al. |
| 5,520,701 A | 5/1996 | Lerch |
| 5,522,873 A | 6/1996 | Jackman et al. |
| 5,527,313 A | 6/1996 | Scott et al. |
| 5,527,321 A | 6/1996 | Hinchliffe |
| 5,527,322 A | 6/1996 | Klein et al. |
| 5,536,251 A | 7/1996 | Evard et al. |
| 5,540,705 A | 7/1996 | Meade et al. |
| 5,542,949 A | 8/1996 | Yoon |
| 5,554,185 A | 9/1996 | Block et al. |
| 5,569,274 A | 10/1996 | Rapacki et al. |
| 5,571,085 A | 11/1996 | Accisano, III |
| 5,571,137 A | 11/1996 | Marlow et al. |
| 5,571,215 A | 11/1996 | Sterman et al. |
| 5,575,802 A | 11/1996 | McQuilkin et al. |
| 5,582,611 A | 12/1996 | Tsuruta et al. |
| 5,593,424 A | 1/1997 | Northrup, III |
| 5,593,435 A | 1/1997 | Carpentier et al. |
| 5,609,598 A | 3/1997 | Laufer et al. |
| 5,618,306 A | 4/1997 | Roth et al. |
| 5,620,452 A | 4/1997 | Yoon |
| 5,626,588 A | 5/1997 | Sauer et al. |
| 5,634,932 A | 6/1997 | Schmidt |
| 5,636,634 A | 6/1997 | Kordis |
| 5,639,277 A | 6/1997 | Mariant et al. |
| 5,640,955 A | 6/1997 | Ockuly et al. |
| 5,649,937 A | 7/1997 | Bito et al. |
| 5,662,681 A | 9/1997 | Nash et al. |
| 5,669,917 A | 9/1997 | Sauer et al. |
| 5,690,671 A | 11/1997 | McGurk et al. |
| 5,695,504 A | 12/1997 | Gifford, III et al. |
| 5,695,505 A | 12/1997 | Yoon |
| 5,702,825 A | 12/1997 | Keital et al. |
| 5,706,824 A | 1/1998 | Whittier |
| 5,709,707 A | 1/1998 | Lock et al. |
| 5,713,910 A | 2/1998 | Gordon et al. |
| 5,713,911 A | 2/1998 | Racene et al. |
| 5,715,817 A | 2/1998 | Stevens-Wright et al. |
| 5,716,367 A | 2/1998 | Koike et al. |
| 5,718,725 A | 2/1998 | Sterman et al. |
| 5,719,725 A | 2/1998 | Nakao |
| 5,722,421 A | 3/1998 | Francese et al. |
| 5,725,542 A | 3/1998 | Yoon |
| 5,725,556 A | 3/1998 | Moser et al. |
| 5,738,649 A | 4/1998 | Macoviak |
| 5,741,280 A | 4/1998 | Fleenor |
| 5,749,828 A | 5/1998 | Solomon et al. |
| 5,769,812 A | 6/1998 | Stevens et al. |
| 5,769,863 A | 6/1998 | Garrison |
| 5,772,578 A | 6/1998 | Heimberger et al. |
| 5,782,845 A | 7/1998 | Shewchuk |
| 5,797,927 A | 8/1998 | Yoon |
| 5,797,960 A | 8/1998 | Stevens et al. |
| 5,810,847 A | 9/1998 | Laufer et al. |
| 5,810,849 A * | 9/1998 | Kontos ................ 606/144 |
| 5,810,853 A * | 9/1998 | Yoon ................ 606/151 |
| 5,810,876 A | 9/1998 | Kelleher |

| | | | | | | |
|---|---|---|---|---|---|---|
| 5,814,029 A | 9/1998 | Hassett et al. | | 6,267,781 B1 | 7/2001 | Tu |
| 5,820,592 A | 10/1998 | Hammerslag | | 6,269,819 B1 | 8/2001 | Oz et al. |
| 5,820,631 A | 10/1998 | Nobles | | 6,277,555 B1 | 8/2001 | Duran et al. |
| 5,823,955 A | 10/1998 | Kuck et al. | | 6,283,127 B1 | 9/2001 | Sterman et al. |
| 5,823,956 A | 10/1998 | Roth et al. | | 6,283,962 B1 | 9/2001 | Tu et al. |
| 5,824,065 A | 10/1998 | Gross | | 6,299,637 B1 | 10/2001 | Shaolian et al. |
| 5,827,237 A | 10/1998 | Macoviak et al. | | 6,306,133 B1 | 10/2001 | Tu et al. |
| 5,829,447 A | 11/1998 | Stevens et al. | | 6,312,447 B1 | 11/2001 | Grimes |
| 5,833,671 A | 11/1998 | Macoviak et al. | | 6,319,250 B1 | 11/2001 | Falwell et al. |
| 5,836,955 A | 11/1998 | Buelna et al. | | 6,322,559 B1 | 11/2001 | Daulton et al. |
| 5,840,081 A | 11/1998 | Anderson et al. | | 6,332,893 B1 | 12/2001 | Mortier et al. |
| 5,843,031 A | 12/1998 | Hermann et al. | | 6,352,708 B1 | 3/2002 | Duran et al. |
| 5,849,019 A | 12/1998 | Yoon | | 6,355,030 B1 | 3/2002 | Aldrich et al. |
| 5,853,422 A | 12/1998 | Huebsch et al. | | 6,358,277 B1 | 3/2002 | Duran |
| 5,855,271 A | 1/1999 | Eubanks et al. | | 6,368,326 B1 | 4/2002 | Dakin et al. |
| 5,855,614 A | 1/1999 | Stevens et al. | | 6,402,780 B1 | 6/2002 | Williamson et al. |
| 5,860,990 A | 1/1999 | Nobles et al. | | 6,402,781 B1 | 6/2002 | Langberg et al. |
| 5,868,733 A | 2/1999 | Ockuly et al. | | 6,406,420 B1 | 6/2002 | McCarthy et al. |
| 5,876,399 A | 3/1999 | Chia et al. | | 6,419,669 B1 | 7/2002 | Frazier et al. |
| 5,879,307 A | 3/1999 | Chio et al. | | 6,461,366 B1 | 10/2002 | Seguin |
| 5,885,271 A | 3/1999 | Hamilton et al. | | 6,464,707 B1 | 10/2002 | Bjerken |
| 5,928,224 A | 7/1999 | Laufer | | 6,482,224 B1 | 11/2002 | Michler et al. |
| 5,944,733 A | 8/1999 | Engelson | | 6,485,489 B1 | 11/2002 | Teirstein et al. |
| 5,947,363 A | 9/1999 | Bolduc et al. | | 6,508,828 B1 | 1/2003 | Akerfeldt et al. |
| 5,954,732 A | 9/1999 | Hart et al. | | 6,533,796 B1 | 3/2003 | Sauer et al. |
| 5,957,949 A | 9/1999 | Leonhard et al. | | 6,537,314 B2 | 3/2003 | Langberg et al. |
| 5,972,020 A | 10/1999 | Carpentier et al. | | 6,540,755 B2 | 4/2003 | Ockuly et al. |
| 5,972,030 A | 10/1999 | Garrison et al. | | 6,551,331 B2 | 4/2003 | Nobles et al. |
| 5,980,455 A | 11/1999 | Daniel et al. | | 6,562,037 B2 | 5/2003 | Paton et al. |
| 5,989,284 A | 11/1999 | Laufer | | 6,562,052 B2 | 5/2003 | Nobles et al. |
| 6,015,417 A | 1/2000 | Reynolds, Jr. | | 6,575,971 B2 | 6/2003 | Hauck et al. |
| 6,019,722 A | 2/2000 | Spence et al. | | 6,585,761 B2 | 7/2003 | Taheri |
| 6,022,360 A | 2/2000 | Reimels et al. | | 6,599,311 B1 | 7/2003 | Biggs et al. |
| 6,033,378 A | 3/2000 | Lundquist et al. | | 6,616,684 B1 | 9/2003 | Vidlund et al. |
| 6,036,699 A | 3/2000 | Andreas et al. | | 6,619,291 B2 | 9/2003 | Hlavka et al. |
| 6,048,351 A | 4/2000 | Gordon et al. | | 6,626,899 B2 | 9/2003 | Houser et al. |
| 6,059,757 A | 5/2000 | Macoviak et al. | | 6,626,930 B1 * | 9/2003 | Allen et al. ................. 606/213 |
| 6,060,628 A | 5/2000 | Aoyama et al. | | 6,629,534 B1 | 10/2003 | St. Goar et al. |
| 6,060,629 A | 5/2000 | Pham et al. | | 6,641,592 B1 | 11/2003 | Sauer et al. |
| 6,063,106 A | 5/2000 | Gibson | | 6,656,221 B2 | 12/2003 | Taylor et al. |
| 6,066,146 A | 5/2000 | Carroll et al. | | 6,669,687 B1 | 12/2003 | Saadat |
| 6,068,628 A | 5/2000 | Fanton et al. | | 6,685,648 B2 | 2/2004 | Flaherty et al. |
| 6,068,629 A | 5/2000 | Haissaguerre et al. | | 6,689,164 B1 | 2/2004 | Seguin |
| 6,077,214 A | 6/2000 | Mortier et al. | | 6,695,866 B1 * | 2/2004 | Kuehn et al. ................. 606/213 |
| 6,086,600 A | 7/2000 | Kortenbach | | 6,701,929 B2 | 3/2004 | Hussein |
| 6,088,889 A | 7/2000 | Luther et al. | | 6,702,825 B2 | 3/2004 | Frazier et al. |
| 6,099,553 A | 8/2000 | Hart et al. | | 6,702,826 B2 | 3/2004 | Liddicoat et al. |
| 6,110,145 A | 8/2000 | Macoviak | | 6,709,382 B1 | 3/2004 | Horner |
| 6,117,144 A * | 9/2000 | Nobles et al. ................. 606/144 | | 6,709,456 B2 | 3/2004 | Langberg et al. |
| 6,117,159 A | 9/2000 | Huebsch et al. | | 6,718,985 B2 | 4/2004 | Hlavka et al. |
| 6,123,699 A | 9/2000 | Webster, Jr. | | 6,719,767 B1 | 4/2004 | Kimblad |
| 6,126,658 A | 10/2000 | Baker | | 6,723,038 B1 | 4/2004 | Schroeder et al. |
| 6,132,447 A | 10/2000 | Dorsey | | 6,726,716 B2 | 4/2004 | Marquez |
| 6,136,010 A | 10/2000 | Modesitt et al. | | 6,740,107 B2 | 5/2004 | Loeb et al. |
| 6,143,024 A | 11/2000 | Campbell et al. | | 6,746,471 B2 | 6/2004 | Mortier et al. |
| 6,159,240 A | 12/2000 | Sparer et al. | | 6,755,777 B2 | 6/2004 | Schweich et al. |
| 6,162,233 A | 12/2000 | Williamson, IV et al. | | 6,764,510 B2 | 7/2004 | Vidlund et al. |
| 6,165,164 A | 12/2000 | Hill et al. | | 6,767,349 B2 | 7/2004 | Ouchi |
| 6,165,183 A * | 12/2000 | Kuehn et al. ................. 606/139 | | 6,770,083 B2 | 8/2004 | Seguin |
| 6,165,204 A | 12/2000 | Levinson et al. | | 6,797,001 B2 | 9/2004 | Mathis et al. |
| 6,168,614 B1 | 1/2001 | Andersen et al. | | 6,797,002 B2 | 9/2004 | Spence et al. |
| 6,171,320 B1 | 1/2001 | Monassevitch | | 6,860,179 B2 | 3/2005 | Hopper et al. |
| 6,182,664 B1 | 2/2001 | Cosgrove | | 6,875,224 B2 | 4/2005 | Grimes |
| 6,187,003 B1 | 2/2001 | Buysse et al. | | 6,926,715 B1 | 8/2005 | Hauck et al. |
| 6,190,408 B1 | 2/2001 | Melvin | | 6,949,122 B2 | 9/2005 | Adams et al. |
| 6,203,531 B1 | 3/2001 | Ockuly et al. | | 8,945,978 | 9/2005 | Hyde |
| 6,203,553 B1 | 3/2001 | Robertson et al. | | 6,966,914 B2 | 11/2005 | Abe |
| 6,206,893 B1 | 3/2001 | Klein et al. | | 6,986,775 B2 | 1/2006 | Morales et al. |
| 6,206,907 B1 | 3/2001 | Marino et al. | | 7,004,970 B2 | 2/2006 | Cauthen, III et al. |
| 6,210,419 B1 | 4/2001 | Mayenberger et al. | | 7,011,669 B2 | 3/2006 | Kimblad |
| 6,210,432 B1 | 4/2001 | Solem et al. | | 7,048,754 B2 | 5/2006 | Martin et al. |
| 6,245,079 B1 | 6/2001 | Nobles et al. | | 7,112,207 B2 | 9/2006 | Allen et al. |
| 6,267,746 B1 | 7/2001 | Bumbalough | | 7,288,097 B2 | 10/2007 | Séguin |

| Patent/Pub. No. | Date | Name |
|---|---|---|
| 7,381,210 B2 | 6/2008 | Zarbatany et al. |
| 7,464,712 B2 | 12/2008 | Oz et al. |
| 7,497,822 B1 | 3/2009 | Kugler et al. |
| 7,533,790 B1 | 5/2009 | Knodel et al. |
| 7,563,267 B2 | 7/2009 | Goldfarb et al. |
| 7,563,273 B2 | 7/2009 | Goldfarb et al. |
| 7,635,329 B2 | 12/2009 | Goldfarb et al. |
| 2001/0004715 A1 | 6/2001 | Duran et al. |
| 2001/0005787 A1 | 6/2001 | Oz et al. |
| 2001/0018611 A1 | 8/2001 | Solem et al. |
| 2001/0022872 A1 | 9/2001 | Marui |
| 2001/0037084 A1 | 11/2001 | Nardeo |
| 2001/0039411 A1 | 11/2001 | Johansson et al. |
| 2001/0044568 A1 | 11/2001 | Langberg et al. |
| 2002/0013571 A1 | 1/2002 | Goldfarb et al. |
| 2002/0022848 A1 | 2/2002 | Garrison et al. |
| 2002/0026233 A1 | 2/2002 | Shaknovich |
| 2002/0035361 A1 | 3/2002 | Houser et al. |
| 2002/0035381 A1 | 3/2002 | Bardy et al. |
| 2002/0042651 A1 | 4/2002 | Liddicoat et al. |
| 2002/0055774 A1 | 5/2002 | Liddicoat |
| 2002/0055775 A1 | 5/2002 | Carpentier et al. |
| 2002/0058995 A1 | 5/2002 | Stevens |
| 2002/0077687 A1 | 6/2002 | Ahn |
| 2002/0087148 A1 | 7/2002 | Brock et al. |
| 2002/0087169 A1 | 7/2002 | Brock et al. |
| 2002/0087173 A1 | 7/2002 | Alferness et al. |
| 2002/0103532 A1 | 8/2002 | Langberg et al. |
| 2002/0107534 A1 | 8/2002 | Schaefer et al. |
| 2002/0147456 A1 | 10/2002 | Diduch et al. |
| 2002/0156526 A1 | 10/2002 | Hilavka et al. |
| 2002/0158528 A1 | 10/2002 | Tsuzaki et al. |
| 2002/0161378 A1 | 10/2002 | Downing |
| 2002/0169360 A1 | 11/2002 | Taylor et al. |
| 2002/0183766 A1 | 12/2002 | Seguin |
| 2002/0183835 A1 | 12/2002 | Taylor et al. |
| 2003/0050693 A1 | 3/2003 | Quijano et al. |
| 2003/0069570 A1 | 4/2003 | Witzel et al. |
| 2003/0069593 A1 | 4/2003 | Tremulis et al. |
| 2003/0069636 A1 | 4/2003 | Solem et al. |
| 2003/0074012 A1 | 4/2003 | Nguyen et al. |
| 2003/0078654 A1 | 4/2003 | Taylor et al. |
| 2003/0083742 A1 | 5/2003 | Spence et al. |
| 2003/0105519 A1 | 6/2003 | Fasol et al. |
| 2003/0105520 A1 | 6/2003 | Alferness et al. |
| 2003/0120340 A1 | 6/2003 | Lisk et al. |
| 2003/0120341 A1 | 6/2003 | Shennib et al. |
| 2003/0130669 A1 | 7/2003 | Damarati |
| 2003/0130730 A1 | 7/2003 | Cohn et al. |
| 2003/0144697 A1 | 7/2003 | Mathis et al. |
| 2003/0167071 A1 | 9/2003 | Martin et al. |
| 2003/0171776 A1 | 9/2003 | Adams et al. |
| 2003/0187467 A1 | 10/2003 | Schreck |
| 2003/0195562 A1 | 10/2003 | Collier et al. |
| 2003/0208231 A1 | 11/2003 | Williamson, IV et al. |
| 2003/0229395 A1 | 12/2003 | Cox |
| 2003/0233038 A1 | 12/2003 | Hassett |
| 2004/0002719 A1 | 1/2004 | Oz et al. |
| 2004/0003819 A1 | 1/2004 | St. Goar et al. |
| 2004/0019377 A1 | 1/2004 | Taylor et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0039443 A1 | 2/2004 | Solem et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0049211 A1 | 3/2004 | Tremulis et al. |
| 2004/0073302 A1 | 4/2004 | Rourke et al. |
| 2004/0078053 A1 | 4/2004 | Berg et al. |
| 2004/0087975 A1 | 5/2004 | Lucatero et al. |
| 2004/0088047 A1 | 5/2004 | Spence et al. |
| 2004/0092962 A1 | 5/2004 | Thorton et al. |
| 2004/0097878 A1 | 5/2004 | Anderson et al. |
| 2004/0097979 A1 | 5/2004 | Svanidze et al. |
| 2004/0106989 A1 | 6/2004 | Wilson et al. |
| 2004/0111099 A1 | 6/2004 | Nguyen et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0133082 A1 | 7/2004 | Abraham-Fuchs et al. |
| 2004/0133192 A1 | 7/2004 | Houser et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138744 A1 | 7/2004 | Lashinski et al. |
| 2004/0138745 A1 | 7/2004 | Macoviak et al. |
| 2004/0148021 A1 | 7/2004 | Cartledge et al. |
| 2004/0152847 A1 | 8/2004 | Emri et al. |
| 2004/0152947 A1 | 8/2004 | Schroeder et al. |
| 2004/0153144 A1 | 8/2004 | Seguin |
| 2004/0158123 A1 | 8/2004 | Jayaraman |
| 2004/0162610 A1 | 8/2004 | Laiska et al. |
| 2004/0186486 A1 | 9/2004 | Roue et al. |
| 2004/0186566 A1 | 9/2004 | Hindrichs et al. |
| 2004/0193191 A1 | 9/2004 | Starksen et al. |
| 2004/0215339 A1 | 10/2004 | Drasler et al. |
| 2004/0220593 A1 | 11/2004 | Greenhalgh |
| 2004/0220657 A1 | 11/2004 | Nieminen et al. |
| 2004/0225300 A1 | 11/2004 | Goldfarb et al. |
| 2004/0236354 A1 | 11/2004 | Seguin |
| 2004/0243229 A1 | 12/2004 | Vidlund et al. |
| 2004/0249452 A1 | 12/2004 | Adams et al. |
| 2004/0249453 A1 | 12/2004 | Cartledge et al. |
| 2005/0004583 A1 | 1/2005 | Oz et al. |
| 2005/0004665 A1 | 1/2005 | Aklog |
| 2005/0004668 A1 | 1/2005 | Aklog et al. |
| 2005/0021056 A1 | 1/2005 | St. Goar et al. |
| 2005/0021057 A1 | 1/2005 | St. Goar et al. |
| 2005/0021058 A1 | 1/2005 | Negro |
| 2005/0033446 A1 | 2/2005 | Deem et al. |
| 2005/0038508 A1 | 2/2005 | Gabbay |
| 2005/0049698 A1 | 3/2005 | Bolling et al. |
| 2005/0055089 A1 | 3/2005 | Macoviak et al. |
| 2005/0059351 A1 | 3/2005 | Cauwels et al. |
| 2005/0149014 A1 | 7/2005 | Hauck et al. |
| 2005/0159810 A1 | 7/2005 | Filsoufi |
| 2005/0197694 A1 | 9/2005 | Pai et al. |
| 2005/0197695 A1 | 9/2005 | Stacchino et al. |
| 2005/0216039 A1 | 9/2005 | Lederman |
| 2005/0228422 A1 | 10/2005 | Machold et al. |
| 2005/0228495 A1 | 10/2005 | Macoviak |
| 2005/0251001 A1 | 11/2005 | Hassett |
| 2005/0267493 A1 | 12/2005 | Schreck et al. |
| 2005/0273160 A1 | 12/2005 | Lashinski et al. |
| 2005/0287493 A1 | 12/2005 | Novak et al. |
| 2006/0004247 A1 | 1/2006 | Kute et al. |
| 2006/0015003 A1 | 1/2006 | Moaddes et al. |
| 2006/0020275 A1 | 1/2006 | Goldfarb et al. |
| 2006/0030866 A1 | 2/2006 | Schreck |
| 2006/0030867 A1 | 2/2006 | Zadno |
| 2006/0030885 A1 | 2/2006 | Hyde |
| 2006/0058871 A1 | 3/2006 | Zakay et al. |
| 2006/0064115 A1 | 3/2006 | Allen et al. |
| 2006/0064116 A1 | 3/2006 | Allen et al. |
| 2006/0064118 A1 | 3/2006 | Kimblad |
| 2006/0089671 A1 | 4/2006 | Goldfarb et al. |
| 2006/0089711 A1 | 4/2006 | Dolan |
| 2006/0135993 A1 | 6/2006 | Seguin |
| 2006/0184203 A1 | 8/2006 | Martin et al. |
| 2006/0195012 A1 | 8/2006 | Mortier et al. |
| 2006/0229708 A1 | 10/2006 | Powell et al. |

| | | | |
|---|---|---|---|
| 2006/0252984 A1 | 11/2006 | Rahdert et al. | |
| 2007/0038293 A1 | 2/2007 | St.Goar et al. | |
| 2007/0100356 A1 | 5/2007 | Lucatero et al. | |
| 2007/0118155 A1 | 5/2007 | Goldfarb et al. | |
| 2007/0129737 A1 | 6/2007 | Goldfarb et al. | |
| 2007/0198082 A1 | 8/2007 | Kapadia et al. | |
| 2008/0039935 A1 | 2/2008 | Buch et al. | |
| 2008/0051703 A1 | 2/2008 | Thorton et al. | |
| 2008/0051807 A1 | 2/2008 | St. Goar et al. | |
| 2008/0097489 A1 | 4/2008 | Goldfarb et al. | |
| 2008/0167714 A1 | 7/2008 | St. Goar et al. | |
| 2008/0183194 A1 | 7/2008 | Goldfarb et al. | |
| 2009/0156995 A1 | 6/2009 | Martin et al. | |
| 2009/0163934 A1 | 6/2009 | Raschdorf, Jr. et al. | |
| 2009/0177266 A1 | 7/2009 | Powell et al. | |
| 2009/0198322 A1 | 8/2009 | Deem et al. | |
| 2009/0270858 A1 | 10/2009 | Hauck et al. | |
| 2009/0326567 A1 | 12/2009 | Goldfarb et al. | |
| 2010/0016958 A1 | 1/2010 | St. Goar et al. | |
| 2010/0022823 A1 | 1/2010 | Goldfarb et al. | |

FOREIGN PATENT DOCUMENTS

| | | |
|---|---|---|
| EP | 179562 | 4/1986 |
| EP | 0179562 B1 | 7/1989 |
| EP | 558031 | 9/1993 |
| EP | 684012 | 11/1995 |
| EP | 0 727 239 | 8/1996 |
| EP | 727239 | 8/1996 |
| EP | 01674040 A2 | 6/2006 |
| FR | 2768324 | 3/1999 |
| GB | 1598111 | 9/1981 |
| GB | 2151142 | 7/1985 |
| JP | 11089937 | 6/1999 |
| WO | WO 81/00668 | 3/1981 |
| WO | WO 91/01689 | 2/1991 |
| WO | WO 91/18881 | 12/1991 |
| WO | WO 92/12690 | 8/1992 |
| WO | WO 94/18881 | 9/1994 |
| WO | WO 94/18893 | 9/1994 |
| WO | WO 95/15715 A1 | 6/1995 |
| WO | WO 96/14032 A1 | 5/1996 |
| WO | WO 96/22735 | 8/1996 |
| WO | WO 96/30072 A1 | 10/1996 |
| WO | WO 97/25927 A1 | 7/1997 |
| WO | WO 97/26034 A1 | 7/1997 |
| WO | WO 97/38748 A2 | 10/1997 |
| WO | WO 97/39688 | 10/1997 |
| WO | WO 97/48436 A2 | 12/1997 |
| WO | WO 98/07375 | 2/1998 |
| WO | WO 98/24372 | 6/1998 |
| WO | WO 98/30153 | 7/1998 |
| WO | WO 98/32382 | 7/1998 |
| WO | WO 98/35638 | 8/1998 |
| WO | WO 99/00059 | 1/1999 |
| WO | WO 99/01377 | 1/1999 |
| WO | WO 99/07354 | 2/1999 |
| WO | WO 99/13777 A1 | 3/1999 |
| WO | WO 99/66967 A1 | 12/1999 |
| WO | WO 00/02489 | 1/2000 |
| WO | WO 00/03651 A1 | 1/2000 |
| WO | WO 00/03759 | 1/2000 |
| WO | WO 00/12168 A1 | 3/2000 |
| WO | WO 00/44313 A1 | 8/2000 |
| WO | WO 00/60995 | 10/2000 |
| WO | WO 01/00111 | 1/2001 |
| WO | WO 01/00114 A1 | 1/2001 |
| WO | WO 01/03651 A2 | 1/2001 |
| WO | WO 01/26557 | 4/2001 |
| WO | WO 01/26586 | 4/2001 |
| WO | WO 01/26587 A1 | 4/2001 |
| WO | WO 01/26588 A2 | 4/2001 |
| WO | WO 01/26703 A1 | 4/2001 |
| WO | WO 01/28432 | 4/2001 |
| WO | WO 01/28455 | 4/2001 |
| WO | WO 01/47438 A1 | 7/2001 |
| WO | WO 01/49213 A2 | 7/2001 |
| WO | WO 01/49213 A3 | 7/2001 |
| WO | WO 01/50985 A1 | 7/2001 |
| WO | WO 01/54618 | 8/2001 |
| WO | WO 01/56512 A1 | 8/2001 |
| WO | WO 01/66001 | 9/2001 |
| WO | WO 01/70320 A1 | 9/2001 |
| WO | WO 01/89440 A2 | 11/2001 |
| WO | WO 01/95831 A2 | 12/2001 |
| WO | WO 01/95832 A2 | 12/2001 |
| WO | WO 01/97741 A2 | 12/2001 |
| WO | WO 02/00099 A2 | 1/2002 |
| WO | WO 02/01999 A2 | 1/2002 |
| WO | WO 02/03892 | 1/2002 |
| WO | WO 02/34167 A2 | 5/2002 |
| WO | WO 02/34167 A3 | 5/2002 |
| WO | WO 02/060352 A1 | 8/2002 |
| WO | WO 02/062263 A2 | 8/2002 |
| WO | WO 02/062270 A1 | 8/2002 |
| WO | WO 02/062408 A2 | 8/2002 |
| WO | WO 03/001893 | 1/2003 |
| WO | WO 03/003930 A1 | 1/2003 |
| WO | WO 03/020179 | 3/2003 |
| WO | WO 03/028558 | 4/2003 |
| WO | WO 03/037171 | 5/2003 |
| WO | WO 03/047467 | 6/2003 |
| WO | WO 03/049619 | 6/2003 |
| WO | WO 03/073910 | 9/2003 |
| WO | WO 03/073913 | 9/2003 |
| WO | WO 00/59382 A1 | 10/2003 |
| WO | WO 03/105667 A3 | 12/2003 |
| WO | WO 2004/004607 | 1/2004 |
| WO | WO 2004/012583 | 2/2004 |
| WO | WO 2004/012789 | 2/2004 |
| WO | WO 2004/012789 A2 | 2/2004 |
| WO | WO 2004/014282 A2 | 2/2004 |
| WO | WO 2004/019811 | 3/2004 |
| WO | WO 2004/082538 A2 | 3/2004 |
| WO | WO 2004/030570 | 4/2004 |
| WO | WO 2004/037317 | 5/2004 |
| WO | WO 2004/045370 | 6/2004 |
| WO | WO 2004/045378 A2 | 6/2004 |
| WO | WO 2004/045463 | 6/2004 |
| WO | WO 2004/047679 | 6/2004 |
| WO | WO 2004/062725 | 7/2004 |
| WO | WO 2004/082523 A2 | 9/2004 |
| WO | WO 2004/093730 | 11/2004 |
| WO | WO 2004/112585 | 12/2004 |
| WO | WO 2004/112651 | 12/2004 |
| WO | WO 2005/002424 | 1/2005 |
| WO | WO 2005/018507 | 3/2005 |
| WO | WO 2005/027797 A1 | 3/2005 |
| WO | WO 2005/032421 A2 | 4/2005 |
| WO | WO 2005/062931 A2 | 7/2005 |
| WO | WO 2005/112792 | 12/2005 |
| WO | WO 2006/105008 | 10/2006 |
| WO | WO 2006/105009 | 10/2006 |
| WO | WO 2006/115875 | 11/2006 |
| WO | WO 2006/115876 | 11/2006 |

OTHER PUBLICATIONS

Abe et al., "Updated: De Vega's annuloplasty for acquired tricuspid disease: Early and late results in 110 patients" Ann. Thorac. Surg. (1996) 62:1876-1877.

Ali Khan et al., "Blade Atrial Septostomy: Experience With the First 50 Procedures," Cathet. Cardiovasc. Diagn., (1991) 23:257-262.

Alvarez at al., "Repairing the degenerative mitral valve: Ten-to fifteen-year follow-up" J. Thorac. Cardiovasc. Surg. (1996) 112:238-247.

Bach et al., "Improvement following correction of secondary mitral regurgitation in end-stage cardiomyopathy with mitral annuloplasty" Am. J. Cardiol. (1996) 78:966-969.
Bach et al., "Early improvement in congestive heart failure after correction of secondary mitral regurgitation in end-stage cardiomyopathy" Am. Heart J. (1995) 129:1165-1170.
Bailey, "Surgery of the Heart" Chapter 20 (1995) pp. 686-737.
Bolling et al., "Surgery for acquired heart disease" (1995) 109:676-683.
Dec et al., "Idiopathic dilated cardiomyopathy" N. Engl. J. Med. (1994) 331:1564-1575.
Fucci et al., "Improved results with mitral valve repair using new surgical techniques" Eur. J. Cardiothorac.Surg. (1995) 9:621-627 (Medline Record enclosed herewith).
Kameda et al., "Annuloplasty for severe mitral regurgitation due to dilated cardiomyopathy" Am. Thorac. Surg. (1996) 61:1829-1832.
Khan et al., "Blade atrial septostomy: Experience with the first 50 procedures" Cathet. Cardiovasc. Diagn. (1991) 23: 257-262.
Maisano et al., "The edge-to-edge technique: A simplified method to correct mitral insufficiency" Eur. J. Cardiothorac. Surg. (1998) 13:240-246.
McCarthy et al., "Tricuspid valve repair with the Cosgrove-Edwards annuloplasty system" Am. Thorac. Surg. (1997) 64: 267-268.
Park et al., "Clinical use of a blade atrial septostomy" Circulation (1978) 58:600-608.
Reul, Ross M. and Cohn, Lawrence II, Mitral Valve Reconstruction for Mitral Insufficiency, Progress in Cardiovascular Diseases, No. 6, May/Jun. 1997, pp. 567-599, vol. XXXIX.
Ricchi et al., "Linear segmental annuloplasty for mitral valve repair" Ann. Thorac. Surg. (1997) 63:1805-1806.
Tager et al., "Long-term follow-up of Rheumatic patients undergoing left-sided valve replacement with tricuspid annuloplasty—Validity of preoperative echocardiographic criteria in the decision to perform tricuspid annuloplasty" Am.J. Cardiol. (1998) 81:1013-1016.
Uchida et al., "Percutaneous cardiomyotomy and valvultomy with angioscopic guidance" Am. Heart J. (1991) 121:1221-1224.
Umana et al., "'Bow-tie' mitral valve repair: An adjuvant technique for ischemic mitral regurgitation" Ann. Thorac. Surg. (1998) 66:1640-1646.
Umana et al., "'Bow-tie' mitral valve repair successfully addresses subvalvular dysfunction in ischemic mitral regurgitation," (1997) Surgical Forum pp. 279-280.
Agricola et al., "Mitral valve reserve in double orifice technique: an exercise echocardiographic study," Journal of Heart Valve Disease, (2002)11(5):637 643.
Alfieri et al., "An effective technique to correct anterior mitral leaflet prolapse," J Card Surg, (1999) 14(6):468-470.
Alfieri et al., "Novel suture device for beating heart mitral leaflet approximation," Annals of Thoracic Surgery, (2002)74:1488 1493.
Alfieri et al., "The double orifice technique in mitral valve repair: a simple solution for complex problems," Journal of Thoracic Cardiovascular Surgery, (2001)122:674 681.
Alfieri et al., "The edge to edge technique," The European Association for Cardio-Thoracic Surgry 14th Annual Meeting, (Oct. 7-11, 2000), Book of Proceedings.
Alfieri, "The edge-to-edge repair of the mitral valve," [Abstract] 6th Annual NewEra Cardiac Care: Innovation & Technology, Heart Surgery Forum, (2003) pp. 103.
Arisi et al., "Mitral valve repair with Alfieri technique in mitral regurgitation of diverse etiology: early echocardiographic results," Circulation Supplement II, (2001) 104(17):3240.
Bernal et al., "The 'Valve Racket': a new and different concept of atrioventricular valve repair," Eur. J. Cardio-thoracic Surgery 29:1026-29 (2006).
Bhudia, S., "Edge-to-edge mitral repair: a versatile mitral repair technique," The Cleveland clinic Foundation, (date unknown).
Borghetti et al., "Preliminary observations on haemodynamics during physiological stress conditions following 'double-orifice' mitral valve repair," European Journal of Cardio-thoracic Surgery, Apr. 18, 2001 20:262-269.
Castedo, "Edge-to-edge tricuspid repair for redeveloped valve incompetence after DeVega's annuloplasty," AnnThora Surg, (2003) 75;605-6.
Derwent citing German language patent EP 684012 published Nov. 12, 1995 for: "Thread for constructing surgical seam has flexible section with two ends, with lower fastening part on thread first end having hollow cylinder with continuous hole through which surgical needle threads" 2 pgs.
Derwent citing Japanese language patent JP 11089937 published Jun. 4, 1999 for: "Catheter for mitral regurgitation test—includes jet nozzles provided on rear side of large diametered spindle shaped portion attached to end of narrow diametered tube" 1 pg.
Dottori et al., "Echocardiographic imaging of the Alfieri type mitral valve repair," Ital Heart J, (2001) 2(4):319-320.
Downing et al., "Beating heart mitral valve surgery: Preliminary model and methodology," Journal of Thoracic and Cardiovascular Surgery, (2002) 123(6):1141-1146.
Falk et al., "Computer-enhanced mitral valve surgery: toward a total endoscopic procedure," Seminars in thoracic and cardiovascular surgery, (1999) 11(3):224-249.
Filsoufi et al., "Restoring Optimal Surface of Coaptation With a Mini Leaflet Prosthesis: A New Surgical Concept for the Correction of Mitral Valve Prolapse," Int'l. Soc. for Minimally Invasive Cardiothoracic Surgery 1(4):186-87 (2006).
Fundaro et al., "Chordal plication and free edge remodeling for mitral anterior leaflet prolapse repair: 8-year follow-up," Annals of Thoracic Surgery, (2001) 72:1515-1519.
Garcia-Rinaldi et al., "Left ventricular volume reduction and reconstruction is ischemic cardiomyopathy," Journal of Cardiac Surgery, (1999) 14:199-210.
Gateliene, "Early and postoperartive results of mitral and tricuspid valve insufficiency surgical treatment using edge-to-edge central coaptation procedure," (2002) 38 Suppl 2:172-5.
Gatti et al., "The edge to edge technique as a trick to rescue an imperfect mitral valve repair," Eur J Cardiothorac Surg, (2002) 22(5):817 20.
Gillinov et al., "Is minimally invasive heart valve surgery a paradigm for the future?," Current Cardiology Reports, (1999) 1:318-322.
Gundry, "Facile mitral valve repair utilizing leaflet edge approximation: midterm results of the Alfieri figure of eight repair," Presented at the Meeting of The Western Thoracic Surgical Association, (1999).
Ikeda et al., "Batista's operation with coronary artery bypass grafting and mitral valve plasty for ischemic dilated cardiomyopathy," The Japanese Journal of Thoracic and Cardiovascular Surgery, (2000) 48:746-749.
Izzat et al., "Early experience with partial left ventriculectomy in the Asia-Pacific Region," Annals of Thoracic Surgery, (1999) 67:1703-1707.
Källner et al., "Transaortic approach for the Alfieri Stitch," Ann Thorac Surg, (2001) 71:378-380.
Kavarna et al., "Transaortic repair of mitral regurgitation," Presented at the third annual New Era Cardiac Care conference, San Diego, CA, (Jan. 13-16, 2000), http://www.hsforum.com/vol3/issue1/2000-2389print.html.
Kaza et al., "Ventricular reconstruction results in improved left ventricular function and amelioration of mitral insufficiency," Annals of Surgery, (2002) 235(6):828 832.
Kherani, The edge-to-edge mitral valve repair: the Columbia Presbyterian experience, Columbia University, (date unknown).
Konertz et al., "Results after partial left ventriculectomy in a European heart failure population," Journal of Cardiac Surgery, (1999) 14(2):129-135.
Kron et al., "Surgical relocation of the posterior papillary muscle in chronic Ischemic mitral regurgitation," Annals. of Thoracic Surgery, (2002)74:600 601.
Krüger et al, "Edge to edge technique in complex mitral valve repair," Thorac Cardiovasc Surg, (2000) Thema: Poster, http://www.thieme.de/thoracic/abstracts/abstracts/p_73.html.
Langer et al., "Posterior mitral leaflet extensions: An adjunctive repair option for ischemic mitral regurgitation?," J. Thorac. Cardiovasc. Surf. 131:868-77 (2006).
Lorusso et al., "Double-Orifice technique to repair extensive mitral valve excision following acute endocarditis," J Card Surg. (1998) 13:24-26.

Lorusso et al., "The double-orifice technique for mitral valve reconstruction: predictors of postoperative outcome," Eur J. Cardiothorac Surg, (2001) 20(3):583-589.

Maisano et al., "The double orifice repair for Barlow Disease: a simple solution for a complex repair," Supplement I Circulation, (1999) 100(18):I-94.

Maisano et al., "The double orifice technique as a standardized approach to treat mitral regurgitation due to severe myxomatous disease: surgical technique," European Journal of Cardiothoracic Surgery, (2000) 17:201-215.

Maisano et al., "The hemodynamic effects of double-orifice valve repair for mitral regurgitation: a 3D computational model," European Journal of Cardio-thoracic Surgery, (1999) 15:419-425.

Maisano et al., "Valve repair for traumatic tricuspid regurgitation," Eur J. Cardio-thorac Surg, (1996) 10:867-873.

Mantovani et al., "Edge-to-edge repair of congenital familiar tricuspid regurgitation: case report," J. Heart Valve Dis., (2000) 9 (5):641-643.

McCarthy et al., "Partial left ventriculectomy and mitral valve repair for end-stage congestive heart failure," European Journal of Cardiothoracic Surgery, (1998) 13:337-343.

Moainie et al., Correction of traumatic tricuspid regurgitation using the double orifice technique, Annals of Thoracic Surgery, (2002) 73:963 965.

Morales et al., "Development of an off bypass mitral valve repair," The Heart Surgery Forum #1999-4963, (1999) 2(2):115-120.

Nakanishi et al., "Early outcome with the Alfieri mitral valve repair," J Cardiol, (2001) 37(5):263-266, (Abstract in English; Article in Japanese.).

Nielsen et al., "The edge-to-edge mitral repair: tension on the approximating suture and leaflet deformation during acute Ischemic mitral regurgitation in the ovine heart," Circulation, (2001)104 [suppl I]:I-29-I-35.

Osawa et al., "Partial left ventriculectomy in a 3 year old boy with dilated cardiomyopathy," Japanese Journal of Throacic and Cardiovascular Surgery, (2000) 48(9):590-593.

Privitera et al., "Alfieri Mitral Valve Repair: Clinical Outcome and Pathology; Circulation," (2002) 106:173.

Redaelli, et al., A computational study of the hemodynamics after 'edge-to-edge' mitral valve repair, Journal of Biomechanical Engineering, (2001) 123:565-570.

Tamura et al., Edge to edge repair for mitral regurgitation in a patient with chronic hemodialysis: report of a case, Kyobu Geka, (2001) 54(9):788-790.

Timek, "Edge-to-edge mitral repair: gradients and three-dimensional annular dynamics in vivo during inotropic stimulation," European Journal of Cardio-thoracic Surgery, (2001) 19:431-437.

Supplementary European Search Report of EP Application No. 00921854.6, dated Oct. 22, 2008, 6 pages total.

Bhudia et al., "Edge-to-edge (Alfieri) mitral repair: results in diverse clinical settings," Ann Thorac Surg, 77: 1598-1606, (2004).

Frazier et al., #62 Early Clinical Experience With An Implantable, Intracardiac Circulatory Support Device: Operative Considerations and Physiologic Implications, 2003 STS Presentation, 1 page total. [Abstract Only].

Gupta et al., #61 Influence of Older Donor Grafts on Heart Transplant Survival: Lack of Recipient Effects, 2003 STS Presentation, [Abstract Only].

Krüger et al, "Edge to edge technique in complex mitral valve repair," Thorac Cardiovasc Surg, 2000, Thema: Poster, http://www.thieme.de/thoracic/abstracts/abstracts/p_73.html.

Noera et al. ., "Tricuspid Valve Incompetence Caused by Nonpenetrating Thoracic Trauma", Annals of Thoracic Surgery, 1991, 51 (2), 320-322.

Patel et al., #57 Epicardial Atrial Defibrillation: Novel Treatment of Postoperative Atrial Fibrillation, 2003 STS Presentation, [Abstract Only].

Robicsek et al., #60 The Bicuspid Aortic Valve: How Does It Function? Why Does It Fail?, 2003 STS Presentation, [Abstract Only].

Tibayan et al., #59 Annular Geometric Remodeling in Chronic Ischemic Mitral Regurgitation, 2003 STS Presentation, [Abstract Only].

Partial European Search Report of EP Application No. 09152208.6, mailed Jun. 10, 2009, 6 pages total.

Timek, "Edge-to-edge mitral valve repair without annuloplasty ring in acute ischemic mitral regurgitation," [Abstract] Clinical Science, Abstracts from Scientific Sessions, (2002) II-461.

Totaro, "Mitral valve repair for isolated prolapse of the anterior leaflet: an 11-year follow-up," European Journal of Cardio-thoracic Surgery, (1999) 15:119-126.

Votta et al., "3 D computational analysis of the stress distribution on the leaflets after edge to edge repair of mitral regurgitation," Journal of Heart Valve Disease, (2002)11:810 822.

* cited by examiner

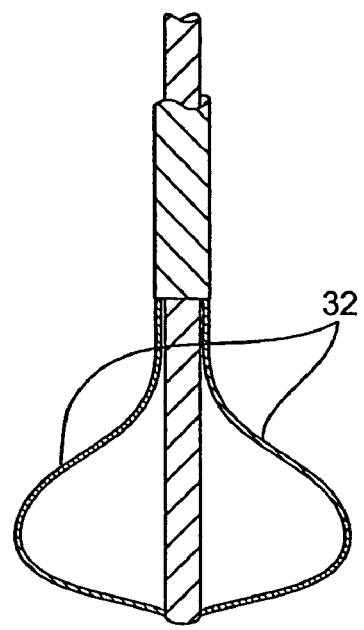
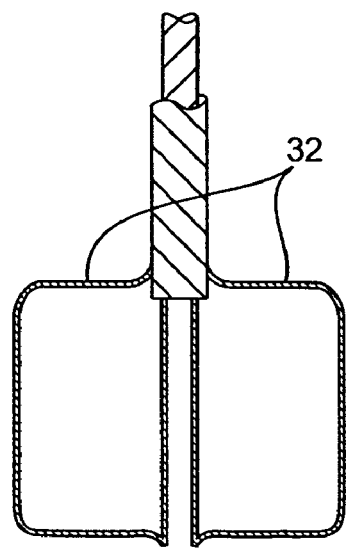
FIG. 31A        FIG. 31B
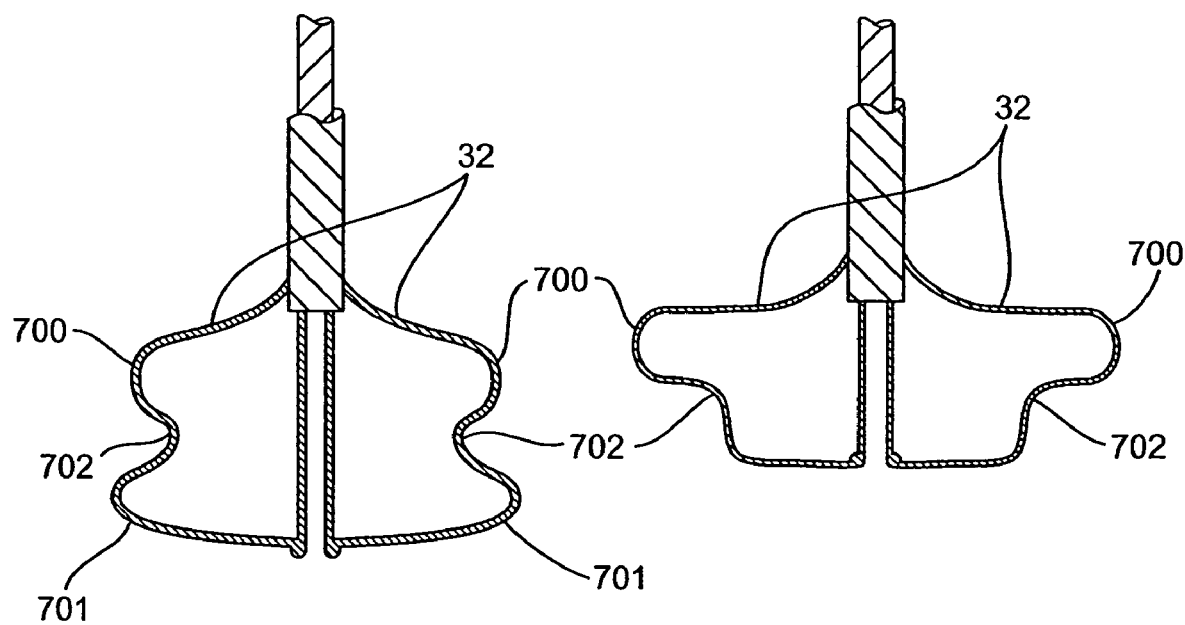
FIG. 31C        FIG. 31D

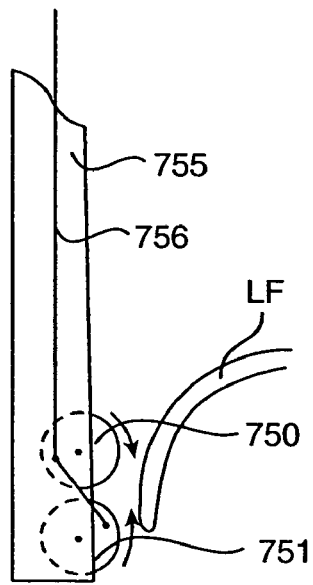
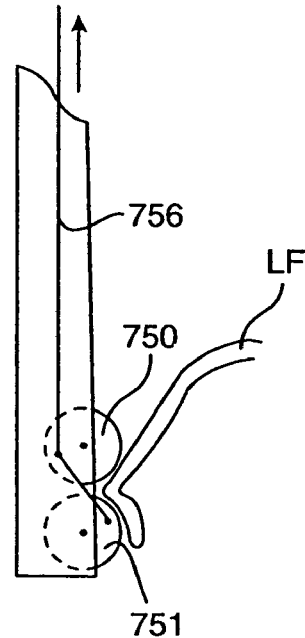
FIG. 45A　　　　　　　FIG. 45B
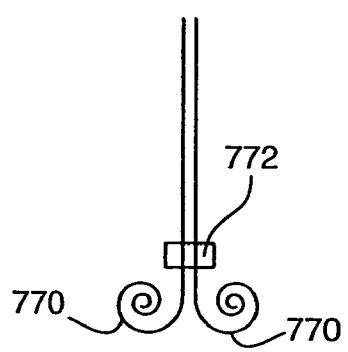
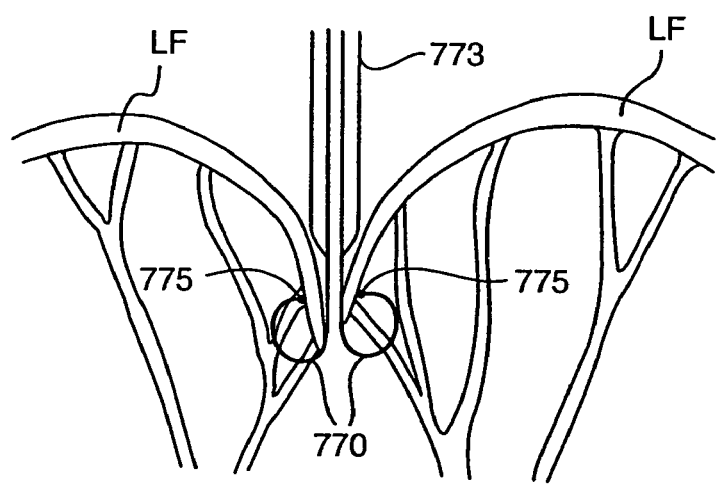
FIG. 46A　　　　　　　FIG. 46B

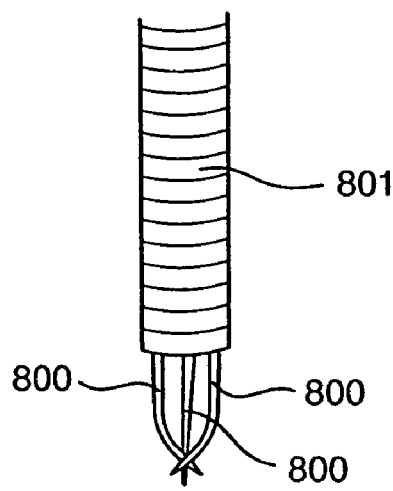
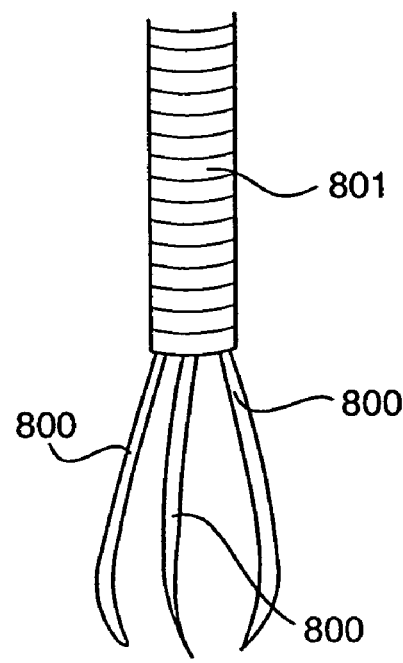
FIG. 47A  FIG. 47B
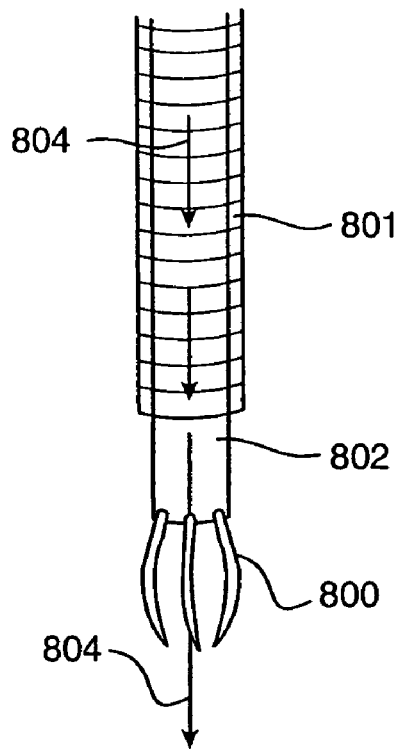
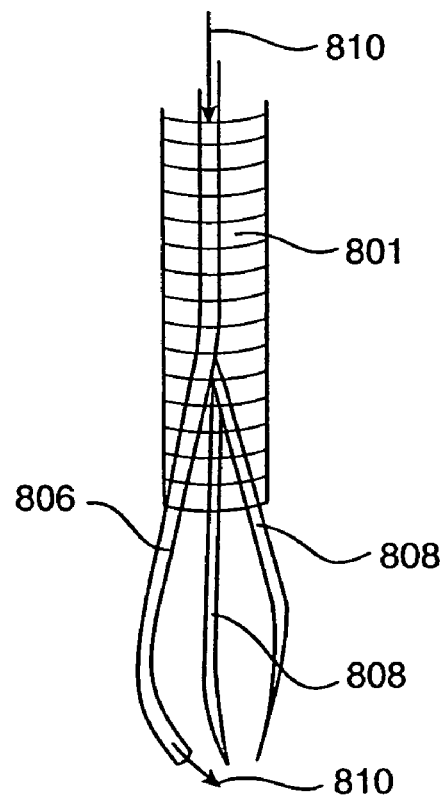
FIG. 47C  FIG. 47D

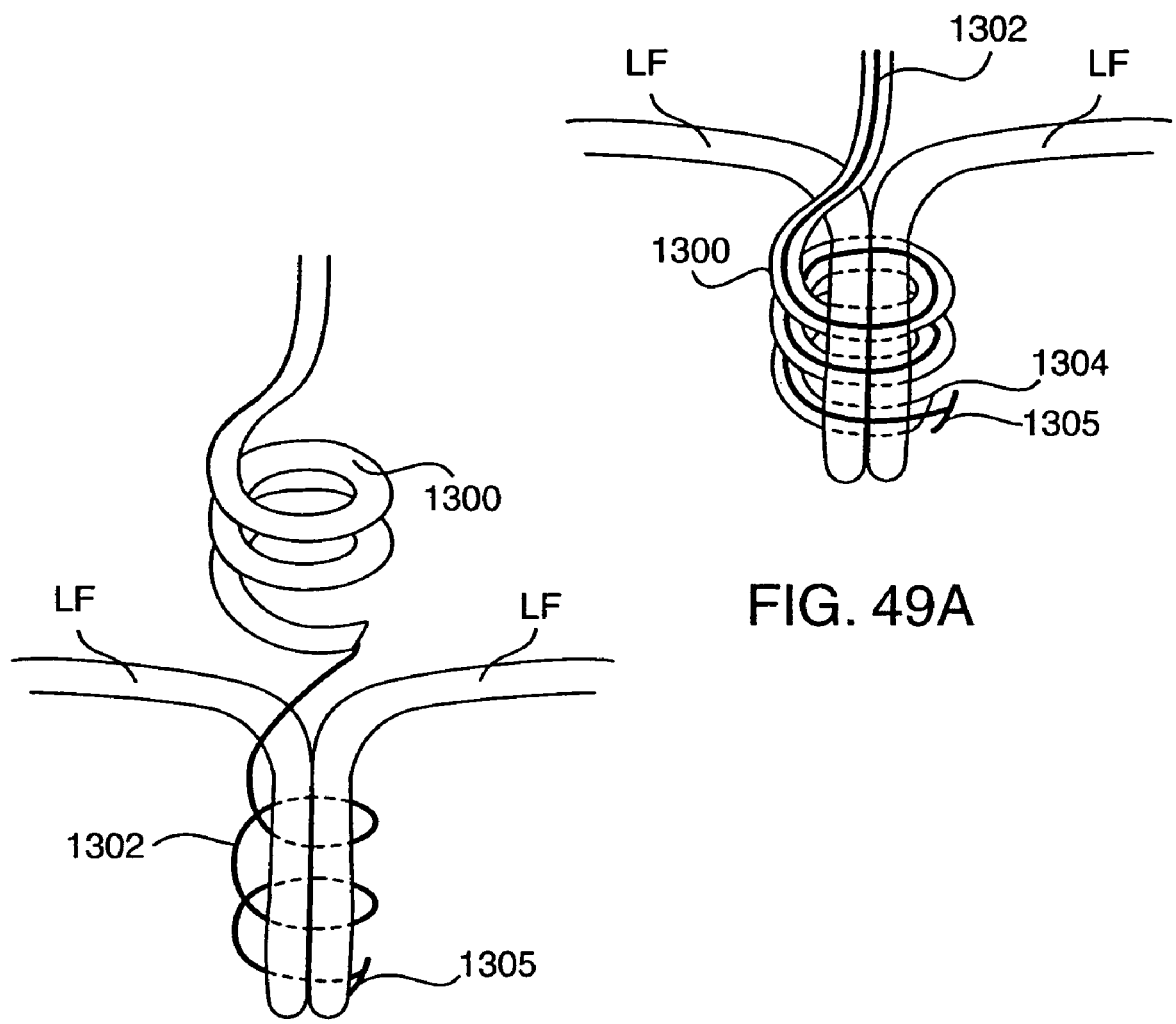
FIG. 49A
FIG. 49B
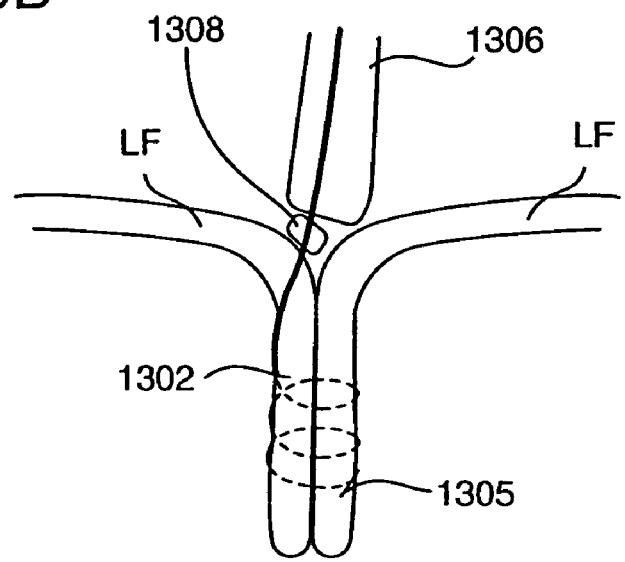
FIG. 49C

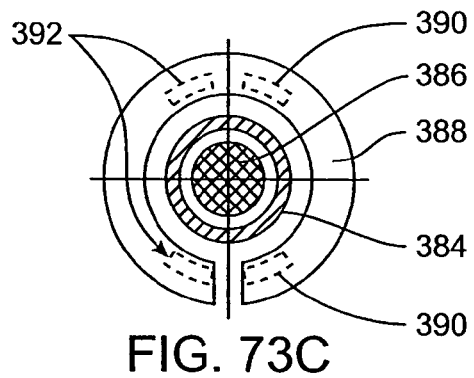
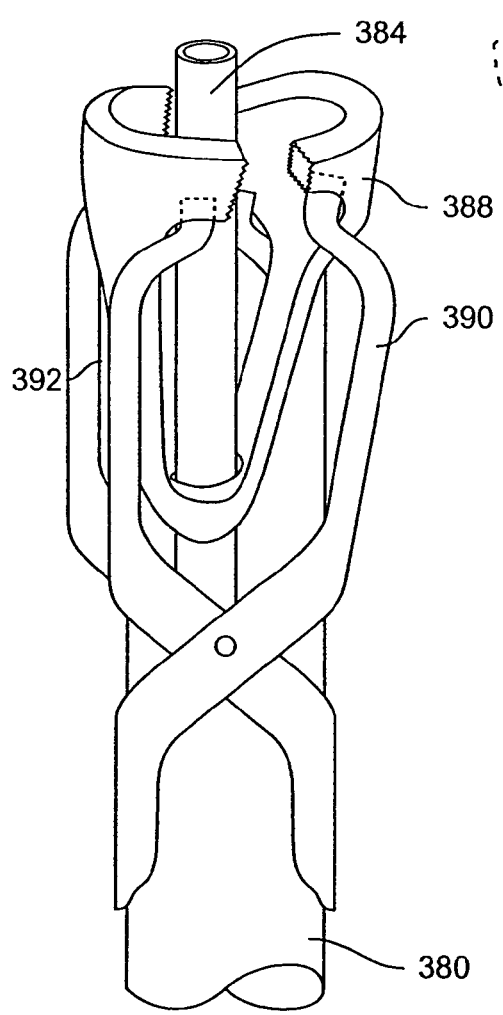
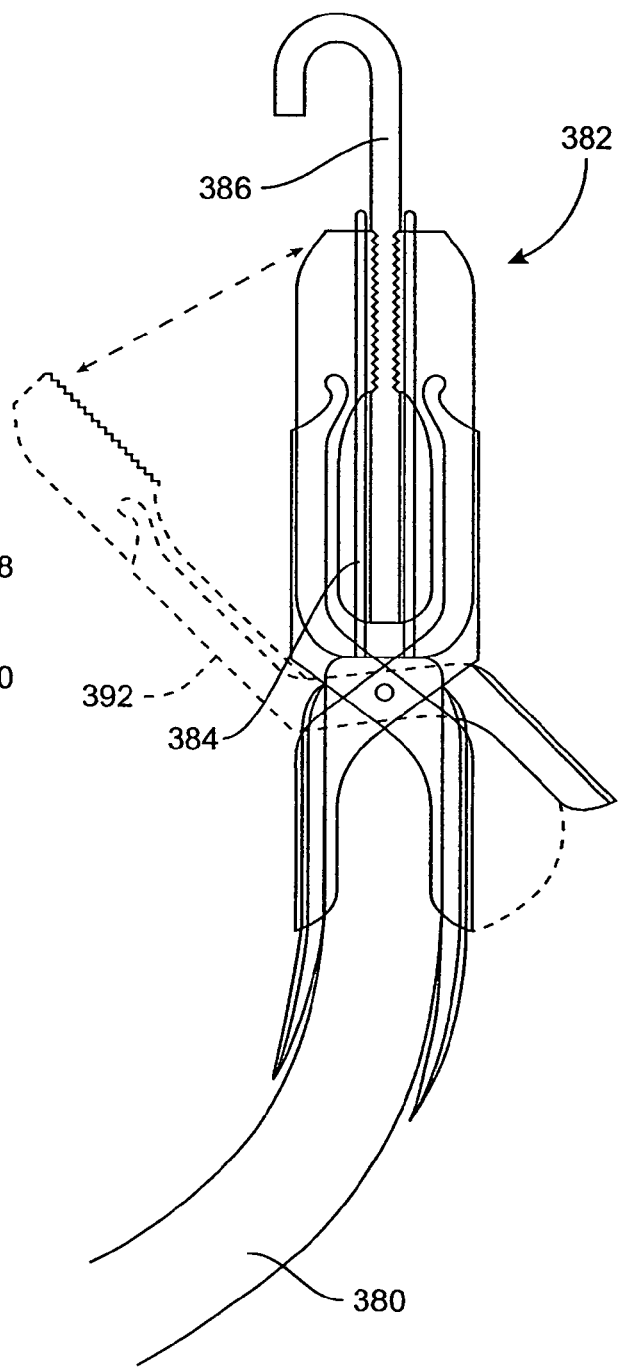
FIG. 73C
FIG. 73B
FIG. 73A

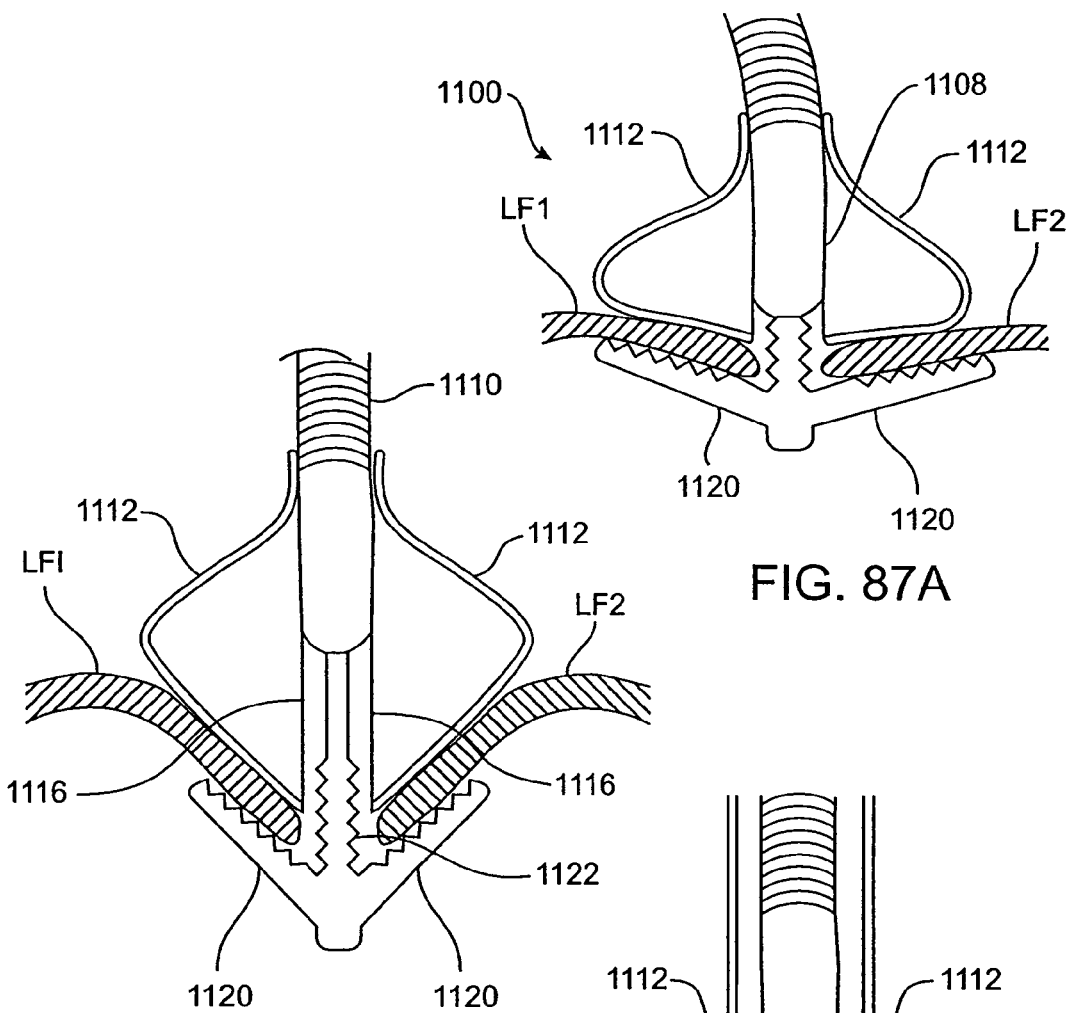
FIG. 87A
FIG. 87B
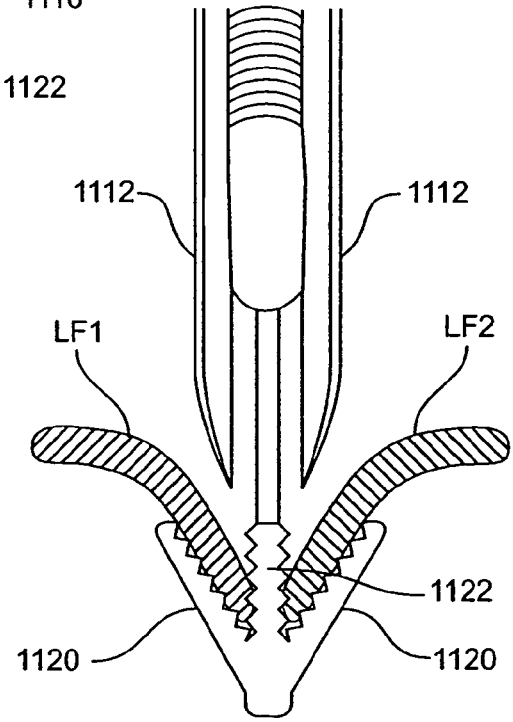
FIG. 87C

LEAFLET SUTURING

This application is a continuation of U.S. application Ser. No. 10/638,022, filed Aug. 7, 2003, which was a continuation of U.S. application Ser. No. 09/544,930, filed Apr. 7, 2000, which application claimed the benefit under 35 U.S.C. §119 (e) of U.S. Provisional Application No. 60/128,690, filed on Apr. 9, 1999 under 37 CFR §1.78(a). The full disclosures of which are incorporated herein by reference.

BACKGROUND OF THE INVENTION

1. Field of the Invention

The present invention relates generally to medical methods, devices, and systems. In particular, the present invention relates to methods, devices, and systems for the endovascular or minimally invasive surgical repair of the atrioventricular valves of the heart, particularly the mitral valve.

Mitral valve regurgitation is characterized by retrograde flow from the left ventricle of a heart through an incompetent mitral valve into the left atrium. During a normal cycle of heart contraction (systole), the mitral valve acts as a check valve to prevent flow of oxygenated blood back into the left atrium. In this way, the oxygenated blood is pumped into the aorta through the aortic valve. Regurgitation of the valve can significantly decrease the pumping efficiency of the heart, placing the patient at risk of severe, progressive heart failure.

Mitral valve regurgitation can result from a number of different mechanical defects in the mitral valve. The valve leaflets, the valve chordae which connect the leaflets to the papillary muscles, or the papillary muscles themselves may be damaged or otherwise dysfunctional. Commonly, the valve annulus may be damaged, dilated, or weakened limiting the ability of the mitral valve to close adequately against the high pressures of the left ventricle.

The most common treatments for mitral valve regurgitation rely on valve replacement or strengthening of the valve annulus by implanting a mechanical support ring or other structure. The latter is generally referred to as valve annuloplasty. A recent technique for mitral valve repair which relies on suturing adjacent segments of the opposed valve leaflets together is referred to as the "bow-tie" or "edge-to-edge" technique. While all these techniques can be very effective, they usually rely on open heart surgery where the patient's chest is opened, typically via a sternotomy, and the patient placed on cardiopulmonary bypass. The need to both open the chest and place the patient on bypass is traumatic and has associated morbidity.

For these reasons, it would be desirable to provide alternative and additional methods, devices, and systems for performing the repair of mitral and other cardiac valves, particularly the tricuspid valve which is the other atrioventricular valve. Such methods, devices, and systems should preferably not require open chest access and be capable of being performed endovascularly, i.e., using devices which are advanced to the heart from a point in the patient's vasculature remote from the heart. Still more preferably, the methods, devices, and systems should not require that the heart be bypassed, although the methods, devices, and systems should be useful with patients who are bypassed and/or whose heart may be temporarily stopped by drugs or other techniques. At least some of these objectives will be met by the inventions described hereinbelow.

2. Description of the Background Art

Minimally invasive and percutaneous techniques for coapting and modifying mitral valve leaflets to treat mitral valve regurgitation are described in WO 98/35638; WO 99/00059; WO 99/01377; and WO 00/03759.

Dec and Fuster (1994) N. Engl. J. Med. 331:1564-1575 and Alvarez et al. (1996) J. Thorac. Cardiovasc. Surg. 112:238-247 are review articles discussing the nature of and treatments for dilated cardiomyopathy.

Maisano et al. (1998) Eur. J. Cardiothorac. Surg. 13:240-246; Fucci et al. (1995) Eur. J. Cardiothorac. Surg. 9:621-627; and Umana et al. (1998) Ann. Thorac. Surg. 66:1640-1646, describe open surgical procedures for performing "edge-to-edge" or "bow-tie" mitral valve repair where edges of the opposed valve leaflets are sutured together to lessen regurgitation.

Mitral valve annuloplasty is described in the following publications. Bach and Bolling (1996) Am. J. Cardiol. 78:966-969; Kameda et al. (1996) Ann. Thorac. Surg. 61:1829-1832; Bach and Bolling (1995) Am. Heart J. 129: 1165-1170; and Bolling et al. (1995) 109:676-683. Linear segmental annuloplasty for mitral valve repair is described in Ricchi et al. (1997) Ann. Thorac. Surg. 63:1805-1806. Tricuspid valve annuloplasty is described in McCarthy and Cosgrove (1997) Ann. Thorac. Surg. 64:267-268; Tager et al. (1998) Am. J. Cardiol. 81:1013-1016; and Abe et al. (1989) Ann. Thorac. Surg. 48:670-676.

Percutaneous transluminal cardiac repair procedures are described in Park et al. (1978) Circulation 58:600-608; Uchida et al. (1991) Am. Heart J. 121:1221-1224; and Ali Khan et al. (1991) Cathet. Cardiovasc. Diagn. 23:257-262.

Endovascular cardiac valve replacement is described in U.S. Pat. Nos. 5,840,081; 5,411,552; 5,554,185; 5,332,402; 4,994,077; and 4,056,854. See also U.S. Pat. No. 3,671,979 which describes a catheter for temporary placement of an artificial heart valve.

Other percutaneous and endovascular cardiac repair procedures are described in U.S. Pat. Nos. 4,917,089; 4,484,579; and 3,874,338; and WO 91/01689.

Thoracoscopic and other minimally invasive heart valve repair and replacement procedures are described in U.S. Pat. Nos. 5,855,614; 5,829,447; 5,823,956; 5,797,960; 5,769,812; and 5,718,725.

BRIEF SUMMARY OF THE INVENTION

The present invention provides methods, devices, and systems for the endovascular repair of cardiac valves, particularly the atrioventricular valves which inhibit back flow of blood from a heart ventricle during contraction (systole), most particularly the mitral valve between the left atrium and the left ventricle. By "endovascular," it is meant that the procedure(s) of the present invention are performed with interventional tools and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach the heart. Thus, the procedures of the present invention will generally not require penetrations made directly through the exterior heart muscle, i.e., myocardium, although there may be some instances where penetrations will be made interior to the heart, e.g., through the interatrial septum to provide for a desired access route. While the procedures of the present invention will usually be percutaneous and intravascular, many of the tools will find use in minimally invasive and open surgical procedures as well. In particular, the tools for capturing the valve leaflets prior to attachment can find use in virtually any type of procedure for modifying cardiac valve function.

The atrioventricular valves are located at the junctions of the atria and their respective ventricles. The atrioventricular valve between the right atrium and the right ventricle has three valve leaflets (cusps) and is referred to as the tricuspid or right atrioventricular valve. The atrioventricular valve between the left atrium and the left ventricle is a bicuspid valve having only two leaflets (cusps) and is generally referred to as the mitral valve. In both cases, the valve leaflets are connected to the base of the atrial chamber in a region referred to as the valve annulus, and the valve leaflets extend generally downwardly from the annulus into the associated ventricle. In this way, the valve leaflets open during diastole when the heart atria fill with blood, allowing the blood to pass into the ventricle. During systole, however, the valve leaflets are pushed together and closed to prevent back flow of blood into the atria. The lower ends of the valve leaflets are connected through tendon-like tissue structures called the chordae, which in turn are connected at their lower ends to the papillary muscles. Interventions according to the present invention may be directed at any one of the leaflets, chordae, annulus, or papillary muscles, or combinations thereof. It will be the general purpose of such interventions to modify the manner in which the valve leaflets coapt or close during systole so that back flow or regurgitation is minimized or prevented. While the procedures of the present invention will be most useful with the atrioventricular valves, at least some of the tools described hereinafter may be useful in the repair of other cardiac valves, particularly the aortic valve.

The methods of the present invention will usually comprise accessing a patient's vasculature at a location remote from the heart, advancing an interventional tool through the vasculature to a ventricle and/or atrium, and engaging the tool against a tissue structure which forms or supports the atrioventricular valve. By engaging the tool against the tissue structure, the tissue structure is modified in a manner that reduces valve leakage or regurgitation during ventricular systole. The tissue structure may be any of one or more of the group consisting of the valve leaflets, chordae, the valve annulus, and the papillary muscles. Optionally, the interventional tool will be oriented relative to the atrioventricular valve and/or tissue structure prior to engaging the tool against the tissue structure. The interventional tool may be self-orienting (e.g., pre-shaped) or may include active mechanisms to steer, adjust, or otherwise position the tool. Alternatively, orientation of the interventional tool may be accomplished in whole or in part using a separate guide catheter, where the guide catheter may be pre-shaped and/or include active steering or other positioning means. In all cases, it will usually be desirable to confirm the position prior to engaging the valve leaflets or other tissue structures. Such orienting step may comprise positioning the tool relative to a line of coaptation in the atrioventricular valve, e.g., engaging positioning elements in the valve commissures.

In a first aspect of the method of the present invention, the tissue structure comprises the valve leaflets and the engaging step comprises attaching one or more opposed points on or along the valve leaflets together. In the case of the bicuspid mitral valve, the attachment points may be located at or near the center of each leaflet, creating a generally symmetric structure with two openings, i.e., between the attachment point(s) and each of the two commissures. Alternatively, the attachment points may be close to each of the commissures. Both will effectively reduce the area in which the valve can open. In the case of the tricuspid valve, any two of the three leaflets can be partially or totally closed together or all three may be partially closed together.

In both cases, the attachment of the valve leaflets may be performed in a variety of ways, including suturing, clipping, stapling, riveting, gluing, fusing, or the like. While each of these approaches may differ significantly in the protocols and devices used for performing them, the end result will be the same, i.e., improved ability of the atrioventricular valve to close against the elevated pressures within the ventricle during systole. In order to improve apposition of the valve leaflets, it may be preferred to attach the leaflets at a point spaced inwardly from the free edge of the leaflet. Usually, the attachment point within the valve leaflet will be located from 1 mm to 4 mm inward from the free edge.

It will frequently be desirable to stabilize the interventional tool relative to the valve leaflets and other heart tissue structures at least some points during the interventional procedure. In a broad sense, such stabilization is intended primarily to couple motion of the interventional tool to the motion of the heart so that the tool may then engage the valve leaflets or other target tissue structures with minimum differential motion. The stabilization may be achieved either through the interventional tool or through a guide catheter or other platform which is used to deliver the interventional tool. In both cases, stabilization will usually be achieved by engaging a tissue structure of the heart, such as the interatrial septum, the atrial wall, the valve annulus, the valve chordae, the papillary muscles, or the like. For antegrade approaches, immobilization of either the guide catheter, the interventional tool, or both relative to the valve annulus or valve commissures will be particularly effective. For retrograde approaches, immobilization against the papillary muscles, the chordae, or the valve leaflets themselves may be particularly effective. Stabilization should be distinguished from valve capture which is usually performed after the interventional tool and/or guide catheter have been stabilized within the heart. Thus, the methods of the present invention may comprise up to four separate steps or phases prior to valve affixation. First, the interventional tool and/or guide catheter may be positioned, either actively or passively. Second, the interventional tool and/or guide catheter may be stabilized within the heart. Next, the interventional tool may be used to capture the valve leaflets. Then, prior to affixation, the valve leaflets may be positioned and, if necessary, repositioned in order to determine that a particular coaptation and affixation are capable of inhibiting the valve regurgitation. Finally, once adequate regurgitation inhibition has been confirmed, the valve leaflets may be affixed in any of the manners described below.

In a particular approach, the interventional tool may be stabilized by mechanically fixing the shape of the tool after the tool has been advanced to a position proximate the atrioventricular valve. For example, the interventional tool can comprise a plurality of linked elements which can be locked into place, e.g., a "goose-neck" device. Such mechanically lockable devices may be used by themselves or in conjunction with any of the other stabilization devices described herein.

When attaching portions of the valve leaflets together, it will frequently be desirable to temporarily capture the valve leaflets before implementing the final attachment step. For example, the leaflets can be captured using forceps or other graspers introduced as part of or separately from the interventional tool. After capturing the valve leaflets, flow through the valve can be observed by conventional cardiac imaging techniques, such as trans-esophegeal echocardiography (TEE), intracardiac echocardiography (ICE) or other ultrasonic imaging technique, fluoroscopy, angioscopy, catheter based magnetic resonance imaging (MRI), computed tomography (CT) and the like. By thus observing the flow through the valves, and more importantly whether or not back flow or regurgitation continues or has been sufficiently inhibited, the desired attachment configuration for the leaflets can be determined. If continued regurgitation is observed, the valve leaflets may be repositioned and the presence or absence of regurgitation again determined. Such repositioning steps may be continued until a position is identified in which the regurgitation is sufficiently inhibited. Additionally, other considerations, such as position of the attachment within the leaflet, stress placed on the leaflet, and other factors can be visualized before deciding on the final attachment point(s). In a preferred example, the valve leaflets may be coapted by a grasping instrument which also has a fixation mechanism, such as stapling, suturing, clipping or riveting as previously described, so that once a desirable attachment configuration is temporarily achieved, the final attachment can be made using the same instrument. Grasping of the valve leaflets can be accomplished using articulated graspers, vacuum-assisted graspers, grasping pins, or other temporary attachment modes as described in more detail below. After the leaflets are in the desired configuration, they may be permanently secured together by any of the techniques described above.

In a second aspect of the method of the present invention, the tissue structure comprises the chordae and the engaging step comprises linking opposed chordae together, i.e., chordae attached to different valve leaflets. Usually, the chordae will be partially gathered or coupled together using a suture or other loop structure. In some instances it may be desirable to closely tie the chordae together at one or more locations.

In a third aspect of the method of the present invention, the tissue structure comprises the chordae and the engaging step comprises applying energy to shorten the chordae. Particular forms of heat energy, most particularly radiofrequency energy, have been found to be able to modify and shrink collagen so that supporting chordae may be tightened. By applying energy to shorten one or more of the chordae attaching either or both (or all three in the case of the tricuspid valve) valve leaflets, the flow through the atrioventricular valve can be modified and regurgitation minimized. In a preferred aspect of the present invention, the chordae will be initially grasped or captured and manipulated to temporarily apply tension to the valve leaflets. The effect of such temporary shortening can then be visually assessed and, if a desired improvement in valve performance is observed, energy can be applied to shorten the chordae. In many cases, however, it may be preferable to apply a clip, ring, suture loop, or other mechanical element to permanently twist, plicate, or otherwise shorten the chordae, as described elsewhere herein.

In a fourth aspect of the method of the present invention, the tissue structure comprises the valve annulus and the engaging step comprises circumferentially tightening or shortening the annulus. In a preferred technique, the annulus will be strengthened by positioning and attaching a supporting structure over the annulus in a manner broadly analogous to the open surgical placement of an annuloplasty ring. Alternatively, the annulus can be tightened by surgical plication techniques, or in some instances by shrinking tissue within the annulus by applying radiofrequency energy as generally described above in connection with shortening of the chordae.

In a fifth aspect of the method of the present invention, the tissue structure comprises the papillary muscles and the engaging step comprises capturing and drawing opposed points or portions of the papillary muscles together. This approach is similar in many respects to capture of the chordae, and will generally comprise suturing or otherwise forming a linkage between the opposed portions of the papillary muscles. As with the chordae, it will generally not be desirable to fully close the papillary muscles together, although in some instances such an approach may also find use.

In all the aspects of the method described above, the heart will usually remain beating while the interventional tool is engaged against the tissue structure. When the heart is beating, however, it may be desirable to temporarily stop valve action during at least a portion of the procedure, particularly to facilitate grasping of the valve leaflets when such a technique is being employed. The valve action can be slowed temporarily by decreasing the heart rate with intravenous infusion of a beta blocker, such as esmolol, or can be completely stopped for a brief time, e.g., five to ten seconds, by infusion of a drug, such as adenosine. Alternatively, the valve action can be stopped by temporarily raising the pressure in the associated ventricle to a pressure above that in the atrium during diastole. While the heart will continue to beat, the motion of the valve leaflets opening and closing will be stopped to facilitate grasping. As a further alternative, it will be possible to mechanically restrain the leaflets directly or by capturing the chordae, as described in more detail below. While such an approach may be effective for some purposes, the difficulty in capturing the valve leaflets initially may still be present.

While the methods of the present invention are particularly desirable since they permit interventions to occur without stopping the heart, they may also be used with patients undergoing cardiopulmonary bypass. Such cardiopulmonary bypass can be achieved by any presently available technique, including both conventional systems and recently developed endovascular bypass systems, such as those available from Heartport, Inc., Redwood City, Calif.

During the procedures performed while the heart is beating, it will often be desirable to stabilize the interventional tool against one or more cardiac structures prior to grasping the leaflets with the interventional tool. Such stabilization will lessen the relative motion between the tool and the structure. Stabilization mechanisms may be separate from or integral with any part of the system or device, including but not limited to guidewires, guiding catheters and interventional tools. Likewise, the stabilization mechanisms may provide one or more additional functions in the tissue modification procedure, such as steering, orientation assessment, grasping, coaptation, adjustment and fixation. Therefore, many components in the system may have dual purposes.

Coaptation may be performed by a number of methods, such as capturing the leaflets or by releasably capturing the chordae attached to each leaflet. An exemplary capture device will comprise a snare, or a pair of snares, which are advanced through the chordae to capture or entangle individual chordae. This snare or snares may then be tightened to draw the chordae partially together and limit valve motion, at least partially. After such coaptation is achieved, the valve leaflets, chordae, papillary muscles, or annulus may then be engaged and modified, e.g., the leaflets may be attached, using a separate interventional tool, as described above and elsewhere herein. Alternatively, it will be possible to form a permanent link, bridge, or capture of the chordae if the temporary coaptation appears sufficient to repair valve function. In some instances, it may be sufficient to simply detach the snare or other capture mechanism and leave it in place permanently. In other instances, it will be possible to exchange the snare for a more permanent attachment structure, such as a suture loop or metallic coil. For example, once the snare is in place, if the valve function is acceptably repaired, the snare may be drawn out from the chordae through the placement catheter, where the snare pulls a length of suture in the manner of a needle passing through tissue. The suture can then be tied or otherwise fastened to form a permanent capture loop for the chordae. Alternatively, a separate attachment structure, such as a metal coil, barb, malecot, or the like, may be advanced around the snared chordae to effect permanent capture, where a structure will be detached and left in place.

The methods described above may be performed using either antegrade or retrograde endovascular access through the vasculature. The following description will describe both antegrade and retrograde access approaches for gaining access to the mitral valve. Mitral valve access is generally more difficult than tricuspid valve access. In a retrograde approach, the interventional tool, optional guiding catheter, and any other supporting devices, will be introduced through distal arterial vasculature and over the aortic arch and into the left ventricle through the aortic valve. Typically, the aortic arch or via a brachial approach will be approached through a conventional femoral artery access route, but could also be approached through the brachial artery, axillary artery, or a carotid artery. When entering the left ventricle, the interventional tool will generally be directed downwardly and away from the mitral valve structure. Thus, the interventional tool will usually be curved or turned so that it approaches the mitral valve from below, usually through the chordae toward the valve annulus. For example, the interventional tool can enter the left ventricle through the aortic valve and then be deflected or otherwise steered to turn 90° to directly approach the mitral valve and chordae. Steering of the tool can be accomplished by deflecting a supporting catheter using pull wires, pre-formed curved catheters, or the like. In some instances, the papillary muscles could be more directly accessed since they generally lie below the aortic valve and inline with the tool as it enters the left ventricle.

Often, it will be desirable to position the interventional tool toward the target tissue structure using a preformed and/or steerable guide catheter. In a retrograde approach, the guide catheter may be placed from an access point, e.g., the femoral artery at the patient's groin, so that it passes over the aortic arch, through the aortic valve, and into the left ventricle where it will form an access path to the target tissue structure. When the tissue structure is the chordae or valve leaflets, the guide catheter will usually have to be curved or be everted or turned backward so that it can turn the interventional tool around. Additionally, it may be desirable to provide for stabilization of the distal end of the guide catheter. Stabilization may be provided by extendible elements, wires, cages, balloons, or other structures which engage the valve annulus, chordae or ventricular wall portions. Alternatively, two or more stabilizing extensions may be provided to project forwardly from the guide catheter and seat in the valve commissures to position and hold the guide catheter in place. Such extendible elements may also be used to stabilize guidewires, interventional tools and other types of catheter systems. Specific stabilization structures will be described in more detail below.

Access for an antegrade endovascular approach will be through the inferior vena cava or superior vena cava into the right atrium. Such antegrade access may, in itself, be sufficient to perform procedures on the tricuspid valve from the top of the valve. Such procedures, however, will not be described in detail herein. To access the mitral valve, it will be necessary to pass from the right atrium into the left atrium, typically by passing the tool through the interatrial septum. The interatrial septum may be endovascularly penetrated by conventional techniques, typically using a Brockenbrough needle, as described in the valvuloplasty literature. Once the interatrial septum has been penetrated, the interventional tool may be passed into the left atrium so that it approaches the mitral valve from the top. Such an approach will require that the access path turn downward, typically through an angle in the range from 0° to 120°.

The superior vena cava may be accessed through a variety of conventional peripheral access sites, such as the internal jugular vein, while the inferior vena cava may be accessed through the femoral vein. Such access may be performed percutaneously or by surgical cut down techniques.

As with the retrograde arterial approach, the antegrade venous approach may utilize placement of a guide catheter. With the use of a guidewire, the guide catheter will be configured to pass from the initial access location, through either the superior vena cava or inferior vena cava into the right atrium. The guide catheter will then be adapted to pass through an interatrial penetration and into the left atrium, where it will be pre-shaped or deflected to approach the mitral valve from the top. The guidewire, guide catheter and/or the interventional catheter which carries the interventional tool may be steerable and may optionally have stabilizing elements. For example, in this specific embodiment, the guide catheter may have two or more laterally extensible steering wires and/or a plurality of stabilizing arms which project forwardly and seat around the valve annulus or commissures to hold the guide catheter in place. The interventional tool may then be deployed through the guide catheter to perform the desired valve repair technique.

Systems according to the present invention comprise a guide catheter configured to pass from the remote vasculature of a patient to a position within the heart adjacent to a target atrioventricular or other cardiac valve. The systems further comprise an interventional catheter configured to pass through the guide catheter and to engage the atrioventricular or other cardiac valve and/or associated cardiac structures and an interventional tool on the interventional catheter adapted to modify the atrioventricular or other cardiac valve leaflets, valve annulus, valve chordae or papillary muscles to reduce regurgitation. In particular, the guide catheter can be configured for either an antegrade or retrograde approach to the mitral valve, as described above. The guide catheter may further comprise a stabilizing element for engaging tissue within the heart to reduce relative movement between the guide catheter and the tissue while the heart remains beating. The structure can be any of the cages, wires, or the like, which have previously been described in connection with the method. Additionally, the interventional catheter may also comprise a stabilizing element for engaging a tissue structure within the heart to reduce relative motion between the interventional catheter and the tissue. The stabilizing element can also be an expansible cage, steering wires, or the like and may include vacuum and/or surface finishes to enhancing coupling. Specific interventional tools include suturing devices, stapling devices, clip-applying devices, radiofrequency electrodes, surgical adhesive applicators, annuloplasty rings, and the like.

Both the interventional tool and the guide catheter may employ stabilizing mechanisms intended to engage a tissue structure within the heart to reduce relative movement between the interventional tool and/or guide catheter relative to the heart, and in particular relative to the atrioventricular valve. The stabilization mechanisms in both cases may be the same. Typically, the stabilization mechanisms will be adapted to engage at least one tissue structure selected from the group consisting of the interatrial septum, the atrial wall, the valve annulus, the valve commissures, the valve chordae, and the papillary muscles. For example, the stabilizing mechanism may comprise one or more extensible wires which are deployable radially outwardly to engage the tissue structure, such as the valve commissures. Alternatively, the stabilizing mechanism could comprise an expansible cage that can be deployed to occupy all or at least a major portion of the atrium above the atrioventricular valve. As a still further alternative, the stabilizing mechanism could be a pair of inflatable balloons which are spaced-apart and adapted to engage the interatrial septum when the interventional tool and/or guide catheter are passed therethrough.

In further specific aspects of the systems of the present invention, the interventional tool may comprise a valve leaflet capture device intended for temporarily holding the valve leaflets prior to modification, e.g., affixation. For example, the valve leaflet capture device may comprise a pair of extensible elements which may be advanced from a distal end of the interventional tool to engage and capture the two mitral valve leaflets or three aortic valve leaflets. The particular capture tools may grasp the leaflets by pinching, partially or fully penetrating or piercing, and/or suctioning the leaflets. The tools may comprise jawed devices, looped devices, coiled devices or pronged devices, or vacuum devices to grasp and hold the leaflets.

The present invention further provides methods for grasping an atrioventricular or other cardiac valve, particularly the mitral valve, to facilitate subsequent intervention or for other purposes. The grasping method comprises capturing chordae attached to at least one leaflet of the valve while the heart is beating. Capture of the chordae from beneath the valve can modify leaflet movement and improve valve function, optionally closing portions of opposed valve leaflets against each other. Usually, chordae attached to valve leaflets (or possibly three valve leaflets in the case of tricuspid valves) are captured simultaneously. For example, one or more snares, such as helical coils, can be advanced into the chordae to capture and immobilize portions thereof. Alternatively, a loop element can be advanced through the valve chordae and tightened in order to modify valve function. In some instances, capture of the chordae can be made permanent and will be sufficient to treat the underlying regurgitation. In other cases, capture of the chordae will be primarily for leaflet coaptation, and the leaflets will be affixed by a subsequent interventional step. Preferably, the subsequent interventional step is performed while the chordae remain captured. The chordae can then be released after the leaflets or other tissue structures have been modified.

The present invention still further provides a chordae capture catheter comprising a catheter body having a proximal end and a distal end. Means are provided at or near the distal end of the catheter body for capturing the chordae. A first exemplary means comprises one or more coils which are extensible from the distal end of the catheter and which engage and entangle the chordae when they are advanced therein. A second exemplary capture means comprises a loop element which is extensible from the distal end of the catheter and which is pre-formed to pass through the chordae on one or both, preferably both valve leaflets in order to draw the chordae together and modify valve function.

A further method according to the present invention for grasping an atrioventricular or other cardiac valve leaflets comprises capturing two valve leaflets separately and preferably sequentially. Such capture is effected by a leaflet capture catheter having at least three grasping jaws or prongs. A first valve leaflet is captured between a first pair of prongs, and second valve leaflet is captured between a second pair of prongs. Optionally, the two prong pairs can have a common center prong, typically where the center prong is fixed (immobile) and the two outer prongs pivot in order to provide a pair of adjacent jaw-type graspers. By separately and sequentially grasping the two leaflets, the leaflets can be held in a preferred apposition and the improvement in valve function observed. Alternatively, the leaflets may be grasped simultaneously. If the improvement is adequate, the valves can be permanently affixed in a separate step. Optionally, the leaflet capture catheter can include a device for fixing the valves, e.g., it can carry a clip which can be applied on to the valves as the capture catheter is withdrawn.

The present invention still further provides leaflet capture catheters suited for performing the method just described. The catheters comprise a catheter body having a proximal end and a distal end. A leaflet grasper is provided at or near the distal end of the catheter body and includes at least three prongs wherein at least two of the three prongs are pivotable so that they may be separately actuated to separately capture individual leaflets or simultaneously actuated to capture the leaflets together. Optionally, the catheters further comprise means for affixing the valve leaflets after they have been captured, preferably comprising a clip-applier.

The present invention further includes leaflet capture catheters and tools which utilize a vacuum for grasping the valve leaflets and manipulating the post leaflets into a desired apposition. Usually, the catheter will have at least two vacuum channels at a distal end where the channels are preferably separately positionable and independently actuable. In that way, at least two valve leaflets can be separately captured and positioned while the base catheter remains stationary. The catheter may be positioned in an antegrade or retrograde manner with the tool entering between the valve leaflets and optionally between the chordae. The tool and/or catheter may optionally further include modification devices, such as suture appliers, clip appliers, staplers, rivet appliers, adhesive applicators, heating elements for shortening the chordae, and others of the specific interventional tools described hereinafter. Likewise, the present invention further includes catheters and tools which include lumens for monitoring pressures within the chambers of the heart, and/or infusion of radiopaque contrast solution.

BRIEF DESCRIPTION OF THE DRAWINGS

FIG. 3A shows normal closure of the leaflets, while

FIGS. 30, and 31A-31D illustrate stabilization mechanisms which utilize coupling with the valve commissures and/or leaflets.

FIGS. 45A-45B are schematic illustrations of a grasping device which utilizes rollers in a pinching method.

FIGS. 46A-46B are schematic illustrations of a grasping device which utilizes a pair of opposing coils in a pinching method.

FIGS. 47A-D illustrate a pronged valve leaflet device which utilizes a pinching, partially penetrating or piercing method.

FIGS. 49A-49C illustrate an additional embodiment of a valve suturing device according to the present invention.

FIGS. 73A-73C illustrate a three-jaw clip-applier.

FIGS. 86, and 87A-87C illustrate an embodiment of an atrial-ventricular device for valve tissue modification.

DESCRIPTION OF THE SPECIFIC EMBODIMENTS

I. Cardiac Physiology

Figure 1:
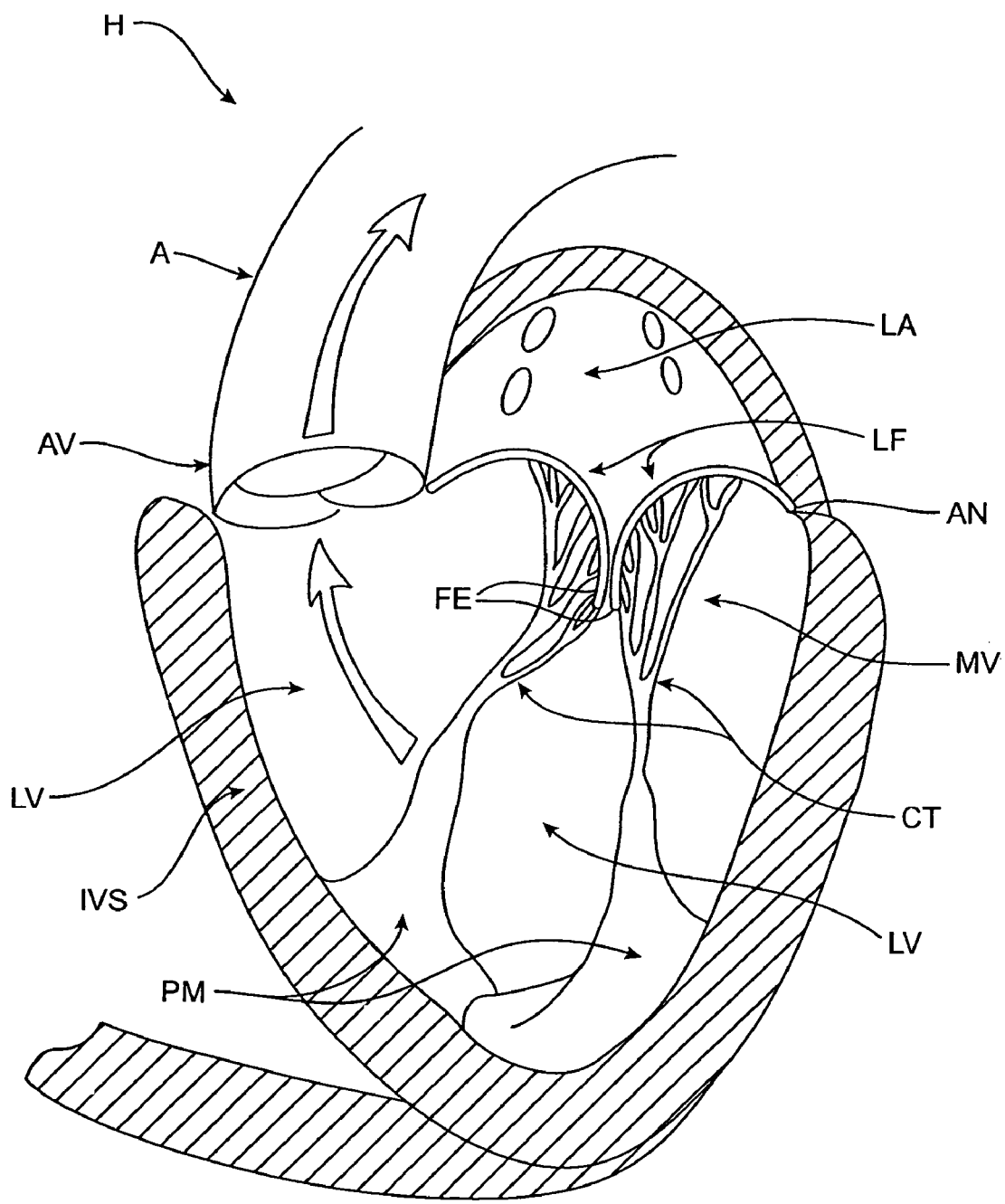
FIG. 1 is a schematic illustration of the left ventricle of a heart showing blood flow during systole with arrows.

The left ventricle LV of a normal heart H in systole is illustrated in FIG. 1. The left ventricle LV is contracting and blood flows outwardly through the tricuspid (aortic) valve AV in the direction of the arrows. Back flow of blood or "regurgitation" through the mitral valve MV is prevented since the mitral valve is configured as a "check valve" which prevents back flow when pressure in the left ventricle is higher than that in the left atrium LA. The mitral valve MV comprises a pair of leaflets having free edges FE which meet evenly to close, as illustrated in FIG. 1. The opposite ends of the leaflets LF are attached to the surrounding heart structure along an annular region referred to as the annulus AN. The free edges FE of the leaflets LF are secured to the lower portions of the left ventricle LV through chordae tendineae CT (referred to hereinafter as the chordae) which include plurality of branching tendons secured over the lower surfaces of each of the valve leaflets LF. The chordae CT in turn, are attached to the papillary muscles PM which extend upwardly from the lower portions of the left ventricle and interventricular septum IVS.

Figure 2:
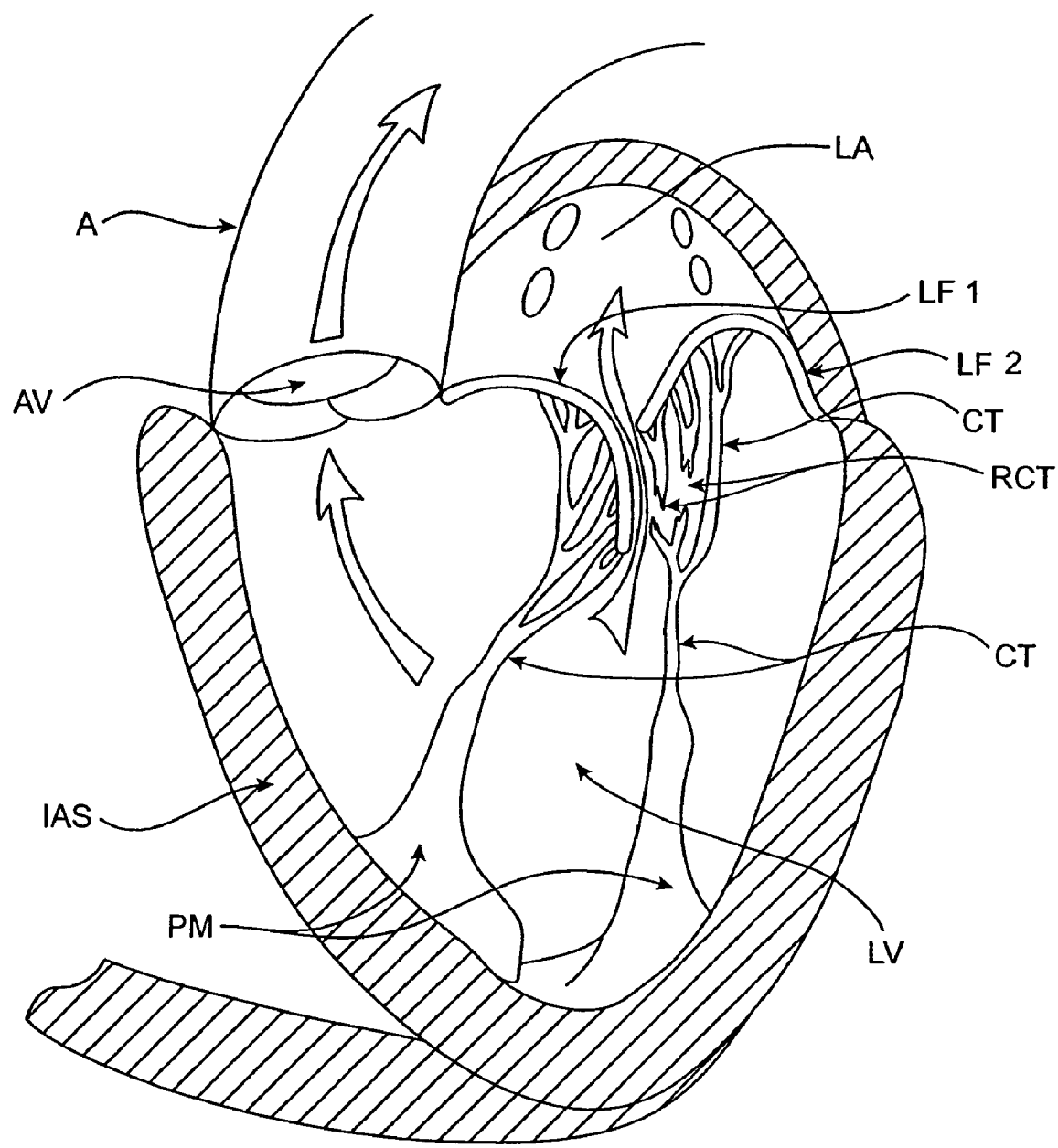
FIG. 2 is a schematic illustration of the left ventricle of a heart having prolapsed leaflets in the mitral valve.
Figure 3:
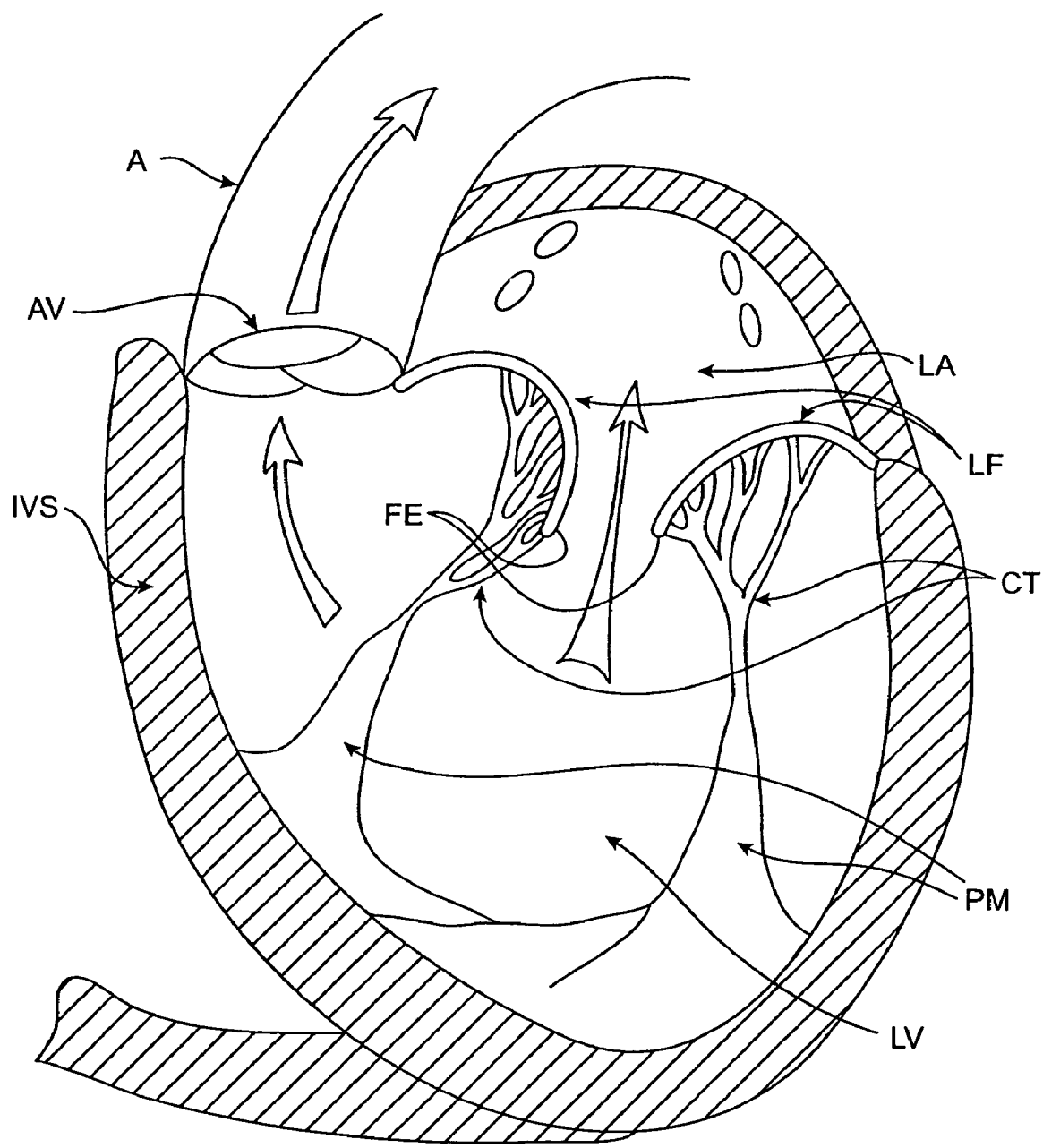
FIG. 3 is a schematic illustration of a heart in a patient suffering from cardiomyopathy where the heart is dilated and the leaflets do not meet.
Figure 4:
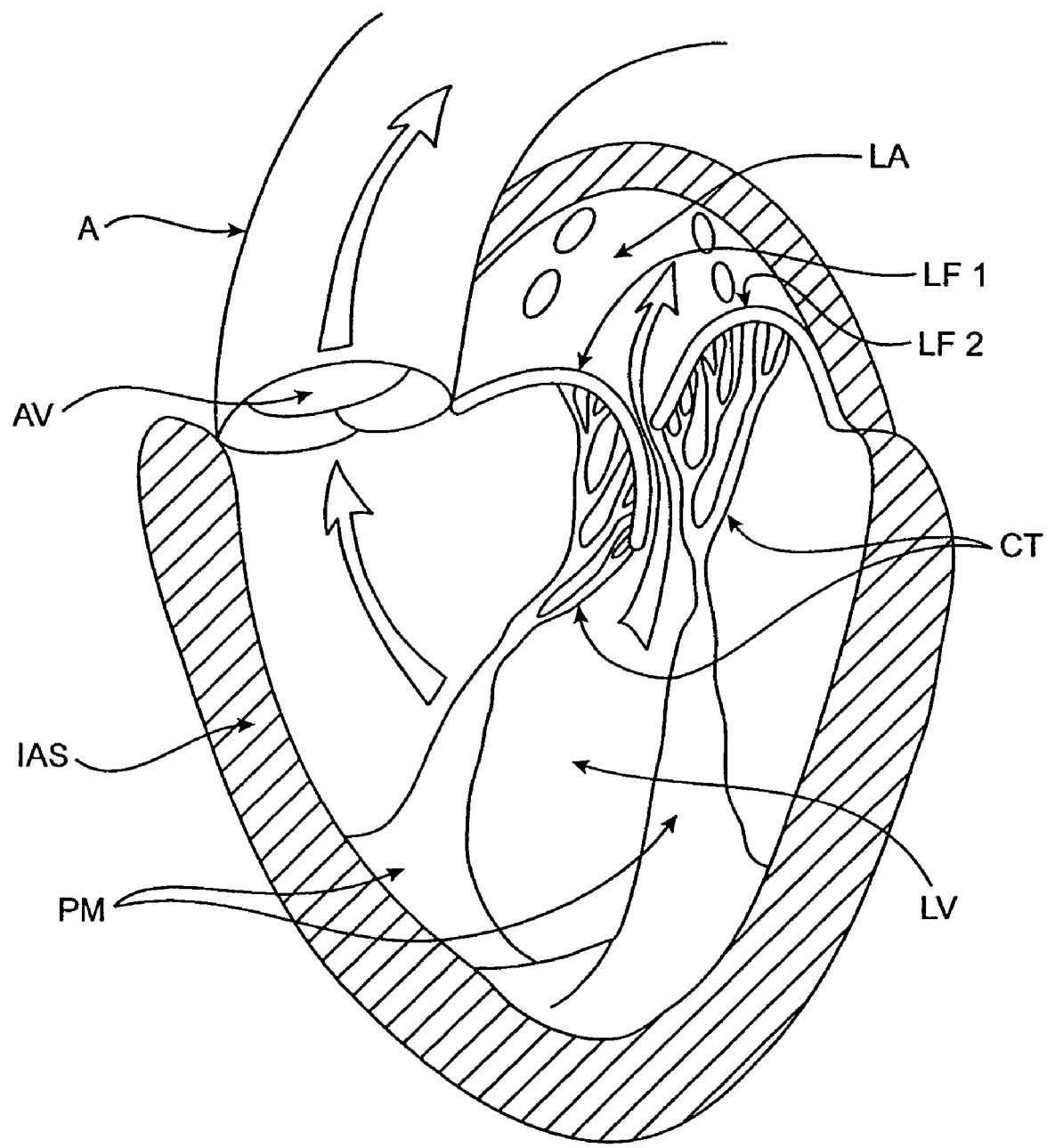
FIG. 4 illustrates mitral valve regurgitation in the left ventricle of a heart having impaired papillary muscles.

Referring now to FIGS. 2-4, a number of structural defects in the heart can cause mitral valve regurgitation. Ruptured chordae RCT, as shown in FIG. 2, can cause a valve leaflet LF2 to prolapse since inadequate tension is transmitted to the leaflet via the chordae. While the other leaflet LF1 maintains a normal profile, the two valve leaflets do not properly meet and leakage from the left ventricle LV into the left atrium LA will occur, as shown by the arrow.

Figure 3A:
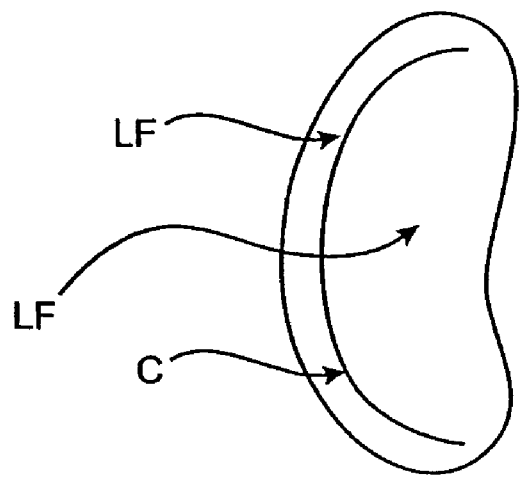
Figure 3B:
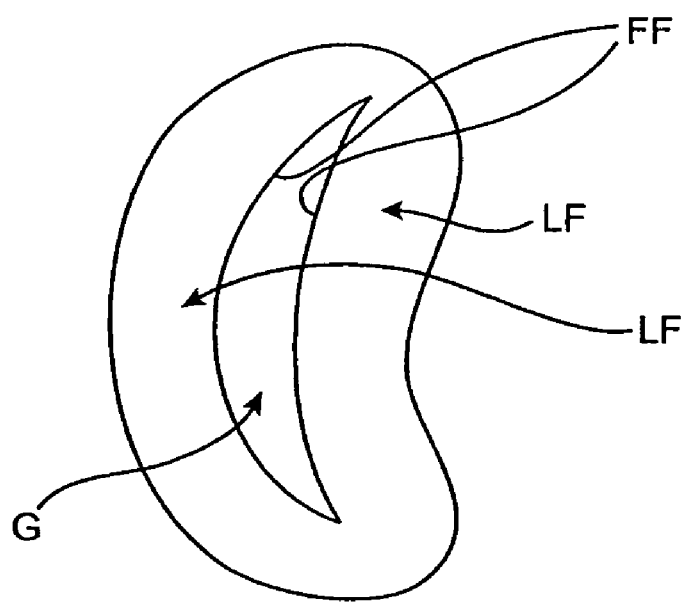
FIG. 3B shows abnormal closure in the dilated heart.

Regurgitation also occurs in the patients suffering from cardiomyopathy where the heart is dilated and the increased size prevents the valve leaflets LF from meeting properly, as shown in FIG. 3. The enlargement of the heart causes the mitral annulus to become enlarged, making it impossible for the free edges FE to meet during systole. The free edges of the anterior and posterior leaflets normally meet along a line of coaptation C as shown in FIG. 3A, but a significant gap G can be left in patients suffering from cardiomyopathy, as shown in FIG. 3B.

Mitral valve regurgitation can also occur in patients who have suffered ischemic heart disease where the functioning of the papillary muscles PM is impaired, as illustrated in FIG. 4. As the left ventricle LV contracts during systole, the papillary muscles PM do not contract sufficiently to effect proper closure. The leaflets LF1 and LF2 then prolapse, as illustrated. Leakage again occurs from the left ventricle LV to the left atrium LA, as shown by the arrow.

II. Interventional Approaches

Figure 5:
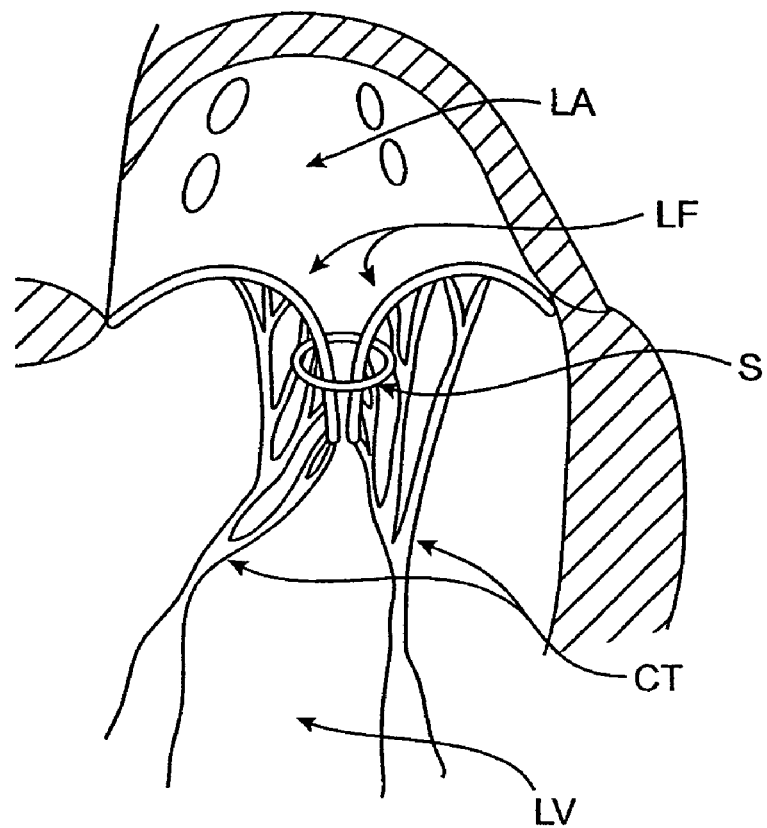
FIG. 5 is a schematic illustration showing direct attachment of opposed valve leaflets to reduce valve regurgitation according to the methods of the present invention.

The present invention treats cardiac valve regurgitation, particularly mitral valve regurgitation, by intervention at either of two locations. First, as shown in FIG. 5, the valve leaflets LF may be directly attached or coupled to each other by a structure S or other means. Typical structures include suture, staples, clips, pins, or other closure devices of a type commonly used in attaching opposed tissue surfaces. Alternatively, the opposed surfaces on the valve leaflets could be attached using adhesives, fusion energy, including radiofrequency current, laser energy, microwave, ultrasonic energy, or the like. A variety of specific techniques for valve leaflet attachment will be described hereinafter.

Figure 6:
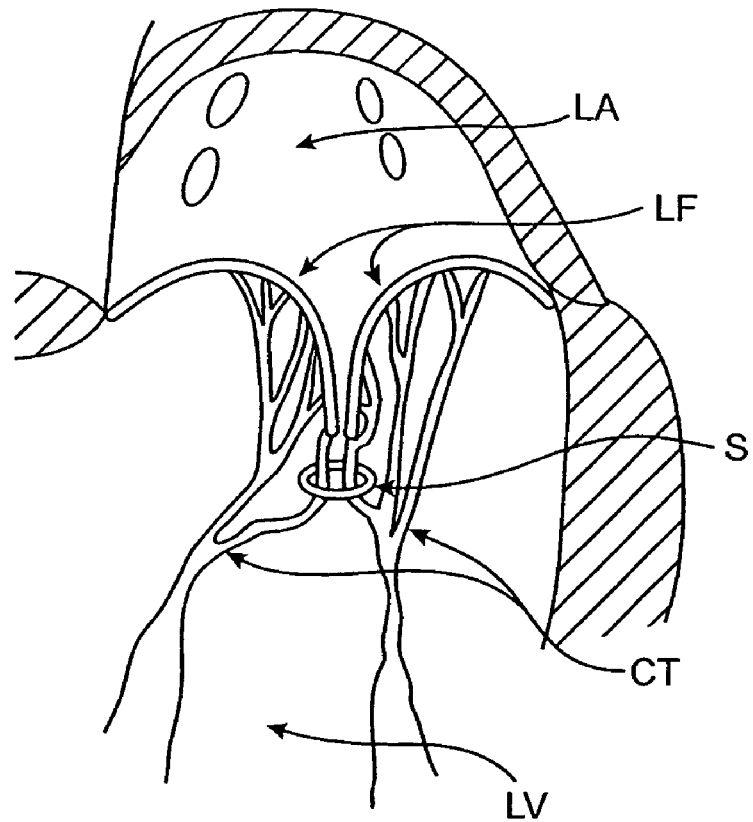
FIG. 6 is a schematic illustration showing attachment of valve chordae to treat valve regurgitation according to the methods of the present invention.

A second and often preferred interventional point will be in the chordae, as shown in FIG. 6. There, an attachment structure S is shown to couple individual chordae or tendons which are attached to each of the two leaflets LF. A variety of specific structures can be utilized, such as snares, staples, sutures, coils, clips, snaps, rivets, adhesives, and the like. Opposed chordae will usually also be attached directly, optionally employing any of the same structures listed above. Alternatively, opposed chordae may be indirectly tied or coupled together by a structure which links or couples their movement, but which does not physically attach chordae from each of the valve leaflets directly together. In addition to attaching the chordae, chordal intervention can include shortening the chordae, e.g., by applying energy to shrink the collagen therein, or may utilize mechanical plication devices, such as clips, to physically shorten the chordae.

III. Access to the Mitral Valve

Access to the mitral valve or other atrioventricular valve will preferably be accomplished through the patient's vasculature in a "percutaneous" manner. By "percutaneous" it is meant that a location of the vasculature remote from the heart is accessed through the skin, typically using a surgical cut down procedure or a minimally invasive procedure, such as using needle access through, for example, the Seldinger technique. The ability to percutaneously access the remote vasculature is well-known and described in the patent and medical literature. Depending on the point of vascular access, the approach to the mitral valve may be "antegrade" and require entry into the left atrium by crossing the interatrial septum. Alternatively, approach to the mitral valve can be "retrograde" where the left ventricle is entered through the aortic valve. Once percutaneous access is achieved, the interventional tools and supporting catheter(s) will be advanced to the heart intravascularly where they may be positioned adjacent the target cardiac valve in a variety of manners, as described elsewhere herein. While the methods will preferably be percutaneous and intravascular, many of the tools described herein will, of course, also be useful for performing open surgical techniques where the heart is stopped and the heart valve accessed through the myocardial tissue. Many of the tools will also find use in minimally invasive procedures where access is achieved thorascopically and where the heart will usually be stopped but in some instances could remain beating.

Figure 7:
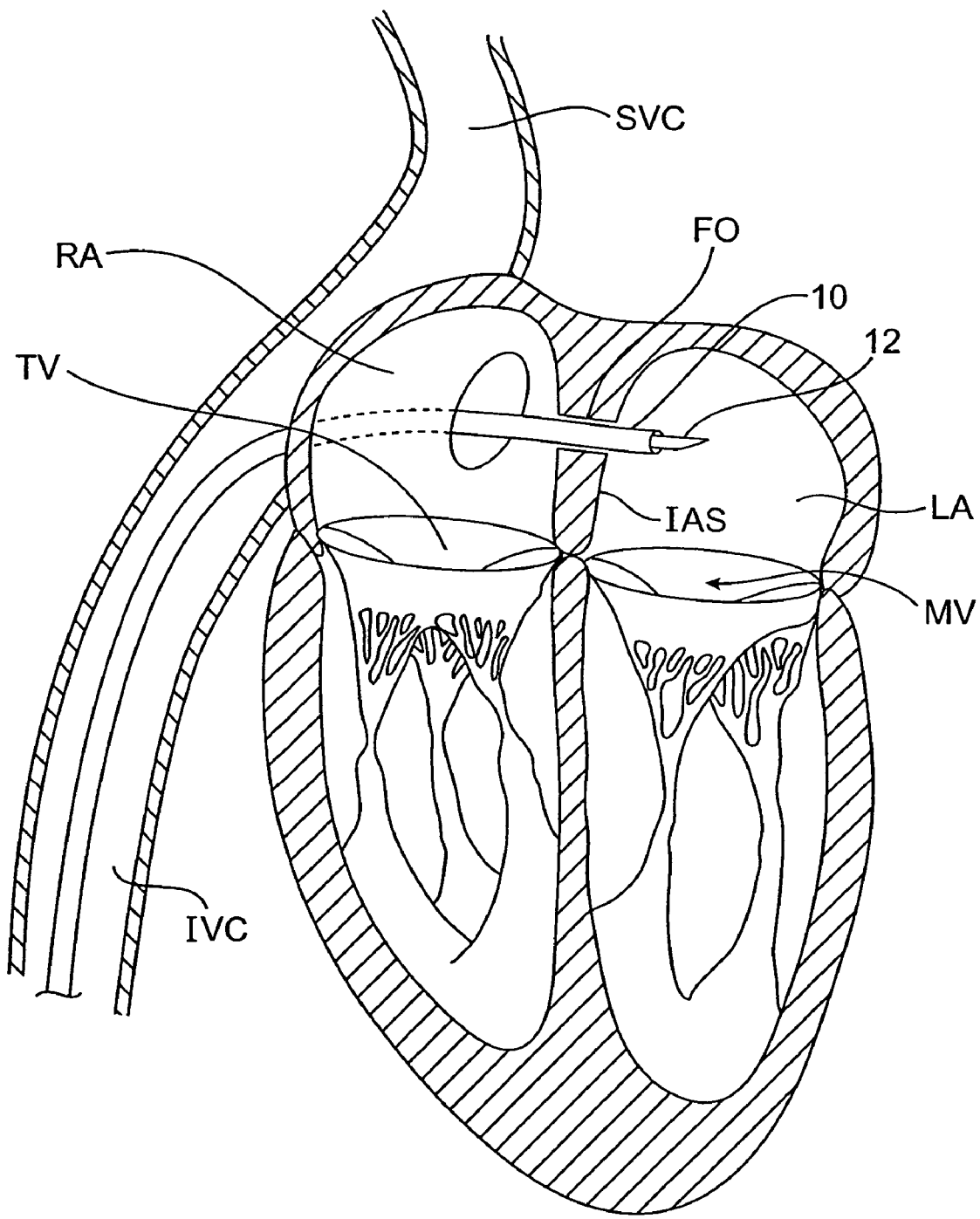
FIGS. 7-8 show exemplary antegrade approaches to the mitral valve from the venous vasculature.
Figure 8:
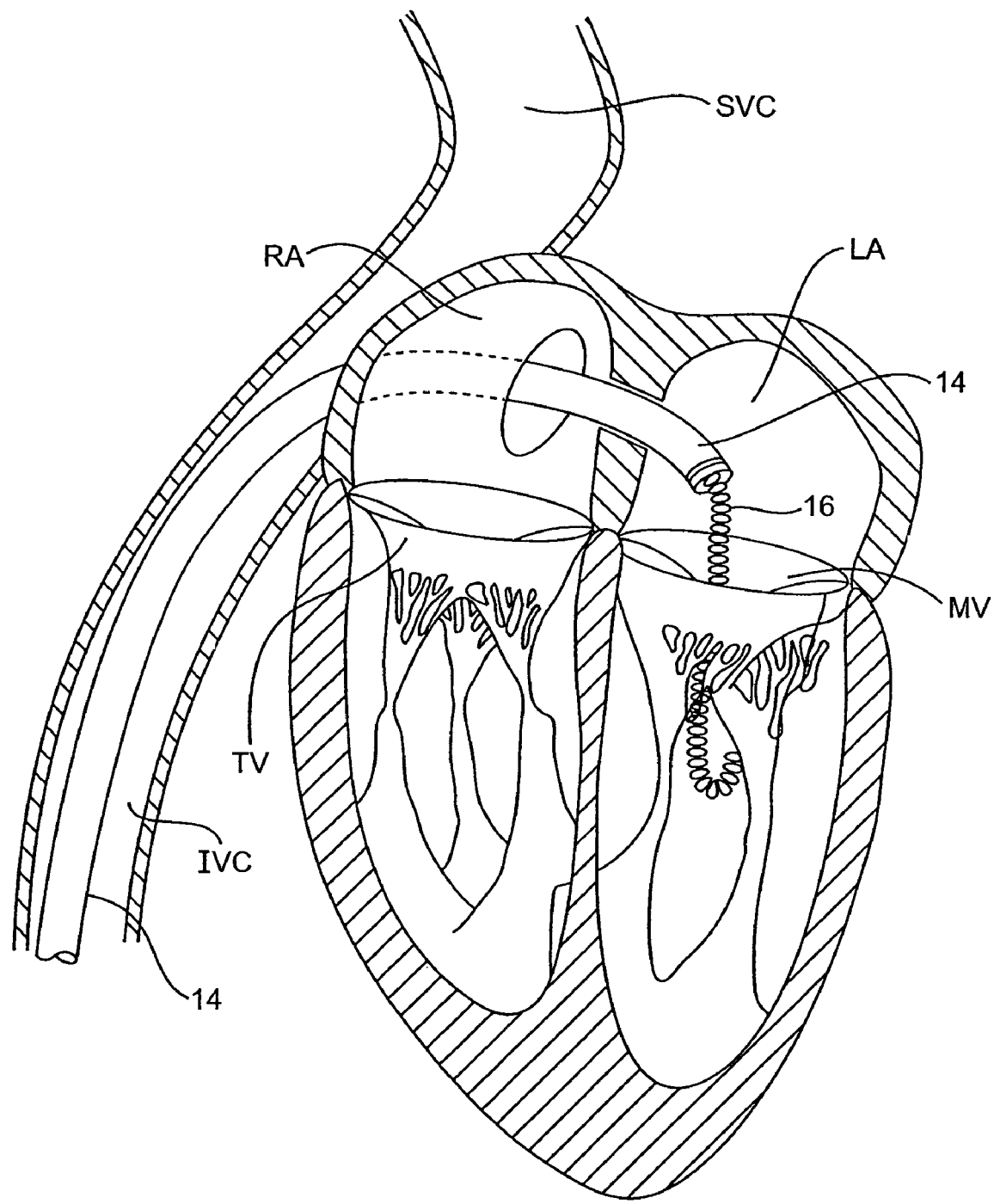

A typical antegrade approach to the mitral valve is depicted in FIGS. 7 and 8. The mitral valve MV may be accessed by an approach from the inferior vena cava IVC or superior vena cava SVC, through the right atrium RA, across the interatrial septum IAS and into the left atrium LA above the mitral valve MV. As shown in FIG. 7, a catheter 10 having a needle 12 may be advanced from the inferior vena cava IVC into the right atrium RA. Once the catheter 10 reaches the anterior side of the interatrial septum IAS, the needle 12 may be advanced so that it penetrates through the septum at the fossa ovalis FO or the foramen ovale into the left atrium LA. At this point, a guidewire may be exchanged for the needle 12 and the catheter 10 withdrawn.

As shown in FIG. 8, access through the interatrial septum IAS will usually be maintained by the placement of a guide catheter 14, typically over a guidewire 16 which has been placed as described above. The guide catheter 14 affords subsequent access to permit introduction of the interventional tool(s) which will be used for performing the valve or tissue modification, as described in more detail below.

The antegrade approach to the mitral valve, as just described, is advantageous in a number of respects. For example, the use of the antegrade approach will usually allow for more precise and effective centering and stabilization of the guide catheter and/or interventional tool. Precise positioning, of course, facilitates accuracy in the tissue modification, particularly affixation of the valve leaflets or chordae. The antegrade approach also reduces the risk of damaging the subvalvular apparatus during catheter and interventional tool introduction and manipulation. Additionally, the antegrade approach eliminates the risks associated with crossing the aortic valve. This is particularly relevant to patients with prosthetic aortic valves which cannot be crossed. When employing chordal fixation, the tools can be placed very close to the free edge of the leaflet since they will be removed in a direction away from the chordae which are being fixed. Additionally, an antegrade approach allows more direct access to the valve leaflets unimpeded by presence of the chordae.

Figure 9:
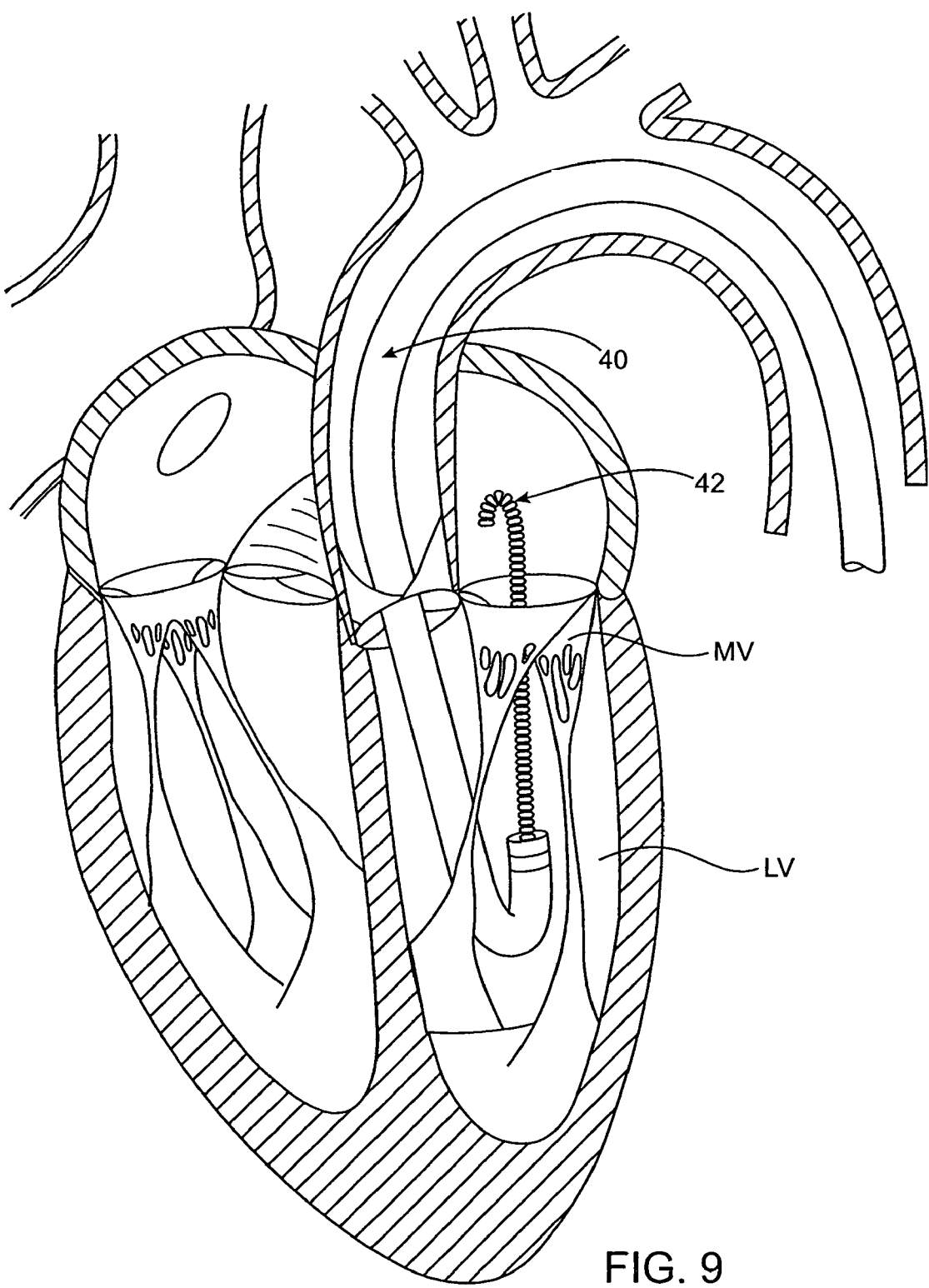
FIGS. 9-10 show exemplary retrograde approaches to the mitral valve through the aortic valve and arterial vasculature.

A typical retrograde approach to the mitral valve is depicted in FIG. 9. Here the mitral valve MV may be accessed by an approach from the aortic arch AA, across the aortic valve AV, and into the left ventricle below the mitral valve MV. The aortic arch AA may be accessed through a conventional femoral artery access route, as well as through more direct approaches via the brachial artery, axillary artery, or a radial or carotid artery. Such access may be achieved with the use of a guidewire 42. Once in place, a guide catheter 40 may be tracked over the guidewire 42. The guide catheter 40 affords subsequent access to permit introduction of the interventional tool(s) which will be used for performing the valve or tissue modification, as described in more detail below.

In some instances, a retrograde arterial approach to the mitral valve will be preferred due to its advantages. Use of the retrograde approach will eliminate the need for a trans-septal puncture. The retrograde approach is also more commonly used by cardiologists and thus has the advantage of familiarity. Additionally, the retrograde approach provides more direct access to the chordae.

The interventional tool(s) used for performing the valve or tissue modifications may be specifically designed for the approach or they may be interchangeable. For example, tools may be specifically designed for an antegrade or retrograde approach, or they may be designed to be used with either approach. In any case, tools may be used in any appropriate fashion to achieve a desired result. However, for the sake of clarity, a nomenclature has been developed to describe the common usage of such tools. Tools which perform the modification procedure while primarily residing in the atrium are referred to as "atrial" tools. These utilize an antegrade approach. Tools which perform the modification procedure while primarily residing in the ventricle are referred to as "ventricular" tools, and likewise utilize a retrograde approach. Tools which cross over the valve to perform the modification procedure, residing in both the atrium and the ventricle, are referred to as "atrial-ventricular" tools, and may utilize either an antegrade or retrograde approach.

IV. Orientation Steering

Approaching the desired valve or tissue structure for effective treatment, as described above, requires proper orientation of the catheters, tools and devices used throughout the procedure. Such orientation may be accomplished by gross steering of the device to the desired location and then refined steering of the device components to achieve a desired result.

Gross steering may be accomplished by a number of methods. First, a steerable guidewire may be used to introduce a guide catheter, interventional tool and/or treatment device into the proper position. The guide catheter may be introduced, for example, using a surgical cut down or Seldinger access to the femoral artery in the patient's groin. After placing a guidewire, the guide catheter may be introduced over the guidewire to the desired position. Alternatively, a shorter and differently shaped guide catheter could be introduced through the other routes described above.

Figure 10:
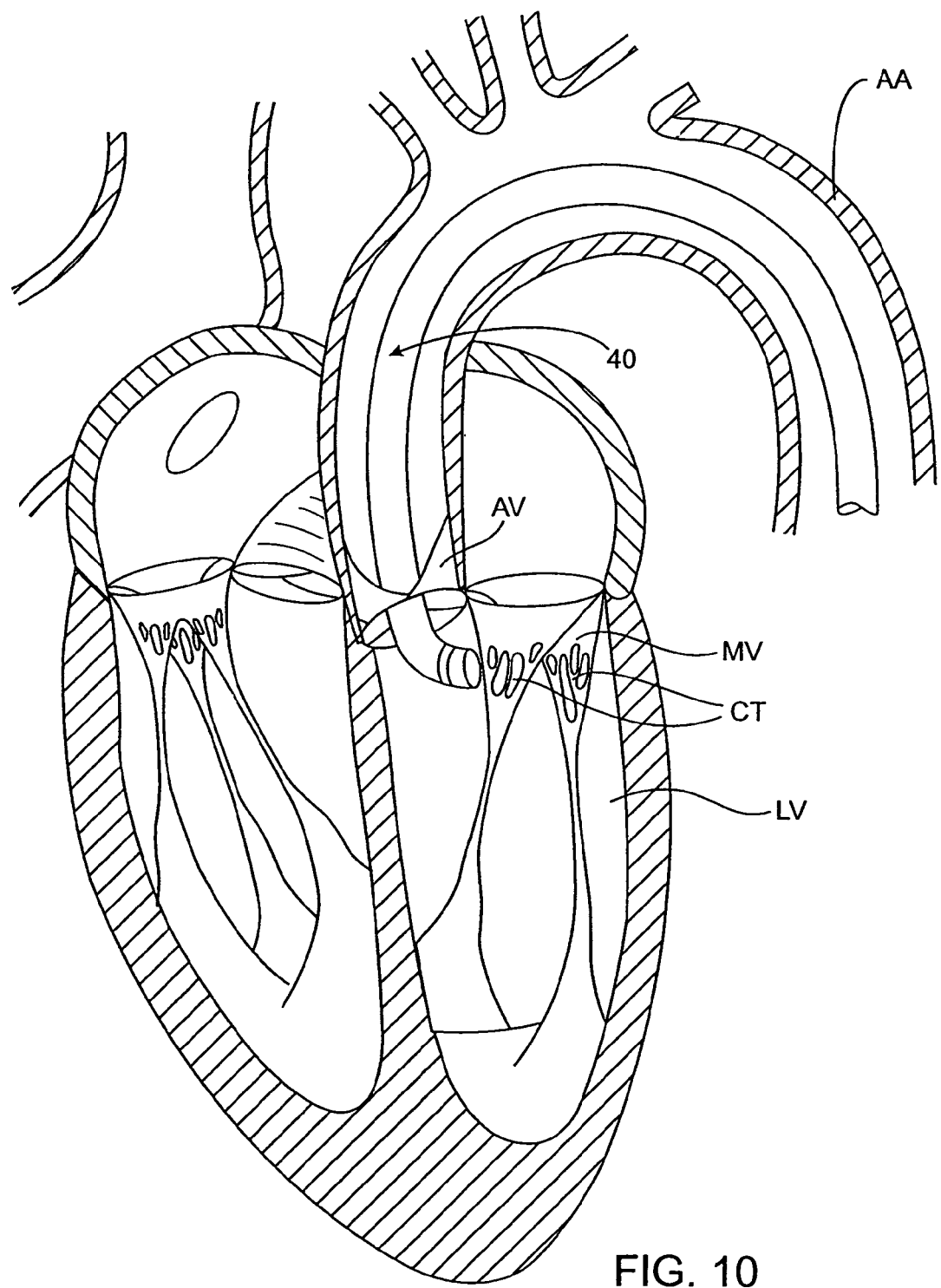

Second, a guide catheter may be pre-shaped to provide a desired orientation relative to the mitral valve. For example, as shown in FIGS. 9 and 10, guide catheter 40 may have a pre-shaped J-tip which is configured so that it turns toward the mitral valve MV after it is placed over the aortic arch AA and through the aortic valve AV. As shown in FIG. 9, the guide catheter 40 may be configured to extend down into the left ventricle LV and to evert so that the orientation of an interventional tool or catheter is more closely aligned with the axis of the mitral valve MV. The guide catheter 40 of FIG. 10 orients an interventional catheter (not shown) in a lateral direction relative to the access of the mitral valve MV. Each of the guide catheters 40 shown in FIGS. 9 and 10 may find use under different circumstances. For example, the guide catheter 40 of FIG. 10 might be particularly suited for introducing tools which modify the chordae CT, while the catheter 40 of FIG. 9 may be more useful for engaging tools against the valve leaflets. As shown in FIG. 9, a guidewire 42 may be positioned from the tip of the guide catheter 40 directly through the opening of the mitral valve MV. Interventional tools can then be directed over the guidewire 42 to form the particular procedures described hereinafter. Likewise, the interventional tool itself may be pre-shaped to provide a desired orientation.

Third, the guidewire, guide catheter or interventional tool may be actively deflected, e.g., having push/pull wires which permit selective deflection of the distal end in 1, 2, 3, or 4 directions depending on the number of pull wires, having shape memory nitinol, or having balloons, wires, wire cages or similar mesh structures to direct the device away from a cardiac structure and therefore into a desired position, to name a few.

Figure 11:
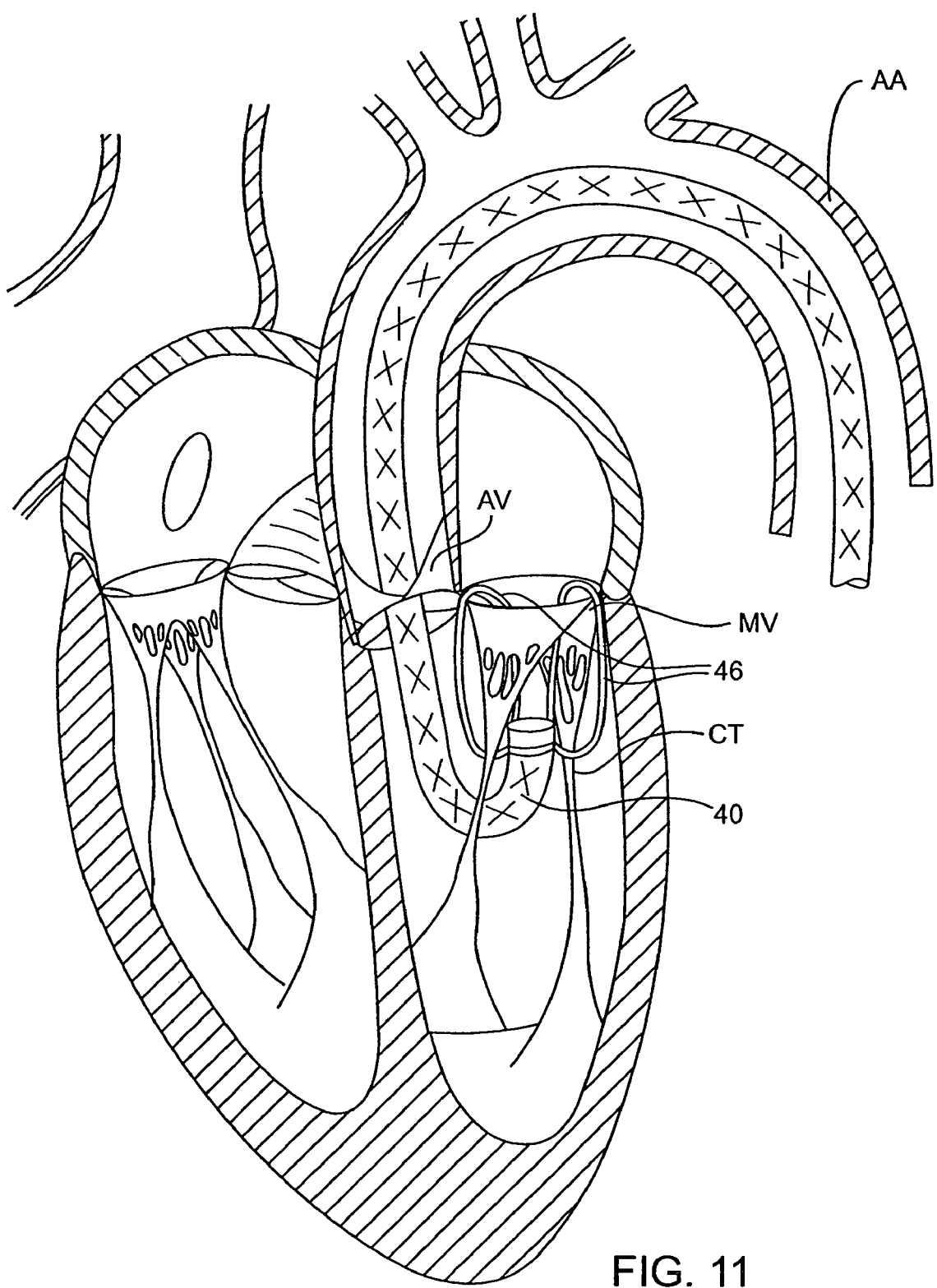
FIGS. 11-14 illustrate the use of adjustment wires for steering capability.
Figure 12A:
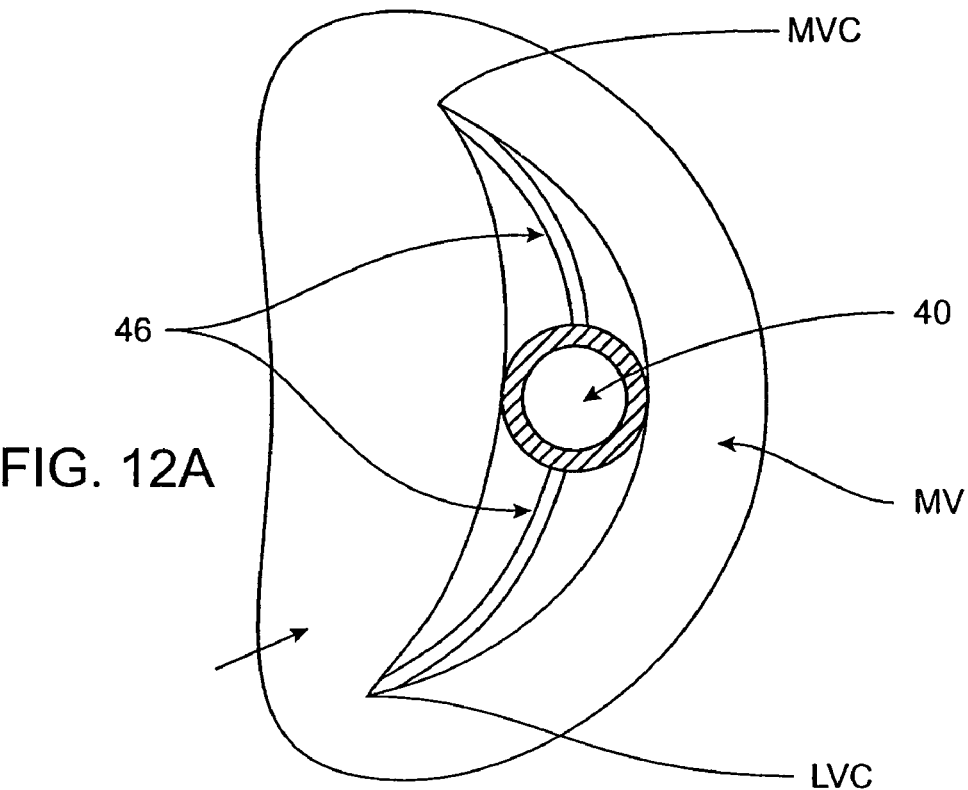
Figure 12B:
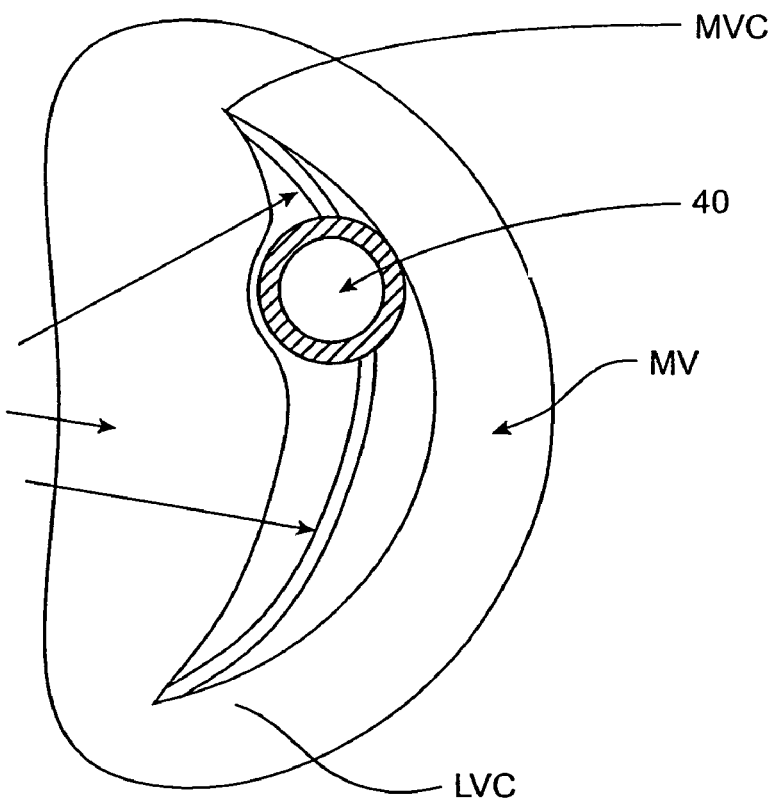

Either of the guide catheters 40 shown in FIGS. 9 or 10 may be provided with steering capabilities. For example, two or more adjustment wires 46 may be provided at the distal tip of the guide catheter 40 as shown in FIG. 11. These adjustment wires may be active or passive, and may be positioned within the valve commissures to enhance alignment of the guide catheter with the mitral valve MV. As shown in FIGS. 12A and 12B, the adjustment wires 46 may be positioned in the medial commissure MVC and lateral commissure LVC, and the guide catheter 40 may thus be moved from a central location, as shown in FIG. 12A to a more medial position, as shown in FIG. 12B. The catheter could of course also be moved in the lateral direction (not shown). The ability to position the guide catheter will be of great benefit in performing the specific interventions and valve modifications described hereinafter. It will be appreciated that similar steering mechanisms could be provided on an interventional catheter introduced through the guide catheter, and in some instances it may be most desirable to provide the guidewire, the guide catheter, and the interventional catheter with steering and positioning capabilities.

Figure 13:
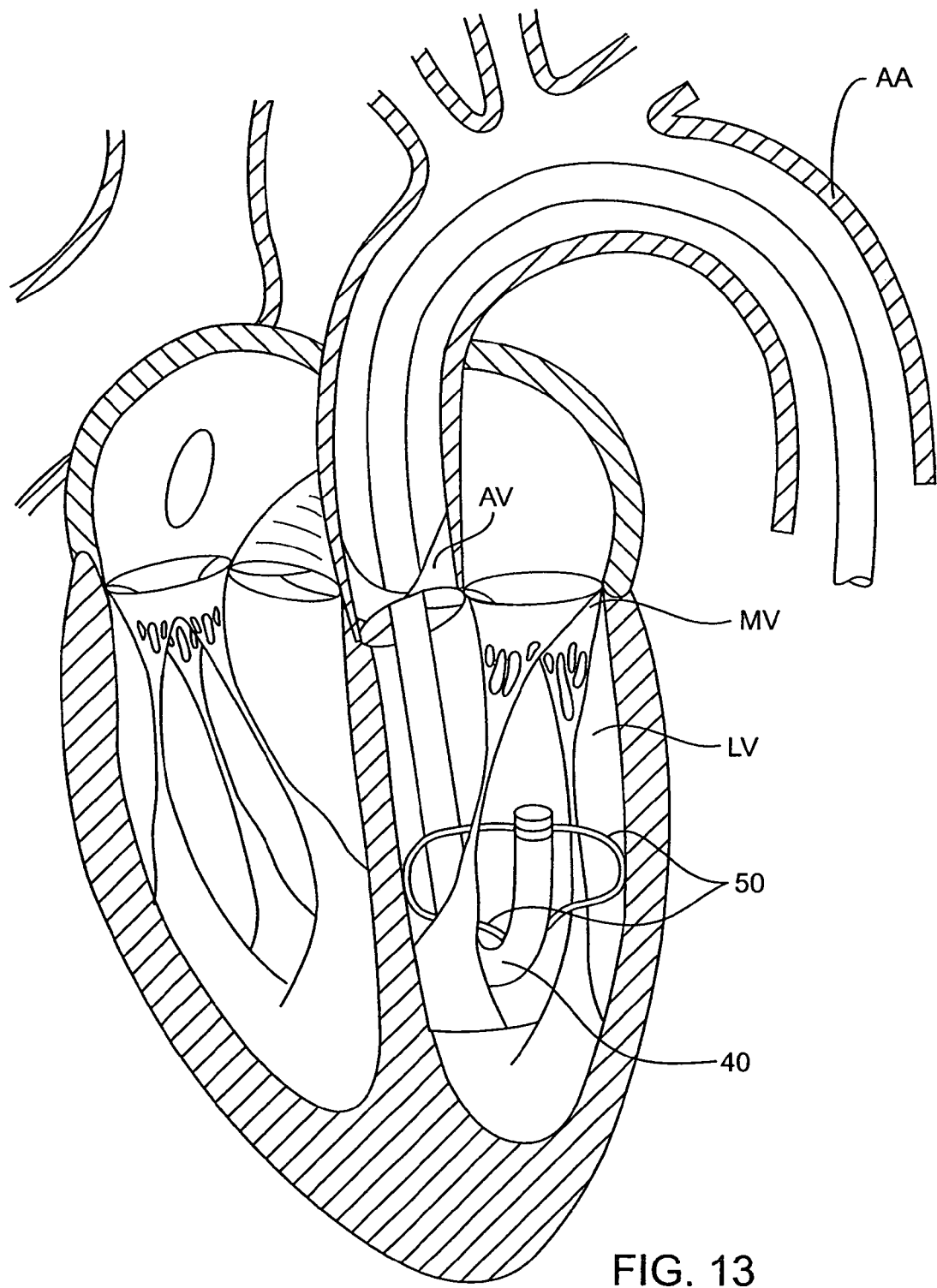

Steering wires 50 on a guide catheter 40 may also be provided to engage opposed surfaces within the left ventricle LV, as shown in FIG. 13. By providing such a steering capability, the distal tip of the guide catheter 40 can be moved further downward from the mitral valve. Catheter 40 of FIG. 13 would be particularly useful in combination with an interventional catheter which itself has steering capabilities which engage portions of the mitral valve, such as the valve commissures as described above.

Figure 14:
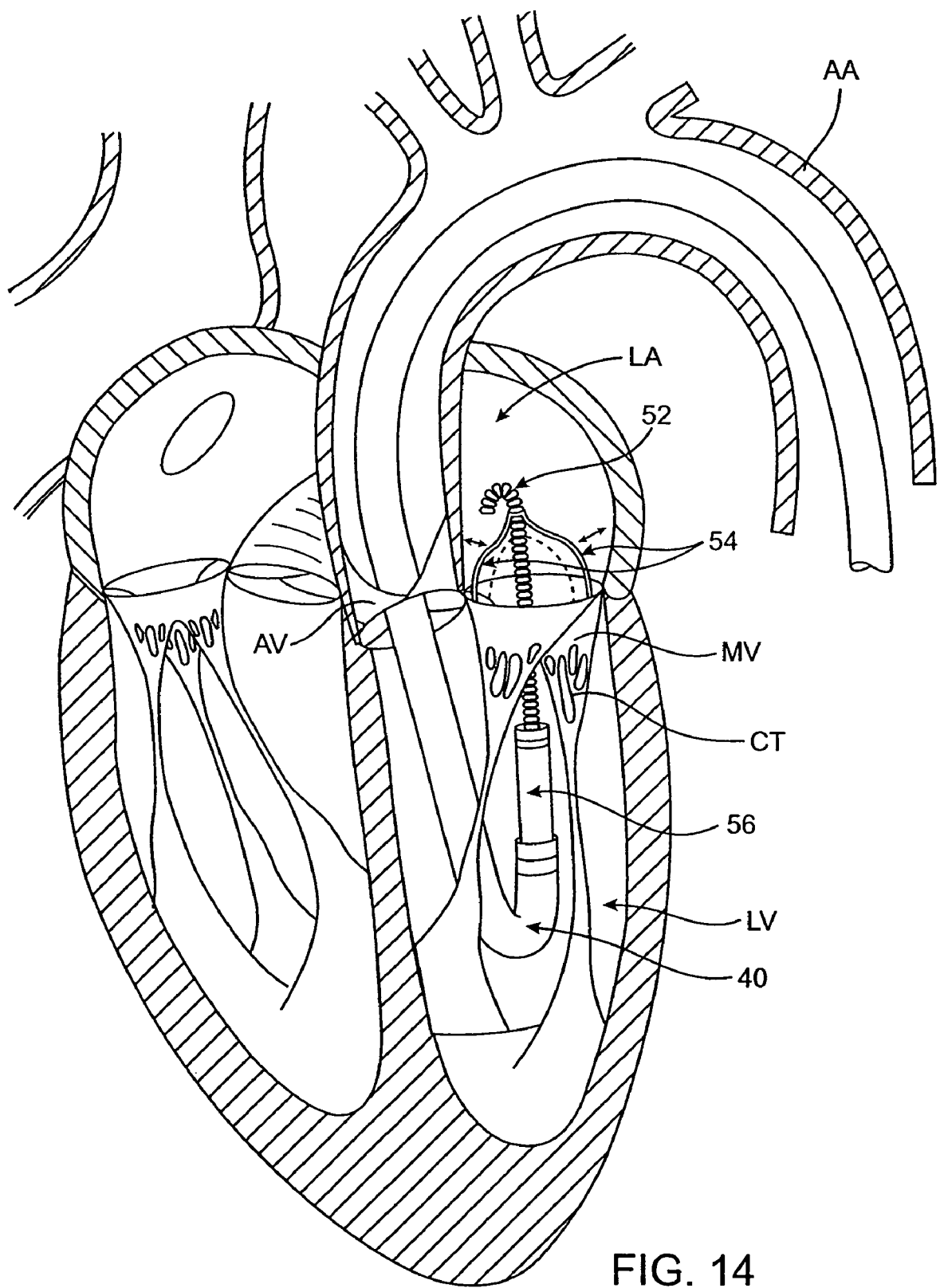
Figure 15A:
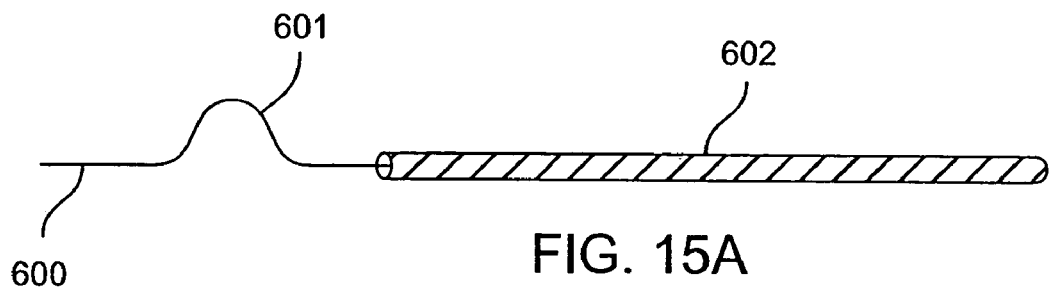
FIGS. 15A-15D illustrate the use of pre-shaped mandrels to steer a component or structure.
Figure 15B:
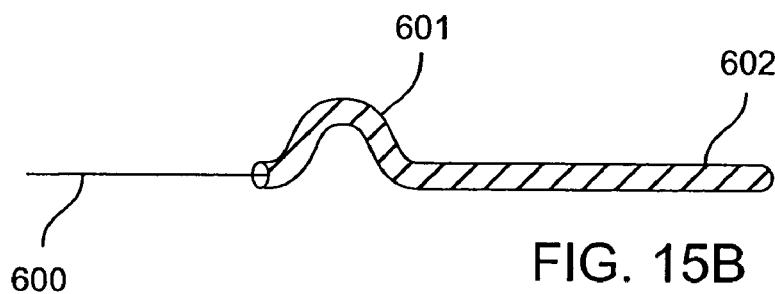
Figure 15C:
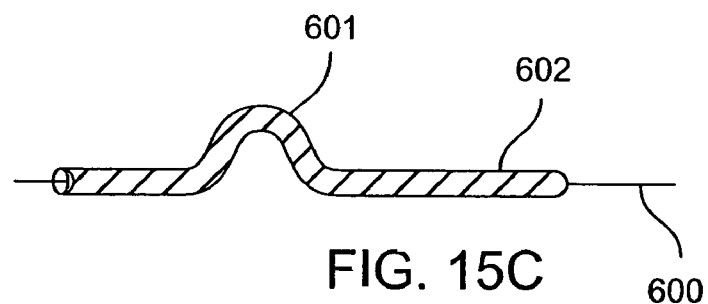
Figure 15D:
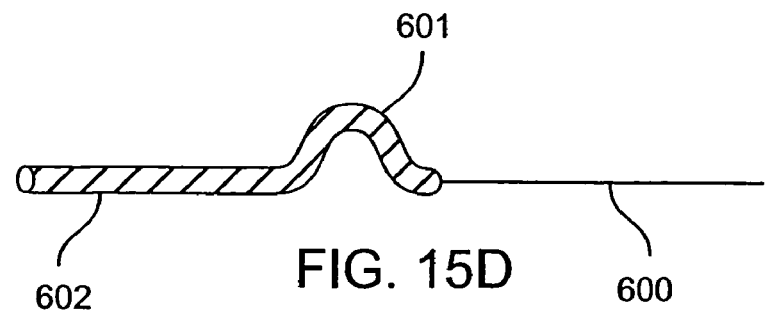

As shown in FIG. 14, the guidewire 52 may have laterally deflectable steering elements 54 which may be positioned in, for example, the valve commissures as described previously. This way, the guidewire 52 may be positioned toward the medial or lateral sides of the mitral valve MV, and an interventional catheter 56 introduced over the guidewire to a desired target structure within or surrounding the mitral valve MV. Providing such a steerable and positionable guidewire, it is particularly advantageous when it is desired to position the tip of an interventional catheter 56 at a region well below the opening of the mitral valve. That is, neither the guide catheter nor the interventional catheter have to be advanced fully to the opening of the mitral valve, leaving them free to be positioned elsewhere.

In some instances, it will be desirable to introduce interventional tools sequentially or simultaneously from both the antegrade and retrograde directions. While it will be possible to separately introduce guiding catheters and guidewires by the approaches described above, in at least some instances it may be preferable to pass a single guidewire between the vena cava and the right atrium, crossing the interatrial septum as previously described. The guidewire may then pass in an antegrade direction through the aortic valve, through the ascending and descending aorta, and then percutaneously out of the vasculature at a location remote from the heart, such as the femoral artery.

Location of a single guidewire in this manner provides a continuous "rail" through the heart, allowing placement of separate devices in both an antegrade and retrograde direction. Additionally, any interaction or cooperation between the devices is facilitated since they will necessarily advance toward one another in an alignment which is controlled and assured by the guidewire, e.g., when fully advanced any two devices will necessarily meet. Thus, one device would extend inward from the venous side of the heart in an anterior antegrade direction to the mitral valve, and a second device would enter through the arterial side of the heart in a retrograde direction. The two devices would then be precisely located relative to each other as they approach and optionally meet at or near the mitral valve. In a particular example, a stabilizing catheter could be introduced in a retrograde direction to approach the chordae and underside of the mitral valve leaflets to provide for temporary stabilization and/or leaflet coaptation, as generally described above. A catheter carrying a fixation device could then be advanced in an antegrade direction to approach the valve leaflets from above. The second device could then be separately actuated to affix the valve leaflets once the proper temporary stabilization has been achieved with the first device.

Fourth, the guidewire, guide catheter or interventional tool may be positioned with the use of a floating balloon. This may be most useful for use with an antegrade approach. The distal balloon of a balloon tipped guidewire or balloon tipped floppy catheter may be inflated and floated antegrade through the mitral valve. If the heart is slowly beating, blood will be flowing from the left atrium, through the mitral valve to the left ventricle. A floating balloon may be carried along this flow trajectory, carrying the guidewire or catheter with it. The balloon may then be deflated and newly placed guidewire or catheter may be utilized as desired.

Fifth, a hollow guidewire, guide catheter or interventional or other tool may be positioned with the use of a rigid, pre-shaped mandrel or insertable member. As shown in FIGS. 15A-D, the mandrel 600 may be comprised of wire, metal, plastic or any suitable material that may be formed to hold a desired shape 601, such as a bend or bump. The mandrel 600 may then be inserted into a lumen in a flexible structure 602 to be positioned. Such a structure may be a hollow guidewire, guide catheter, interventional tool or any other tool or component of a structure. As the shape 601 is advanced, the flexible structure 602 conforms to the shape 601 as it is passed through. This may be utilized to position a structure or component of a structure in a desired location for later steps in the procedure.

It may be appreciated that any of the devices, systems and methods used for gross steering may be also be applied to refined steering of the device or device components to achieve a desired result. In particular, it may be desired to independently or dependently manipulate components of the interventional tools throughout the procedure. Such steering may allow urging of the components relative to the leaflets, annulus, atrial wall or other specific cardiac structures. This may be achieved with any of the devices or methods described above.

V. Orientation Assessment

Proper orientation of the systems and devices is necessary for performing the valve or tissue modification. Both the orientation of the devices and the components of the devices, in relation to cardiac structures and to each other, are of concern. Cardiac structures to which orientation is desired may include the atrial walls, interatrial septum, valve annulus, valve leaflets, valve commissures, valve chordae, papillary muscles and ventricle walls, to name a few. Assessment of the orientation of the components and devices may be achieved by a number of mechanisms and methodologies.

First, orientation may be assessed by tactile feedback. Introduction and manipulation of the devices and components may allow them to contact cardiac structures or other devices. Such contact may guide the devices into proper position and relevant orientation. For example, it may be possible to tactilely sense the force of the distal end of a guidewire, catheter or interventional tool against the leaflets, commissures, annulus, chordae, papillary muscles, ventricular walls, and/or atrial walls, to name a few. The force may be translated along its length to its proximal end to provide feedback to the physician or operator. Similarly, sensors may be used to achieve a similar result. Additionally, the catheter or tool may have a lumen to allow for pressure monitoring. This may provide feedback throughout the procedure which may indicate the presence and level of mitral regurgitation.

Second, orientation may be assessed by visualization of the devices and components themselves. The components or the overall system may be modified for enhanced echogenic and/or fluoroscopic visibility. Echogenicity of a material in a blood medium is dependent on the difference in acoustic impedance (product of velocity of sound and density of the medium through which the sound wave is traveling) between the material and blood. Therefore, a thin polymer coating on the components or the overall system may provide modulation of the acoustic impedance at the interface of the component and blood, thereby improving echovisibility. Likewise, microscopic air bubbles trapped on the surface or embedded within the coating may also improve echovisibility. Similarly, fluoroscopic visibility may be improved with radiopaque coatings, radiopaque marker bands, or the like. Additionally, a lumen within the catheter or tool may be provided to inject radiopaque contrast solution to improve fluoroscopic visibility or surrounding tissues. In any case, such coatings, markings and fluids may provide visualization of the devices and components themselves or any structures or elements used throughout the treatment procedure. Similarly, angioscopic vision may be used to access the orientation throughout the procedure.

Third, one or more orientation elements may be used to assess orientation of the components and/or systems in relation to cardiac structures, specifically the target valve. Thus, orientation elements may be any structure or feature that provides information as to the orientation of the component, device or system of the present invention. The elements may be separate from or integral with any part of the system or device. They may be removably or fixedly mounted on the guidewire, guide catheter, interventional tool and/or other device. Likewise, the elements may be components or parts of components of the device which provide one or more additional functions in the tissue modification procedure, such as stabilization, grasping, coaptation, adjustment or fixation. Further the elements may be atrial, ventricular or atrial-ventricular devices such that they may or may not cross the valve in the orientation assessment process. In addition, such elements may be used to steer and/or orient the components and systems prior to or simultaneous with assessment.

Orientation elements may be in the form of propellers, wings, petals, arms, loops, and the like. One or more of these elements may be present, typically extending radially from a central shaft. When two elements are present, they are commonly placed 120 to 180 degrees apart around the central shaft; more than two elements are typically arranged in a radial pattern around the central shaft. In the preferred embodiments, the orientation elements are typically placed either perpendicular to the line of coaptation or following the line of coaptation. This may provide the most useful reference, however many other placement orientations may be used.

Figure 16:
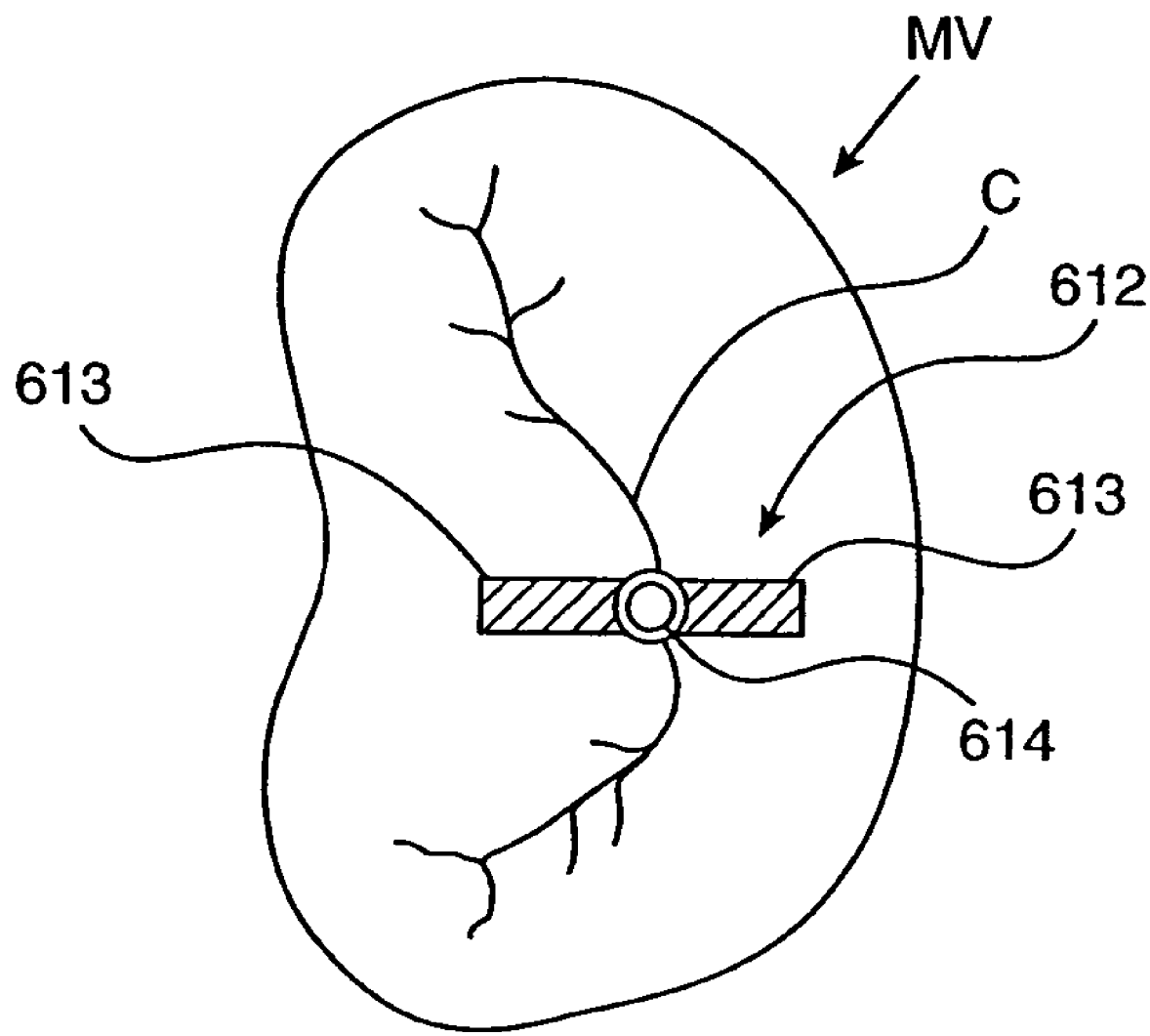
FIGS. 16-20, 21A-21C, and 22A-22B depict various orientation assessment tools.
Figure 17:
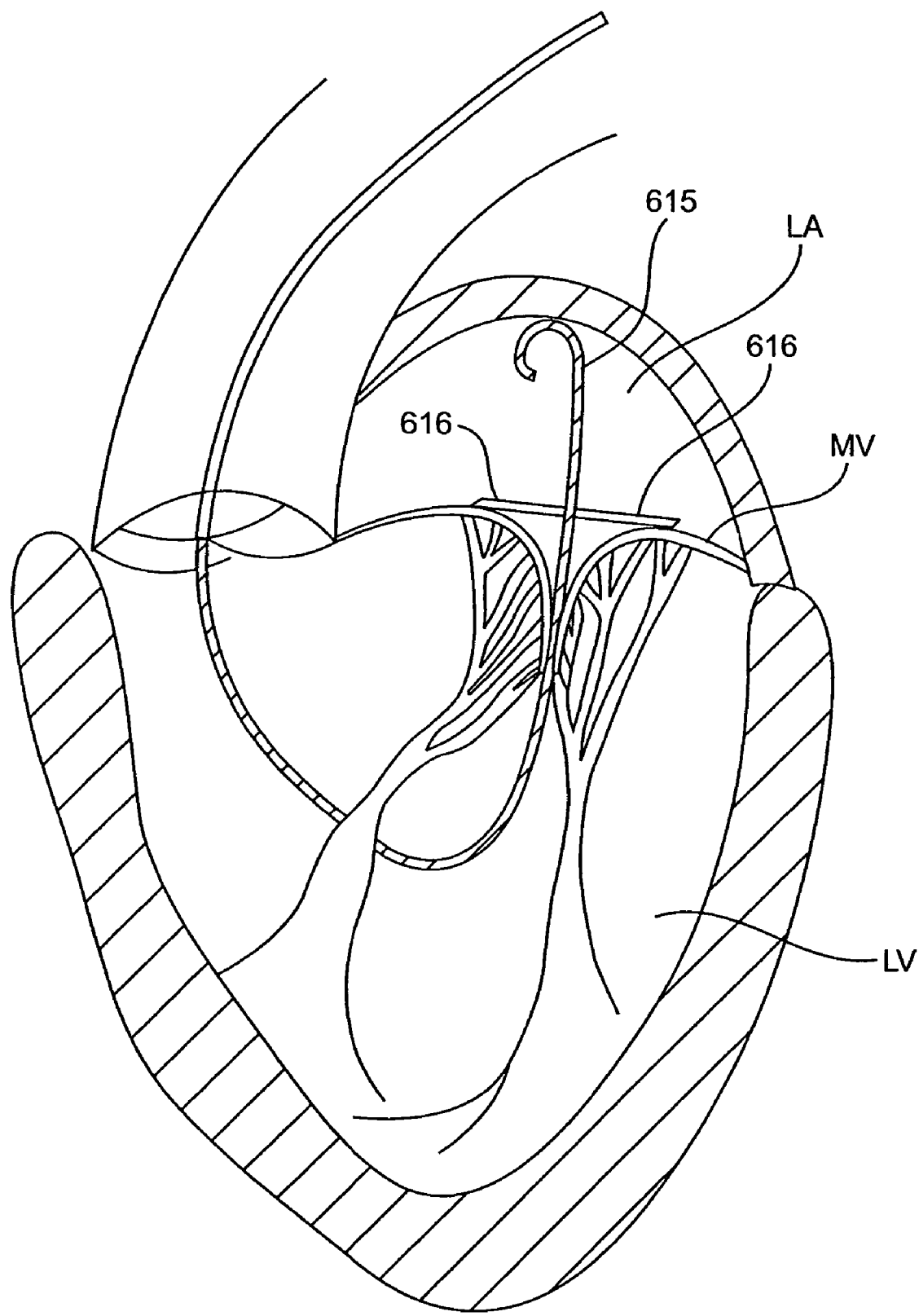

Examples of orientation elements placed perpendicular to the line of coaptation are depicted in FIGS. 16 and 17. FIG. 16 is a short axis view of the mitral valve MV with an orientation element 612 shown having a pair of orientation structures 613 arranged 180 degrees apart around a central shaft 614. The orientation element 612 is shown perpendicular to the line of coaptation C. Such positioning of the element 612 may indicate that the device is in its desired orientation, specific components are in a desired orientation, or devices or components may be oriented in relation to the positioned element which may be more visible than other parts of the device.

FIG. 17 is a long axis view of the mitral valve MV. Here, a guidewire 615 with a pair of orientation propellers 616 is shown inserted through the mitral valve MV via a retrograde approach. Visualization of the propellers 616 may allow repositioning of the guidewire 615 until the propellers are perpendicular to the line of coaptation C. At this point, a guide catheter, interventional or other tool may be tracked over the catheter in the desired orientation. Such tracking may be facilitated with the use of a keyed, notched, oval or similar lumen for guidance. Similarly, such orientation propellers 616 may be mounted on a guide catheter with a keyed lumen for guided insertion of interventional tools.

Figure 18:
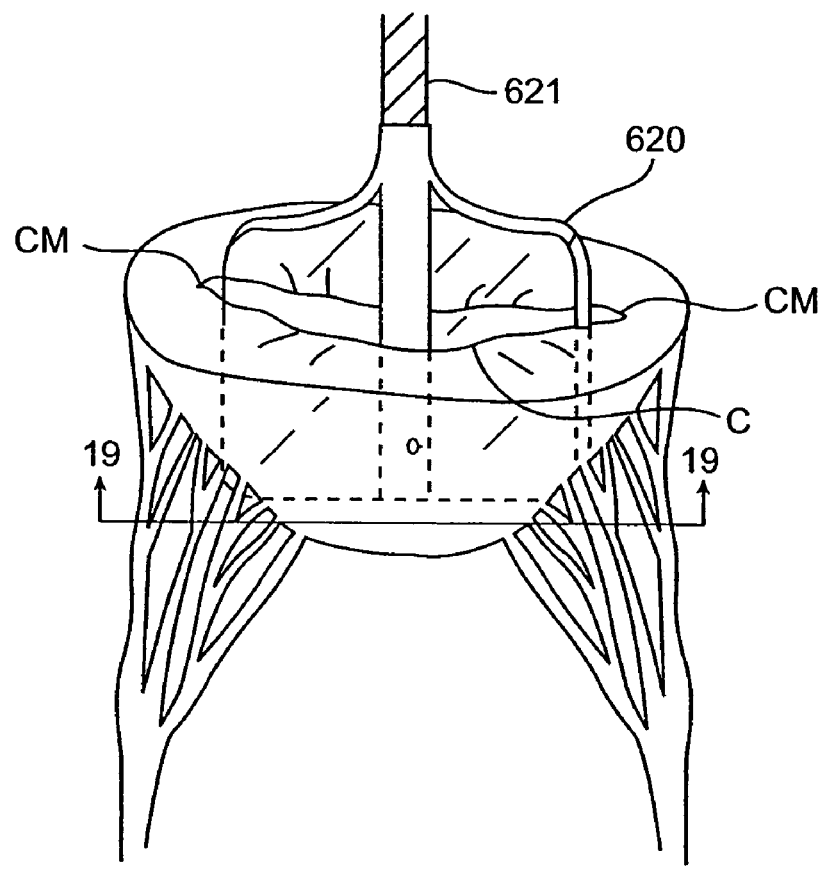
Figure 19:
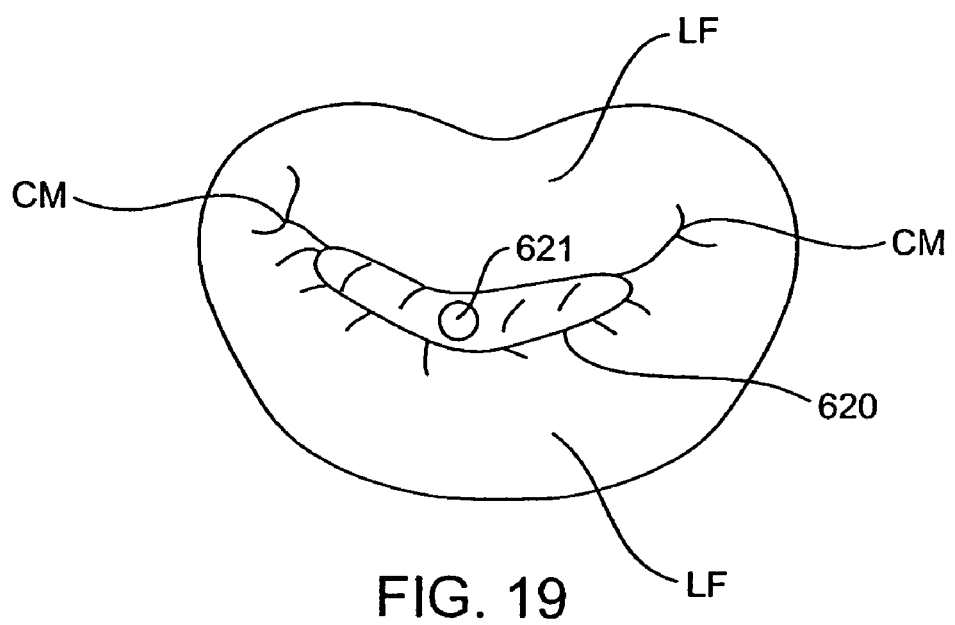

Examples of orientation elements placed along the line of coaptation are depicted in FIGS. 18 and 19. FIG. 18 is a long axis view of an orientation element 620 inserted into the valve opening along the line of coaptation C. An end view shown in FIG. 19 illustrates the penetration of the element 620 through the valve opening and the valve leaflets LF sealing against the element 620. In addition, portions of the orientation element 620 may contact the commissures CM at each end of the valve opening for support and/or for reference. Using the position of the orientation element 620 as a reference, the location of a variety of cardiac structures, particularly the valve leaflets LF, are known. In addition, if the position of specific components of the device are known in relation to the orientation elements 620, such relation may be used to infer the relation of those components to the cardiac structures. For example, if the orientation elements are known to be perpendicular to the graspers of the present invention, positioning of the orientation elements in the manner described above would ensure that the graspers would be aligned perpendicular to the line of coaptation C or in a desirable location to grasp the valve leaflets LF.

In this example, the orientation element 620 is shown as an inflatable bladder coaxially attached to a distal central shaft 621. Such a bladder may be comprised of a compliant or noncompliant material, such as PET, PUR, Silicone, Chronoprene, or the like. The bladder material itself may be echo or fluorogenic, or it may be filled with an echo or fluorogenic liquid or suitable medium, such as carbon dioxide or agitated saline. In its inflated state, it is preferred that the bladder is wide or thick enough to so that the endview of the bladder is visible in a short axis view of the mitral valve, as shown in FIG. 19, and that the bladder is long or high enough so that the anterior and posterior leaflets may seal against the bladder in systole.

Figure 20:
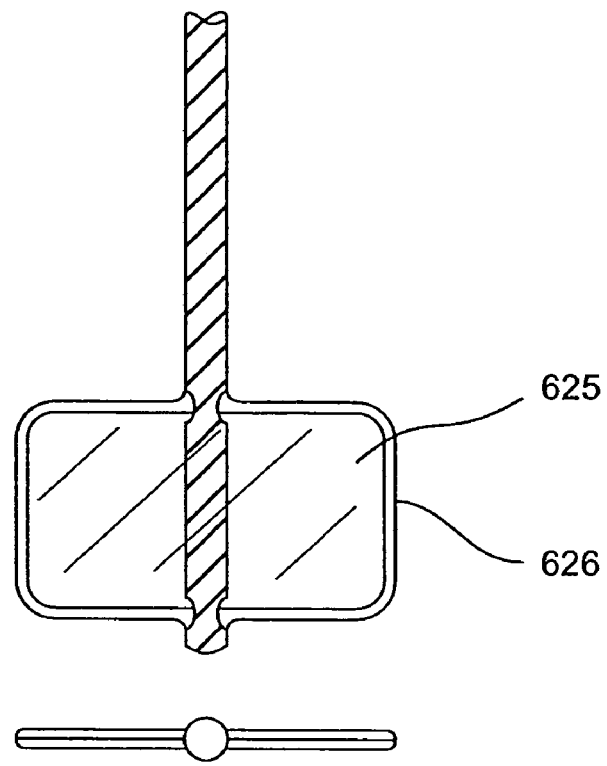
Figures 21A, 21B, 21C:
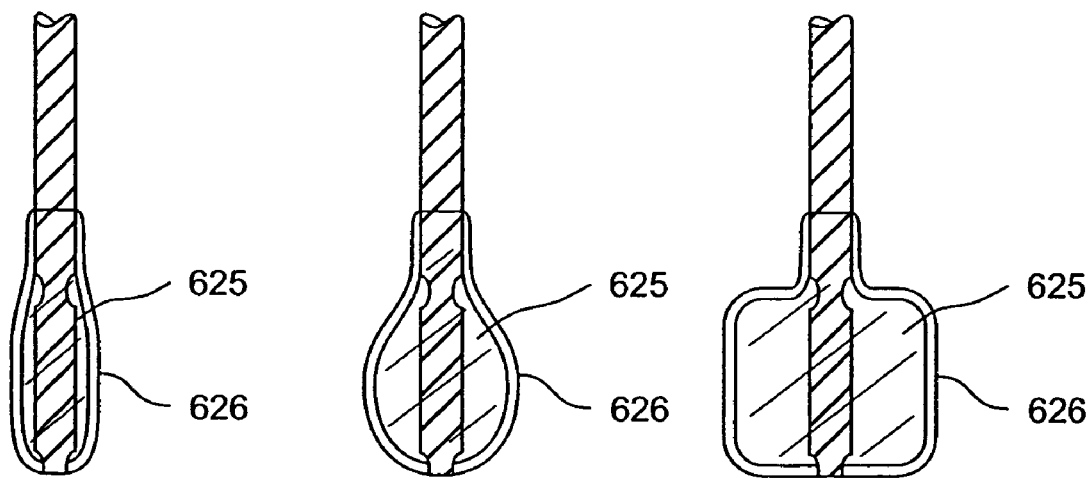

In addition, as shown in FIG. 20, the bladder 625 may be supported by a frame 626. The frame 626 may be comprised of any suitable material, such as nitinol, stainless steel, plastic or any combination thereof, of any consistent or variable flexibility, and any cross-sectional shape, such as round wire, hollow tube or flat ribbon. This material may be echo or fluorogenic or treated for such effects. In addition, the shape of the frame 626 may be of any suitable symmetrical or nonsymmetrical geometry, including but not limited to triangular, rectangular, circular, oblong, and single or multi-humped. A rectangular geometry is depicted in FIG. 20. In addition, the frame 626 may be expandable as shown in FIGS. 21A-C. In the collapsed state, FIG. 21A, the bladder 625 and enclosed frame 626 may be inserted through a lumen in a guide catheter or interventional tool. When appropriately positioned, the frame 626 may be gradually expanded, FIG. 21B, to a desired geometry, FIG. 21C. It may be appreciated that the orientation element may function without inflation of the bladder 625 or with just the frame 625 and no bladder.

Figure 22A:
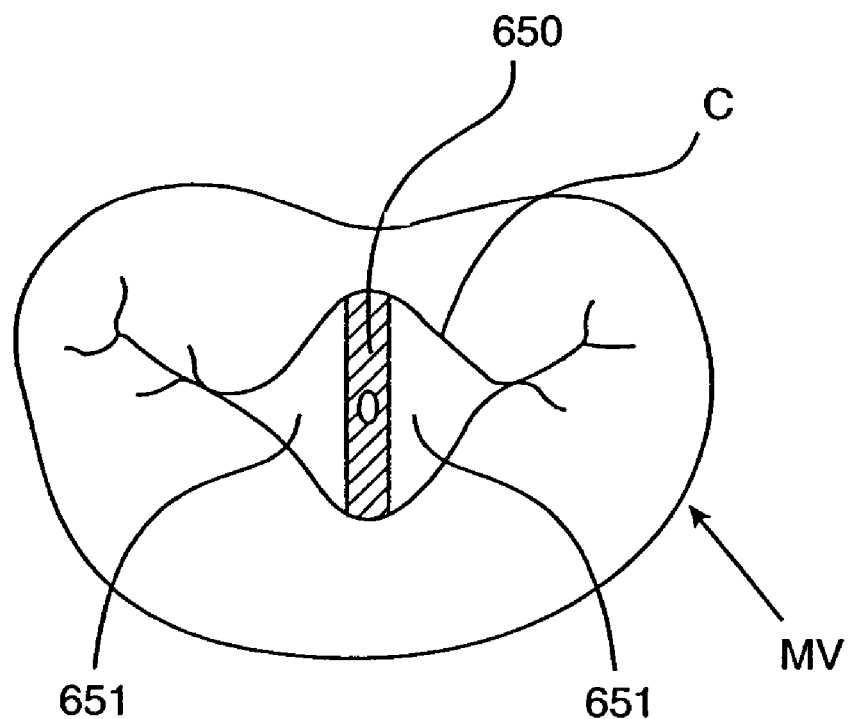
Figure 22B:
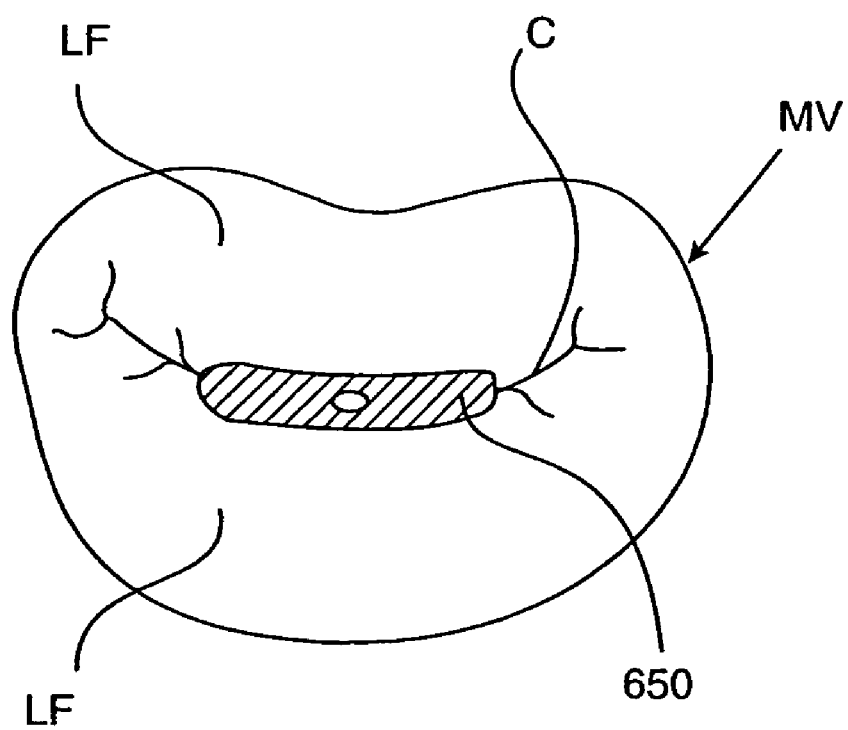

Fourth, orientation may be assessed by visualization of flow patterns resulting from system or component position with respect to cardiac structures. As mentioned, the heart may be slowly beating throughout the tissue modification procedure. As the heart beats, blood may be flowing from the left atrium, through the mitral valve, to the left ventricle. Visualization of these flow patterns using Color Doppler Echocardiography may allow inferences as to how systems or components are positioned. For example, as shown in FIGS. 22A, if a thin planar structure 650 is inserted in the valve opening with its long axis perpendicular to the line of coaptation C, a higher level of regurgitation may result due to blood flow through the unsealed portions 651. If the structure 650 is inserted with its long axis along the line of coaptation C, as shown in FIG. 22B, a lower level of regurgitation may result due to more adequate sealing of the valve leaflets LF against the structure 650. Thus, such a structure 650 or similarly designed device may be used as an orientation element.

VI. Stabilization

Before a valve or tissue modification or intervention is performed, it will usually be desirable to temporarily stabilize the interventional tool in relation to the cardiac structure. By "stabilization" it is meant that the interventional tool will be somehow coupled to a cardiac structure so that any existing relative motion between the tool and the structure is lessened. Cardiac structures which may be utilized for coupling include the atrial walls, interatrial septum, valve annulus, valve leaflets, valve commissures, valve chordae, papillary muscles and ventricle walls, to name a few. Such stabilization is performed in order to facilitate a subsequent intervention. For example, an access catheter may be mechanically coupled to the valve or tissue surrounding the valve, such as the annulus or the chordae, and the interventional tool deployed from the catheter to perform a desired intervention, such as suturing, stapling, snaring, annuloplasty, RF tissue modification, or the like. The stabilization will usually be terminated after the particular valve modification is completed, but in some instances the stabilization could be terminated and redeployed multiple times at various points throughout the procedure.

The stabilization mechanisms may be separate from or integral with any part of the system or device. They may be removably or fixedly mounted on the guidewire, guide catheter, interventional tool and/or other device. Likewise, the elements may be components or parts of components of the device which provide one or more additional functions in the tissue modification procedure, such as steering, orientation assessment, grasping, coaptation, adjustment or fixation. Further the mechanisms may be atrial, ventricular or atrial-ventricular devices such that they may or may not cross the valve in the stabilization process. In particular, such mechanisms may be used to steer and/or orient the components and systems prior to or simultaneous with stabilization.

Figure 23:
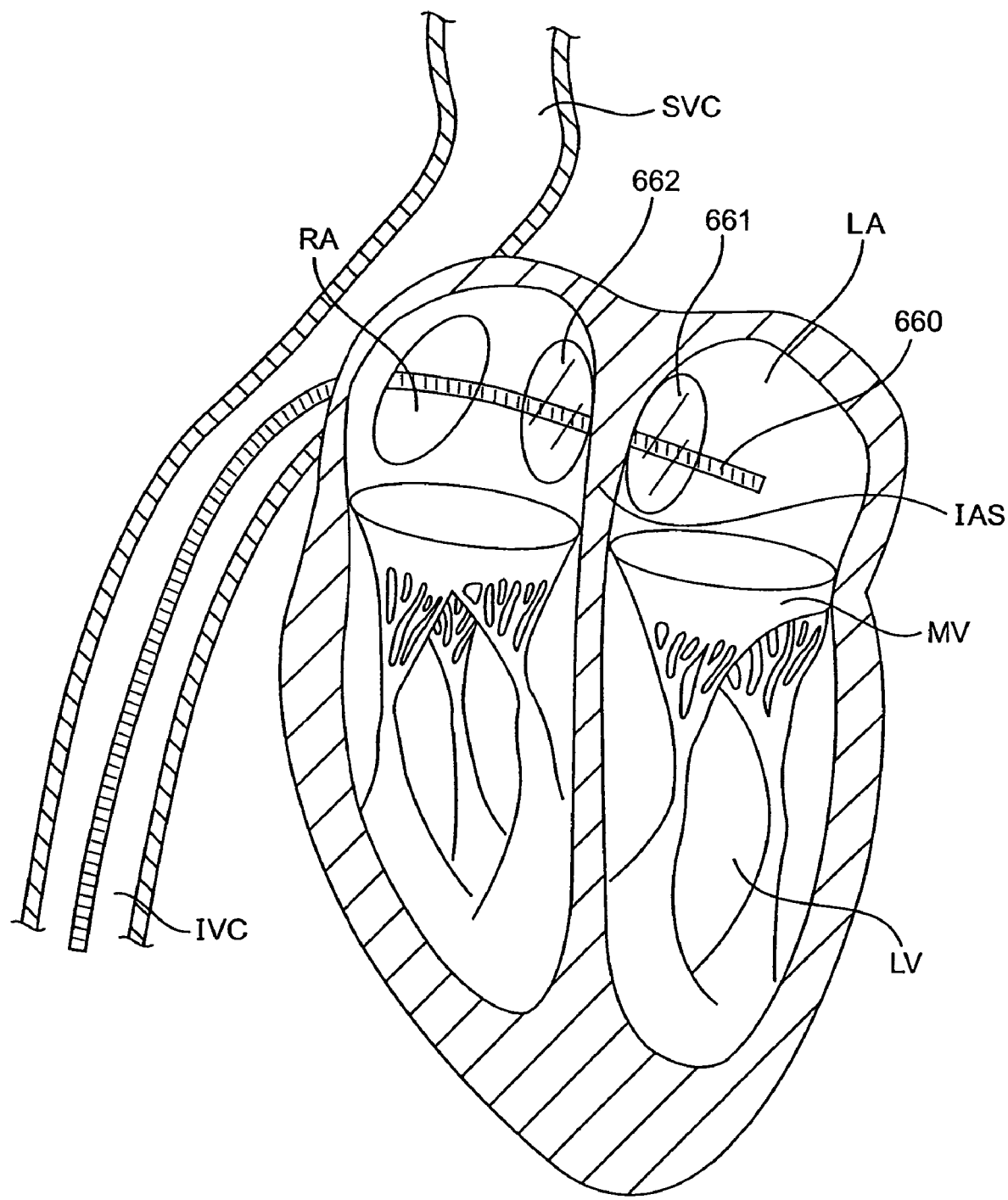
FIG. 23 is a schematic illustration of an interatrial septum stabilization device.

In the preferred embodiments, three general categories of stabilization mechanisms may be formed for descriptive purposes: 1) stabilization against the atrial septum, atrial walls or ventricle walls, 2) stabilization against the valve, and 3) stabilization against the chordae or papillary muscles. Stabilization against the atrial septum may be useful when approaching antegrade with atrial or atrial-ventricular devices. As previously described, an antegrade approach involves crossing from the right atrium RA to the left atrium LA by penetrating the interatrial septum IAS. This may be accomplished with a needle bearing catheter, which may then be exchanged for an introducer, guide catheter or similar catheter. Interventional tools may be introduced through this catheter for tissue modification treatment. To prevent movement of the catheter in an axial direction, a stabilization mechanism may be used to engage and lock the catheter to the interatrial septum. A preferred embodiment is shown in FIG. 23, which depicts a catheter shaft 660 having a distal balloon 661 and a proximal balloon 662 inflated on opposite sides of the interarterial septum IAS. Inflation of the balloons 661, 662 against the septum couples the shaft 660 to the septum and stabilizes the system. It may be appreciated that a number of components, such as disks, cages, balls, mesh, or other structures, may be used in place of one or more of the balloons to achieve a similar result.

Figure 24:
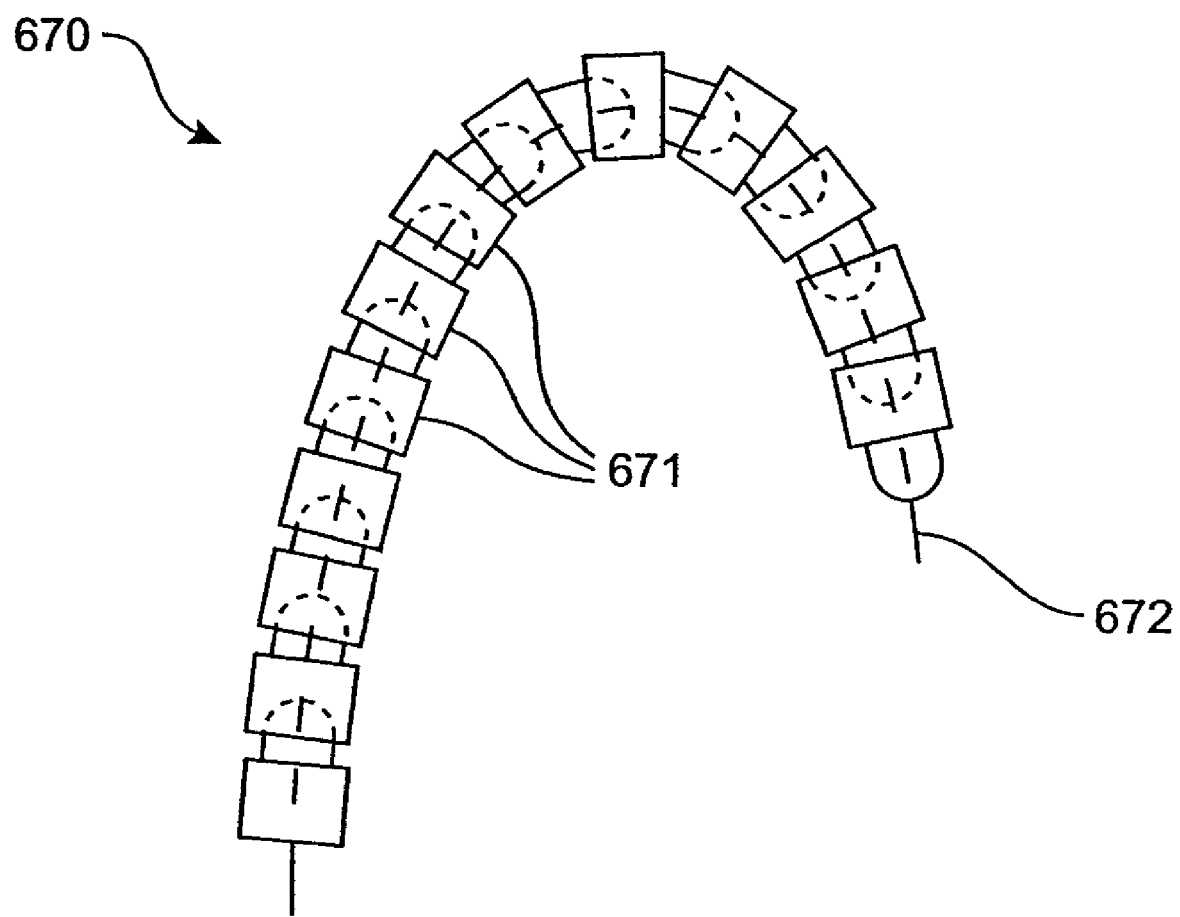
FIG. 24 is a schematic illustration of a catheter shaft designed to provide stabilization against a structure, such as the interatrial septum, or for flexible adjustment and locking stability in various positions.

Stabilization against the atrial septum may also be achieved by forming an introducer or guide catheter which is rigid through the interatrial septum and left atrium. Typically, such introducers or guide catheters are flexible along their length to facilitate introduction through the tortuous paths of the vascular system. In an antegrade approach as described, the catheter may be inserted through the interatrial septum with its distal end suspended in the left atrium. In the case of a flexible catheter, movements at the septum may not be translated linearly to the catheter tip. Therefore, there may be relative movement between the distal end and the portion passing through the septum. This may be reduced by coupling the distal end to the portion passing through the septum. In a preferred embodiment, the catheter shaft between and including the distal end and the portion passing through the septum may be made rigid. Referring to FIG. 24, the catheter shaft 670 may be comprised of stacked elements 671. The elements 671 may be domed disks or collar segments with domed ends which are mechanically coupled by a structure 672. The structure 672 may connect the centers of the elements 671, as shown, in a flexible manner so that the shaft 670 may be shaped in any desired geometry suitable for use in the tissue modification treatment. Once a desired shape is formed, the structure 672 may be rigidified to hold the shape. Such rigidity may allow any movement of the interatrial septum to be translated to the distal end of the catheter shaft, thus coupling the catheter to the movements of the heart. This may improve stabilization of the devices and systems used in the tissue modification treatment. It may be appreciated that a variably rigid shaft as described may be utilized for coupling to any cardiac feature and may be used with or as part of any device component or device in the procedure. Thus, the feature may be utilized to lock any device component, catheter or tool into place once it has been manipulated into a desired shape. This may be useful in a variety of situations in addition to those mentioned above.

Stabilization against the valve may be most useful when approaching antegrade with atrial or atrial-ventricular devices, however it may also be useful when approaching retrograde with ventricular or atrial-ventricular devices. When approaching antegrade, stabilization may be most easily achieved by coupling one or more components of the device to the atrial walls, valve annulus, valve leaflets, and/or valve commissures.

Figure 25:
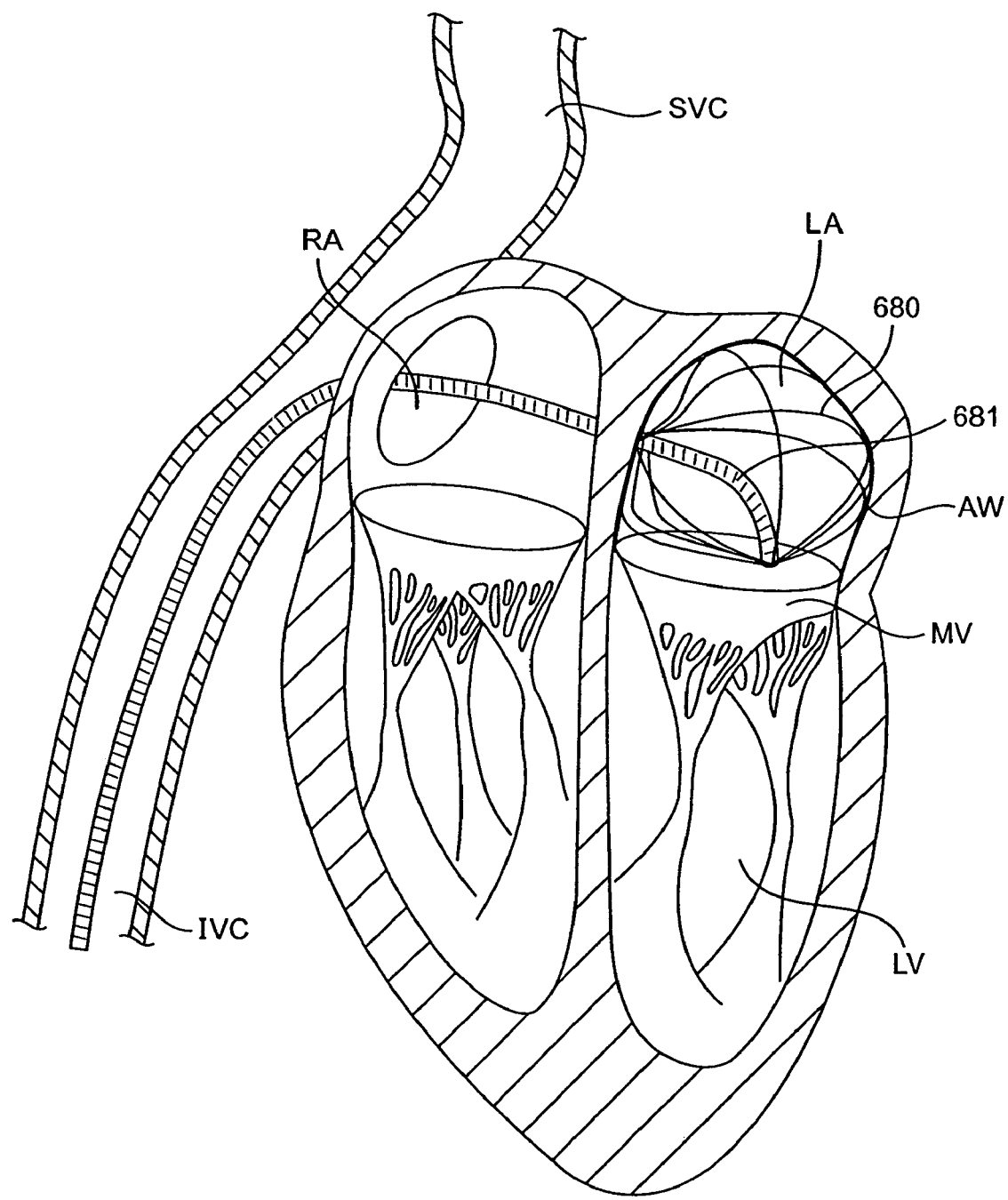
FIG. 25 is a schematic illustration of an atrial stabilization device.

Coupling to the atrial walls may be accomplished by a number of stabilization mechanisms. In each embodiment, structures such as wires, ribbons, mesh, cages or balloons extend outwardly from the device, contacting and applying radial force to the atrial walls. Such contact may couple the movements of the atrium with the device for stabilization. A preferred embodiment is shown in FIG. 25. Here, flexible wires 680 bend out radially from the catheter shaft 681 with curved portions contacting the atrial walls AW. It may be appreciated that any number of wire patterns or means of extending from the shaft may be utilized, as mentioned above.

Coupling to the valve annulus may also be accomplished by a number of stabilization mechanisms, many of which include simultaneous coupling to other valve features, such as the leaflets and/or commissures. In preferred embodiments, such stabilization mechanisms may be comprised of loops, rings, wings, petals, arms, and the like. Coupling can be enhanced by varying surface friction and/or combining structures with vacuum. One or more of these mechanisms may be present, typically extending radially from a central shaft. When two elements are present, they are commonly placed 90 to 180 degrees, preferably 120 to 180 degrees, apart around the central shaft. More than two elements are typically arranged in a radial pattern around the central shaft. Structure, size, angle and arrangement may be adjustable to fit individual patient anatomy.

Figure 26:
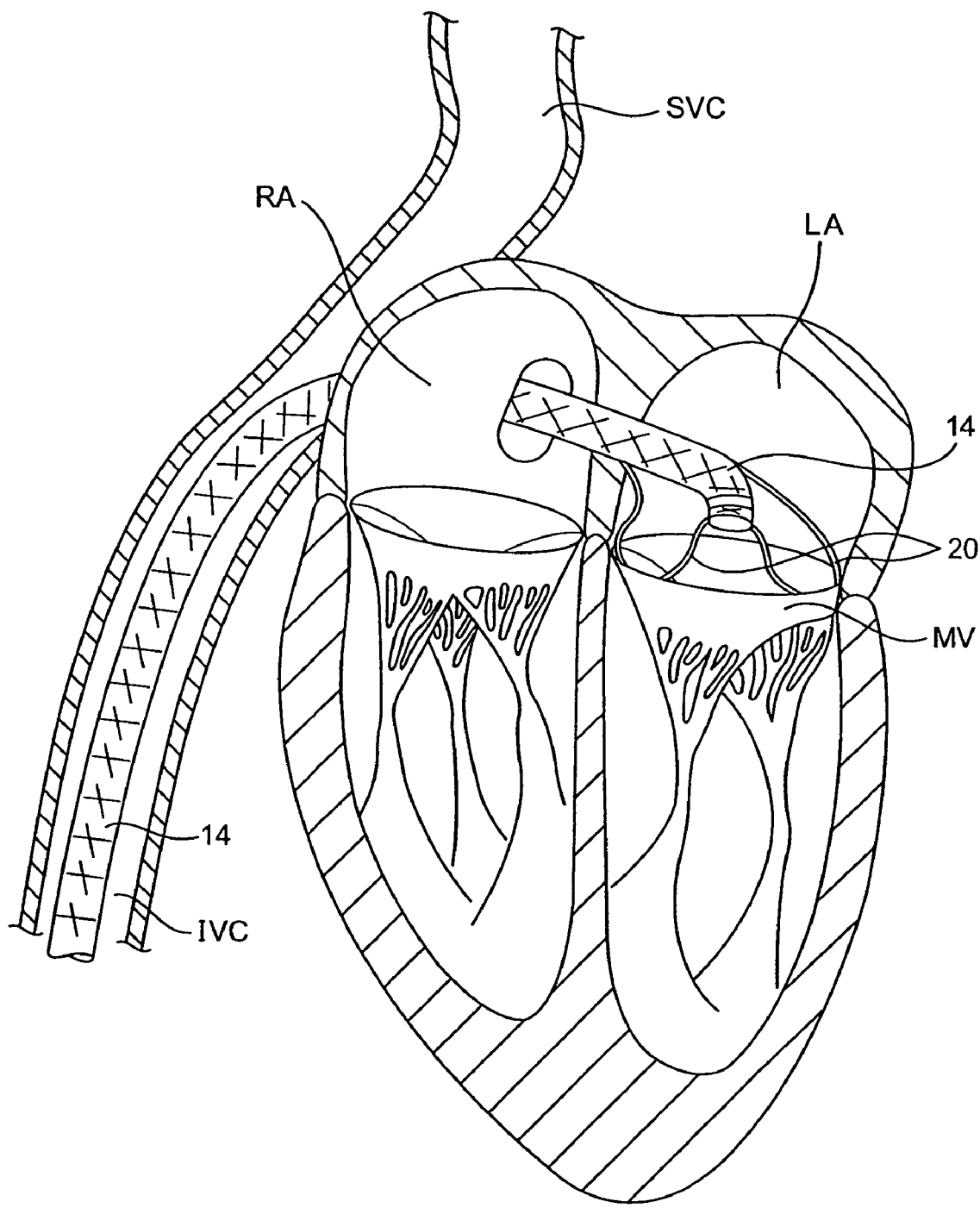
FIGS. 26-29 illustrate stabilization mechanisms which utilize coupling to the valve annulus.

Examples of such embodiments are shown in FIGS. 26-29. Referring to FIG. 26, a guide catheter 14 may have deployable adjustment wires 20 to serve as a stabilization mechanism. The wires 20 are typically attached at one end to the distal tip of the guide catheter 14 and may be advanced at their other ends so that they selectively deploy from the guide catheter to engage the mitral valve MV. The adjustment wires 20 may act to stabilize or anchor the guide catheter relative to the mitral valve MV by coupling to the valve annulus, leaflets or commissures.

Figure 27:
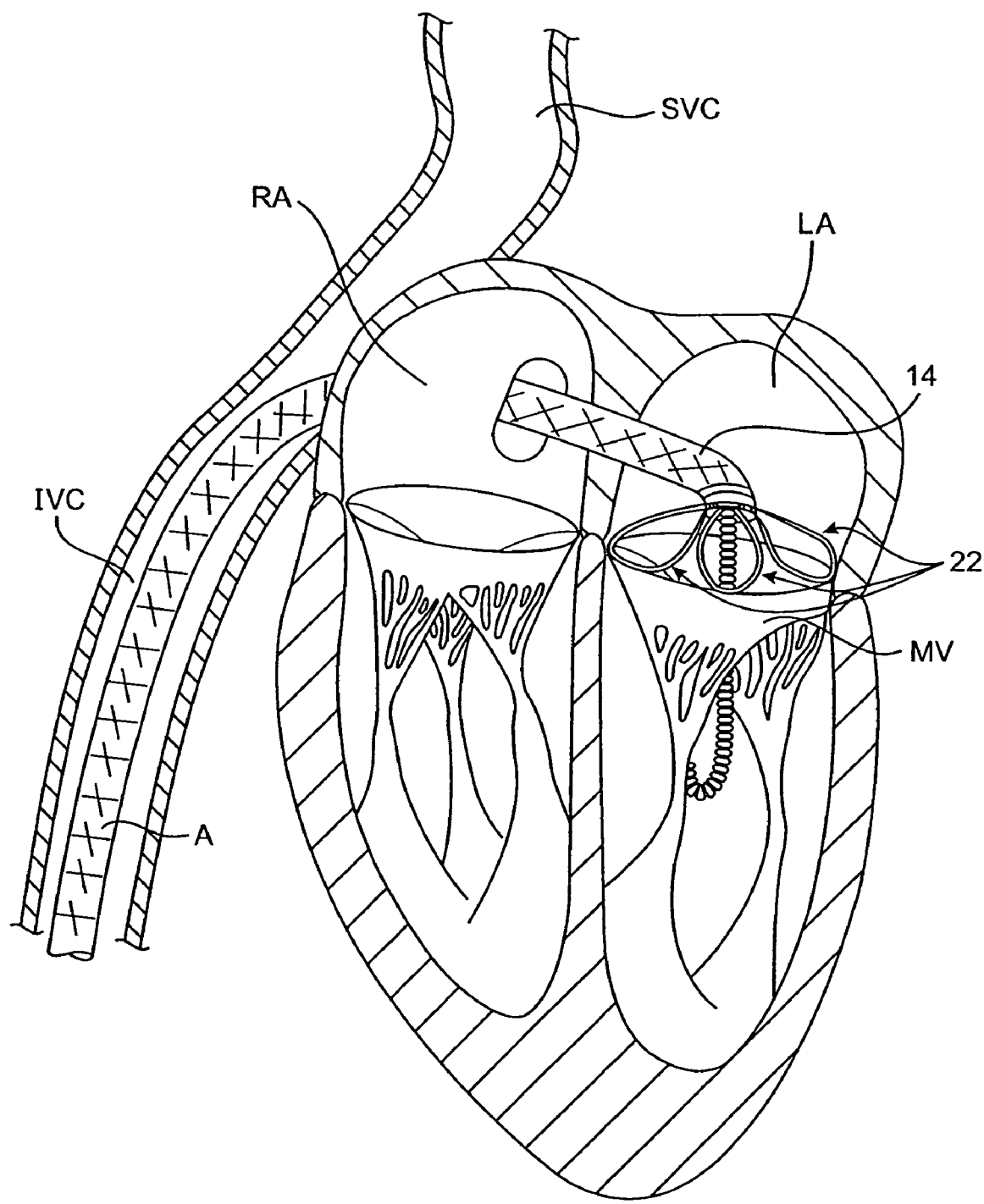
Figure 28:
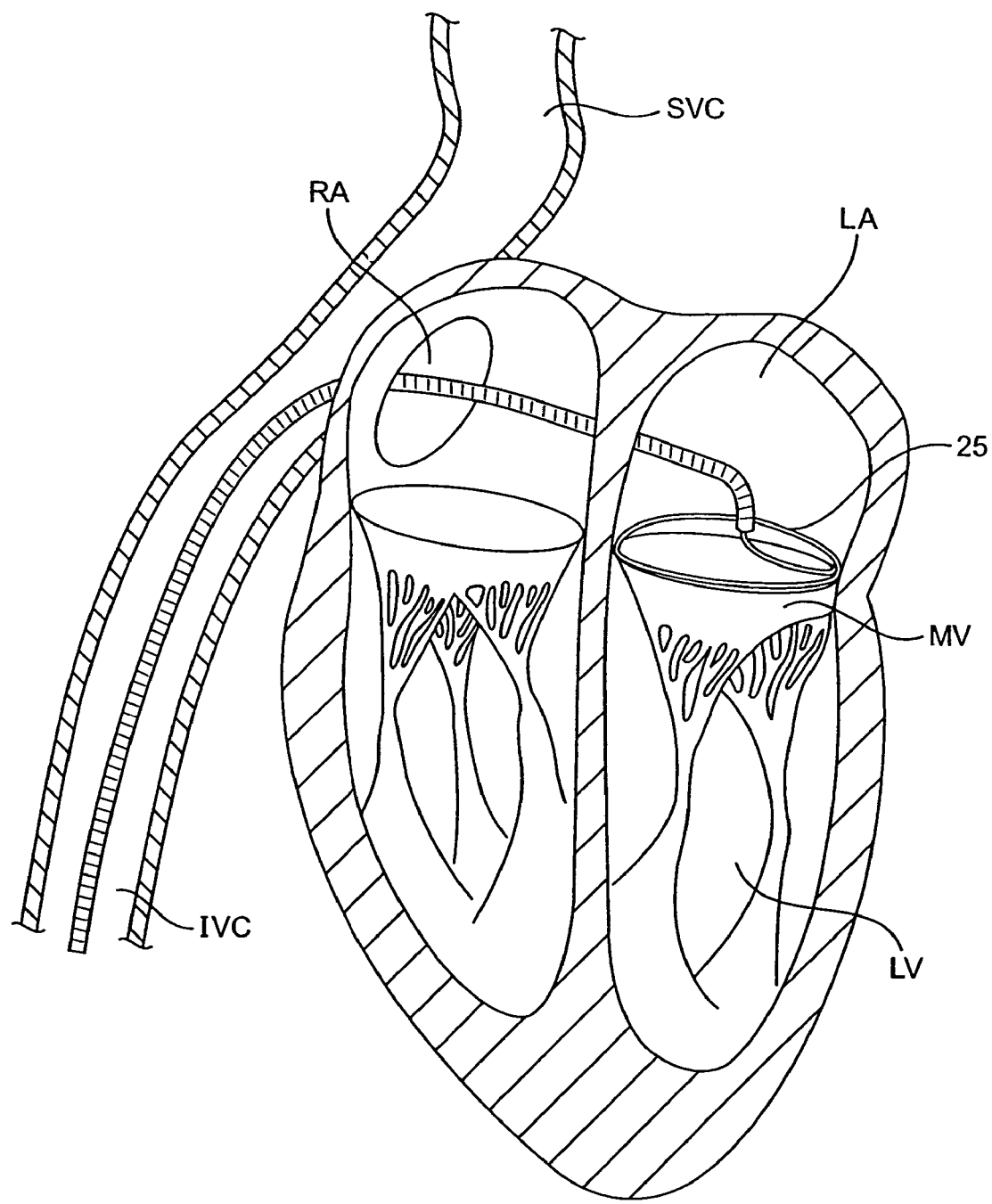
Figure 29:
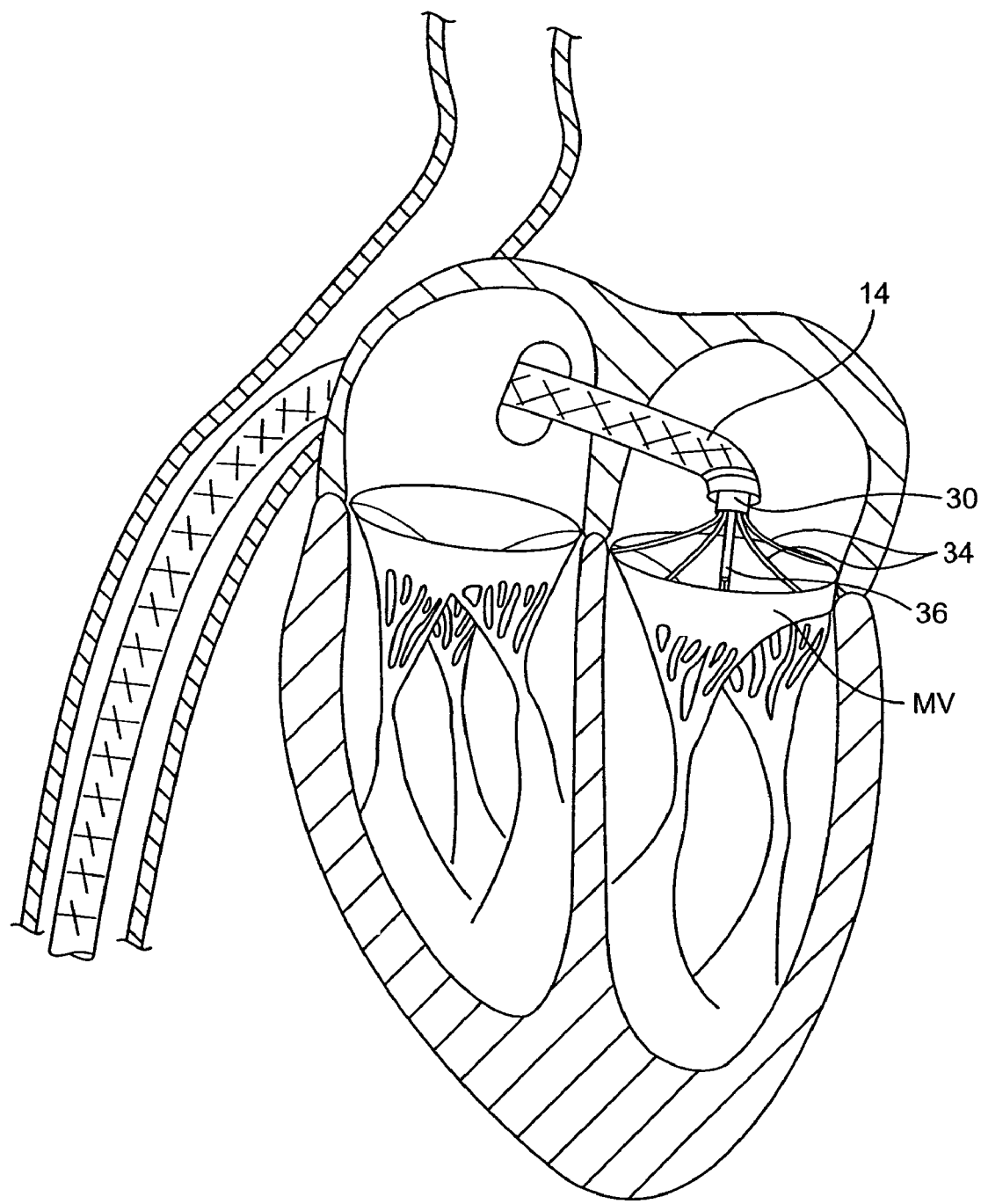

Similarly, the guide catheter 14 may have any number of stabilization elements, as illustrated in FIGS. 27-29. As shown in FIG. 27, the stabilization elements may be comprised of a number of petals 22 arranged around the distal tip of the catheter 14. Similarly, the stabilization element may be a single large loop 25, as depicted in FIG. 28. Alternatively, the interventional catheter 30 may have a plurality of stabilizing arms 34 (FIG. 29) which both position and anchor the distal tip of the interventional catheter 30 relative to the valve annulus. Usually, at least three stabilizing arms will be utilized, with four being illustrated, however any number may be used. The stabilizing arms 34 may be pre-shaped, resilient metal rods (for example, formed from nitinol or other shape memory or superelastic alloy), ribbons, tubes, polymers or composites thereof that may be selectively extended from the tip of the interventional catheter 30 to engage the valve annulus. The interventional catheter 30 of FIG. 29 is shown with a separately extendable interventional tool 36 which performs the desired valve or tissue modification, as described in more detail below. Such stabilization elements may preferably engage the annulus located about the mitral valve MV and apply forward pressure against the annulus to maintain contact and provide axial stabilization.

Figure 30:
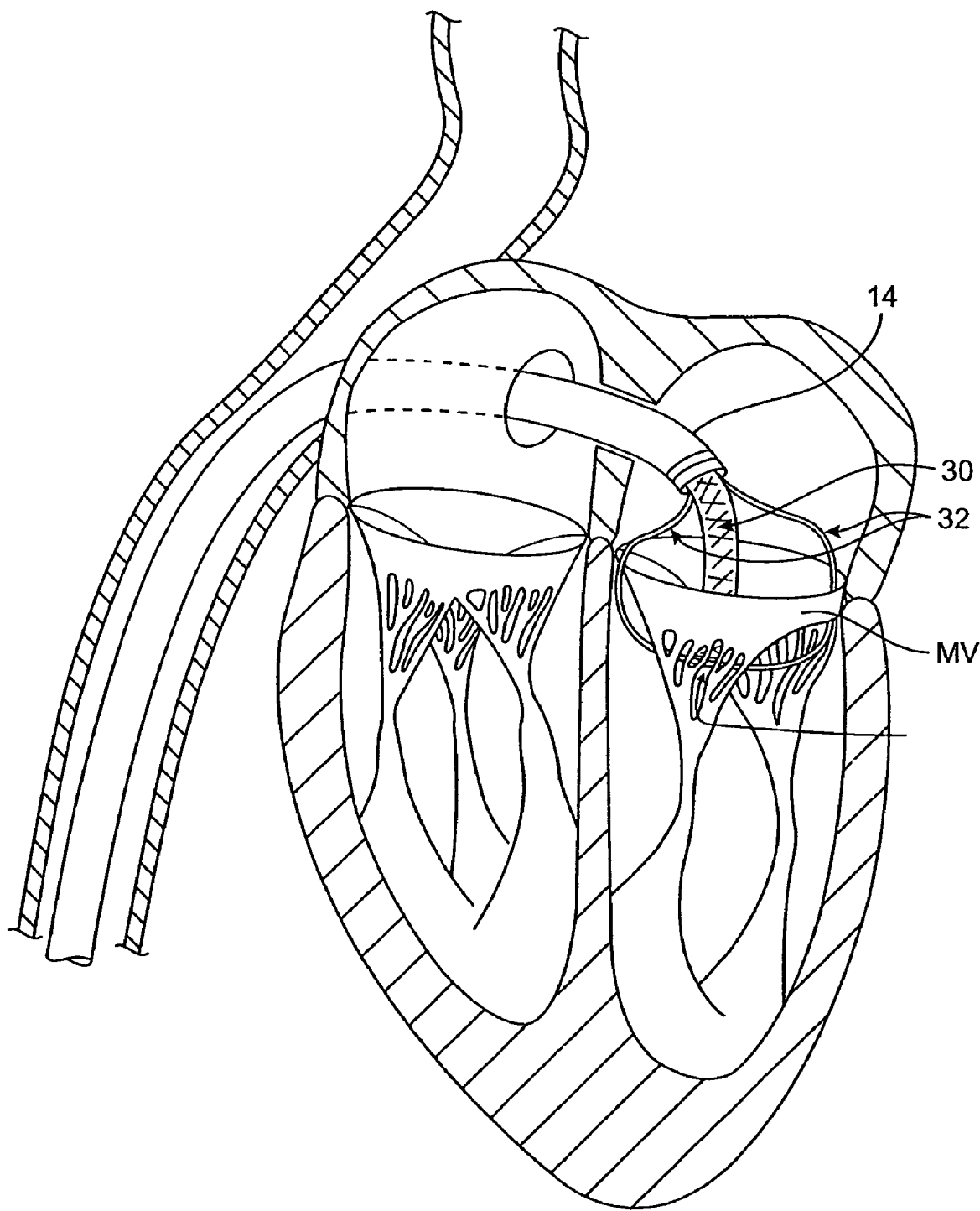

Stabilization may also be achieved by applying radial pressure to the commissures. As shown in FIG. 30, a pair of stabilization elements 32 may extend radially from a guide catheter 14 or interventional tool 30 to contact the commissures. The distance between the elements 32 may be equal to or slightly greater than the distance between the commissures to apply radial force against the commissures. The stabilization elements 32 may be comprised of any suitable material, such as nitinol, stainless steel, plastic or any combination thereof, of any consistent or variable flexibility, and any cross-sectional shape, such as round wire, flat ribbon or hollow tube. As shown in FIGS. 31 A-31D, the shape of the stabilization element may be of any suitable symmetrical or nonsymmetrical geometry, including but limited to triangular (FIG. 31A), rectangular (FIG. 31B), circular, oblong, double-humped (FIG. 31C) or single-humped (FIG. 31D). It may be appreciated that such stabilization mechanisms may also serve in orientation assessment, particularly as the frame 626 (FIG. 20) previously described. Thus, they may be echo or fluorogenic or treated for such effects. In addition, it may be appreciated that such stabilization elements may be passive, i.e., pre-sized and shaped to fit the patient anatomy so that they engage the valve annulus without adjustment, or may be active so that they can be used to steer the guide catheter as previously described.

A number of stabilization mechanisms apply both radial and axial pressure to the valve for stabilization. For example, the double-humped element, shown in FIG. 31C, has a superior hump 700 which may protrude into the left atrium, contacting the superior aspect of the annulus and possibly the left atrial wall, and an inferior hump 701 which may protrude into the left ventricle, contacting the inferior aspect of the annulus and possibly the left ventricle wall or chordal tissue. The superior hump 700 may apply a downward axial force on the annulus and the inferior hump 701 may apply an upward axial force. The waist 702 between the humps may be dimensioned or adjustably sized to fit between the commissures and to apply a radial force on the commissures. Similarly, a single-humped element, shown in FIG. 31D, may provide similar stabilization without the added support from the protruding inferior hump. Additionally, this design may be easier to position in the mitral valve.

The last general category of stabilization mechanisms for descriptive purposes is stabilization against the chordae. Stabilization against the chordae may be most useful when approaching retrograde with ventricular or atrial-ventricular devices. Coupling to the chordae may be useful in stabilization for tissue modification to the valve, the chordae, the annulus or a combination of these. When modifying the valve, the contact with the valve structures (typically grasping of the valve leaflets) may still be necessary. However, when modifying the chordae, additional contact (such as grasping the chordae) may not be necessary since the stabilization methods may include this step. Therefore, stabilization against the chordae will be discussed in Section VIII Grasping.

VII. Immobilization

Immobilization refers to substantially retarding or diminishing the motion of the cardiac structures or intermittently or temporarily stopping the cardiac cycle. This may be accomplished with a variety of methodologies. First, drugs may be injected to temporarily slow or stop the cardiac cycle. Such drugs may include but are not limited to esmolol, adenosine, isofluorane and transarrest mixture, with or without electrical pacing. Likewise, induced atrial fibrillation may interrupt the cardiac cycle.

Mechanical immobilization of the valve can be effected in a variety of ways. Most simply, valve action can be diminished or stopped by raising the pressure in the associated ventricle to a pressure above that in the atrium during diastole. For example, a suitable liquid can be infused into the ventricle to raise the intraventricular pressure, or the aortic valve could be temporarily incapacitated allowing aortic regurgitation and raising the ventricular diastolic pressure. Alternatively, interventional tools and/or catheters carrying such tools may simply be mechanically stabilized against the valve, valve annulus, valve commissures, ventricular wall, atrial wall, generally as described above.

Mechanical valve immobilization will usually involve more interaction with the valve than simple stabilization. Immobilization will usually involve either capture and immobilization of either or both valve leaflets (or all three valve leaflets in the case of a tricuspid valve) or capture and immobilization of the chordae. For example, balloons or mesh cages may be used and placed under one or both leaflets to hold them partially closed. By temporarily immobilizing or adjusting the valve action, such as changing the point of coaptation, it is possible to see if a particular modification will be sufficient to treat the regurgitation. For example, by temporarily grasping the valve leaflets at a particular point and holding the leaflets together, it can be determined whether a permanent suturing, stapling, or other affixation at that point will achieve a sufficient reduction in regurgitation. When the heart is beating, valve regurgitation can be examined in real time via conventional imaging techniques, such as TEE. If the temporary valve modification appears sufficient, it can then be made permanent using any one of a variety of interventional techniques.

VII. Grasping

Valve or tissue modifications or interventions most commonly require grasping a portion of the valve or tissue to be modified. Such grasping may be useful in adjusting tissues (such as coapting valve leaflets) for appropriate modification, checking the positioning of the tissues for improved biological function, and stabilizing or immobilizing the tissue for the modification procedure. As previously described, such grasping may also be useful to stabilize another tissue which will be modified in the procedure, such as the grasping the chordae to stabilize the valve for valve modification. Since the most common procedures may involve valve modification or chordal modification, grasping of these cardiac structures will be discussed. However, it may be appreciated that described grasping devices, systems and methods may apply to any cardiac or other structure.

A. Chordal Grasping

Grasping of the chordae may involve capturing and anchoring the chordae, as illustrated in FIGS. 32-40. As shown in particular in FIGS. 32A and 32B, a guide catheter 40 can deploy a first capture coil 60 and a second capture coil 62 through a pair of deployment catheters 64 and 66, respectively. The coils will be positioned while visualizing so that the first coil 60 captures chordae attached to a first valve leaflet LF and coil 62 captures chordae attached to a second valve leaflet LF. The capture coils will typically be elastic wires, preferably composed of a superelastic material such as nitinol, which are delivered through the deployment catheters in a straightened configuration. When they are advanced out of the deployment catheters, the capture coils will assume a helical or other configuration that can be advanced into and entangle the chordae.

Figure 32A:
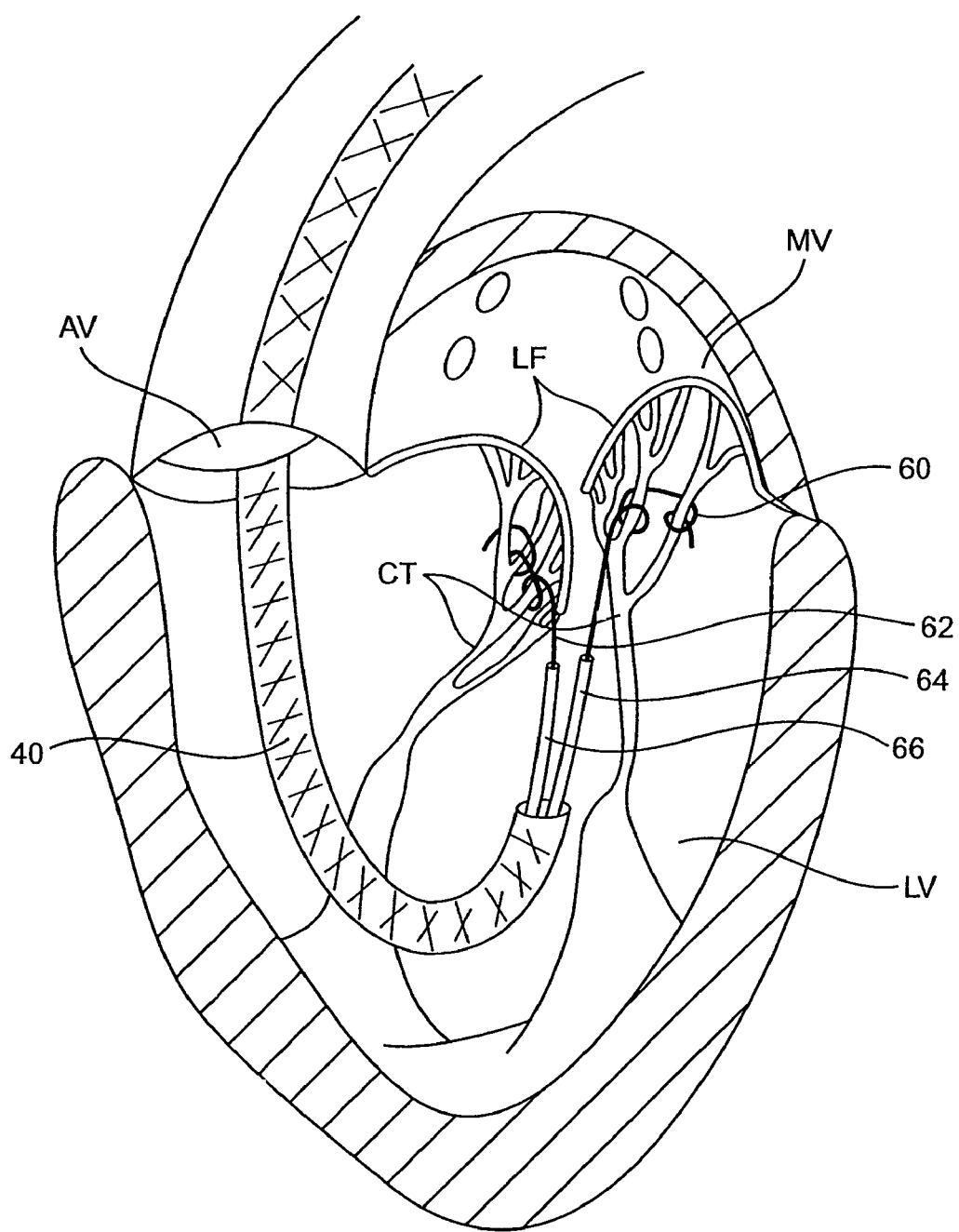
FIGS. 32A and 32B illustrate mitral valve stabilization using snares for capturing the valve chordae.
Figure 32B:
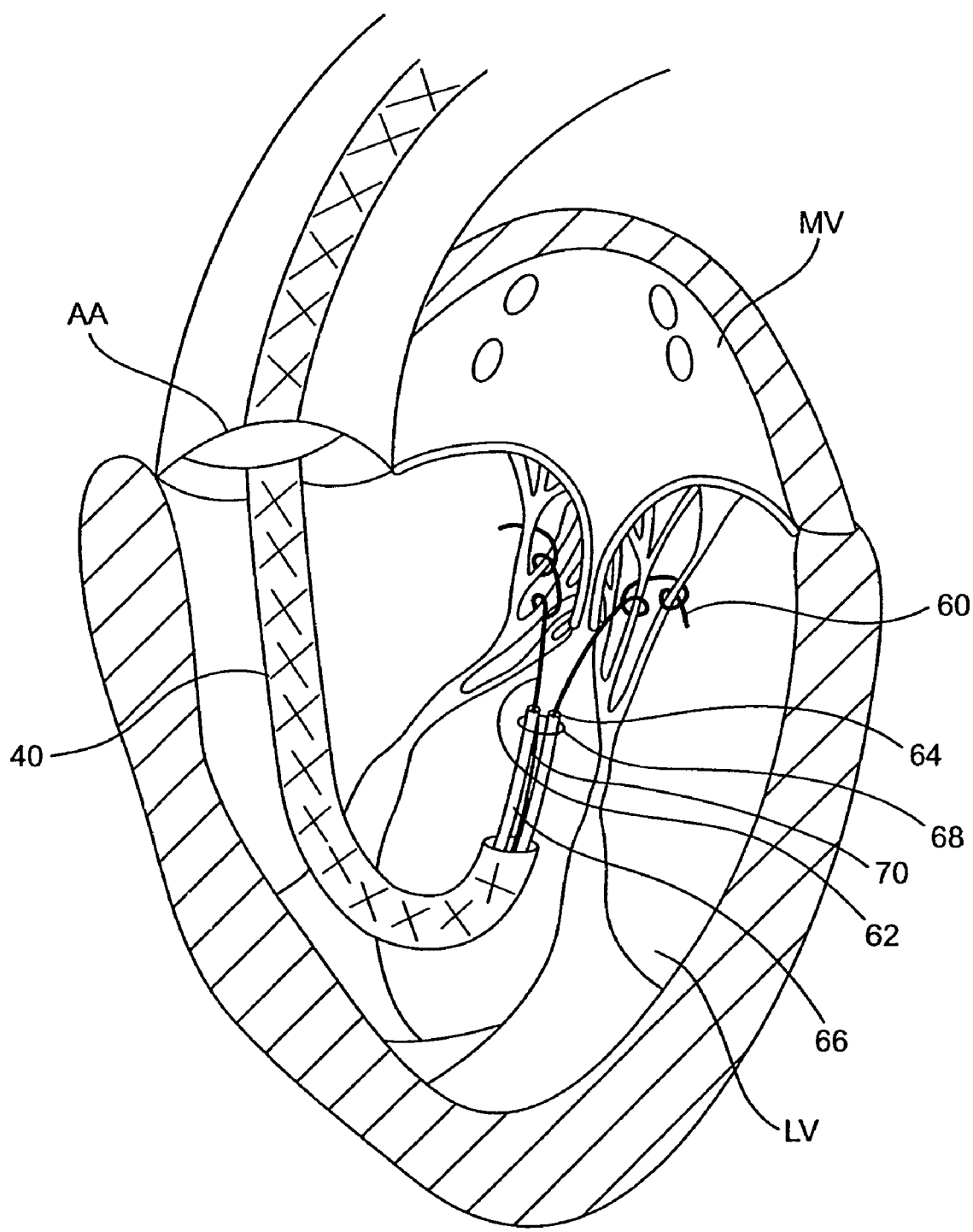

The coils 60 and 62 may then be brought together laterally preferably coapt the leaflets LF together by advancing a retaining ring 68 which is secured at the distal end of a deployment wire 70, as illustrated in FIG. 32B. The leaflets are thus brought together and immobilized for a subsequent intervention. Alternatively, if immobilization via the coils 60 and 62 is sufficient in itself, it will be possible to make the deployment permanent. It is a particular advantage of the temporary immobilization that the valve action can be examined via the real time imaging techniques to see if regurgitation has been adequately addressed. If it hasn't, the coils can be redeployed or the relative positions of the two coils 60 and 62 can be changed until an adequate pair has been effected.

It will be appreciated that if a subsequent interventional step is required, it can be made from either an antegrade or retrograde approach. A variety of specific interventional techniques are described in detail hereinbelow.

Figure 33A:
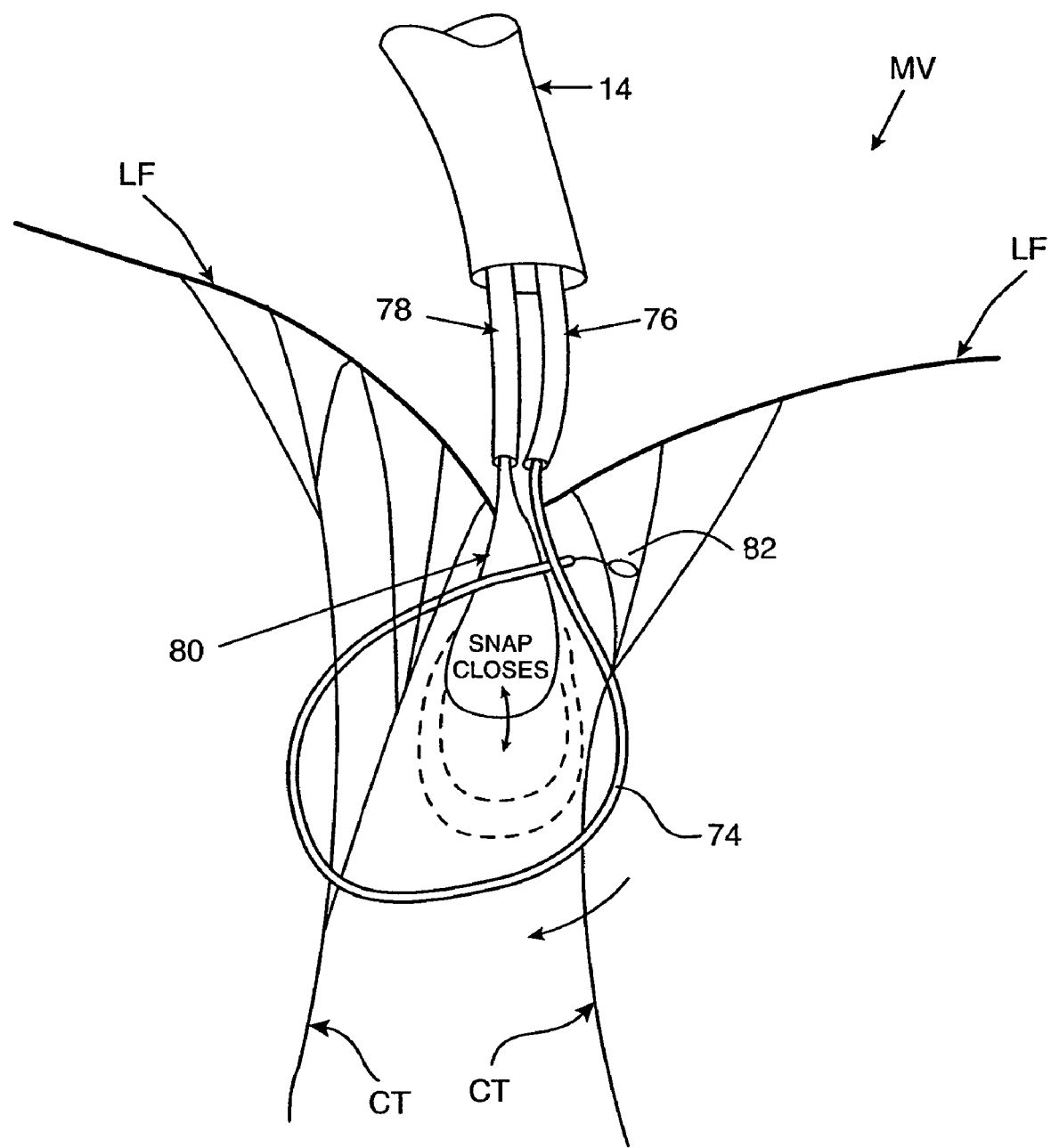
FIGS. 33A and 33B illustrate an antegrade approach for snaring valve chordae and optionally suturing the chordae together to treat valve regurgitation.
Figure 33B:
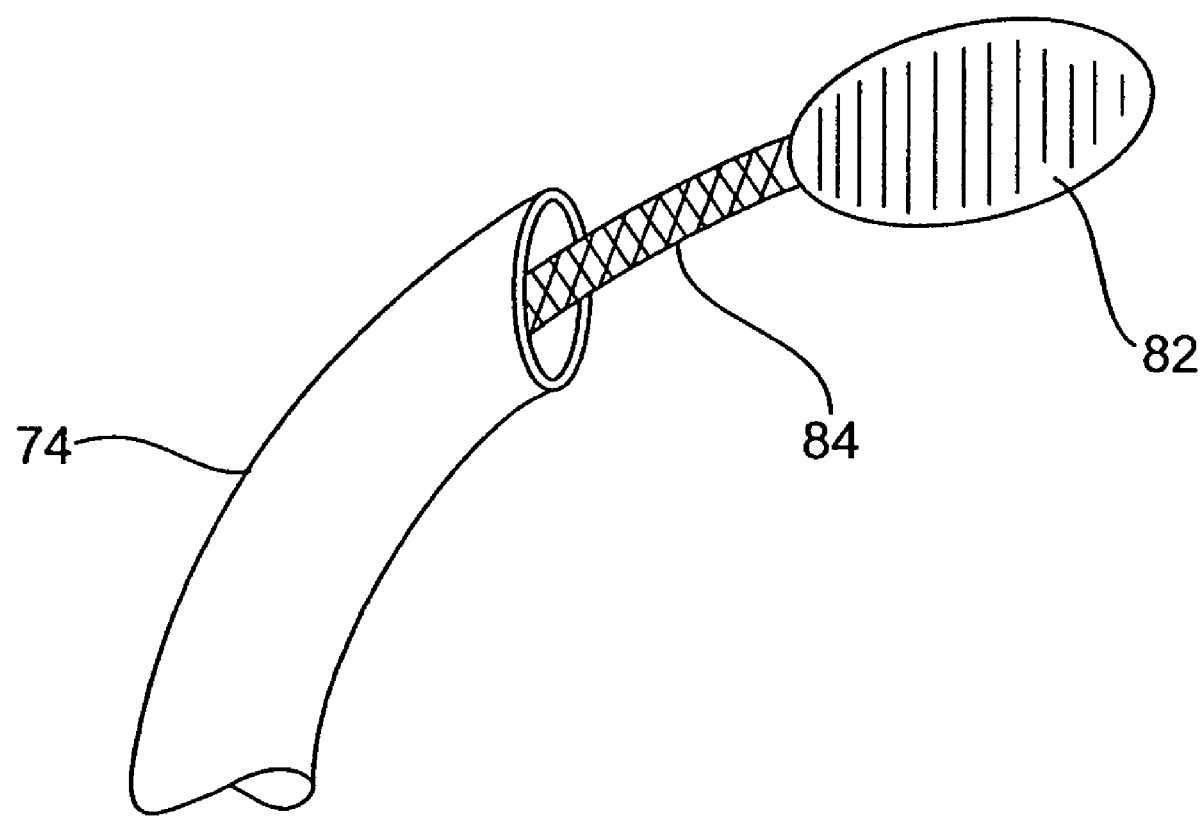

An antegrade approach for deploying a single chordae snare 74 and optionally securing a suture loop about the captured chordae is illustrated in FIGS. 33A and 33B. A guide catheter 14 deployed over the leaflets LF of the mitral valve MV may be deployed as described previously. A pair of deployment catheters 76 and 78 are advanced from the distal end of the guide catheter 14 and observed in real time via any of the imaging techniques described previously. The pre-shaped snare 74 is advanced out of the first deployment catheter 76 and is advanced through both of the chordae CT, as illustrated in FIG. 33A. A capture loop 80 is advanced from the second deployment catheter 78 and positioned so that it lies in the path of the pre-shaped snare 74 as it is advanced through the chordae CT. After a capture tip 82 passes through the capture loop 80, the loop can be tightened to secure to the capture tip 82 and draw the tip into the second deployment catheter 78. The capture tip 82 is attached to an end of a length of suture 84 (FIG. 33B) which runs back through a lumen in the snare 74. In this way, the suture may be pulled into the second deployment catheter 78, while the snare 74 is withdrawn back into the first deployment catheter 76, leaving only the suture in place grasping both the chordae. By then tying or otherwise securing the suture together into a permanent loop through the chordae, the coaptation of the valve leaflets LF can be modified in a desired way. As with the previous embodiments, a particular advantage of this approach is that the valve coaptation can first be viewed using the real time imaging capability to assure that valve regurgitation is adequately addressed before making the chordae capture permanent.

Figure 34:
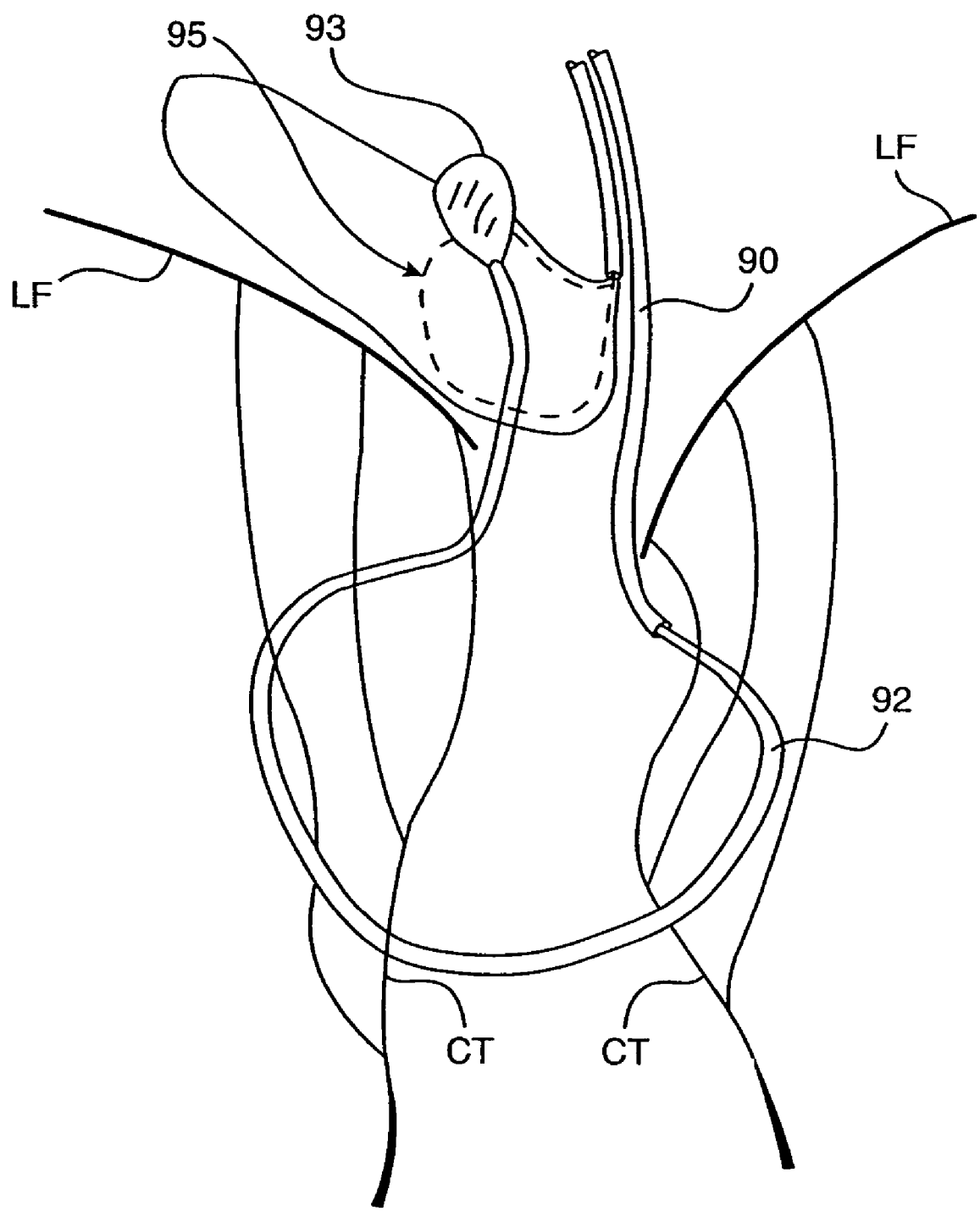
FIG. 34 illustrates an antegrade approach for snaring valve chordae to stabilize the mitral valve.

An alternative technique for deploying suture to capture chordae CT is illustrated in FIG. 34. First deployment catheter 90 (positioned through a guide catheter which is not shown) is positioned through the opening between valve leaflets LF. A balloon 93 at the distal end of chordae snare 92 is extended through the chordae, as described previously. The balloon 93 is inflated and floated through the mitral valve during regurgitation. The balloon will pass through the previously deployed capture snare 95. Alternatively, the chordae snare 92 could be shaped so that it will encircle the chordae and then pass outwardly through the valve opening and into the previously deployed capture snare 95.

Figure 35:
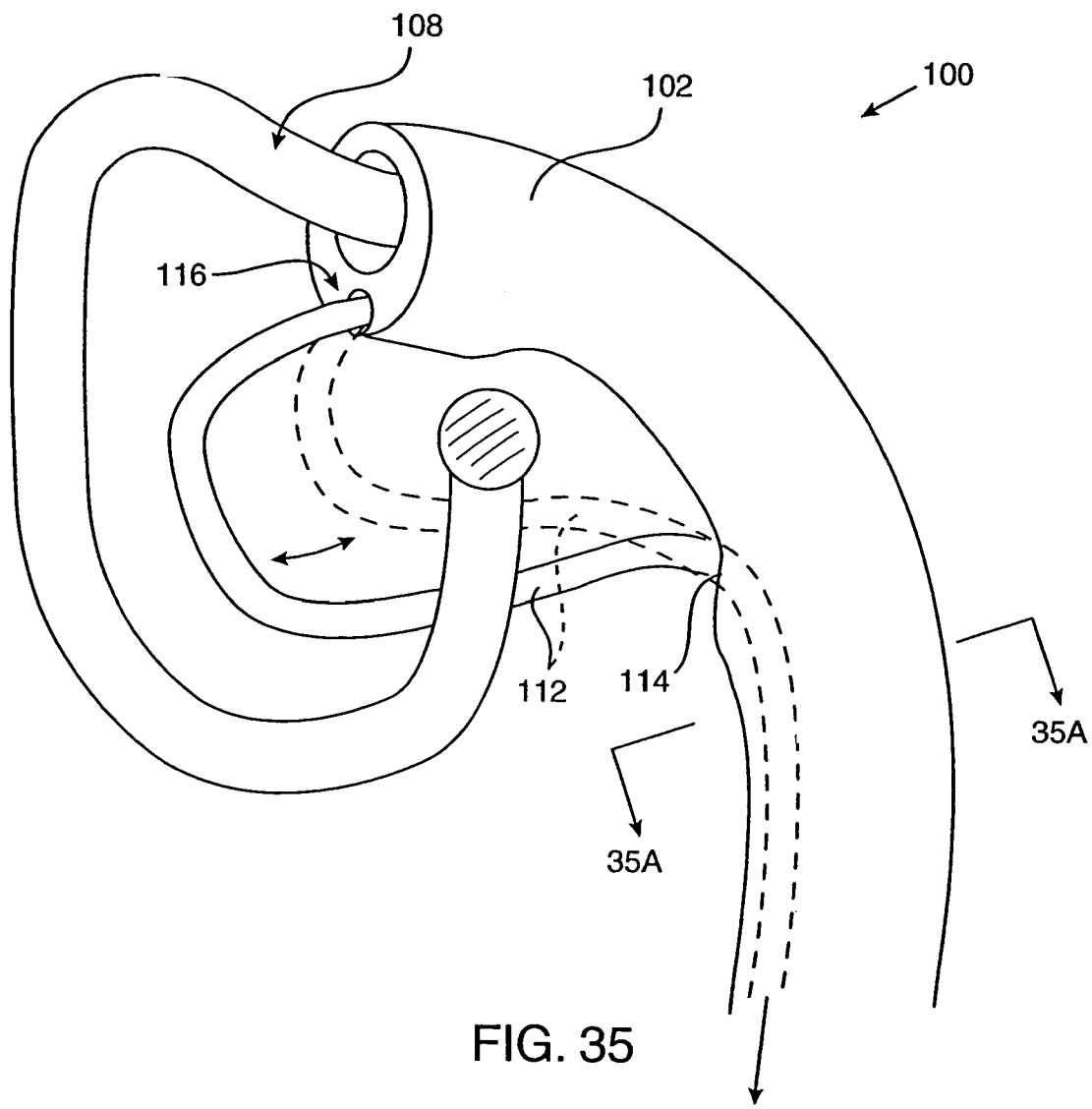
FIGS. 35 and 35A illustrate a snaring catheter particularly intended for capturing valve chordae from a retrograde approach.
Figure 35A:
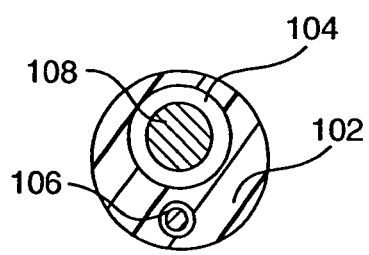

A chordae stabilization catheter 100 which is particularly suited for a retrograde approach is illustrated in FIG. 35. The catheter 100 includes a catheter body 102 having a pair of lumens 104 and 106 extending from a proximal end (not shown) to a distal end which is illustrated in FIG. 35A. The main lumen 104 extends fully to the distal tip of the catheter body 102 and a chordal snare 108 is slidably received in the lumen. The snare 108 has a loop pre-formed over its distal end so that, when extended from the catheter 100, it will assume the shape shown in FIG. 35. The loop has a diameter generally in the range from 3 mm to 20 mm and is shaped so that it will evert backwardly into a secondary loop formed by a capture snare 112. The capture snare 112 is disposed in the secondary lumen 106 and emerges from an opening 114 space proximally from the distal end of the catheter 100. The distal tip of the capture snare 112 is fixed at an anchor point 116 in the distal tip of the catheter body 102. Thus, by extending and retracting the capture snare 112, the capture loop can be moved between the position shown in full line and broken line.

Figure 36A:
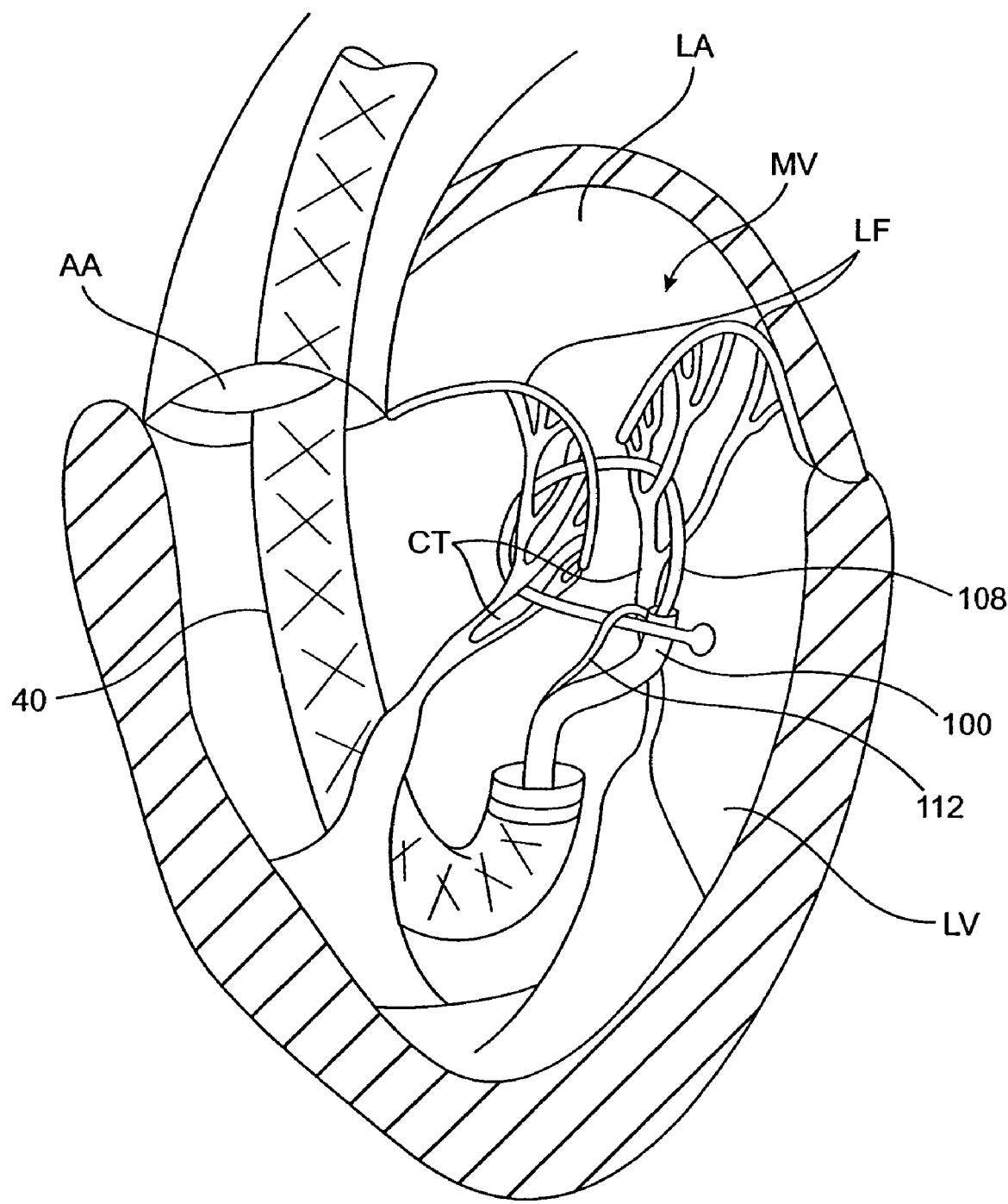
FIGS. 36A and 36B illustrate use of the catheter FIG. 35 for snaring valve chordae.
Figure 36B:
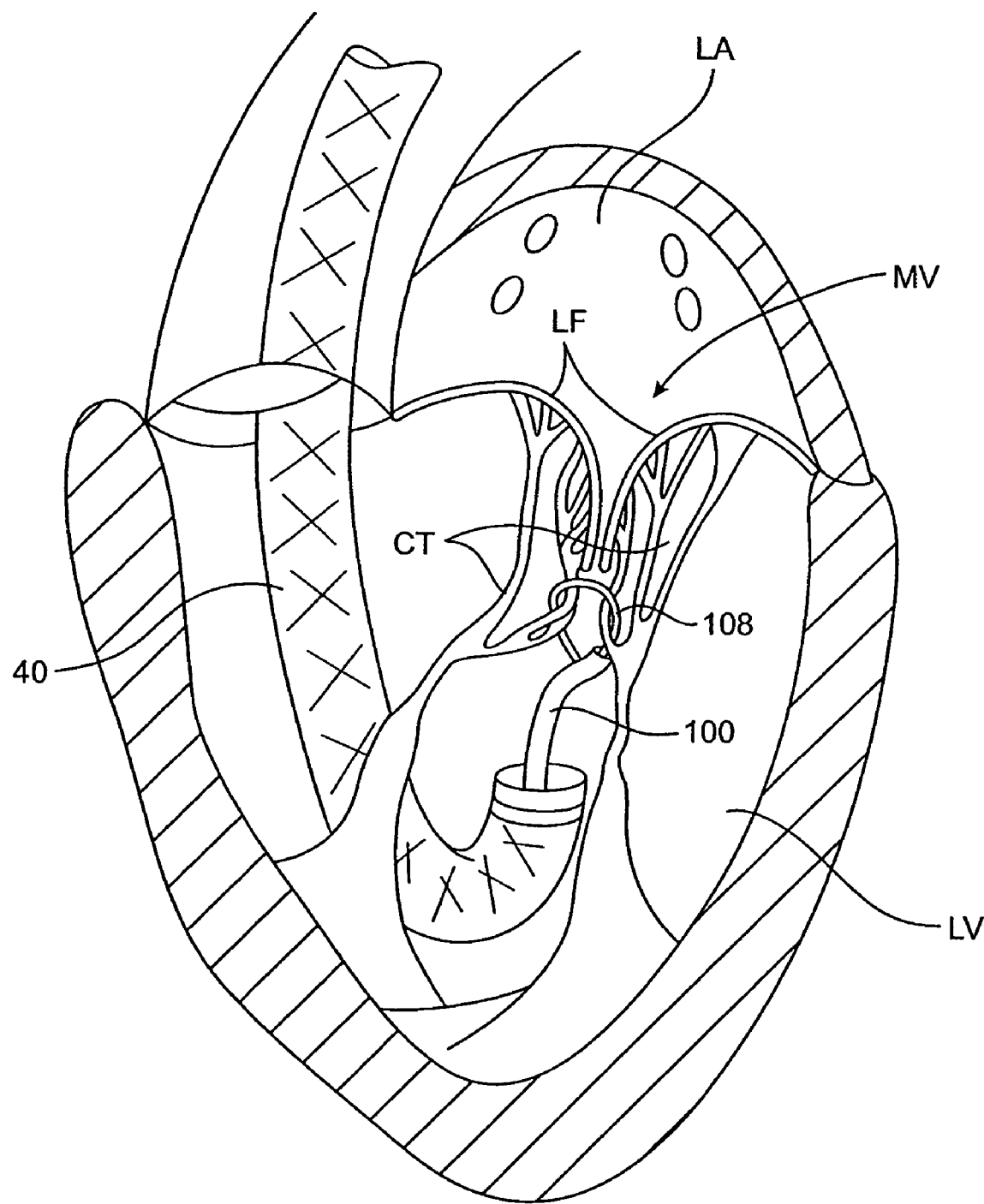

Referring now to FIGS. 36A and 36B, use of the catheter 100 for capturing and stabilizing chordae CT will be described. The catheter 100 is introduced in a retrograde direction (although antegrade would also be possible), typically through a guide catheter 40 as generally described above. Under direct (e.g., fluoroscopic) observation, the distal end of the catheter 100 will be guided to a position generally within the chordae CT, as illustrated in FIG. 36A. The chordae snare 108 will then be extended from the distal tip so that it passes through and becomes entangled with the chordae CT attached to both of the leaflets LF. The distal tip of the chordal snare 108 will eventually pass through the loop defined by the capture snare 112, also as illustrated in FIG. 36A. The capture snare will then be tightened to hold the distal tip of the chordae snare 108, and the chordae snare then retracted so that the loop of the snare which passes through the chordae will be tightened, generally as shown in FIG. 36B. Generally, the catheter 100 will not be intended for permanently affixing the chordae CT. Instead, immobilization of the valve leaflets LF will be intended to facilitate a subsequent treatment step, as described hereinafter. Use of the retrograde approach for immobilizing the chordae CT will be particularly advantageous when used with antegrade interventions.

Figures 37, 38:
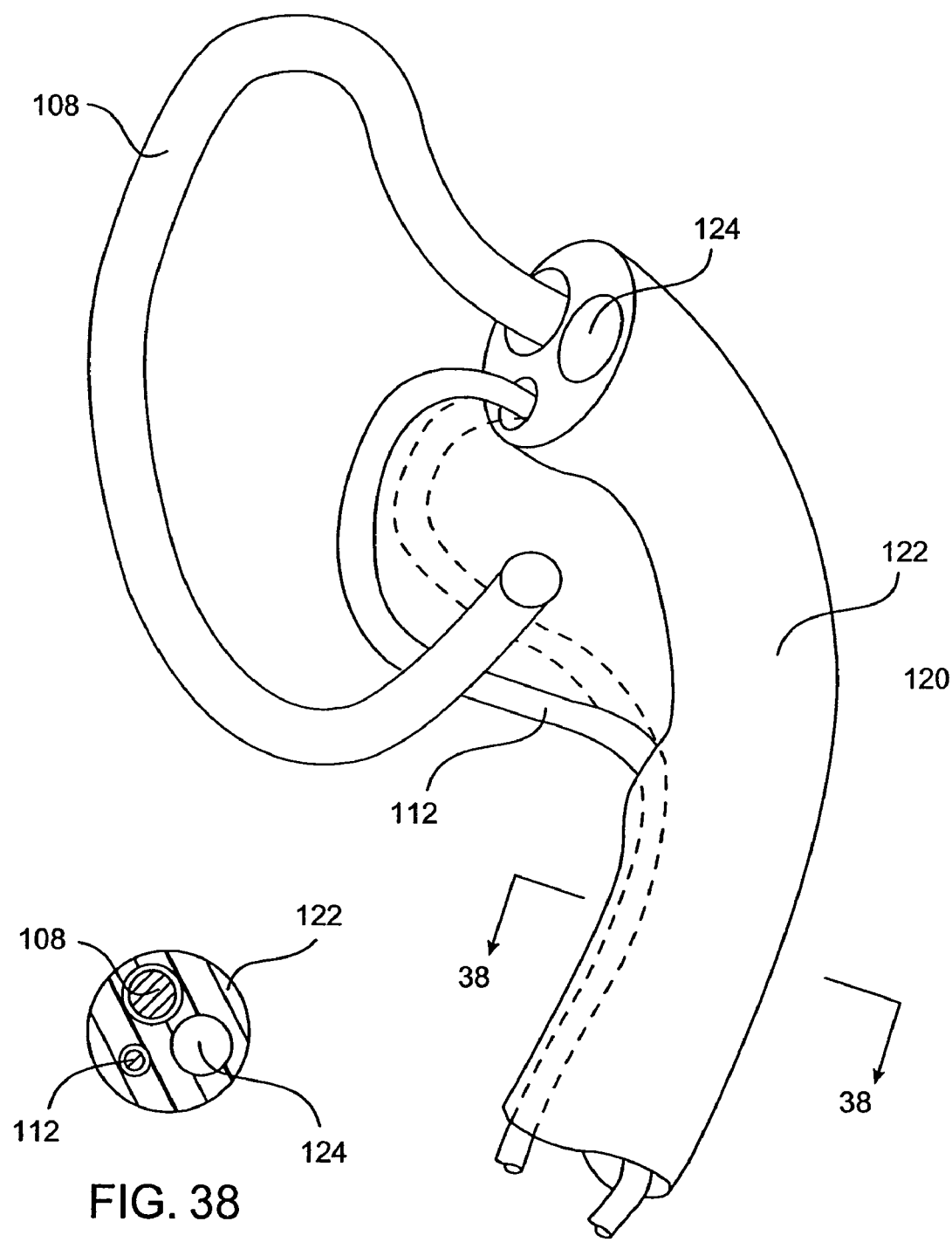
FIGS. 37 and 38 illustrate a catheter similar to that shown in FIGS. 35 and 35A, except that it includes a working channel for introducing interventional catheters and tools to treat the mitral or other atrioventricular valve according to the methods of the present invention.
Figure 39A:
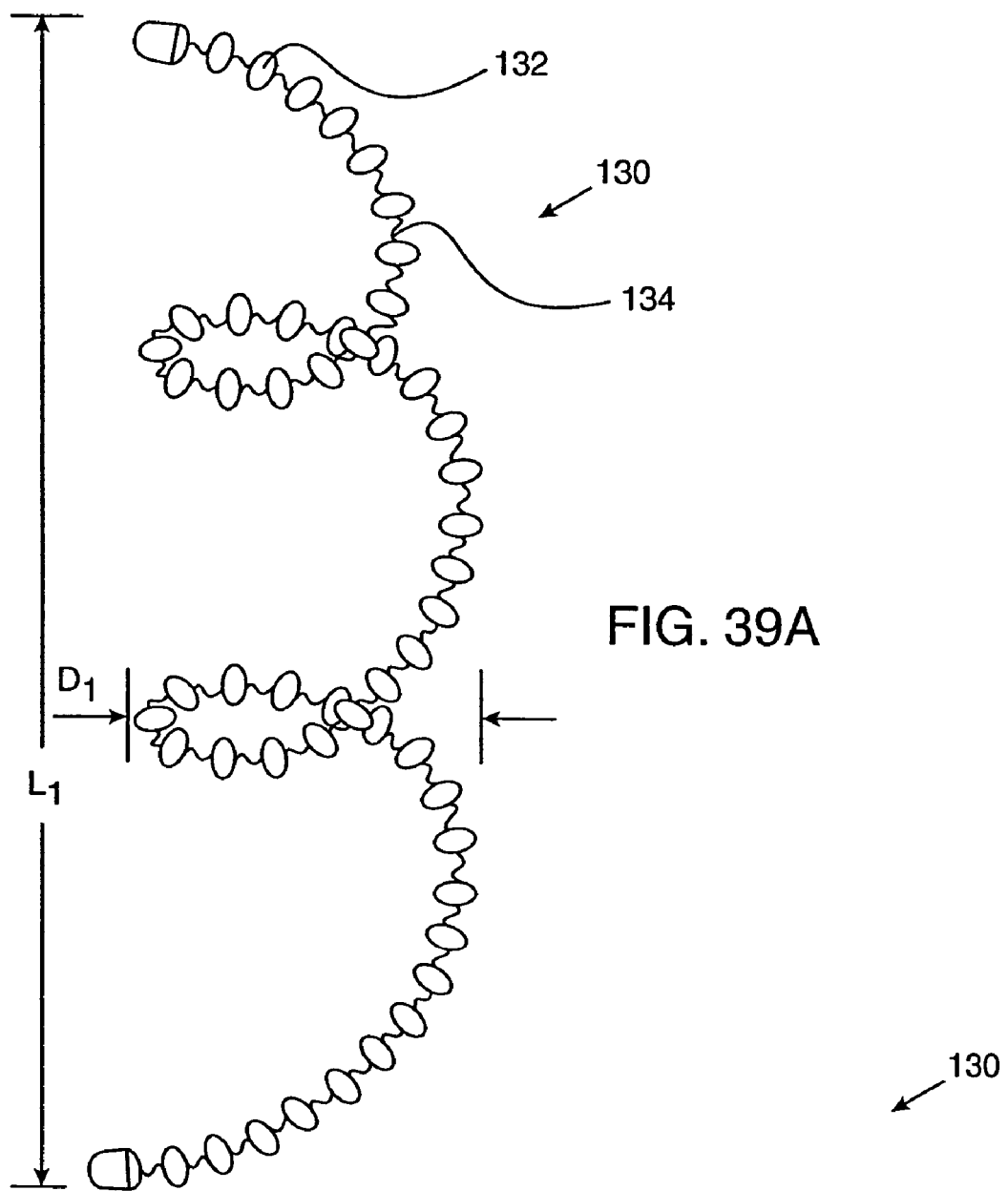
FIGS. 39A and 39B illustrate a coil which can be implanted within the valve chordae to stabilize the mitral valve.
Figure 39B:
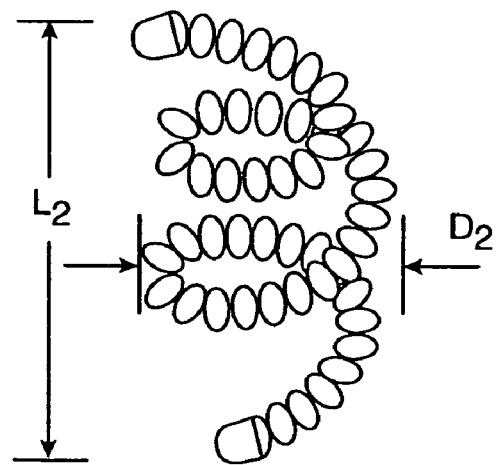
Figure 40:
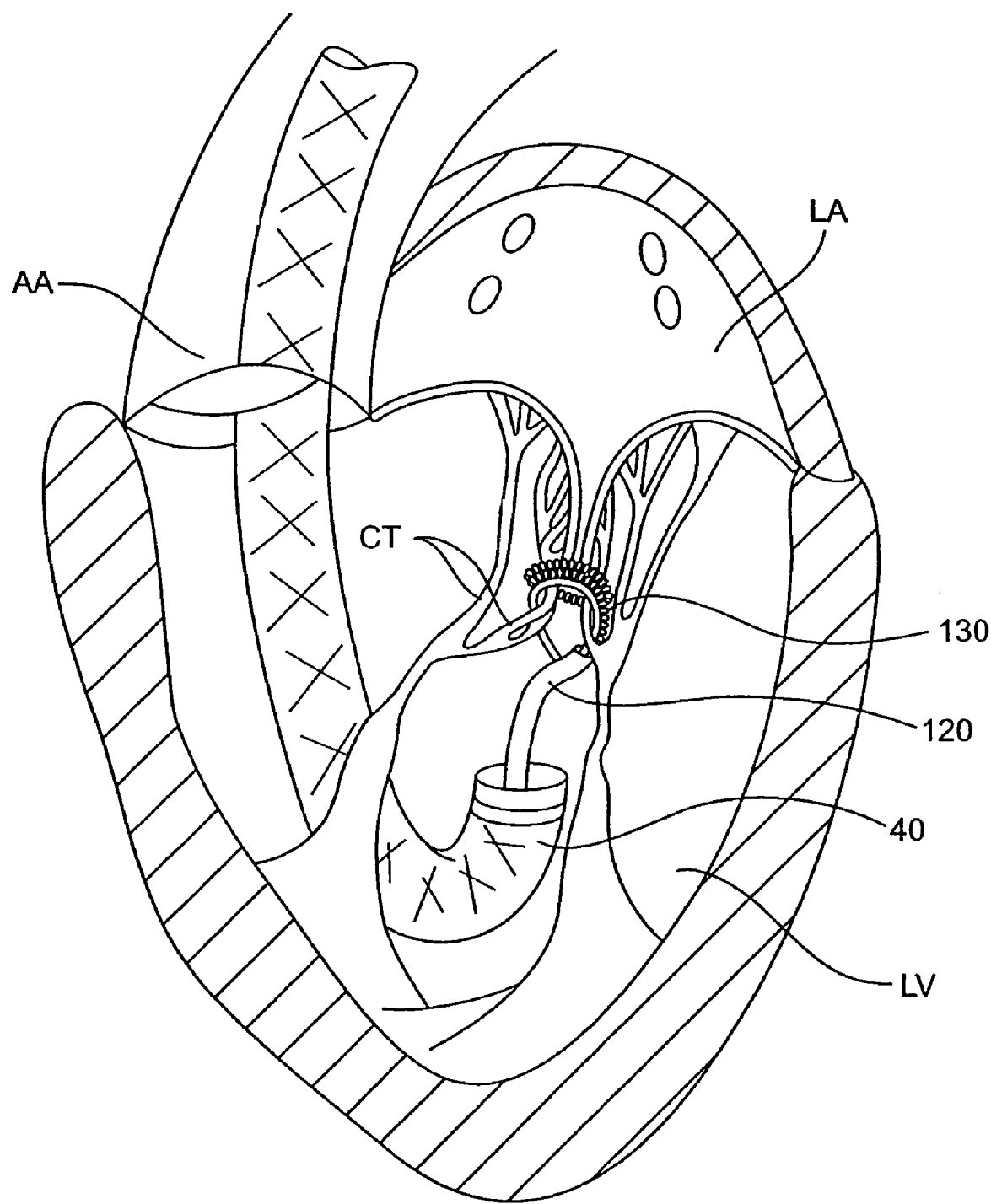
FIG. 40 illustrates placement of the coil of FIGS. 39A and 39B from a retrograde approach.

The catheter of FIG. 35 could, however, be modified to facilitate performance of retrograde interventions while the chordae are stabilized. As shown in FIG. 37, the catheter 120 includes a catheter body 122 which is generally the same as that shown for catheter 100 in FIG. 35 (with common components being given identical reference numbers), except that a third working lumen 124 is provided. The working lumen 124 can be used to deliver and position a wide variety of interventional tools for performing at least most of the specific interventions described elsewhere in this application. The catheter 120 will, of course, be particularly useful for performing interventions which rely on retrograde stabilization of the chordae CT of the type provided by the catheter. For example, the lumen 124 may be used to position an RF energy delivery tool for heating the chordae to cause shrinkage, as described in more detail below. Alternatively, the working lumen 124 could be used to position a chordae stabilization coil 130, generally as described in FIGS. 39A and 39B. The coil is typically a helical filament having a secondary helical structure comprising, for example, three major loops. The coil may comprise an inner element composed of a shape memory material, such as nitinol, inserted into an outer coil 132 made of a radiopaque material, such as a platinum alloy. The shape memory coil 134 is formed into a "stacked coil" configuration (with no space between adjacent windings of the coil) and then programmed so that it will assume the stacked coil configuration at a temperature slightly above body temperature. The coil assembly 130 is formed by heat treating the platinum 132 to a diameter D1 and length L1, as shown in FIG. 39A. The shape memory coil 134 is then stretched to a near linear configuration and inserted into the platinum coil 132, and the two are coupled at the end. Upon heating, the shape memory coil contracts back into its tightly stacked coil shape, compressing the platinum coil 132, and causing the entire assembly 130 to assume a smaller diameter D2 and length L2, as shown in FIG. 39B. The coil 130 may be delivered using a pusher catheter through the working lumen 124 so that it deploys within and entangles the chordae CT, as shown in FIG. 40. The pusher catheter (not shown) could be configured similarly to embolic coil delivery catheters, such as those described in U.S. Pat. Nos. 5,226,911; 5,234,437; 5,250,071; 5,261,916; 5,312,415; 5,350,397; and 5,690,671, the full disclosures of which are incorporated herein by reference.

B. Valve Leaflet Grasping

Valve leaflet grasping may be accomplished using a number of methods, most commonly the following three: 1) pinching, 2) partially or fully penetrating or piercing, and 3) the use of suction or vacuum. Pinching involves grasping the surface or edge of the leaflet without penetrating the tissue. This may be accomplished by an antegrade or retrograde approach using atrial, ventricular or atrial-ventricular devices. It may be appreciated that although the following embodiments are examples which are described relative to a specific approach (antegrade or retrograde), each device or component may be used or adapted to be used in all approaches.

Figure 41A:
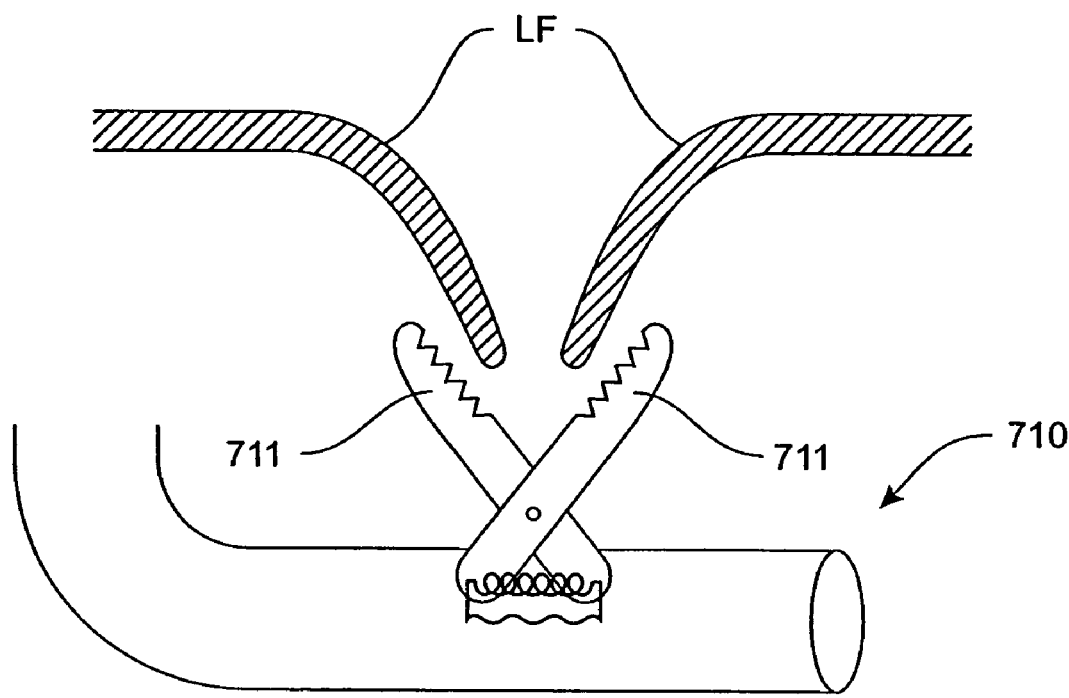
FIGS. 41A-41B, 42A-42B and 43 illustrate valve leaflet grasping devices which utilizes a pinching method.
Figure 41B:
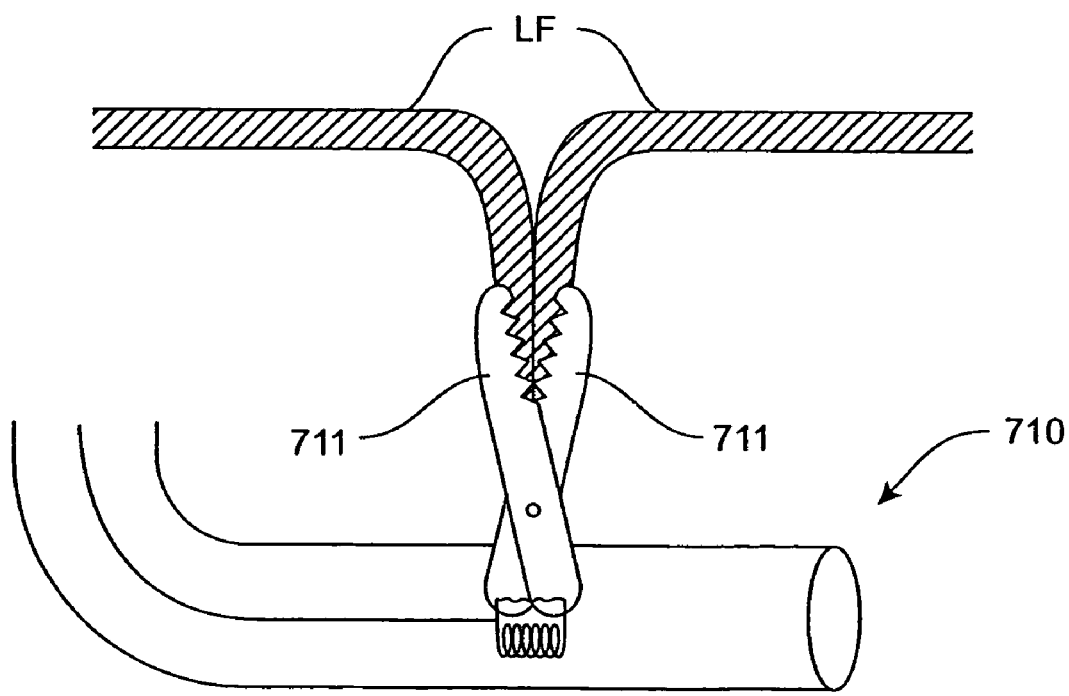
Figures 42A, 42B:
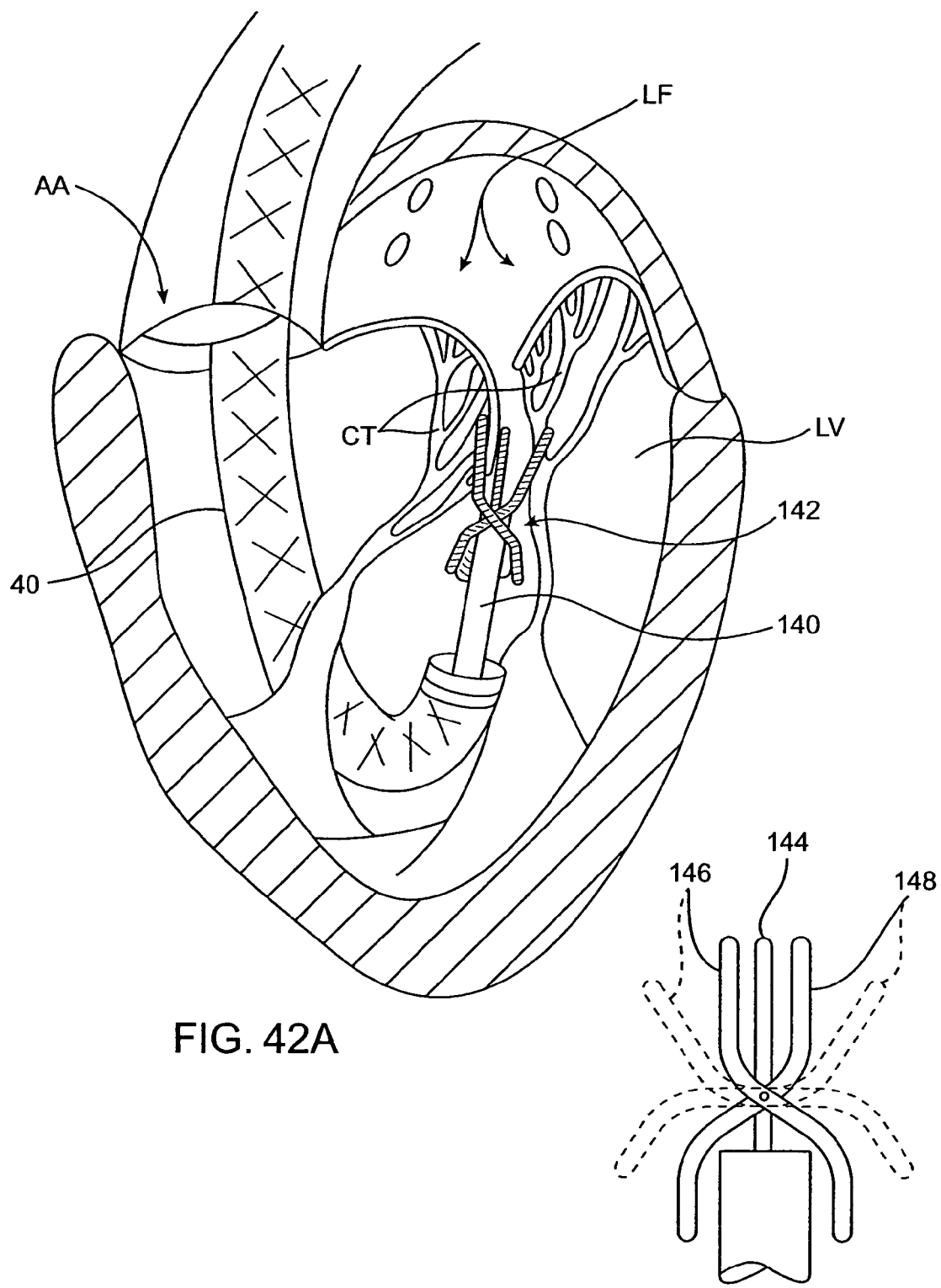
Figure 43:
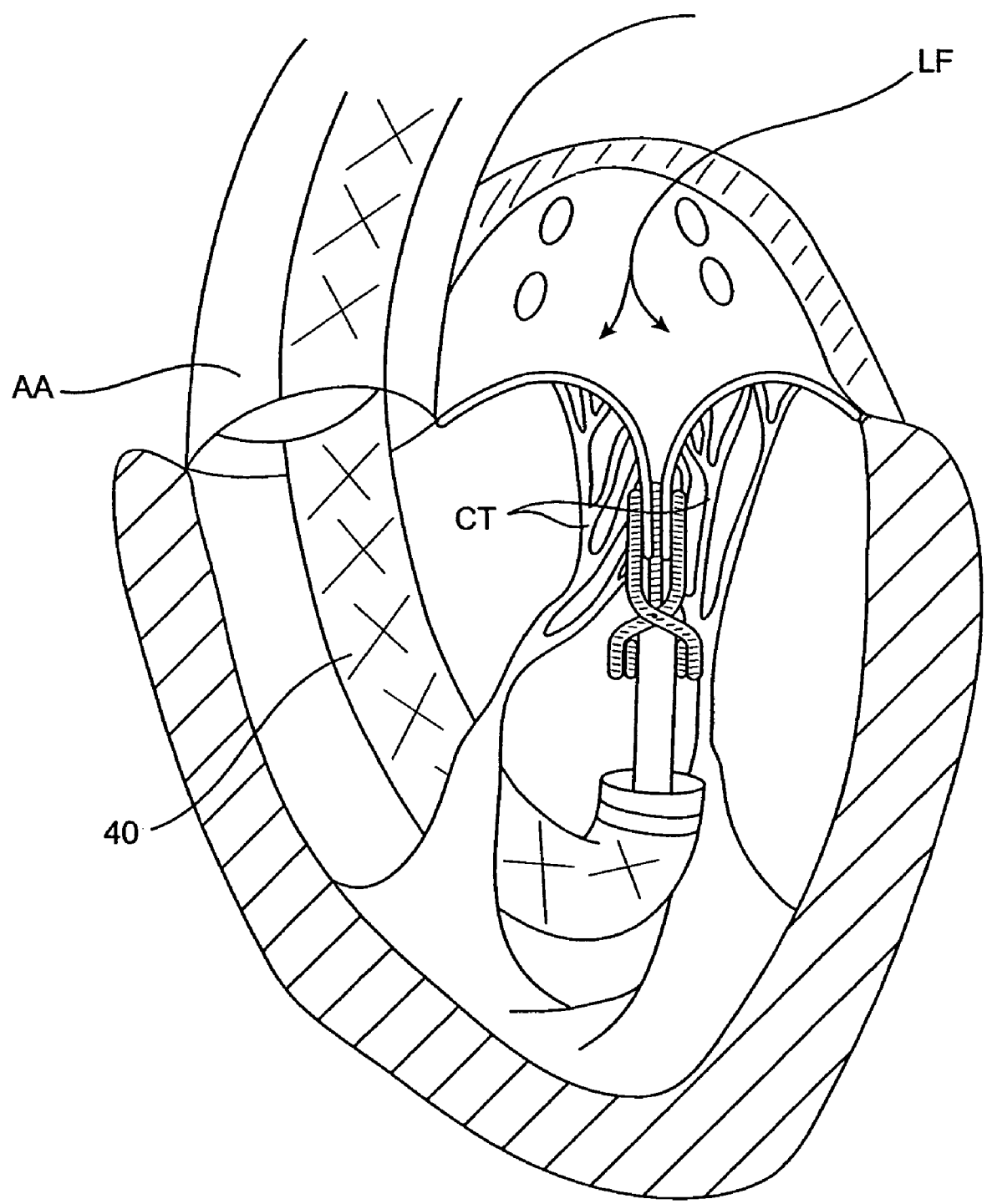

In preferred embodiments, depicted in FIGS. 41-43, pinching of the valve leaflets LF can be achieved, for example, by using a grasping catheter introduced in a retrograde direction to temporarily capture the free ends of the valve leaflets LF. It may be possible to use a simple two-jaw tool at the distal end of a catheter to capture both opposed leaflets. Such a two-jaw tool 710 is depicted in its open position in FIG. 41A. In this position, opposing jaws 711 may be positioned on opposite sides of the free ends of the valve leaflets LF. In its closed position, depicted in FIG. 41 B, the leaflets may be drawn together and pinched to immobilize the valve. Although this may be adequate, it may be preferred to use a three-jaw capture tool as shown in FIGS. 42-43. The catheter 140 can be delivered through a guide catheter generally as described above. The catheter includes a tool 142 at its distal end. Tool 142, as best shown in FIG. 42B, includes a fixed center jaw 144 and a pair of pivotable outer jaws 146 and 148. The jaws 146 and 148 may be independently opened to a "capture" position as shown in broken line in FIG. 42B. Actuation of the jaws 146 and 148 may be achieved in a variety of conventional manners, including pull wires, push wires, inflatable balloons, heat memory alloy motors, and the like. By independently opening and closing the capture jaws 146 and 148 against the fixed jaw 144, the valve leaflets LF can be captured independently.

As shown in FIG. 42A, a first leaflet LF can first be captured. The catheter 140 can then be manipulated and positioned, typically under real time imaging, to capture the second leaflet LF, as shown in FIG. 43. It will be appreciated that independent capture of the leaflets greatly facilitates the procedure. Use of a single pair of capture jaws requires that the leaflets be captured at the instant when they are properly opposed. In the case of prolapsed valves, such an instance may never occur. Once captured and immobilized, as shown in FIG. 43, the valve leaflets can then be modified in any one of a variety of ways, as described elsewhere in the application.

Figures 44A, 44B, 44C:
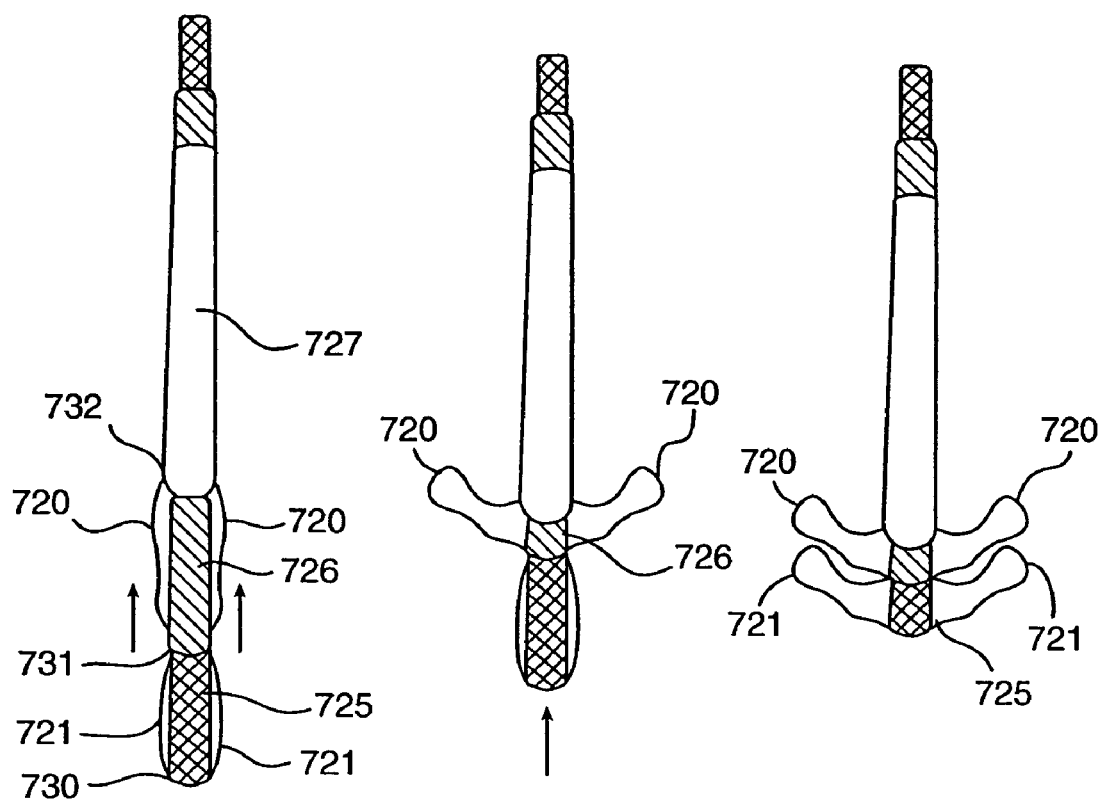
FIGS. 44A-44D are schematic illustrations of an atrial-ventricular valve leaflet grasping device which utilizes a pinching method.
Figure 44D:
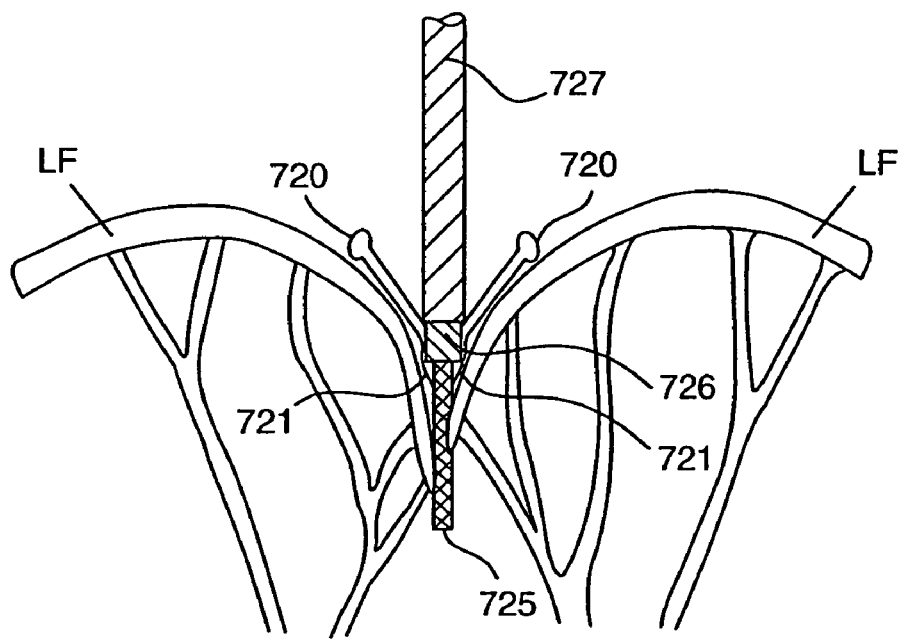

Additional embodiments, depicted in FIGS. 44-46, involve pinching of the valve leaflets LF by using a grasping catheter introduced in an antegrade direction to temporarily capture the surfaces or the free ends of the valve leaflets LF. Referring to FIGS. 44A-44D, the valve leaflets LF may be pinched between a superior loop 720 and an inferior loop 721. In a preferred embodiment, the grasper is comprised of a nitinol flat ribbon heat set in the shape of double loops 720, 721. The ribbon may be mounted on a series of three coaxial shafts, an interior shaft 725, a central shaft 726 and an exterior shaft 727. The distal end of the ribbon may be attached to the distal end 730 of the interior shaft 725, a midportion of the ribbon may be attached to the distal end 731 of the central shaft 726, and the proximal end of the ribbon may be attached to the distal end 732 of the exterior shaft 727. One or more ribbons may be mounted on the coaxial shafts; in this example, two ribbons are shown 180 degrees apart. When extended, as shown in FIG. 44A, the grasper may be pulled flat against the shafts 725, 726 ,727 for ease of insertion through a guide catheter or tool and into a desired position between the valve leaflets LF. When the central shaft 726 is retracted or the exterior shaft 727 advanced, as shown in FIG. 44B, the superior loops 720 may extend radially from the shafts. The superior loops 720 may rest on the superior surface of the valve leaflets LF in the atrium, as shown in FIG. 44D. In this position, the superior loops 720 may aid in orientation assessment, as the superior loops may be echo or fluorogenic and may be easily visible in relation to the cardiac structures or other devices or components. When positioned in a desired location, the interior shaft 725 may then be retracted, as shown in FIG. 44C, to extend the inferior loops 721 radially from the shafts. The inferior loops 721 may be in contact with the inferior surface of the valve leaflets LF in the ventricle. Thus, the valve leaflets LF may be pinched between the inferior loop 721 and superior loop 720. It may also be appreciated that the inferior loops 721 may be deployed prior to the superior loops 720.

Referring to FIGS. 45A-45B, the valve leaflets LF may be pinched between a superior roller 750 and an inferior roller 751. As shown in FIG. 45A, the rollers 750, 751 may be mounted on a shaft 755 and connected by a pull actuation wire 756. The rollers 750, 751 may be serrated or surface treated in a directional pattern to facilitate grasping of the valve leaflets LF. To grasp a leaflet LF, the rollers 750, 751 may be placed against the surface or free edge of the leaflet LF. Pulling of the actuation wire 756 may rotate the superior roller 750 and inferior roller 751 toward each other. This may draw the leaflet LF between the rollers 750, 751, as shown in FIG. 45B. Thus, the leaflets LF may be individually grasped for treatment.

Referring to FIGS. 46A-46B, the valve leaflets LF may be pinched between a pair of flat coils 770. In a preferred embodiment, each coil 770 may be comprised of nitinol flat ribbon heat set in the shape of a coil. As shown in FIG. 46A, the coils 770 may be linked together with opposing curvature by a clip 772. Movement of the clip 772 along the coils 770 may uncurl the coils 770 to a straightened configuration. As shown in FIG. 46B, this may also be accomplished by a catheter shaft 773 placed over the coils 770. In the straightened position, the coils 770 may be inserted between the valve leaflets LF in an atrial-ventricular position so that the distal ends 775 of the coils 770 are in the ventricle. As the shaft 773 or clip 772 is retracted, the coils 770 may begin curling radially beneath the valve leaflets LF and upwardly so that the distal ends 775 of the coils 770 contact the inferior surface of the valve leaflets LF. Similarly, if the coils 770 continue curling, a portion of the flat ribbon proximal to the distal end 775 may contact the valve leaflet. In this manner, the leaflets may be grasped for treatment. Such a grasping device may also serve as a fixation device with the pair of coils 770 left in place, as will be described in a later portion of the application.

A valve or tissue structure may also be grasped by atraumatic partial or full penetration or piercing. This may be accomplished with a variety of grasping mechanisms. Preferred embodiments include one or more prongs extending from an interventional tool in an arrangement to grasp a specific structure. Specifically, three opposing prongs may extend from a grasping sheath with distal ends configured to pinch, partially penetrate or pierce. Such ends may be pointed or may be soft, as in the case of rounded, urethane coated or solder coated ends. Referring to FIG. 47A, the opposing prongs 800 may be retracted into a grasping sheath 801 to hold the prongs 800 in a closed configuration. It may be preferred to orient the device to a desired position in this configuration. When the target tissue has been located, the prongs 800 may be extended to grasp the tissue structure, as shown in FIG. 47B. This may be accomplished by either extending the prongs 800 axially or retracting the grasping sheath 801. The target tissue may be pinched, partially penetrated or pierced with the prongs 800 in this configuration, or such action may be facilitated by closing or partially closing the prongs 800 as previously depicted in FIG. 47A. Alternatively, the prongs 800 may be attached to or integral with a prong-tipped tube 802, as shown in FIG. 47C. Such a design may be more conducive to the insertion of tools or fixation devices for further treatment steps, such as tissue modification. Tools or devices may be inserted through a lumen in the prong-tipped tube 802, depicted by arrows 804, for use at or near the grasping location. Similarly, tools or fixation devices may be inserted through a lumen in a hollow prong 806, as depicted in FIG. 47D. Here, one or more prongs 806 may be hollow, and the remaining prongs 808 may be comprised of solid wire or a suitable material. Tools or devices may be inserted through a lumen in the hollow prong 806, depicted by arrows 810, for use at or near the grasping location. Prongs, hollow or solid, may be made from stainless steel, NiTi, plastic or other suitable material. Additionally, they may be coated or coiled to enhance visibility. Likewise, the geometries of the prongs may be varied to facilitate grasping of the desired amount of tissue. And, the distal tip sharpness and surface finish can be varied to establish the amount, if any, of piercing.

Figure 48:
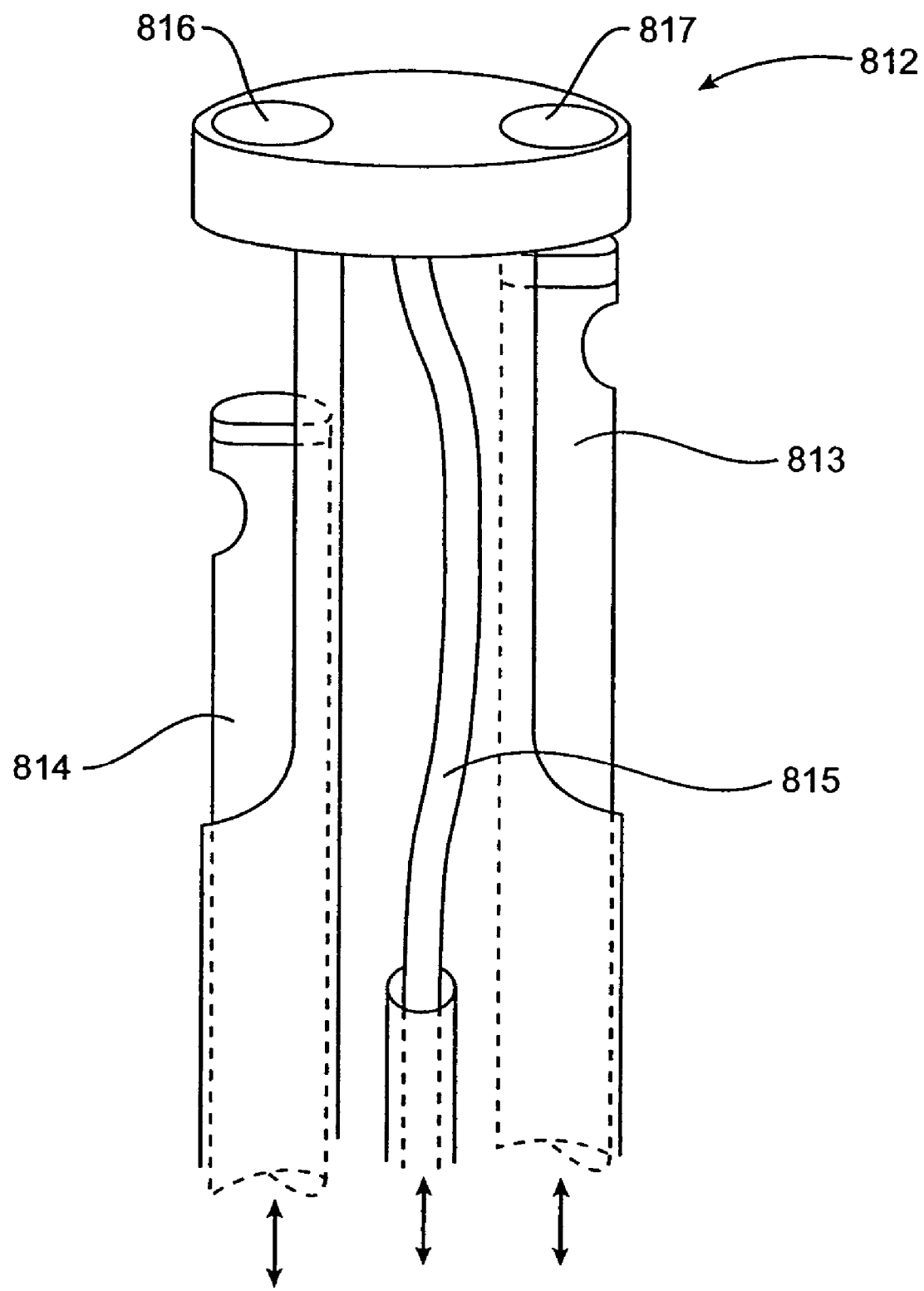
FIG. 48 illustrates a vacuum-assisted stabilization catheter for use in the methods of the present invention.

In addition to directly engaging the valve leaflets to effect stabilization and/or immobilization with the grasper devices described above, the present invention may also employ a catheter or other tool having vacuum or suction applicators to temporarily capture the valve leaflets. As shown in FIG. 48, a catheter 812 comprises a shaft having a pair of vacuum applicator rods 813 and 814. Usually, the vacuum applicator rods 813 and 814 will comprise separate shafts which may be axially translated relative to the main shaft of the catheter. Further optionally, the shafts could be articulated or otherwise manipulable so that they can be independently positioned relative to the valve leaflets or other tissue structures once the catheter 812 is in place. The vacuum applicators have one or more apertures to permit contact and adherence to tissue when the applicators are attached to external vacuum sources. Usually, the shaft will be placed across the valve, either in an antegrade or retrograde fashion, and the applicators positioned to grasp and manipulate the valve leaflets. Optionally, the catheter 812 may comprise additional stabilizing and/or steering wires of the type previously described. For example, a steering wire 815 (and optionally a second steering wire on the opposite side) may be provided for engaging against the valve commissures to permit positioning of the catheter with respect to the valve leaflets. The vacuum applicators would further be independently positionable to engage the valves in the desired fashion. Using this catheter, the leaflets can be grasped and the competency of the valve evaluated using the methods described previously. The valve adjustment can then be effected using any of the interventional approaches described herein. Further, it may be appreciated that in each embodiment, timing of grasping may be facilitated by the use of gating with the patient's EKG, pressure waves of the cardiac cycle, audio heart sounds, electronic pressure or contact sensors on the graspers.

VIII. Coaptation, Adjustment and Evaluation

Once the valve leaflets, chordae or tissue structure is grasped by an interventional tool, the tissue may be manipulated to achieve a desired result, such as improvement in valve function. Such manipulation may occur during the grasping step, or it may require a separate step following grasping. In the case of leaflet modification, valve leaflets may be coapted or brought together and held in a preferred apposition. The valve function may then be evaluated for indications of improved valve function, such as reduced regurgitation. If further improvement is desired, the valve leaflets may be additionally manipulated or adjusted. Adjustment should primarily occur in a superior/inferior (up/down) motion in order to bring the leaflets to a final positioning where regurgitation is minimized. During adjustment, one or both leaflets may be released and recaptured with new positioning. After the final evaluation, the valve leaflets may be fixated in the desired position by an appropriate fixation device. In the case of chordae shortening or other tissue modification, similar steps may be taken.

IX. Tissue Modifications

Repair of atrioventricular or other cardiac valves according to the present invention is effected by modifying the valve or a supporting tissue structure in some way to affect blood flow through the valve during a phase of the cardiac cycle, for example to permit blood flow through the valve during diastole when the associated ventricle is filling with blood but which inhibits or prevents blood regurgitation back through the valve during systole. A number of techniques for modifying the valve closure by capturing or grasping the chordae attached to each valve leaflet have been described above. These techniques are often used just for valve grasping and/or coaptation and adjustment prior to a separate valve modification step, but they may also be made permanent to provide the final valve modification. Other techniques for more directly modifying the leaflets or other supporting structures of the atrioventricular valves will be described in this section. These techniques may be utilized either with or without the valve grasping and/or coaptation and adjustment techniques described above. For purposes of simplicity, however, the following methods will generally be described without specifically illustrating such grasping, coapting and adjustment approaches, focusing primarily on the methods and devices involved with fixation. In addition, it may be appreciated that although the following embodiments are examples which are described relative to a specific approach (antegrade or retrograde), each device or component may be used or adapted to be used in all approaches. Further, although devices and methods are described for fixating specific tissues, such as valve leaflets or chordae, such devices and methods may be used for any cardiovascular tissues and the like.

A. Fixation of Valve Leaflets

Figure 49:
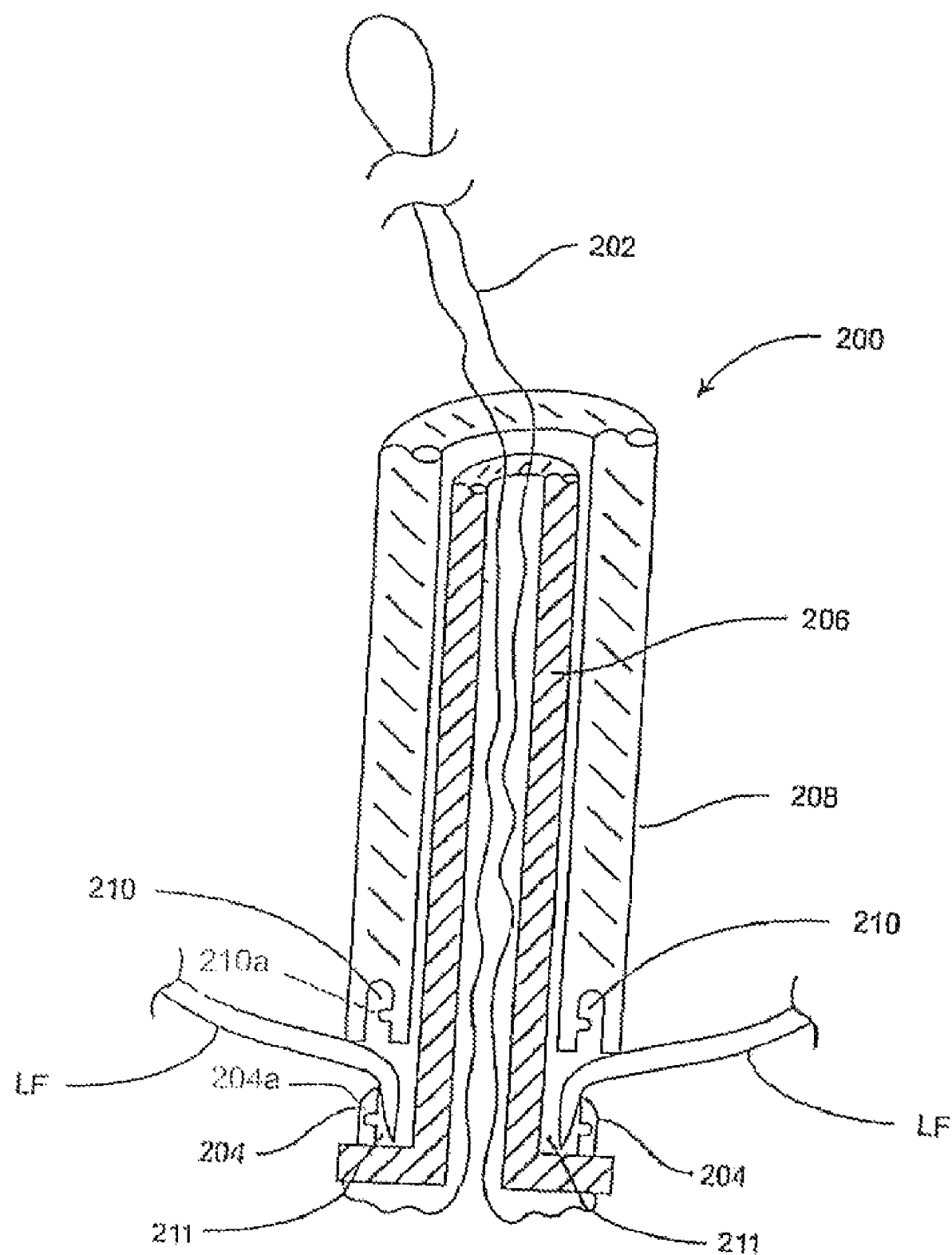
FIG. 49 illustrates an embodiment of a valve suturing device according to the present invention.

Suture can be delivered through the valve leaflets and then tied in a manner analogous to an open surgical procedure. In one embodiment, a suturing tool 200, shown in FIG. 49, may be positioned at the distal end of an interventional catheter. The interventional catheter will usually be advanced in an antegrade direction (i.e., from above the mitral valve), either directly through a guiding catheter or through a working lumen in a stabilization catheter. The tool 200 carries a length of suture 202 attached to a pair of needles 204 at either end thereof. The suture may be comprised of conventional suture material or of wire, typically stainless steel, nitinol or other material. The needles are releasably held on a reciprocating shaft 206 disposed within a lumen of a retrieval sheath 208. The tool 200 can be positioned to capture the opposed free ends of the mitral valve leaflets LF in a leaflet receptacle 211 disposed near a distal end of the interventional catheter, generally as shown in FIG. 49. The needles can then be advanced through the leaflets LF by drawing the shaft 206 toward the sheath 208. Proximal retraction of shaft 206 relative to sheath 208 draws needles 204 into needle receptacles 210. A needle catch or detent mechanism comprising a protuberance 210a extending laterally into the needle receptacle 210 engages a concave region 204a of needle 204 releasably locking the needle 204 with the sheath 208. Further retraction of shaft 206 continues to move the needles so that the needles 204 penetrate the leaflet while they are captured in needle receptacles 210 formed in the sheath 208. The sheath can then be withdrawn so that the suture is at least partially pulled through the leaflets. A knot can be tied in the suture, and the knot then advanced through the associated catheter to tighten over the valve leaflets. The tool 200 can carry two, three, four, or even more lengths of suture which may be simultaneously or sequentially introduced into the valve leaflets in order to permit multiple suture loops to be placed. The resulting tied suture loops will be similar to the "bow tie" sutures placed in open surgical procedures which have been described in the medical literature as described above.

The need to place and draw long lengths of suture through the valve leaflets can, however, be deleterious to the fragile leaflet structures. Thus, alternative needle and suture devices which rely on mechanical fasteners in relatively short suture lengths may be preferred. In one embodiment, a hollow suturing coil 1300, shown in FIG. 49A, may be positioned at or near the distal end of an interventional catheter. The suturing coil 1300 may be comprised of any material of sufficient rigidity to pierce and penetrate through valve leaflets LF, such as stainless steel, various shape memory or superelastic materials, metal alloys and various polymers, to name a few. The hollow suturing coil 1300 may contain a suture 1302 comprised of conventional suture material or of wire, typically stainless steel, nitinol or other material. The suture 1302 may be secured at the tip 1304 of the coil 1300 with a toggle rod 1305. After the valve leaflets LF have been grasped and coapted, the suturing coil 1300 may be advanced in a corkscrew fashion through the valve leaflets LF, as shown in FIG. 49A. Though such advancement is shown from above, advancement may be made from any direction through any number and configuration of valve leaflet layers. When advancing, the sharpened tip 1304 of the coil 1300 may pierce through the leaflets LF any number of times. It may be appreciated that such corkscrew piercing may be made through the middle portions of the leaflets such that a pierce is made at each half-rotation, or the piercings may be made along the edges of the leaflets such that a pierce is made at each full-rotation, to name a few.

Once the coil 1300 has advanced to a desired location, the toggle rod 1305 may be secured against a leaflet LF to hold the suture 1302 in place. At this point, the coil 1300 may be removed by retracting the coil 1300 in a reverse corkscrew fashion, as depicted in FIG. 49B, leaving the suture 1302 behind. Since the coil 1300 may be much larger in diameter than the thickness of the leaflets (to aid in placement), the suture 1302 may be loose-fitting and the valve leaflets LF insufficiently modified. The suture 1302 may then be tightened, as shown in FIG. 49C, so that the suture 1302 holds the leaflets LF together in a desired configuration. This may be aided by the use of a soft-tipped catheter 1306 which may be advanced to contact the surfaces of the leaflets LF when tightening to prevent the leaflets LF from prolapsing. Once the suture 1302 is sufficiently tight, a restrictive collar 1308 may be deployed from the catheter 1306 or another device to secure and terminate the suture 1302. Such a restrictive collar 1308 may be comprised of any suitable material, such as heat-shrink tubing, nitinol shape-memory or superelastic coil or the like. Thus, this embodiment eliminates the need for needle passers and needle receivers providing a simplified method of valve leaflet fixation.

Figure 50:
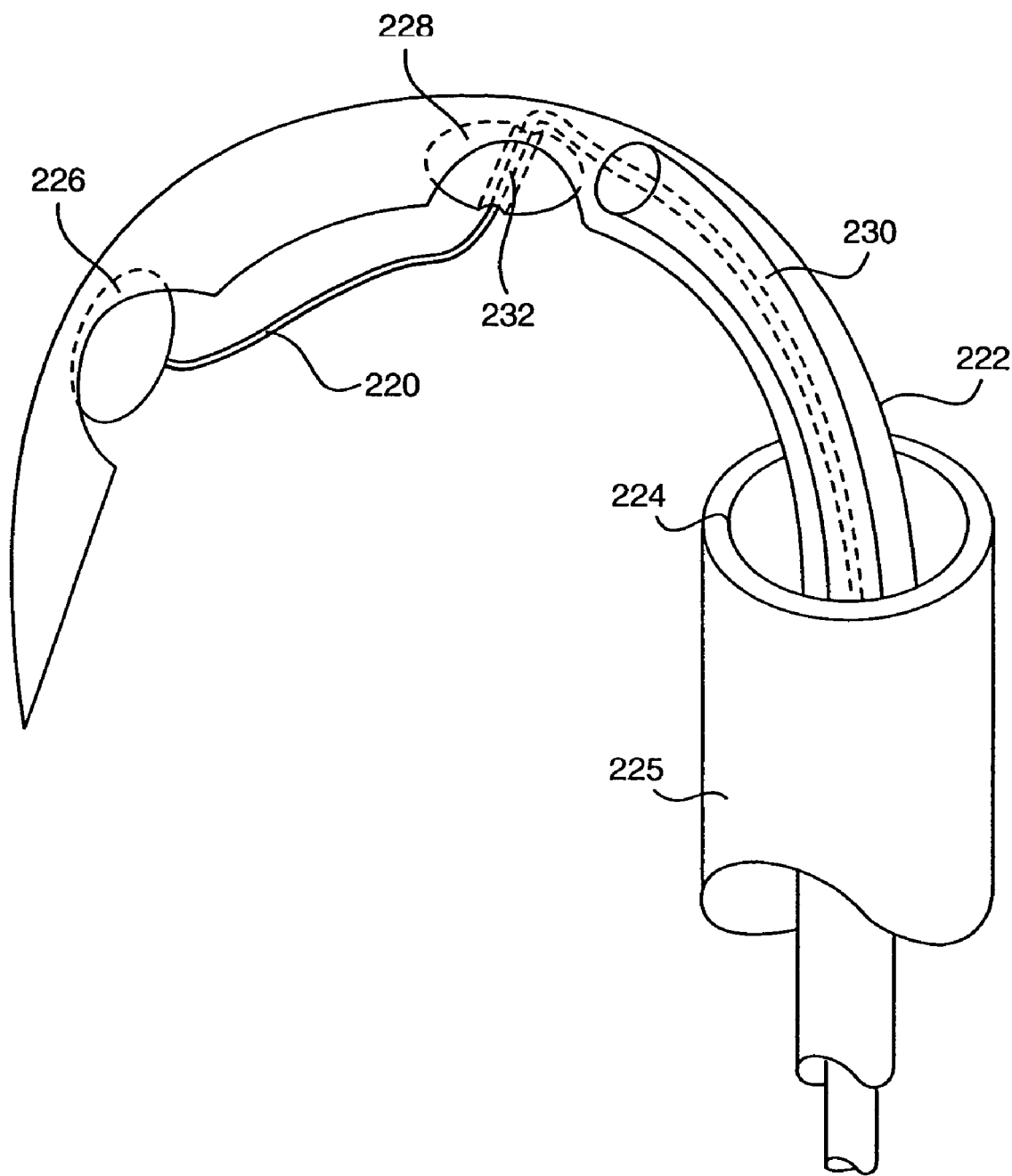
FIG. 50 illustrates a further embodiment of a valve suturing device according to the present invention.
Figure 51:
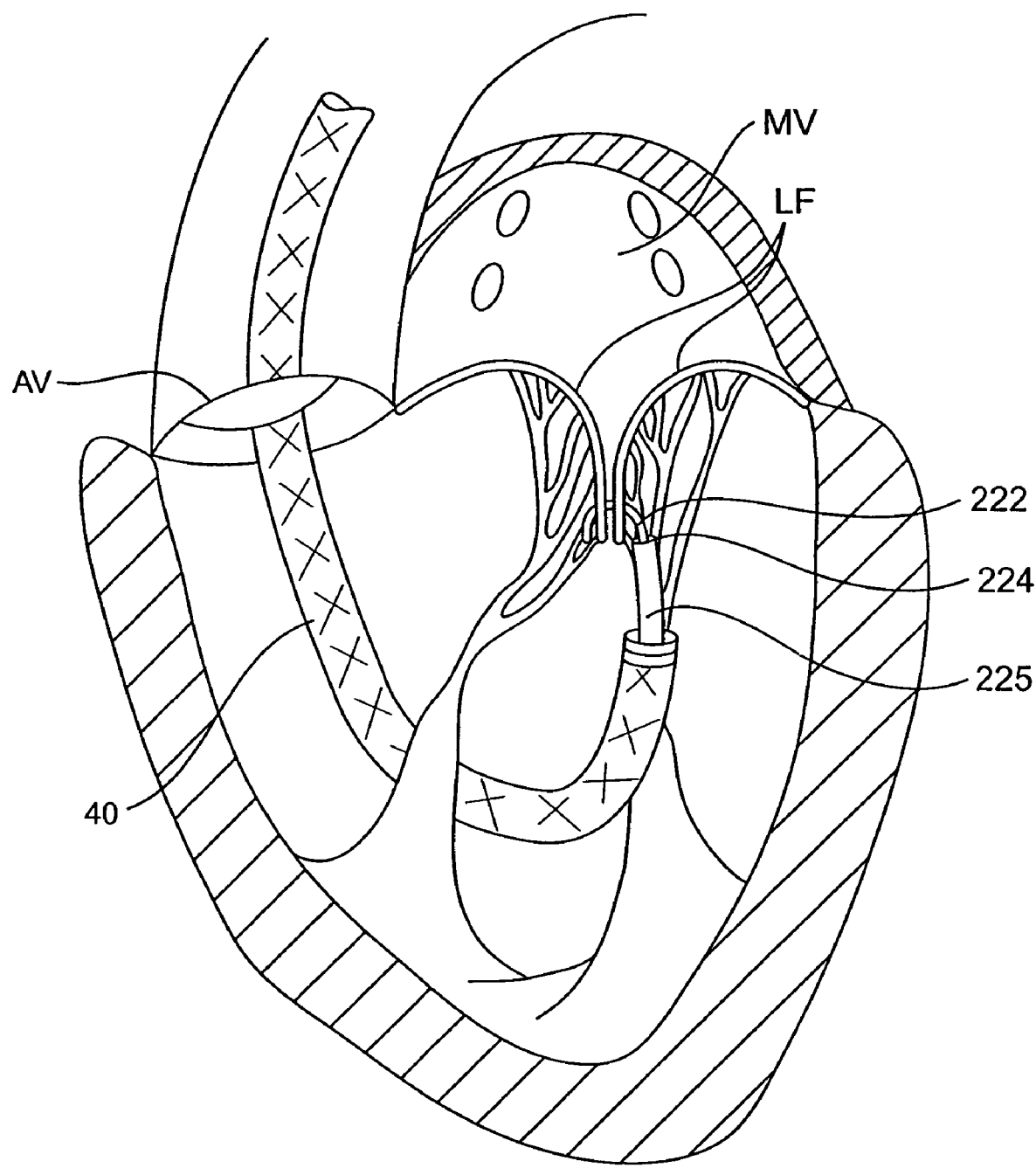
FIG. 51 illustrates use of the catheter for capturing and suturing opposed mitral valve leaflets.

Alternatively, referring to FIGS. 50 and 51, a short length of suture 220 may be positioned using a curved needle 222 which can be extended from the distal tip 224 of an interventional catheter 225. The needle 222 is formed from an elastic material, such as a shape memory alloy, and may be constrained in a generally straightened configuration within the catheter 224. When extended, as shown in FIG. 50, it assumes a curved shape so that it may be advanced through the atrioventricular or other cardiac valve leaflets LF, as shown in FIG. 51. A distal anchor 226 is secured to the distal end of the suture 220 while a slideable, locking anchor 228 is placed over a portion of the suture located proximally to the distal anchor 226 as shown in FIG. 50. The catheter 225 may be advanced to the valve leaflets LF in a retrograde approach, as shown in FIG. 51, using a guide catheter 40, as generally described above. The distal end 224 of the catheter 225 is positioned adjacent to the underside of a valve leaflet, and the needle 222 then advanced outwardly from the distal tip so that it passes through both valve leaflets.

Figure 52:
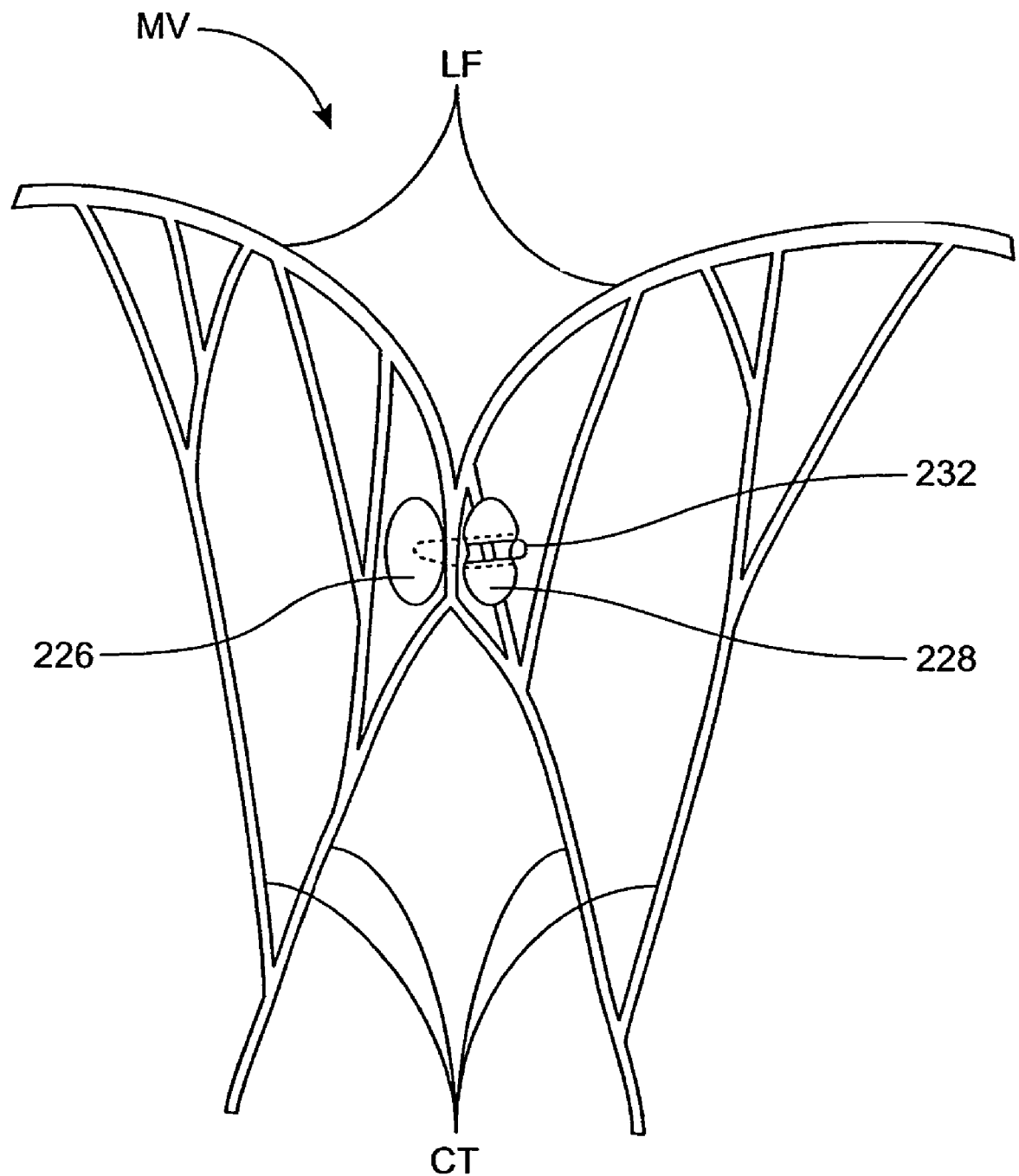
FIG. 52 illustrates the mitral valve leaflets which have been secured as shown in FIG. 51.

In order to assure that the valve leaflets are in a proper orientation prior to needle advancement, the valve leaflets may be coapted and observed using any of the techniques described previously. After the needle has been advanced through the leaflets LF, a deployment sleeve 230 is advanced to release the slideable anchoring catheter 228 from the needle and advance it toward an underside of the valve leaflet LF. As the anchor 228 approaches the valve leaflet, tension on the suture 220 will pull the distal anchor 226 from the needle. The deployment sleeve 230 can be advanced sufficiently to draw the two anchors 226 and 228 together on opposite sides of the valve leaflets, as seen in FIG. 52. The suture can then be tied off or, alternatively, locked in place using a mechanical lock 232. If the suture is comprised of a malleable wire, as previously described, the wire may be twisted together. In either case, the suture is then severed and the catheter 225 withdrawn.

Figure 53:
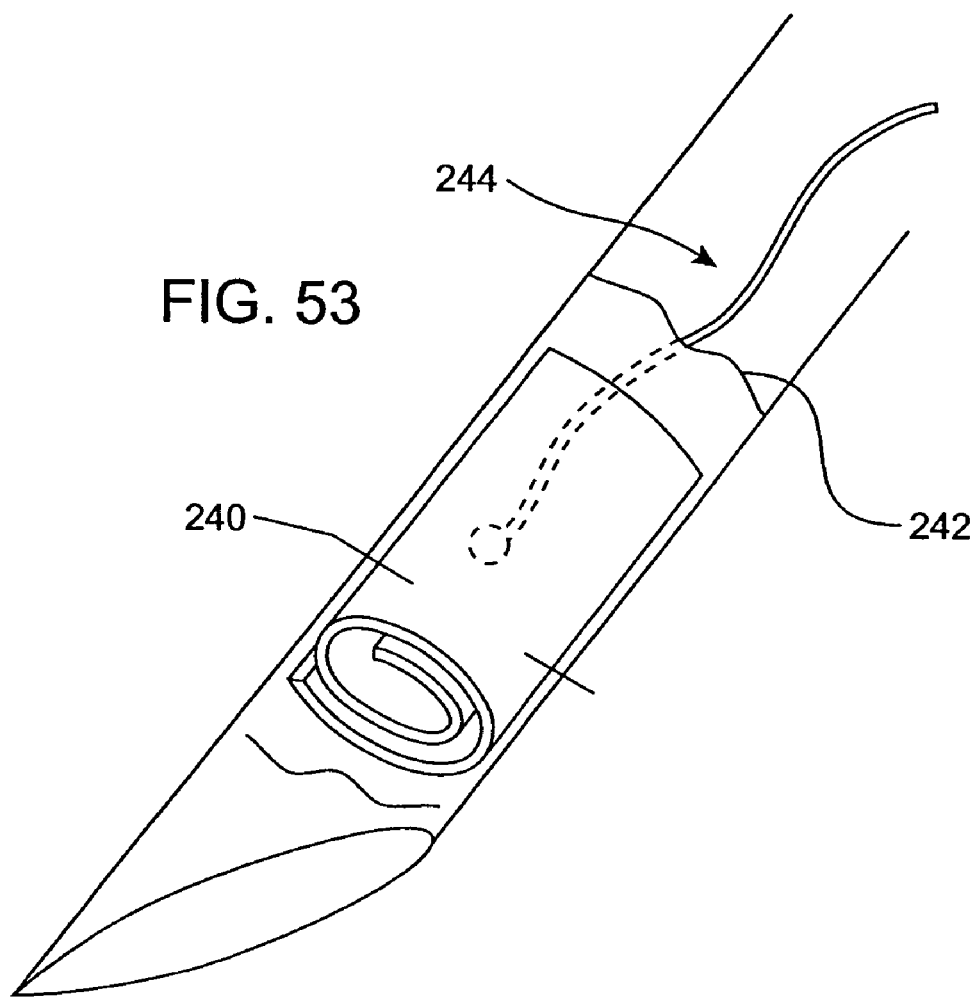
FIGS. 53 and 54 illustrate an alternative anchor which can be used with the suturing devices of the present invention.
Figure 54:
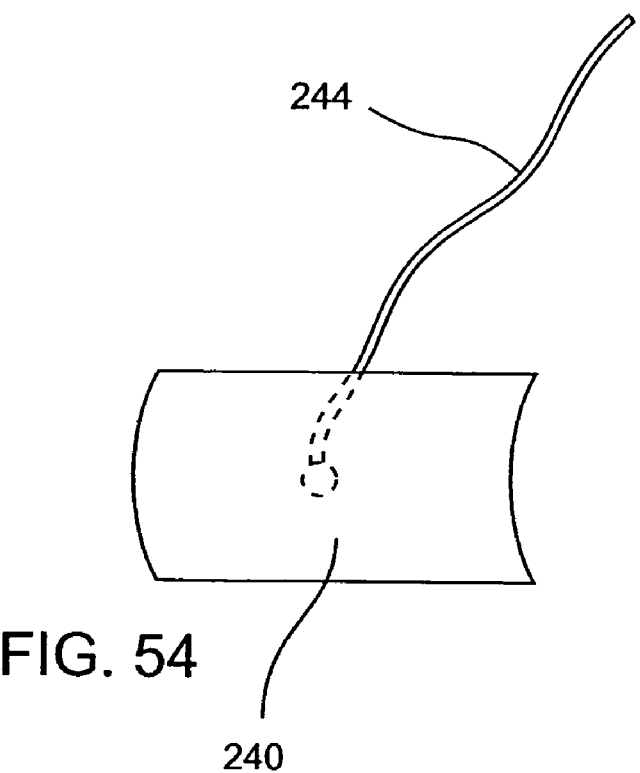

The anchors 226 and 228 shown in FIG. 50 are generally oval shaped and have a length dimension which is greater than the width of the needle used to introduce them. Thus, when pulled laterally, they can seal against the opposed surfaces of the two valve leaflets. In some instances, however, it will be desirable to have anchors which are capable of expanding to a much larger dimension to assure that they do not pull through the relatively fragile tissue of the leaflets. An exemplary expansible anchor 240 is shown in its collapsed configuration within a needle 242 in FIG. 53 and its expanded configuration in FIG. 54. The anchor 240 is connected to a length of suture 244 and could be used with a similar slideable, expansible anchor (not shown) analogous to the non-expansible anchor 228 of FIG. 50.

Figure 55A:
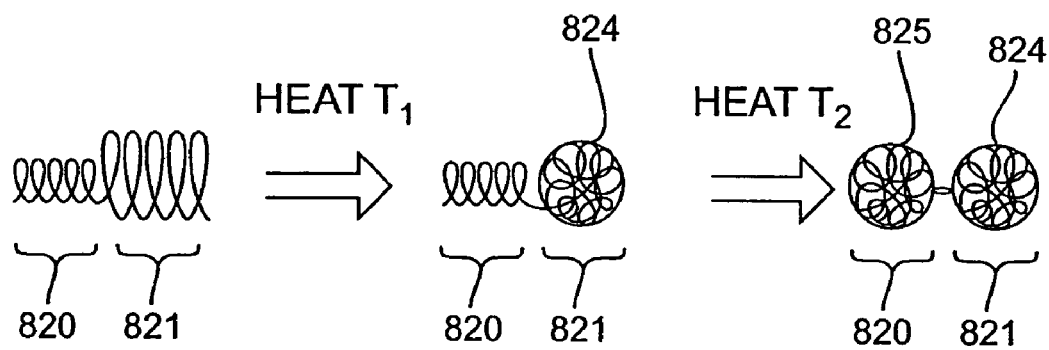
FIGS. 55A-55B illustrate the use of an expansible anchor in fixation.
Figure 55B:
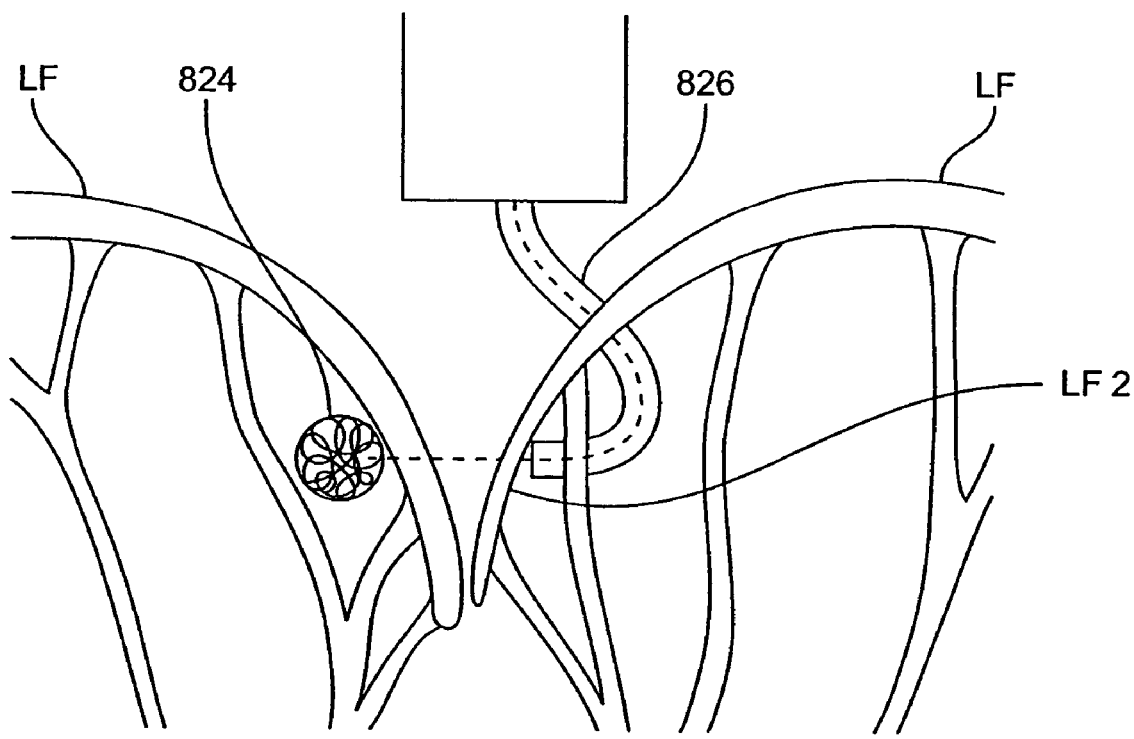

Additional expansible anchors may be seen in FIGS. 55A and 55B. In this embodiment, the anchor is comprised of an expanding randomly oriented wire coil. The coil is made from a shape memory nitinol wire that is annealed (heat set) in a straight configuration and then coiled. As shown in FIG. 55A, different sections 820, 821 of the coil may be processed to have different properties by varying the diameter and tension in the coil along its length. When the coil is heated to a specified level (T1, such as with RF energy, a designated portion 821 of the coil will become a randomly oriented mass of wire 824 with self-locking struts to prevent disentanglement. When the coil is heated to a different specified level (T2), a different designated portion of the coil 825 will become randomly oriented. As each portion of the coil 824, 825 expands and changes shape, a full entanglement of the coils is allowed to occur, effectively compressing and fixing the two halves 824, 825 of each coil together. The coil may be introduced through the valve leaflets LF with the use of a shape memory, super elastic or heat/current activated needle introducer 826. Once the valve leaflets LF are pierced, an anchor 824 may be activated and deployed distally. The introducer 826 may then be retracted to the proximal side of the second leaflet LF2 and the second anchor (not shown) may be deployed in the same manner. The amount of tension between the anchors 824, 825 may be affected with the shape memory or super elastic properties of the expanding anchor. It may be appreciated that the heat activated expanding coil may alternatively take other forms, such as a wire mesh, for example. Additional expansible anchors may be in the form of inflatable chambers filled with a liquid that may optionally partially or fully solidify.

Figure 56:
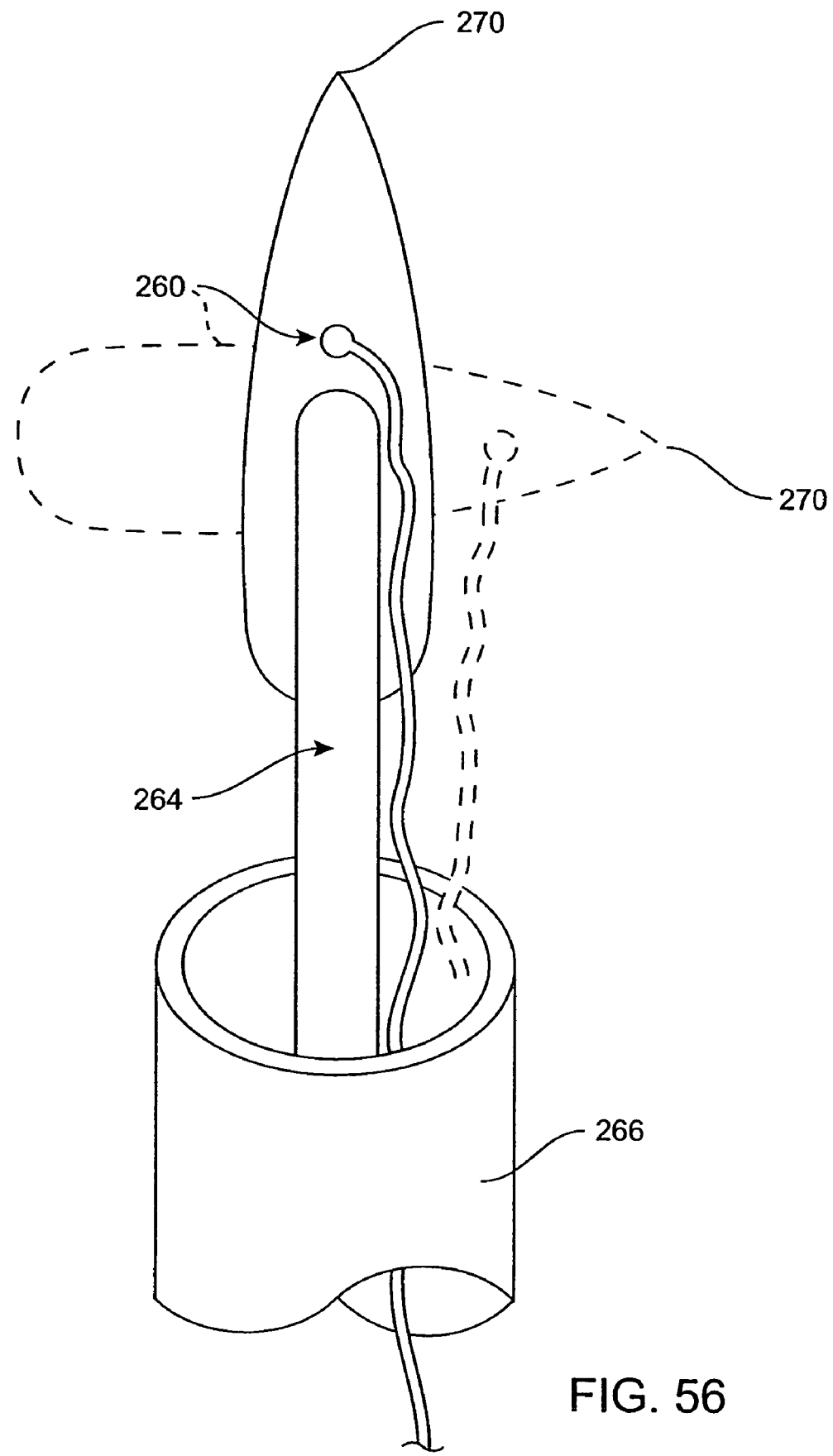
FIGS. 56 and 57 illustrate yet another suturing device according to the present invention.
Figure 57:
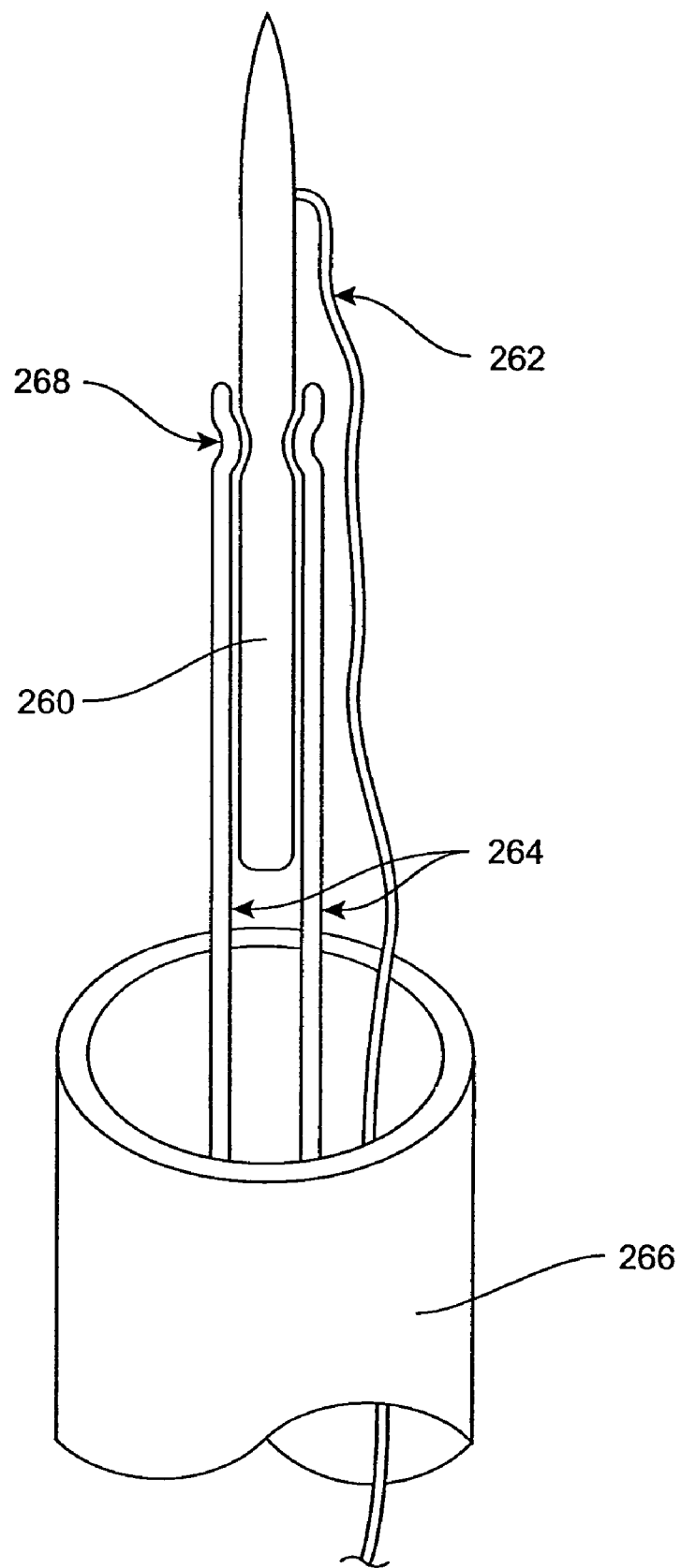

Yet another form of detachable anchor attached to a length of suture is illustrated in FIGS. 56 and 57. FIG. 56 is a front view, while FIG. 57 is a side view of the same structure. A self-penetrating anchor 260 attached to a length of suture 262 is carried on a pair of rods 264. The rods are mounted within an open lumen of a deployment catheter 266. The anchor 260 can pivot on a detent structure 268 formed between the distal ends of the deployment rods 264. The anchor has a sharpened distal tip 270 which permits the anchor to be directly penetrated through the valve leaflet tissue when the rods are extended from the catheter 266.

Figure 58:
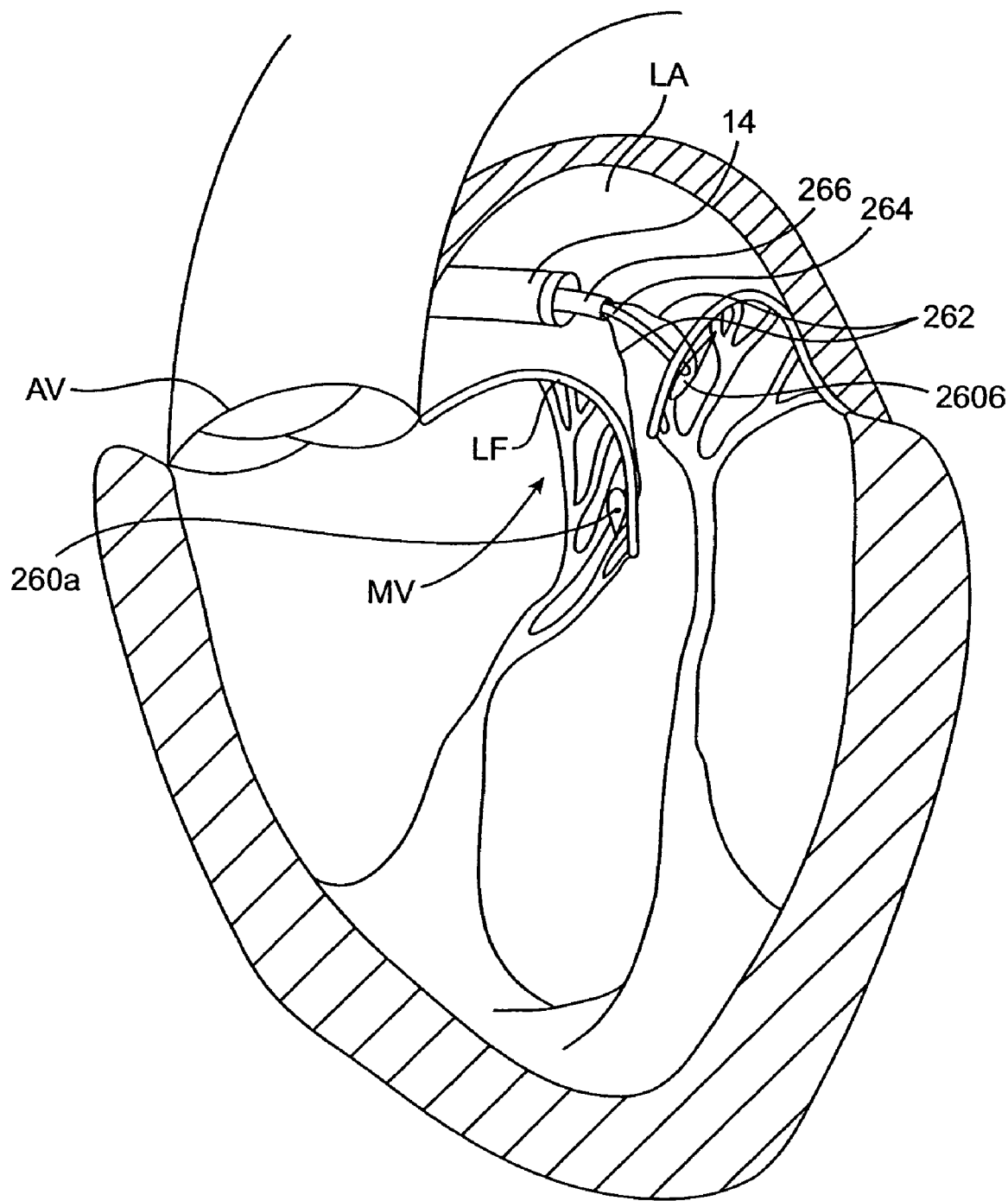
FIG. 58 illustrates use of the suturing device of FIGS. 56 and 57 to place sutures between valve leaflets of the mitral valve.

Referring now to FIG. 57, the catheter 266 may be deployed over the leaflets LF of the mitral valve MV in an antegrade direction through a guide catheter 14 as generally described above. The catheter 266 can be used to deliver a pair of the anchors 260 sequentially. As shown in FIG. 58, a first anchor 260a has been deployed through a first leaflet and a second anchor 260b has just been placed through the second leaflet. The anchors 260a and 260b are deployed by pushing them through the leaflet tissue while the sharpened tip 270 remains generally in a distal or forward direction. After passing through the tissue, the anchor 260a/260b can be turned, either by pulling back on the deployment rods 264 or by pulling backwardly on the suture 262. The two ends of suture 262 can then either be tied or fastened using a mechanical fastener in order to draw the opposed leaflets into proper apposition.

Figure 59:
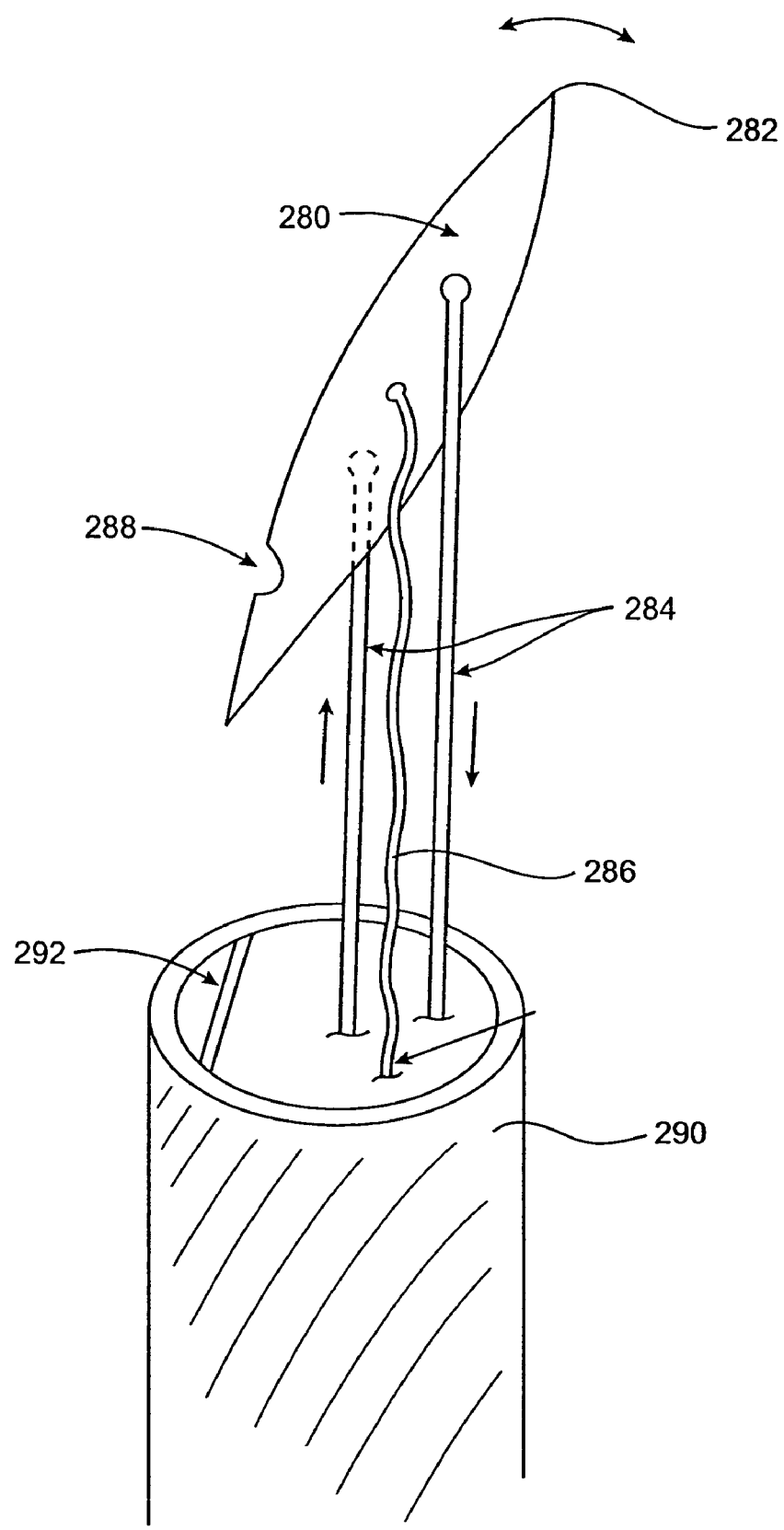
FIG. 59 illustrates yet another embodiment of a suturing device according to the present invention.
Figure 60:
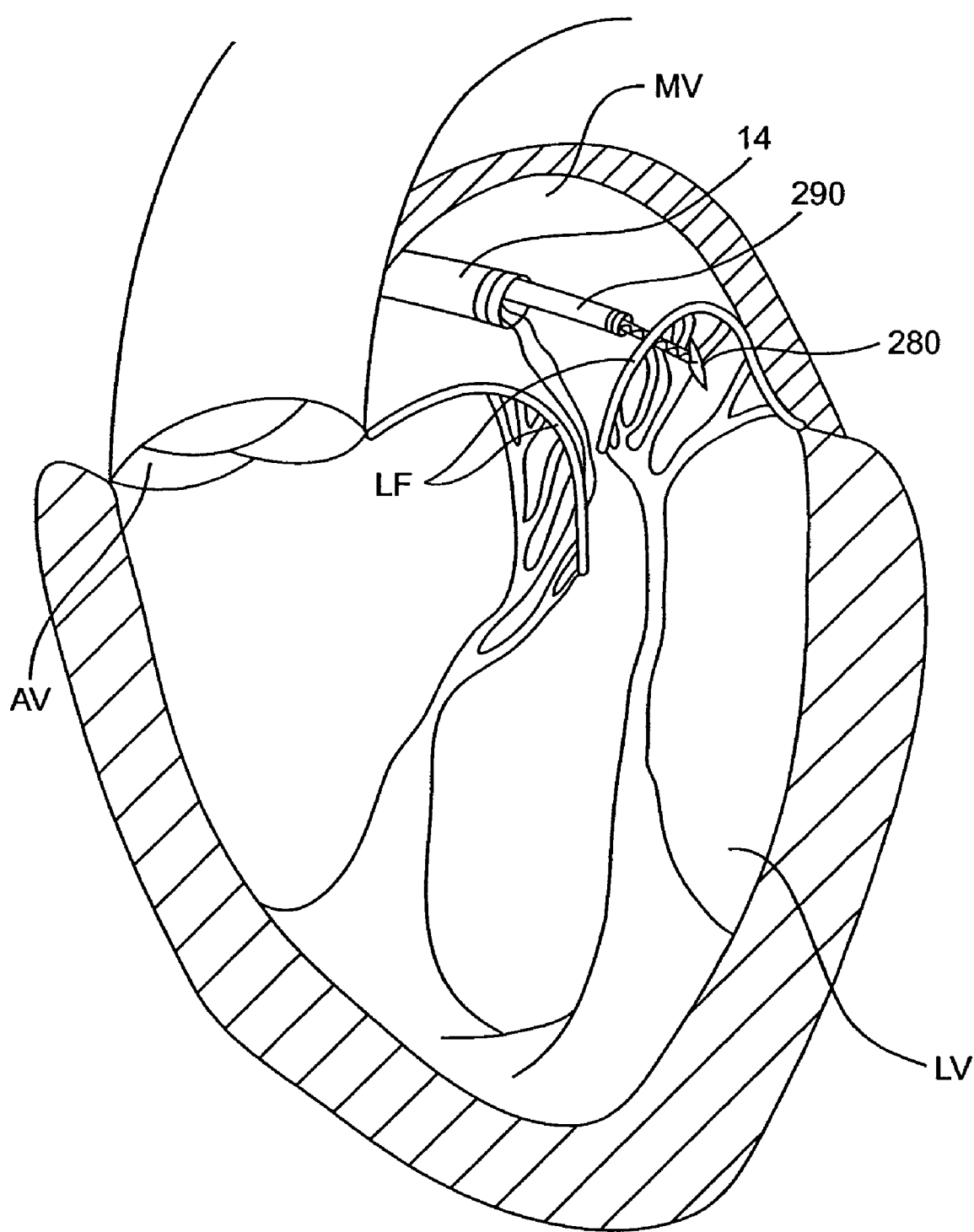
FIG. 60 illustrates use of the device of FIG. 59 and suturing opposed mitral valve leaflets.

Referring now to FIGS. 59 and 60, a deployment catheter 290 having a needle 280 with sharpened distal tip 282 can be used to place suture loops in individual valve leaflets. A needle 280 is carried on a pair of actuator rods 284 with a length of suture 286 attached to the needle. The needle 280 is first passed through the leaflet in a generally axial orientation with respect to the catheter 290. After passing through the leaflet from a guide catheter 14, as shown in FIG. 60, the needle is canted at an angle from 20° to 30° and passed back through the leaflet at a different position. A locking groove 288 on the needle is captured on a bar 292 in the distal end of the catheter 290. The needle 280 may thus be detached from the rods 284 to pull suture 286 in a loop back through the leaflet. This way, loops of suture may be placed successively through both leaflets LF of a mitral valve MV, as shown in FIG. 60. The suture loops may then be tied off, connected with fasteners, fused together using RF, microwave or ultrasound energy, or otherwise secured to close the valves together in a desired apposition.

In addition to sutures and suture-based devices, as just described, opposed points on the valve leaflets and/or chordae can be attached with a variety of staples and tissue-penetrating fasteners. The staples and other fasteners can be delivered through guide catheters, generally as described above, and may be positioned during or after valve grasping, coaptation and adjustment, also as described above.

Figure 61A:
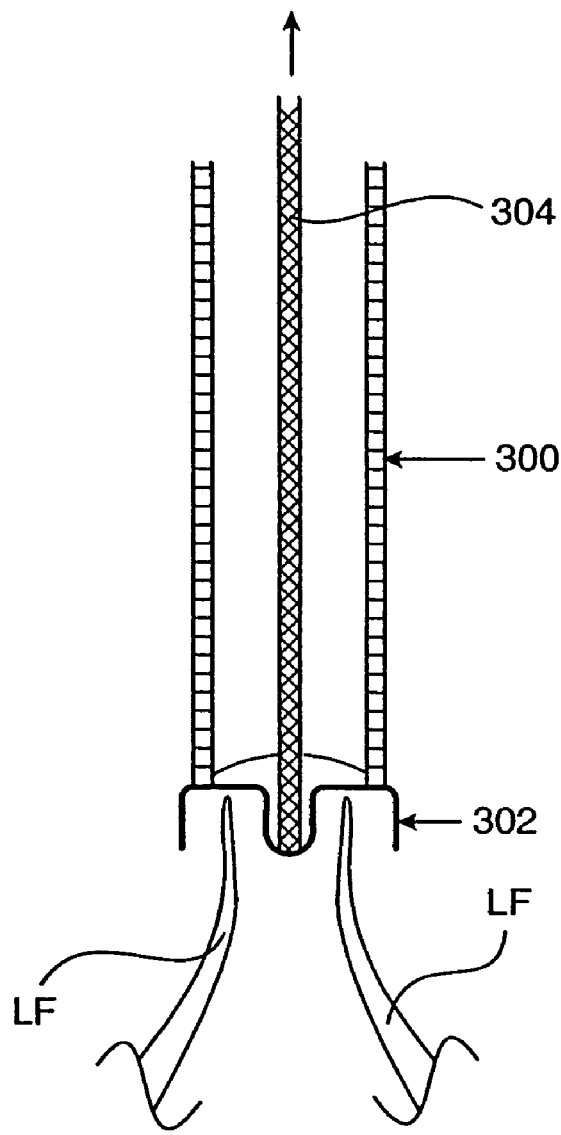
FIGS. 61A and 61B illustrate a stapling device which can be used to staple opposed leaflets of an atrioventricular valve according to the methods of the present invention.
Figure 61B:
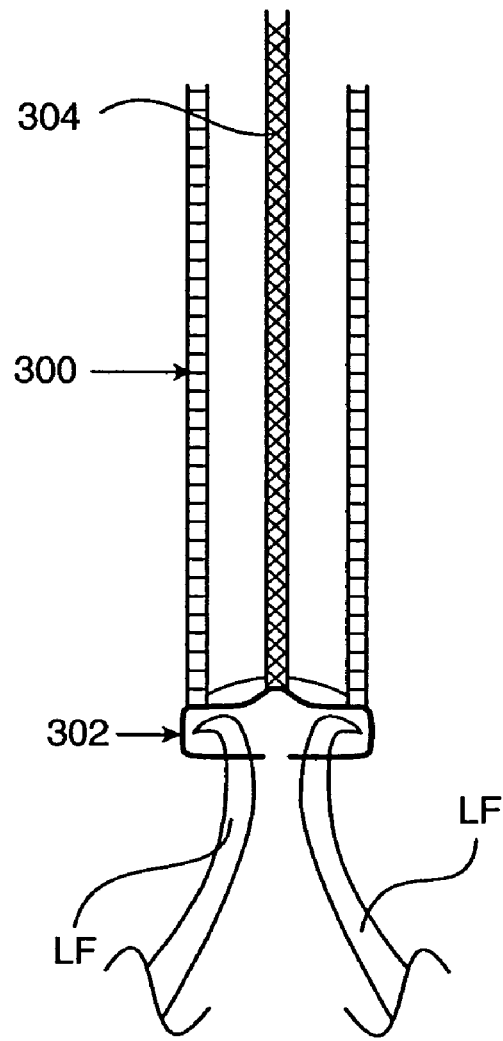

Referring now to FIGS. 61A and 61B, staple applying catheter 300 is schematically illustrated. Typically, the leaflets LF of a mitral or other atrioventricular valve will first be accessed by any of the techniques described above. The catheter 300 will then be introduced in a retrograde fashion, for example, as illustrated previously. A staple 302 is held in an open position at the distal tip of the catheter 300 and has a generally W-shaped profile with two recesses for receiving each of the leaflets LF, as shown in FIG. 61A. After proper positioning is confirmed visually, the staple 302 may be closed over the leaflets so that the tips penetrate opposed points on each leaflet by pulling on an actuator cord 304, as shown in FIG. 61B. The actuator cord can then be detached and the catheter 300 withdrawn, leaving the staple 302 in place to hold the leaflets together. Optionally, additional clips can be placed in a like manner to further strengthen the affixation of the leaflets. As described, the clip is a malleable clip which undergoes plastic deformation for emplacement. Alternatively, the clip could be formed of an elastic material, such as a shape memory alloy, and held in its open position as shown in FIG. 61A. The clip could then be placed by releasing it to return to its memory (closed) configuration, as shown in FIG. 61B. Other actuation mechanisms could also be used, such as the use of heat to induce a shape change in a heat memory alloy staple.

Figure 62A:
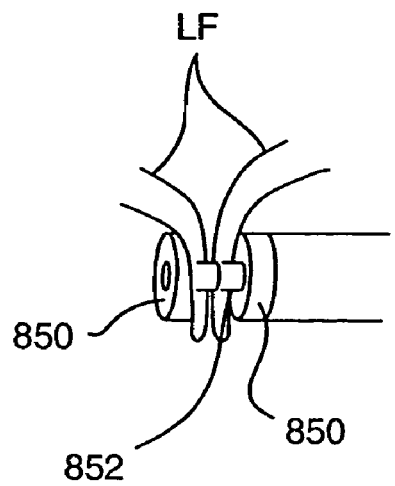
FIGS. 62A-D are schematic illustrations of fixation devices.
Figure 62B:
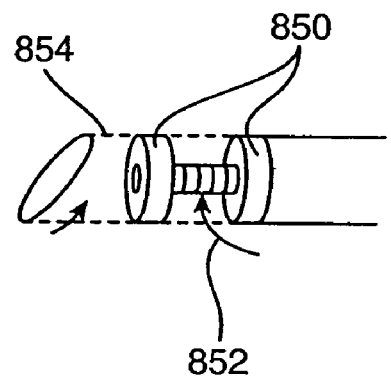
Figure 62C:
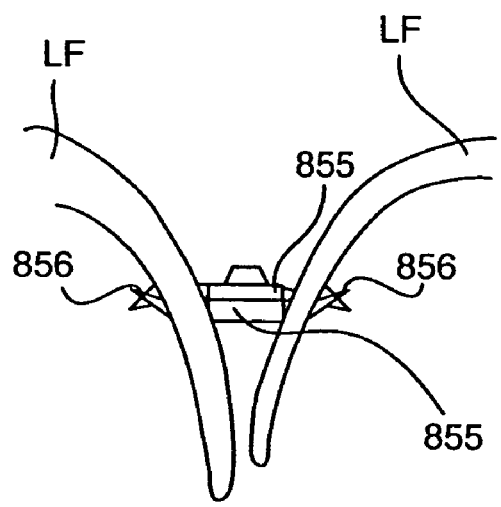
Figure 62D:
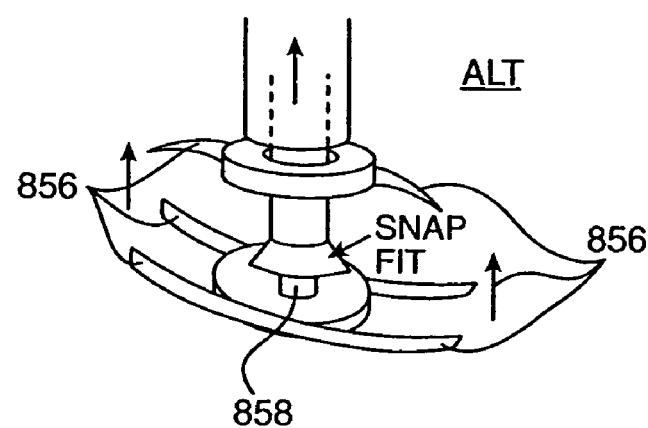

In addition, two part snaps, rivets and staples may be used to hold leaflets in place by locking together. This may be achieved by a number of device designs. Preferred embodiments involve two disks 850, pledgets, or the like, placed on opposite sides of tissues or leaflets LF to be bound together, as shown in FIG. 62A. Typically a shaft 852, pin or needle may pierce the leaflets LF and connect the two disks 850. The disks 850 may then be snapped or joined together by interlocking one or both disks 850 to the shaft 852 and/or portions of the shaft 852 to each other. Such a fixation device may be introduced through a lumen of a specialized catheter 854, introducer or component of an interventional tool, as shown in FIG. 62B. The disks 850 may be solid and/or rigid requiring placement on each side of the tissue, or the disks 850 may be flexible, collapsible and/or inflatable such that they may be inserted through the tissue for placement on the other side of the tissue. Preferred embodiments also involve two disks 855, pledgets, or the like, which are placed between tissues or leaflets LF to be bound together, as shown in FIG. 62C. Here, the disks 855 have penetrating prongs 856 at each end to pierce and grasp tissue. When the disks 855 are snapped or joined together by interlocking one or both disks 855 to a shaft 858, shown in FIG. 62D, and/or portions of the shaft 858 to each other, the leaflets LF may be bound together.

Figure 63:
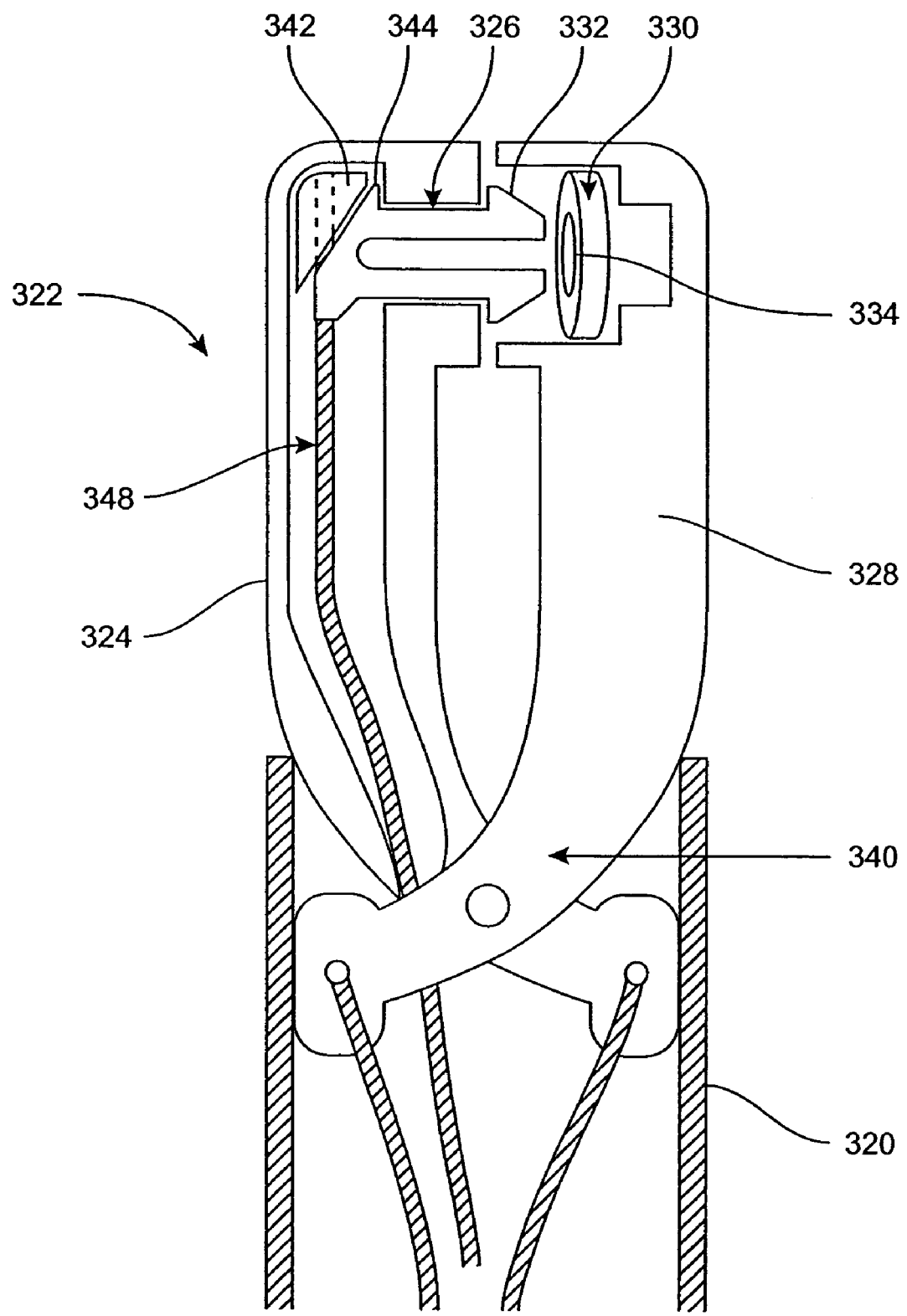
FIG. 63 illustrates an alternative two part fixation stapling device.
Figure 64:
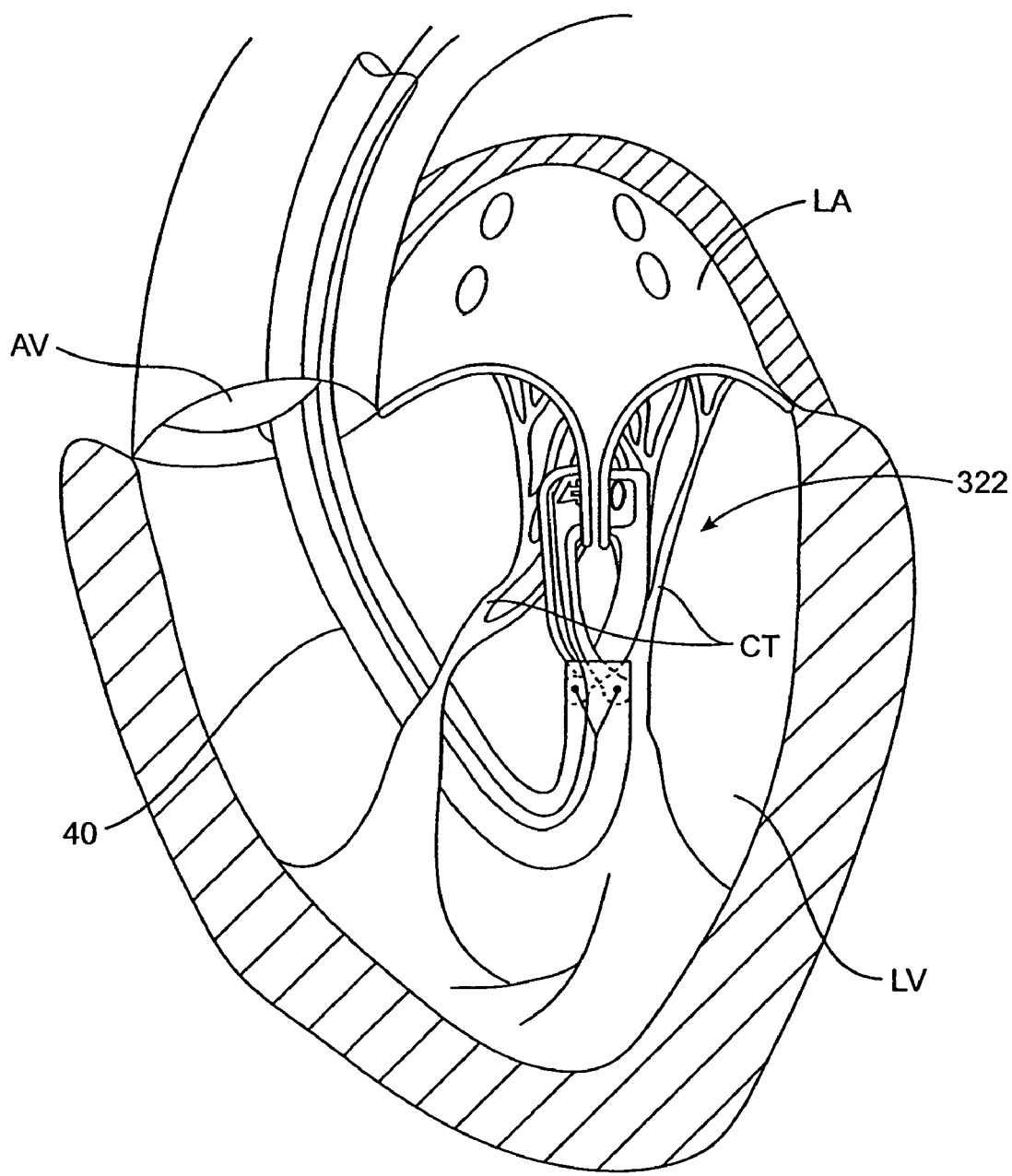
FIG. 64 illustrates use of the stapling device of FIG. 63 for stapling opposed valve leaflets of a mitral valve.

An additional embodiment of a two part rivet-like stapling mechanism is illustrated in FIG. 63. A stapling mechanism 322 at the distal end of a catheter 320 comprises a first jaw 324 which carries a fastener 326 and a second jaw 328 which carries a retaining ring 330. The fastener has a collapsible cone 332 at its distal end so that it may be forced into an aperture 334 in the retaining ring 330. The jaws 324 and 328 are pivotally mounted within the distal end 340 of the catheter so that they may be opened and closed to grasp the free ends of the valve leaflets therebetween. The closing of the jaws 324 and 328, however, does not lock the fastener 326 into the retaining ring 330. Thus, the valve leaflets can be temporarily grasped and the improvement in valve regurgitation visually assessed. If the improvement is sufficient, the fastener 332 can be driven into the tissue and locked in the retaining ring 330. If the improvement is not sufficient, the jaws can be repositioned on the valve leaflets one or more additional times until an adequate or optimized repositioning of the leaflets is obtained. The fastener 332 can be driven into the retaining ring in a variety of ways. In the illustrated embodiment, a cam device 342 is slidably mounted behind an inclined surface 344 on the rear of the fastener 326. By drawing the cam actuator 342 downwardly using draw cord 348, the rivet can be driven through the valve leaflets and into the retaining ring 330, as illustrated in FIG. 64.

Figure 65A:
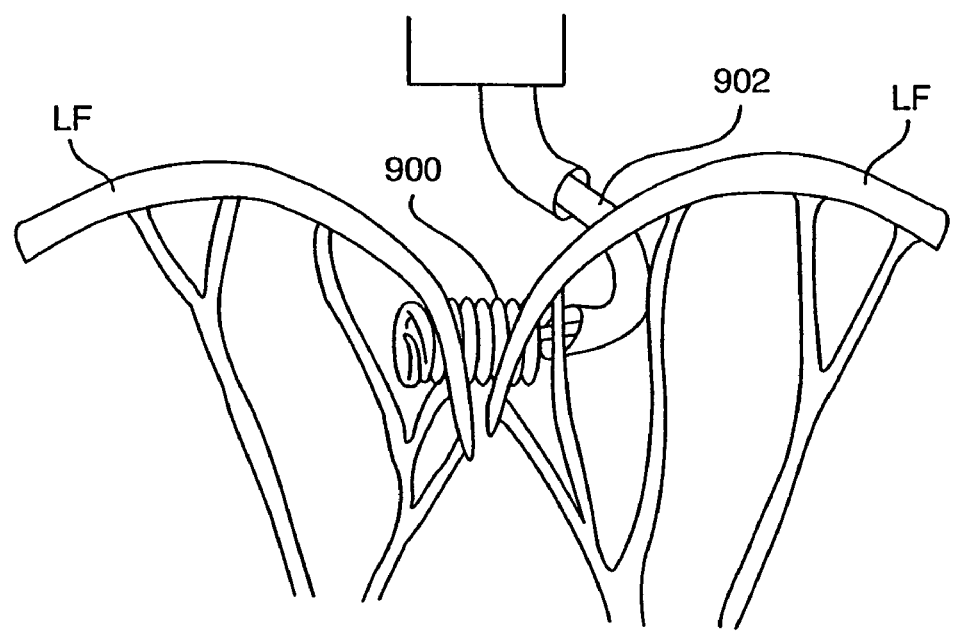
FIG. 65A-65C are schematic illustrations of coiled fixation devices.
Figure 65B:
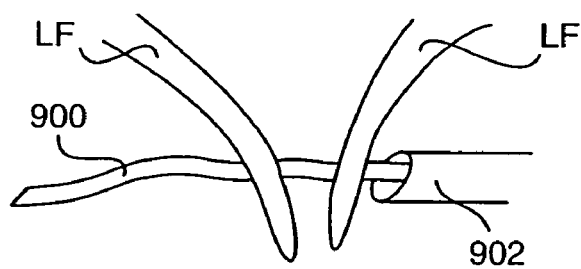
Figure 65C:
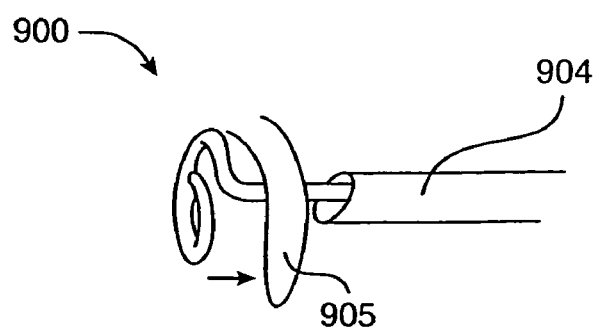

In addition to rivets, snaps, pins and the like, coils may be used in a similar manner to fix valve leaflets in a desirable arrangement, as shown in FIG. 65A. Coils 900 may be comprised of a superelastic material and pre-shaped in a coil configuration for engagement with the leaflets. The coil 900 may be advanced from an introducer sheath 902 to deploy the coil 900 in an orientation that will approximate the leaflets in compression. Alternatively, the coil 900 may be comprised of a heat or current activated shape memory material As depicted in FIG. 65B, the coil 900 may be straightened in its initial configuration for ease of piercing and advancing through the leaflets LF. When positioned, the material may be activated by heat or current to assume a shape memory coil configuration corresponding with FIG. 65A. Again, the coils may be oriented to approximate the leaflets in compression. To achieve maximum leaflet compression at the coaptation points, a super elastic or shape memory coil 900 may be delivered in a manner that places the coil in an inverted orientation across the leaflets, as illustrated in FIG. 65C. This may be accomplished with the use of a specialized delivery system 904. When released from the delivery system 904, the distal end 905 of the coil produces a compressive force as the coil attempts to achieve a non-inverted orientation.

Figure 66:
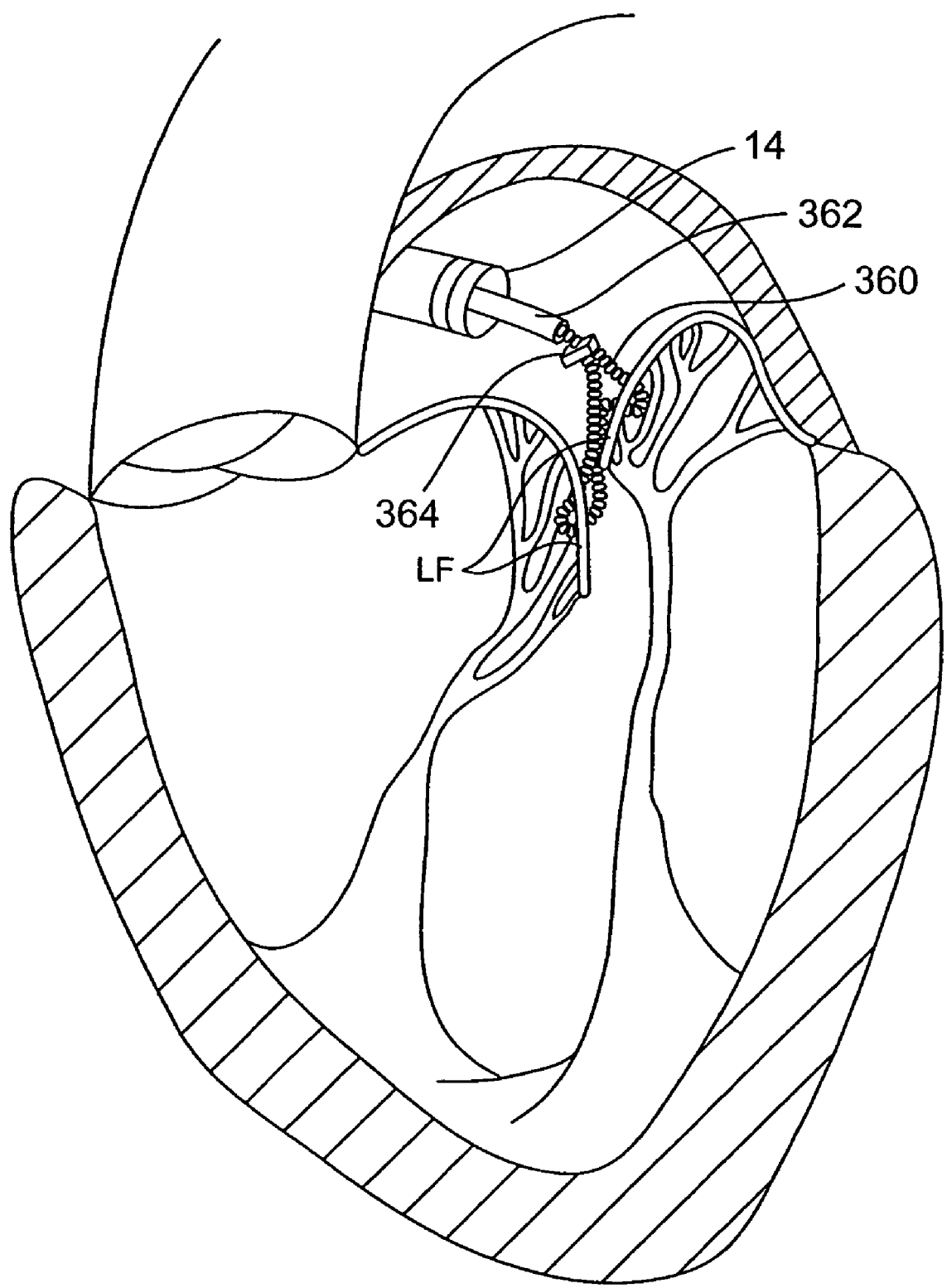
FIG. 66 illustrates use of a self-securing anchor for attaching opposed surfaces on the leaflets of the mitral valve.

As a further alternative, a cinch-type fastener 360 may be positioned in a loop through opposed valve leaflets LF, as shown in FIG. 66. The fastener 360 could be advanced from either a retrograde or antegrade direction, but the antegrade direction is illustrated for convenience. A positioning catheter 362 can be introduced through a guide catheter 14 which has been previously positioned by any of the techniques described above. After advancing the cinch-type fastener 360 through the leaflets, for example by pushing a pre-shaped fastener 360 through the leaflets so that it returns to the distal tip of the placement catheter 360, a fastening collar 364 may then be advanced to tighten the fastener loop 360 until the leaflets are positioned in a desired fashion. Alternatively, the fastener 360 may be twisted to constrict the open loop. Typically, the fastener 360 has chevrons or other one-way surface features so that the locking column may be advanced and will remain in place without loosening over time, or in the case of twisting, untwisting over time. The fastener 360 is then released and, if desired, additional fasteners positioned in a like manner. The fastening collar 364 may alternatively be used to secure the sutures shown previously in FIG. 49. The collar 364 may be crimped onto the sutures 202 or locked in place by the use of a combination of one-way surface features on the collar 364 and sutures 202.

Figure 66A:
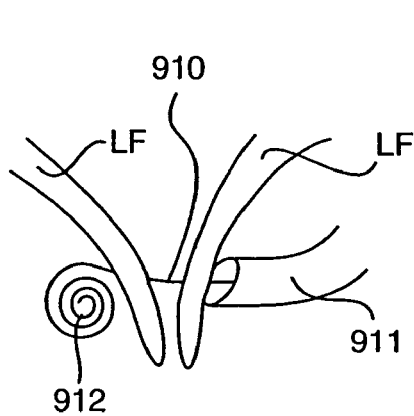
FIGS. 66A-66B are schematic illustrations of penetrating fixation devices.
Figure 66B:
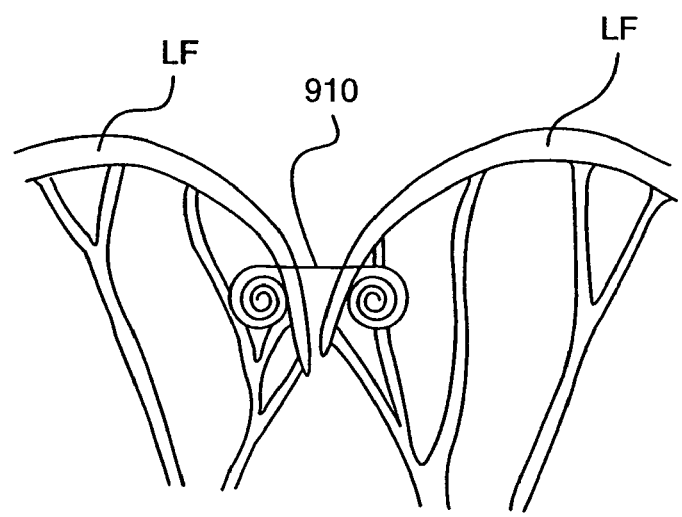

Further, a variety of penetrating and non-penetrating clips, barbs, grappling hooks, and the like, may be used to fasten valve leaflets in a desired configuration. As previously described as a means to grasp the free ends of the valve leaflets in a pinching manner, a pair of flat coils may also be used as a fixation device. As previously shown and described in relation to FIG. 46A, the coils 770 may be linked together with opposing curvature by a clip 772. When inserted as shown in FIG. 46B, the coils 770 may be permanently joined in this orientation and may remain as a permanent implant. Alternatively, the coils 910 may pierce the leaflets LF to hold them in place as shown in FIGS. 66A and 66B. During placement, the coil 910 may be inserted through a delivery catheter 911 in a straight configuration and pierce the leaflets LF in this form, allowing the free distal end 912 of the coil 910 to curl after it has penetrated the leaflets LF, as shown in FIG. 66A. The proximal end may then curl after it disengages from the delivery catheter 911 to remain as an implant as shown in FIG. 66B.

Figure 67:
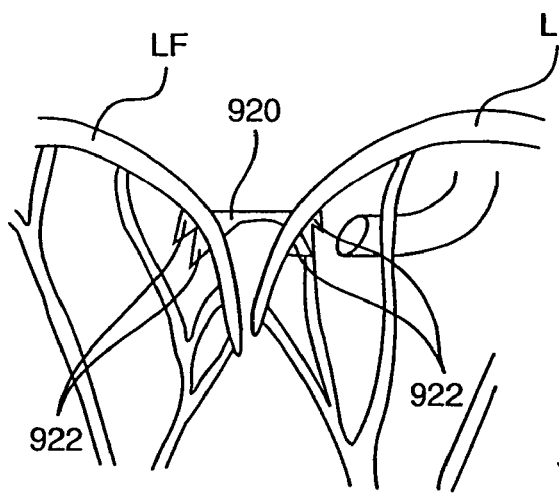
FIGS. 67 and 68 are schematic illustrations of penetrating fixation devices with barb-like distal ends.
Figure 68:
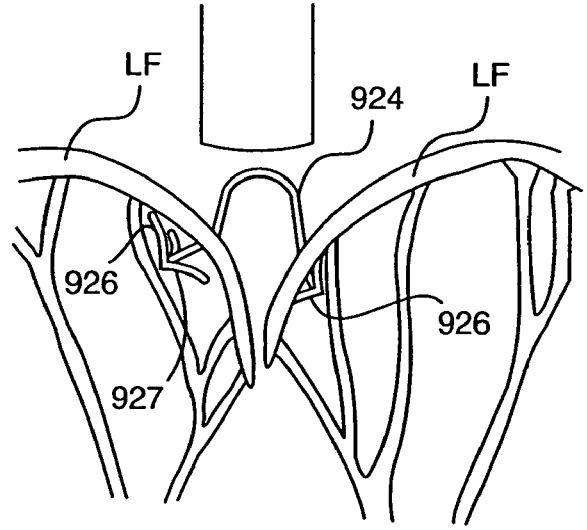

Likewise, a variety of barb-like structures may be used in a similar fashion to fasten valve leaflets in a desired configuration. Referring to FIG. 67, a shaft 920 with one or several curved barb-like distal ends 922 may be positioned so that the distal ends partially or fully penetrate each leaflet LF to be fixed. The shaft 920 may be a shape memory or super elastic wire. By activating the shaft 920 with heat or current, in the case of a shape memory material, or allowing the shaft 920 to assume its pre-configured shape, in the case of a super elastic material, several barbs 922 may be approximated to coapt the leaflets in the desired position. On the other hand, several discontinuous barbs 922 may be tensioned and coapted using a crimping or coupling and trimming system. Similarly, as shown in FIG. 68, a shaft 924 with expanding barb-like distal ends 926 may be positioned so that the distal ends 926 penetrate each leaflet LF to be fixed. Here, however, the distal ends 926 may be comprised of one or more struts 927 which expand to further prevent retraction of the shaft 924. Such expansion may be achieved by activation of the shaft 924 with heat or current or allowing the device to assume its pre-configured shape. In addition to end 926 expansion, the shaft 924 may be approximated to coapt the leaflets or several discontinuous shafts may be tensioned and coapted using a crimping or coupling and trimming system.

Figure 69A:
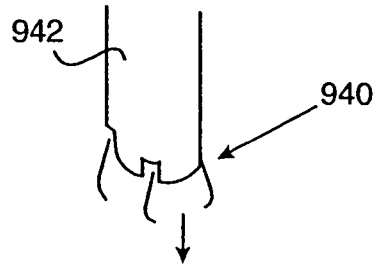
FIGS. 69A-C and 70A-B are schematic illustrations of clips used as fixation devices.
Figure 69B:
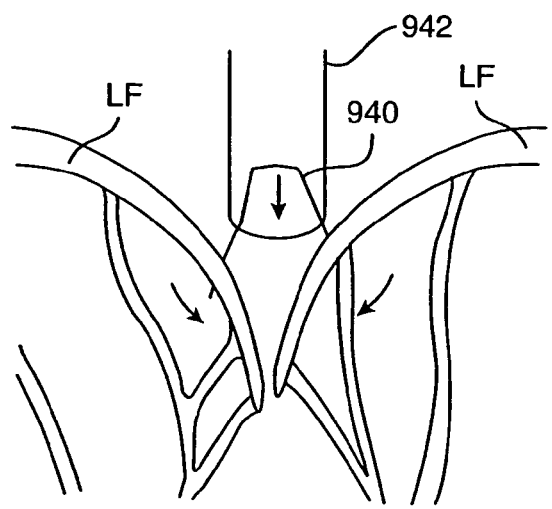
Figure 69C:
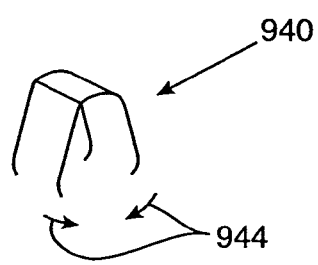
Figure 70A:
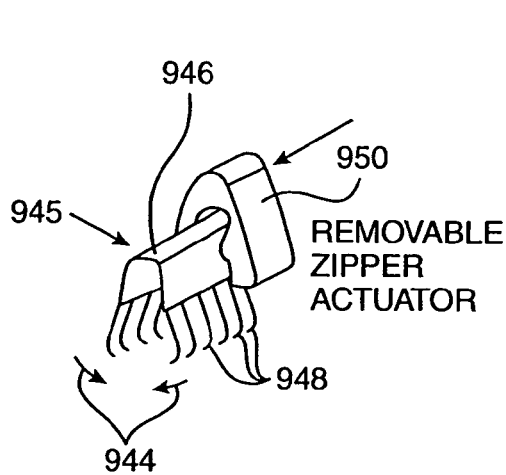
Figure 70B:
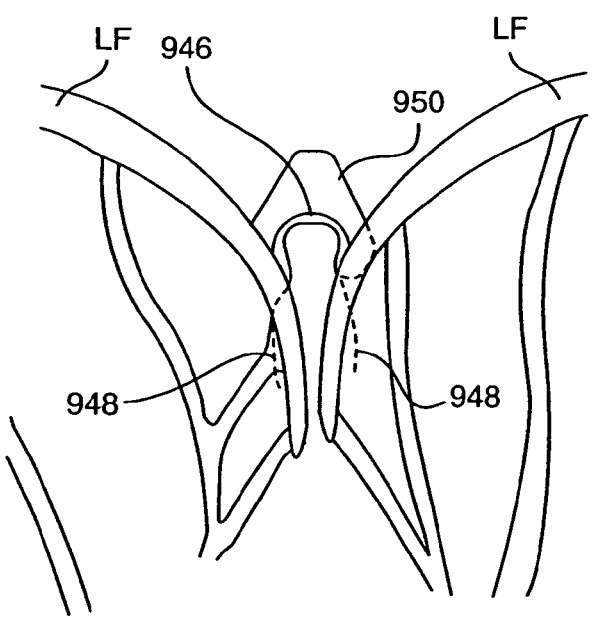

In addition to fixation, clips may be used to draw leaflets together in a suitable coaptation configuration. While temporarily holding two or more leaflets in a desired configuration, such as with grasping tools, a clip may be deployed to maintain the desired position or to further manipulate the leaflets. For example, a clip 940 may be mounted on a delivery catheter or interventional tool 942, as shown in FIG. 69A. It may then be positioned in a desired location to hold the leaflets LF, as shown in FIG. 69B. In the deployed and activated state, depicted in FIG. 69C, the clip 940 may tend to pinch inwardly, pulling the leaflets together, as indicated by arrows 944. This may be achieved by activation of super elastic or shape memory material. Alternatively, referring to FIGS. 70A and 70B, the clip 945 may pinch inwardly, indicated by arrows 944, by manual crimping of the spine 946 or interlocking of the piercing legs 948. When positioned appropriately between the valve leaflets LF, as shown in FIG. 70B, the leaflets may be drawn together by crimping the spine 946 of the clip 945 with the use of a removable actuator 950. As the actuator 950 passes over the spine 946, the spine 946 may be plastically deformed to a new configuration. Or, as the actuator 950 passes over the spine 946, the proximal ends of the piercing legs 948 may become interlocked. In either case, inward movement of the clip 945 may be controlled by passing the actuator 950 only over portions of the spine 946 in which such pinching is desired. Therefore, a single clip may provide variable inward forces.

Figure 71:
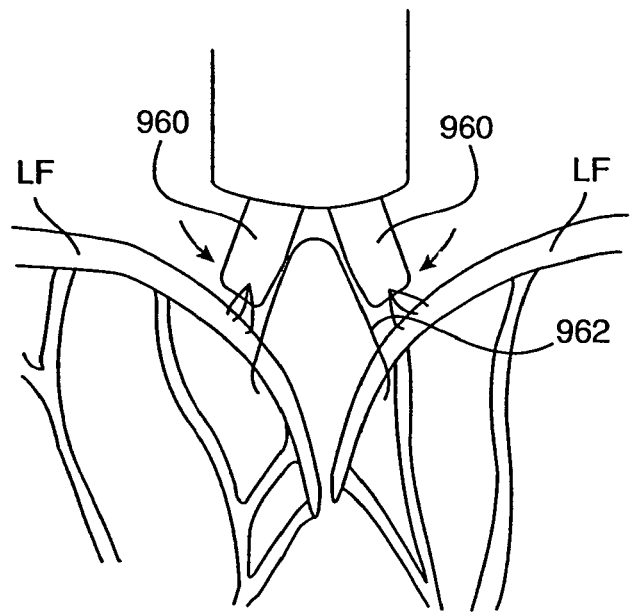
FIGS. 71, and 72A-72B are schematic illustrations of clips involving the use of graspers in the fixation mechanism.
Figure 72A:
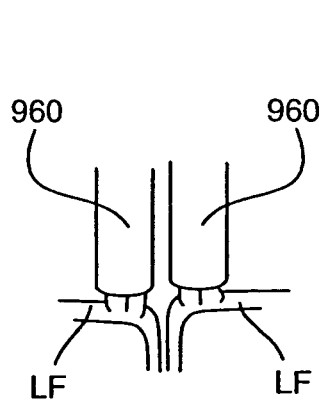
Figure 72B:
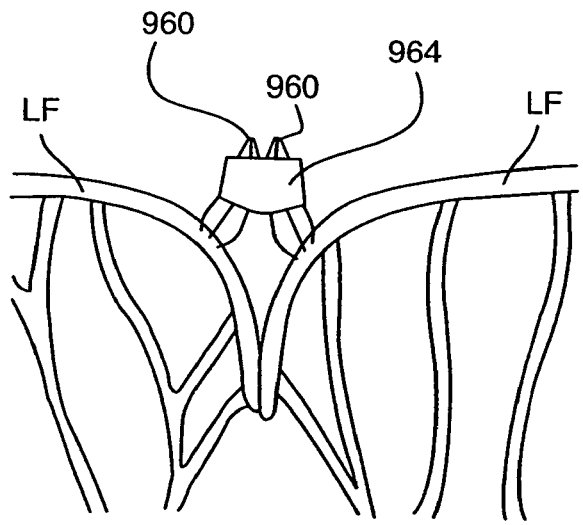

Inward forces may also be applied by components of an interventional tool, such as a by graspers. Graspers, as previously described, are devices which grasp and hold tissues (such as coapting valve leaflets) for appropriate modification, such as fixation. Thus, graspers are most likely in place while a fixation device is deployed and positioned. Referring to FIG. 71, an embodiment of graspers 960 is shown holding the leaflets LF on opposite sides of a deployed clip 962. Inward force may be applied to the clip 962 by moving or applying force to the graspers 960 in an inward direction, as depicted by arrows. In a further embodiment, the graspers may serve as a grasping device and as an implantable fixation device. Referring to FIG. 72A, an embodiment of graspers 960 is shown coapting and holding the leaflets LF together. The graspers 960 may then be joined by a coupling device 964 and detached for implantation, as shown in FIG. 72B.

Because of the fragility of the tissue in the valve leaflets, it will sometimes be preferred to utilize methods or devices which do not completely pierce or penetrate the tissue. For example, leaflets may be fused together in a desired coaptation position by applying laser, RF, microwave or ultrasonic energy at specified coaptation points. In addition or alternatively, external clips which are partially penetrating or non-penetrating may be used. A variety of deformable and elastic clips can be utilized, and clips will usually be deployed in a retrograde fashion so that an opening in the clip can be placed over the undersides of the adjacent valve leaflets.

Figure 74:
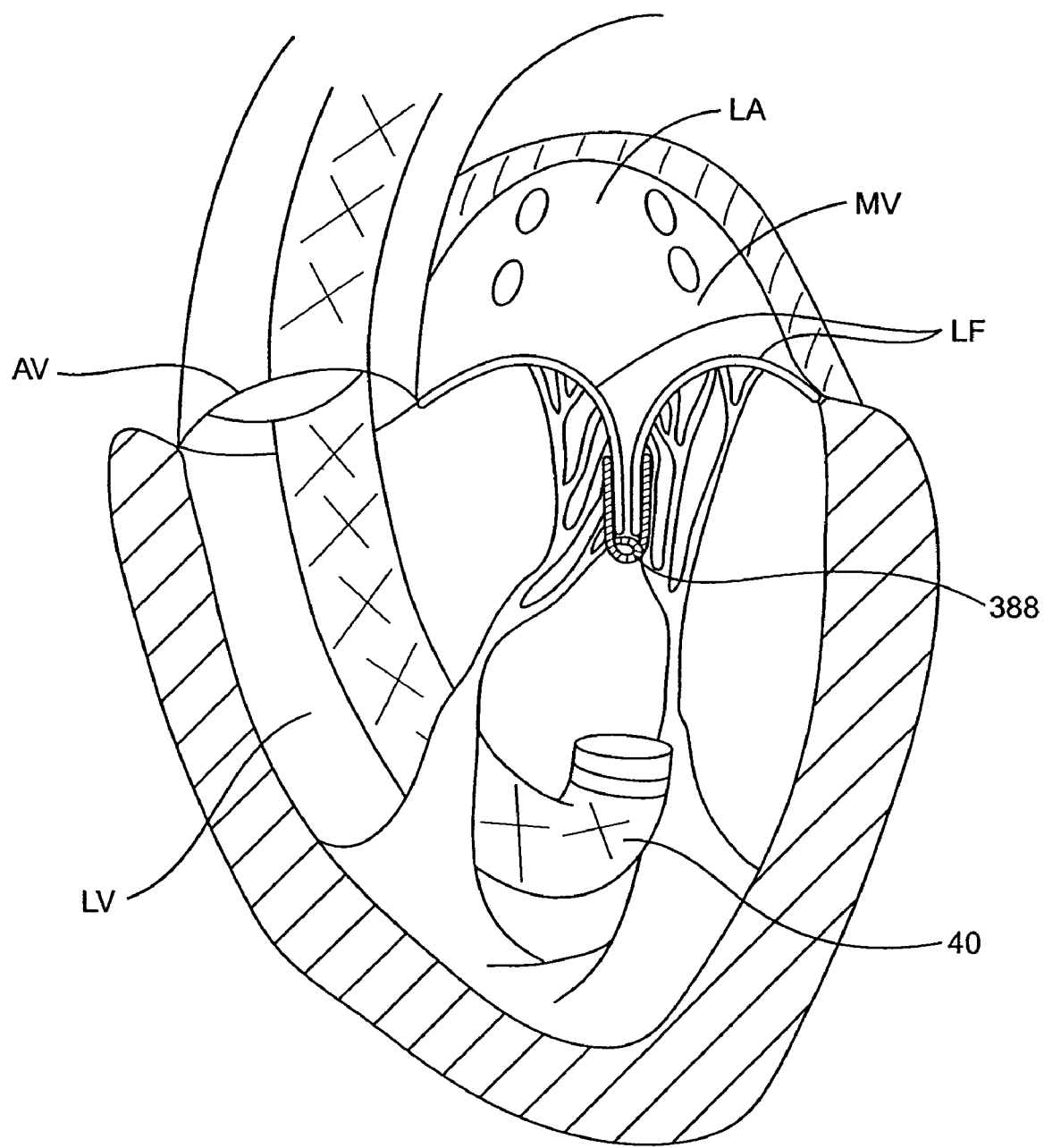
FIG. 74 illustrates a clip which has been applied by the clip-applier of FIGS. 73A-73C.

A preferred clip-applying catheter 380 is depicted in FIGS. 73A, 73B, and 73C. The catheter 380 has a three jaw clip-applying device 382 at its distal end. The three jaw structure allows the clip-applier to be used as a three jaw grasping device before final deployment of the clip. Such grasping has been described earlier with reference to FIGS. 42A, 42B, and 43 above. A center jaw 384 of the device has a tubular structure and allows the catheter to be introduced over a guidewire 386, where the guidewire may be placed through the atrioventricular valve prior to catheter positioning. A clip 388 has a V-shaped structure and is normally closed so that a force is required to open the distal ends of the clip. Jaws 390 and 392 hold the clip and can open the clip by selectively opening either jaw, with jaw 392 shown open, in broken line in FIG. 73A. Thus, jaw 392 may be opened first to capture a free end of a first valve leaflet. With the catheter 380 thus attached to just the first valve leaflet, the catheter can be repositioned so that the other jaw 390 can be opened and used to capture the second valve leaflet. After the valve leaflets are captured and held in a proper orientation, valve improvement can be confirmed by visual observation. If improvement is sufficient, the clip can be detached from the catheter and left in place, as shown in FIG. 74.

B. Shortening of the Chordae

Figure 75:
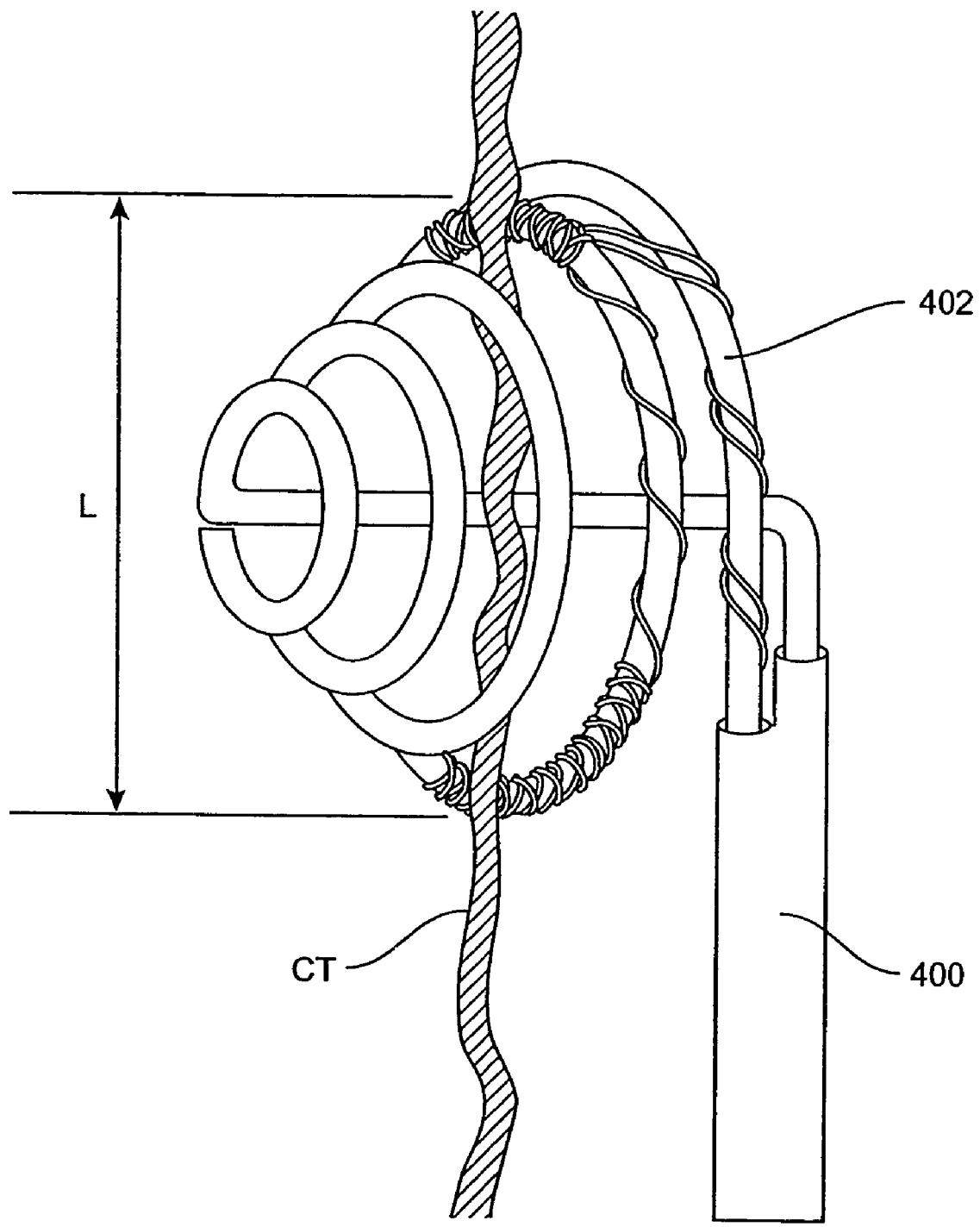
FIG. 75 illustrates a device for applying radiofrequency energy to shorten valve chordae.

In addition to suturing, fastening, and otherwise physically attaching portions of the valve leaflets and/or chordae together, valve leaflet closure can be improved by shrinking portions of either or both of the chordae attached to the two valve leaflets. An exemplary catheter 400 having an energy-applying coil 402 at its distal end is shown in FIG. 75. Such energy may be in the form of radiofrequency (RF), microwave, ultrasound, laser, heat or current. The catheter 400 may be deployed in either an antegrade or retrograde direction, with retrograde generally being preferred to facilitate access to the chordae. One or more chordae CT are captured within the coil and RF energy, for example, applied from a conventional power supply. Application of the RF energy to the chordae, which are composed of collagen and other normal tissue constituents, over a length L will cause shrinkage of the tissue to a length which is shorter than the original length L. Similarly, such application of energy to the chordae may also be achieved with the use of an energy applying chordal snare or similar device. By applying such shortening of the chordae, valve conditions, such as prolapsed valves can be effectively treated.

Figure 76:
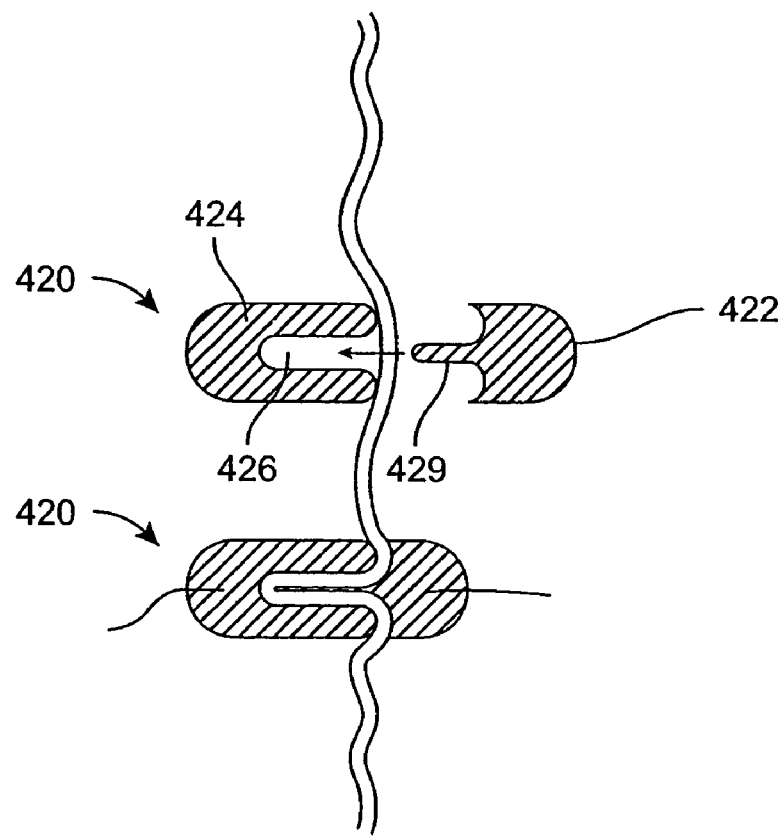
FIGS. 76, and 77A-77B illustrates devices used to plicate and shorten valve chordae.
Figures 77A, 77B:
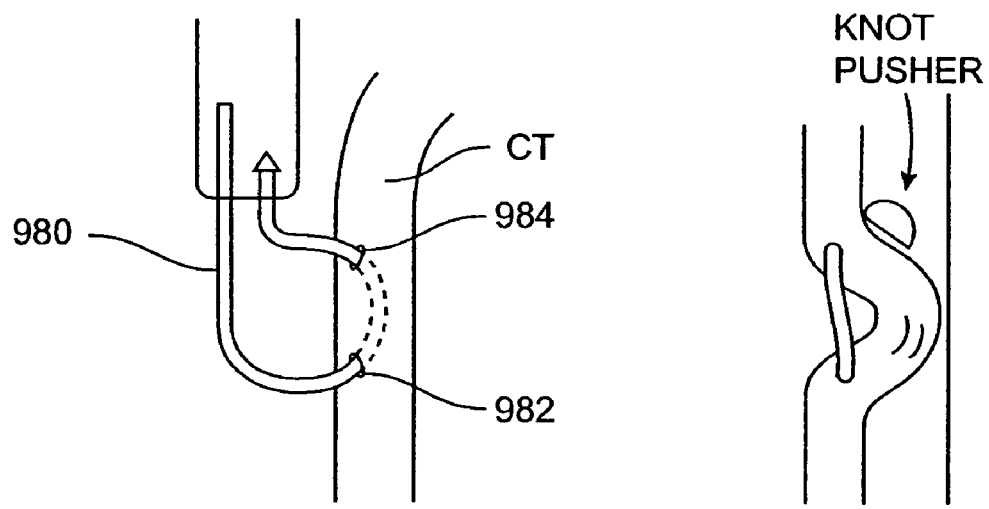

In addition to the use of energy for shortening chordae, the chordae can be plicated sing mechanical plication devices 420, as illustrated in FIG. 76. Each of the devices 420 comprise a cap piece 422 and a receptacle 424. A receptacle has a channel 426 which receives a pin 428 on the cap piece 422. There is sufficient clearance between the pin 428 and channel 426 so that a portion of the chordae CT can be captured and folded therein by placing the cap into the receptacle. Each plication device 420 will thus shorten a portion of the chordae by a predetermined amount. Multiple devices can be used to achieve a desired overall shortening of the chordae. The devices can be placed using jaw-type devices and shortening can be visually observed by any of the techniques described above. Alternatively, chordae may be mechanically plicated with the use of suture loops. Referring to FIG. 77A, a suture 980 may penetrate the chordae CT at a first location 982 and then penetrate the chordae CT again at a second location 984 forming a loop. By pulling closed the loop, as shown in FIG. 77B, the effective length of the chordae CT is reduced. The suture loop may then be fixed and trimmed for implantation. This may be repeated along a chordae to form multiple individual or continuous loops, and/or it may be repeated along more than one chordae. Similarly, such plication may also be achieved with the use of a shape memory or super elastic wire coil which may penetrate a chordae at one or more points and draw the tissue together upon activation.

C. Annuloplasty

The intravascular approaches of the present invention, particularly the antegrade approaches, can also be used to place supporting rings and devices around the atrioventricular valve annulus. Such devices can provide support which is analogous to that provided by annuloplasty rings implanted in open surgical procedures. In one approach, an elastic annuloplasty ring can be delivered through the guide catheter in a collapsed fashion, deployed to open over the annulus, and then stitched or stapled in place using appropriate catheters.

Figure 78:
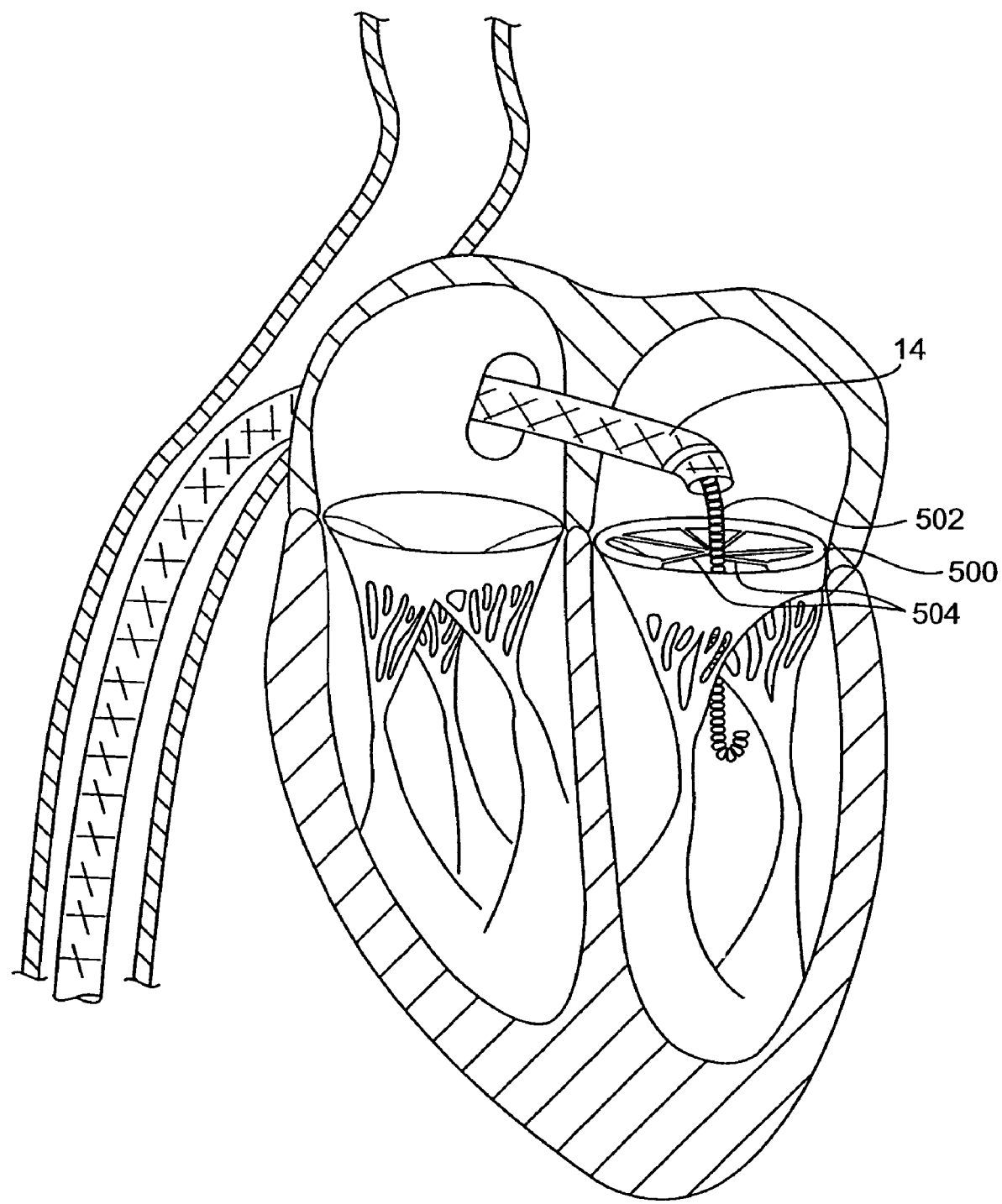
FIG. 78 illustrates a first exemplary approach for placing an annuloplasty ring according to the methods of the present invention.

A first exemplary annuloplasty ring 500 can be deployed using a catheter 502 positioned through a guide catheter 14, as generally shown in FIG. 78. The annuloplasty ring 500 is deployed as an umbrella having spokes 504 which open the outer ring. After deploying the ring, it may be secured in place using sutures, staples, tissue adhesives, or other conventional techniques. The catheter 502 may then be removed, together with the deployment spokes 504, leaving the ring permanently in place.

Figure 79:
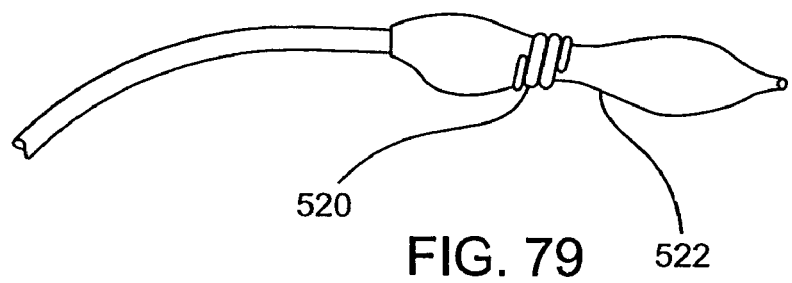
FIGS. 79 and 80 illustrate a second exemplary approach for placing an annuloplasty ring according to the methods of the present invention.
Figure 80:
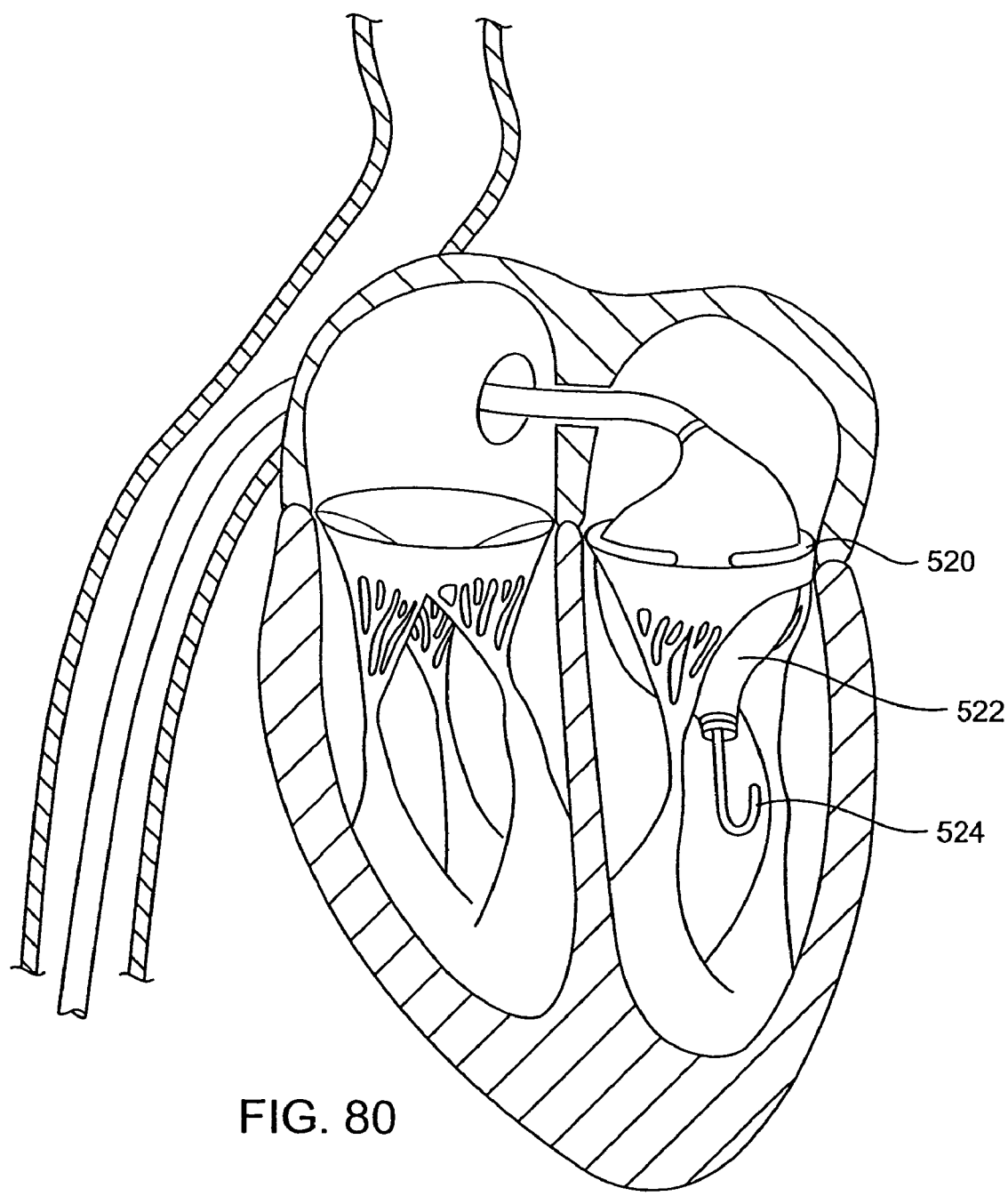

Alternatively, an annuloplasty ring 520 can be delivered on a balloon catheter 522 as shown in FIGS. 79 and 80. The ring 520 can be formed from a deformable material, and the balloon 520 inflated within the valve annulus to expand and deploy the ring, as shown in FIG. 80. The balloon catheter may be placed directly over a guidewire 524, but will more usually be positioned using a combination of a guide catheter and guidewire. Once the ring 520 is deployed, it can be sutured, stapled, glued, or otherwise affixed around the valve annulus.

Figure 81:
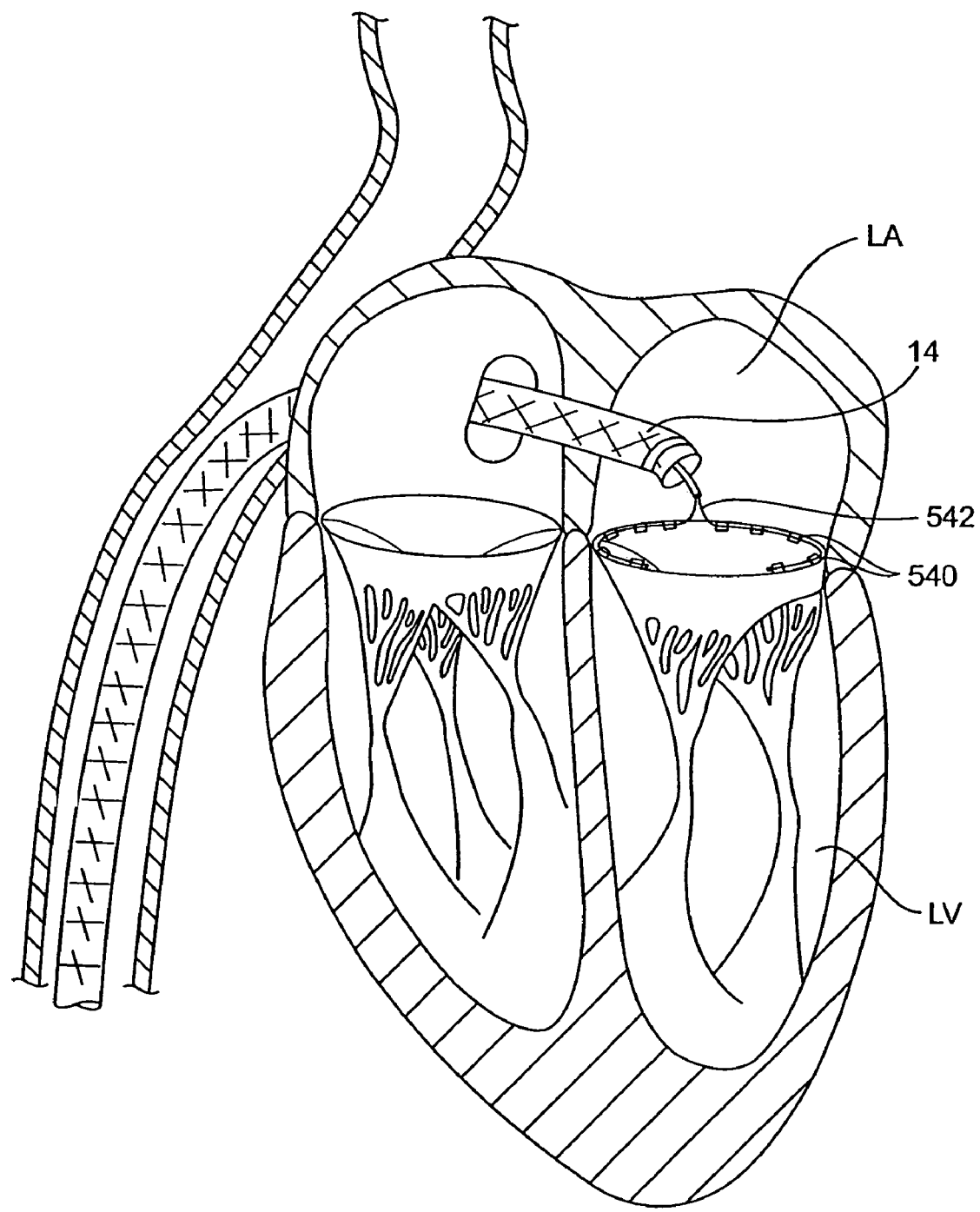
FIG. 81 illustrates a method for placing an anchored filament about a mitral valve annulus that can be used to tighten the annulus.

As an alternative to placement of discrete annuloplasty rings, the valve annulus can be reinforced and tightened by placing a plurality of anchors, such as staples 540 about the annulus of the mitral valve, as shown in FIG. 81. A suture 542 or other filament can then be placed through the anchors 540 and tightened in a "purse string" fashion. The suture filament can then be tied off to maintain the desired tightening and enforcement of the valve annulus.

Figure 82:
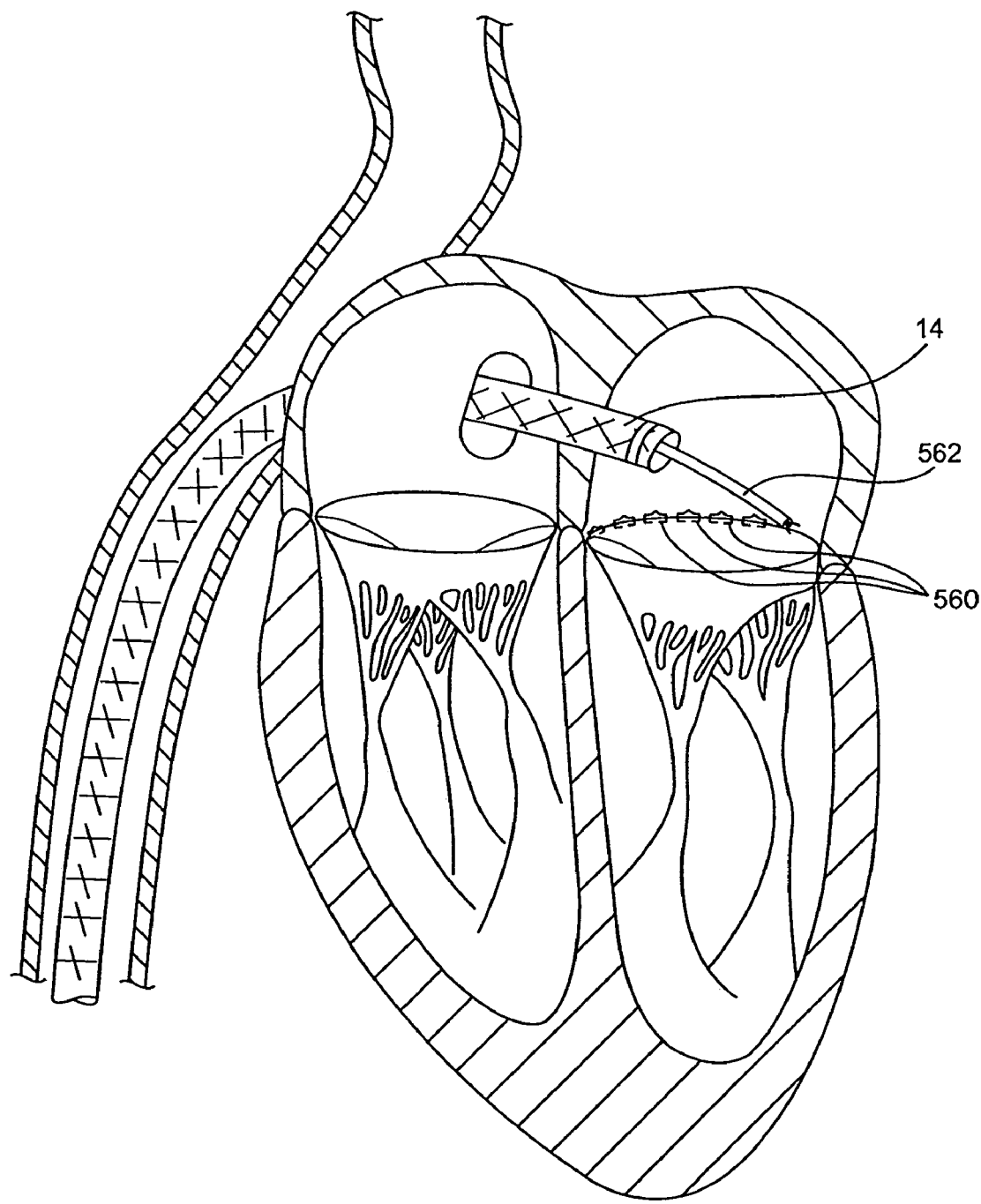
FIG. 82 illustrates a method for placing multiple sutures about a mitral valve annulus, where the individual suture plicate and tighten the annulus.

As yet a further alternative, the valve annulus can be plicated by positioning a plurality of staples about the annulus, as shown in FIG. 82. Here, each staple 560 plicates or shortens a small peripheral segment of the annulus. A staple applying catheter 562 may have the same general structures described above in connection with FIGS. 61A and 61B.

X. Device Embodiments

The following three device embodiments depict complete device designs utilizing a variety of the specific components described above and/or new component designs to accomplish similar objectives.

A. Atrial Device

Figure 83:
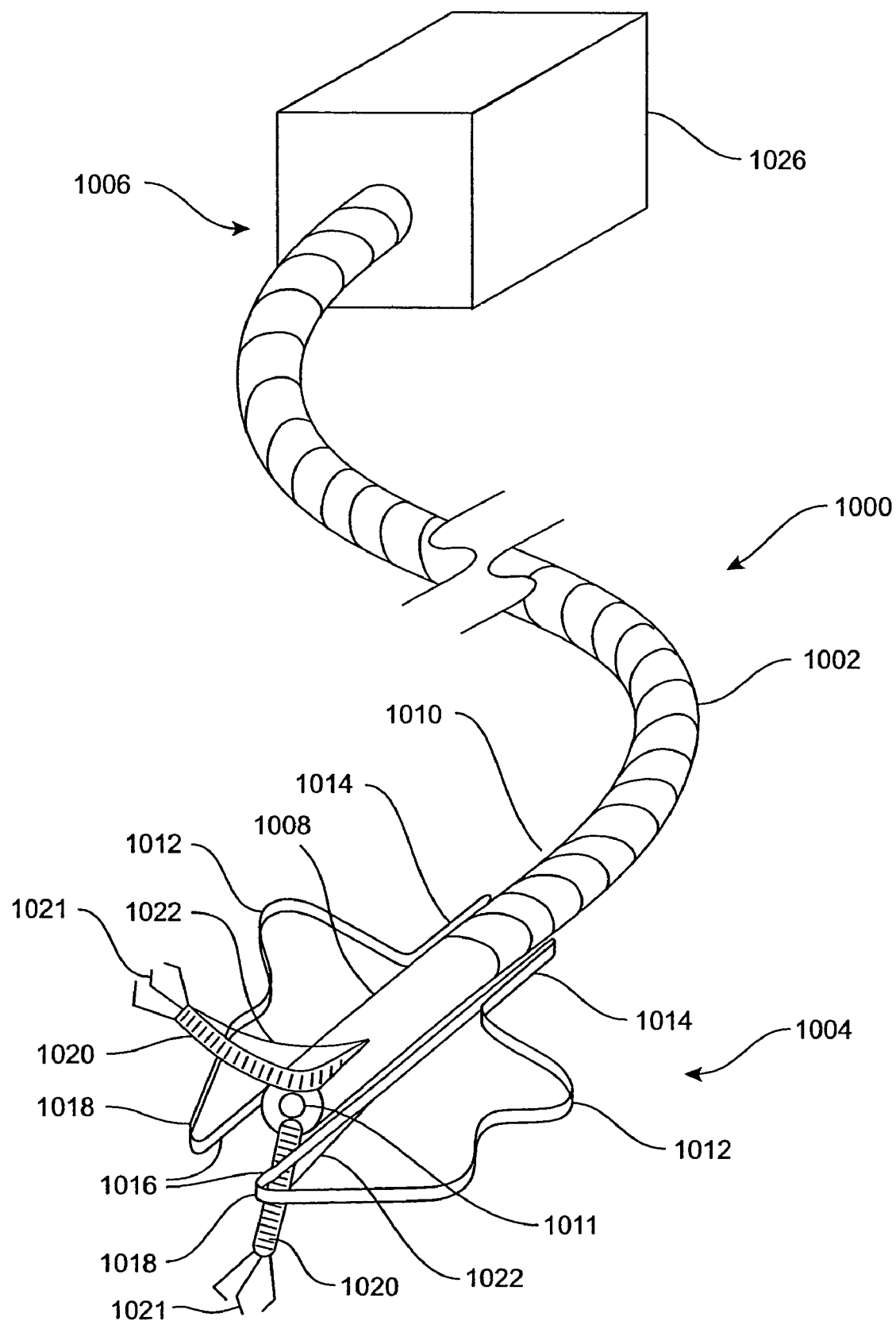
FIGS. 83-85 illustrate an embodiment of an atrial device for valve tissue modification.

Referring to FIG. 83, the atrial device 1000 is comprised of a catheter shaft 1002 having a distal end 1004 and a proximal end 1006. The catheter shaft 1002 is comprised of, among others, a conduit 1008, a coaxial outer sheath 1010, and a central guidewire lumen 1011. Toward the distal end 1004, a pair of stabilizers 1012 having a single-hump shape (previously illustrated in FIG. 31D) are fixedly mounted on the outer sheath 1010 at their proximal end 1014 and fixedly attached or hinged to extenders 1016 at their distal end 1018. The stabilizers 1012 are shown in an outwardly bowed position, however they may be inwardly collapsed by either extending the extenders 1016 or retracting the outer sheath 1010. Bowing may be achieved by the reverse process.

Figure 84:
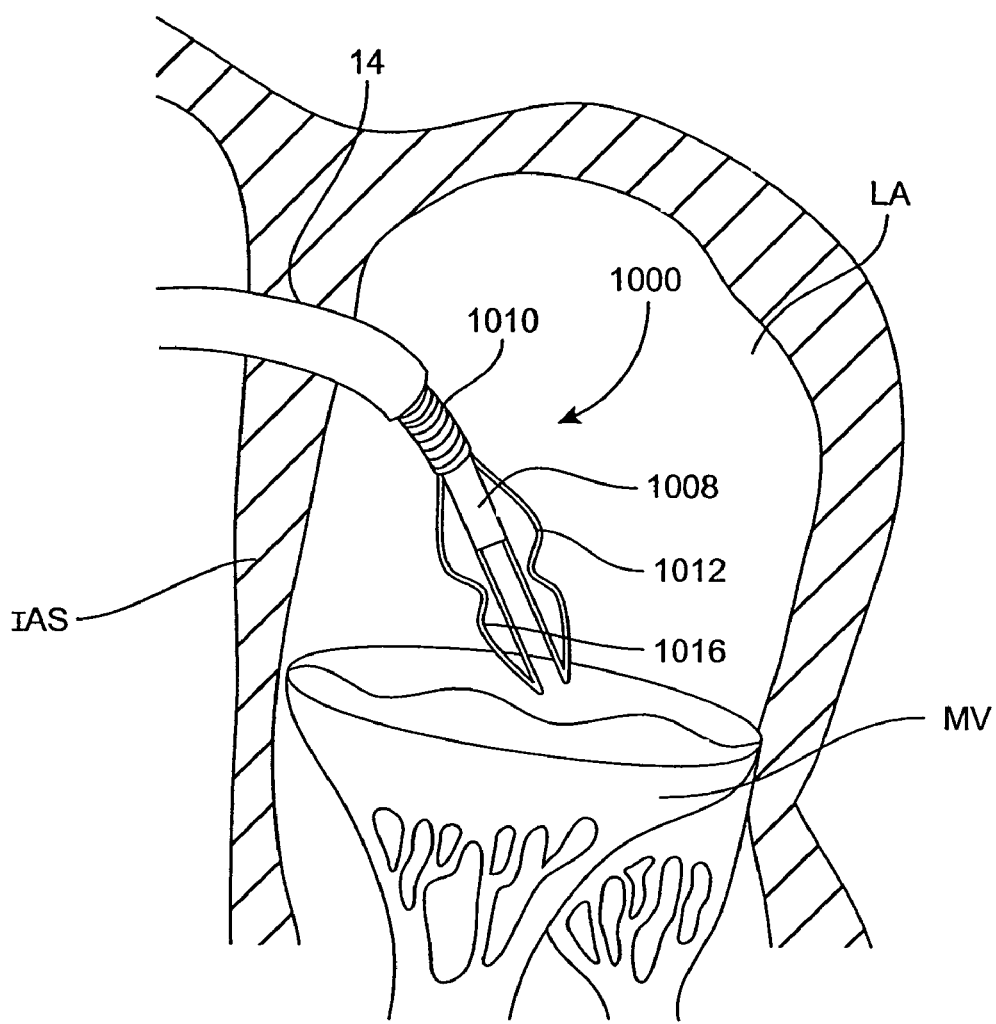

Referring to FIG. 84, the atrial device 1000 may be used with a typical antegrade approach to the mitral valve MV. As previously described and depicted in FIGS. 7 and 8, such an antegrade approach may involve penetrating the interatrial septum IAS and maintaining such access with a guide catheter 14. The guide catheter 14 permits introduction of the atrial device 1000 to the left atrium LA and mitral valve MV. To allow passage of the device 1000 through the guide catheter 14, the stabilizers 1012 must be in a collapsed position as shown. In addition, graspers, described below, may be fully retracted to avoid damage to cardiac structures. Thus, they are not visible in FIG. 84.

Figure 85:
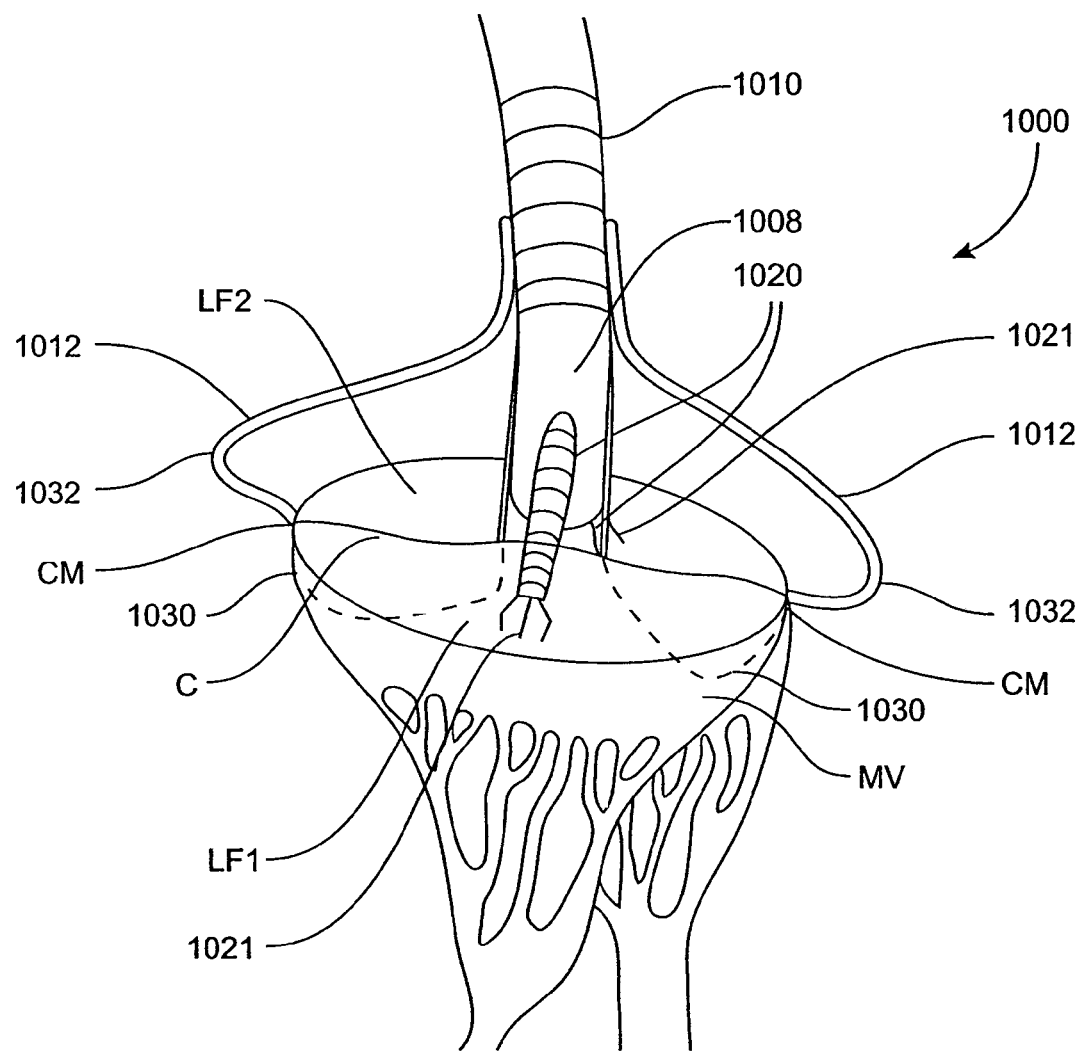

Referring to FIG. 85, the atrial device 1000 may be stabilized against the mitral valve MV. The stabilizers 1012 may be inserted through the mitral valve MV and may be aligned with the line of coaptation C between the valve leaflets LF1, LF2. To minimize mitral valve regurgitation (MVR) due to insertion of the device 1000, the stabilizers 1012 may be located approximately 120 degrees apart. This angle may be fixed or adjustably variable. The single-humped shape of the stabilizers 1012 may allow the inferior portion 1030 to pass within the valve and apply radial pressure to the commissures CM and the superior portion 1032 (or hump) to rest upon and apply axial pressure to the commissures CM.

Referring again to FIG. 83, a pair of graspers, comprised of grasping sheaths 1020 and three opposing prongs 1021 configured to partially or fully penetrate or pierce, are shown extended from the conduit 1008 in the plane bisecting the angle of the stabilizers 1012 (i.e. approaches the middle of the leaflets). This angle may be fixed or variable. When not in use, however, the graspers may be fully retracted within the conduit 1008. Tension from lateral steering wires 1022 cause the graspers to deflect away from each other and approximate the most desirable angle for grasping. Amount of deflection may be controlled from the proximal end of the device by the steering wires 1022. When the graspers are positioned in a desired location as shown in FIG. 85, the prongs 1021 may be deployed and opened by either retraction of the grasping sheath 1020 or advancement of the prongs 1021 beyond the grasping sheath 1020. Retraction of the sheath 1020 does not significantly affect the position of the graspers, thus enabling the user to contact the valve leaflets LF1, LF2 with the prongs 1021 housed within the sheath 1020 and then to initiate grasping the leaflets at the contacted location by retracting the grasping sheaths 1020. The opposing prongs 1021 may be closed to grasp (pinch, partially penetrate or pierce) the leaflet tissue by advancing the grasping sheaths 1020 or retracting the prongs 1021 within the sheaths 1020.

Figure 84A:
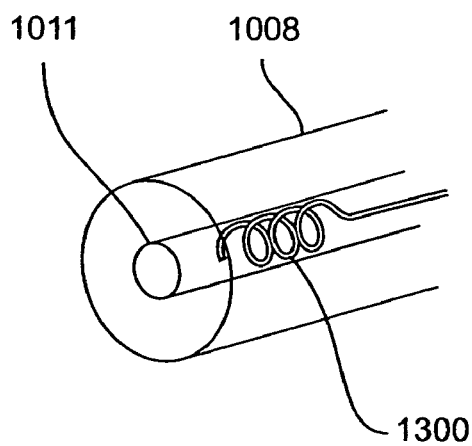
Figure 84B:
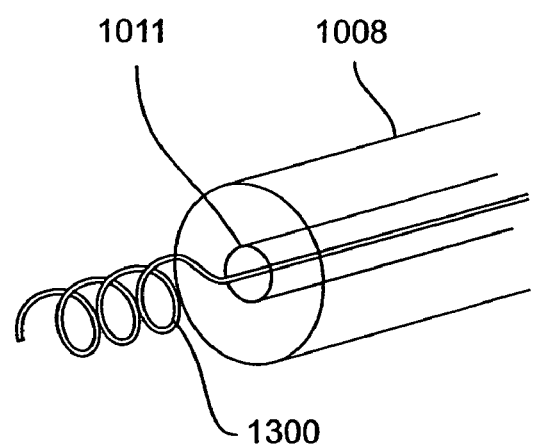

After both leaflets have been grasped, tension in the steering wires 1022 is released and the conduit 1008 is advanced over the grasping sheaths 1020. Such advancement draws the sheaths 1020, and grasped leaflets, together for coaptation. After coaptation, the mitral valve regurgitation is evaluated to determine if the locations which are grasped are appropriate for fixation. If the grasping points are not appropriate, the leaflets may be released and regrasped individually or simultaneously by the above described methods. If the grasping points are appropriate, the preferred embodiment allows for exchange of the guidewire, located in the guidewire lumen 1011, for a fixation device. The fixation device may use, for example, staples, sutures, clips, rivets, coils, fusing devices, zippers, snares, clamps, hooks, chordal fixation or shortening devices to repair the mitral valve regurgitation. Specifically, the fixation device may be the hollow suturing coil 1300 shown previously in FIGS. 49A-C. As shown in FIG. 84A, the hollow suturing coil 1300 containing suture 1302 (not shown) may be deployed through the guidewire lumen 1011 in a coiled configuration. The coil 1300 may expand or change shape once it is deployed from the lumen 1011, providing the coil 1300 is comprised of a suitable shape memory or superelastic material. Similarly, as shown in FIG. 84B, the suturing coil 1300 may be deployed through the guidewire lumen 1011 in a straightened configuration such that it coils and/or expands or changes shape once it is deployed from the lumen 1011.

The above described components may be manipulated and controlled by a handle 1026 connected to the proximal end 1006 of the catheter shaft 1002, as shown in FIG. 83. The handle 1026 permits independent control of the components, including but not limited to retraction and extension of extenders 1016, deployment of stabilizers 1012, adjustment and locking of outer sheath 1010, translation and deflection of grasping sheaths 1020, stopping and locking of grasping sheaths 1020 and axial sliding of the conduit 1008. In addition, the device may be readily adapted to approach the mitral valve trans-atrially for a minimally invasive surgical (MIS) procedure, with either beating or stopped heart.

B. Atrial-Ventricular Device

Figure 86:
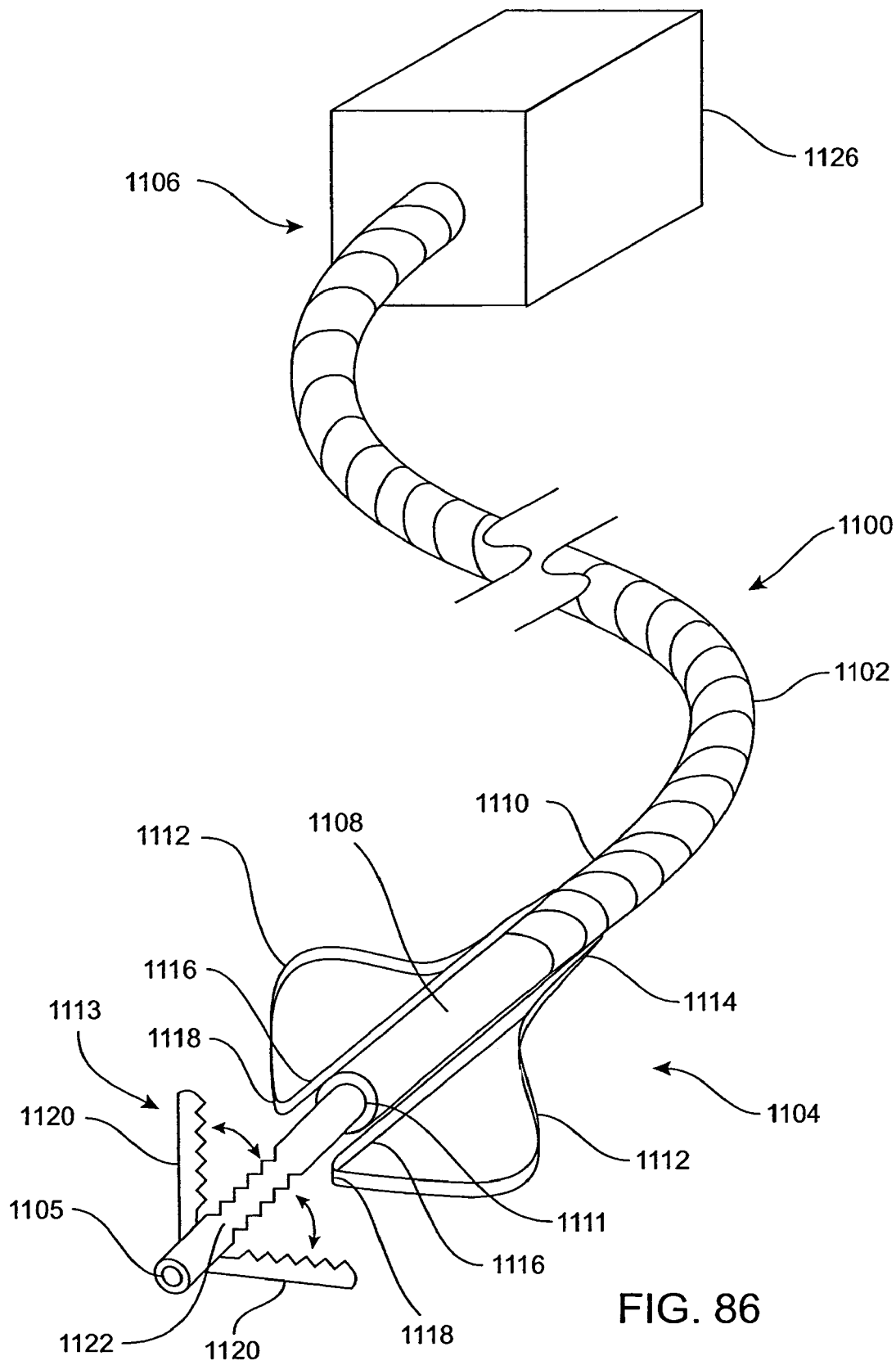

Referring to FIG. 86, the atrial-ventricular device 1100 is comprised of a catheter shaft 1102 having a distal end 1104 and a proximal end 1106. The catheter shaft 1102 is comprised of, among others, a conduit 1108, a coaxial outer sheath 1110, a central lumen 1111 through which a double-jaw grasper 1113 may be inserted, and a central guidewire lumen 1105. Toward the distal end 1104, a pair of stabilizers 1112 having a triangular shape (previously illustrated in FIG. 31A) are fixedly mounted on the outer sheath 1110 at their proximal end 1114 and fixedly attached to extenders 1116 at their distal end 1118. The stabilizers 1112 are shown in an outwardly bowed position, however they may be inwardly collapsed by either extending the extenders 1116 or retracting the outer sheath 1110. Bowing may be achieved by the reverse process. The double-jaw grasper 1113 is comprised of two articulating jaw arms 1120 which may be opened and closed against the central shaft 1122 (movement depicted by arrows) either independently or in tandem. The grasper 1113 is shown in the open position in FIG. 86. The surfaces of the jaw arms 1120 and central shaft 1122 may be toothed, as shown, or may have differing surface textures for varying degrees of friction.

Referring to FIGS. 87A-C, the atrial-ventricular device 1100 may be used with a typical antegrade approach to the mitral valve MV, as previously described and depicted in FIGS. 7 and 8. However, the double-jaw grasper 1113 extends through the valve such that the leaflets L1, L2 are grasped from below. Thus, the device 1100 is termed "atrial-ventricular."

Referring to FIG. 87A, the atrial device 1100 may be stabilized against the mitral valve MV. The stabilizers 1112 may be positioned on the superior surface of the valve leaflets LF1, LF2 at a 90 degree angle to the line of coaptation. The grasper 1113 may be advanced in its closed position from the conduit 1108 between the leaflets LF1, LF2 until the jaw arms 1120 are fully below the leaflets in the ventricle. At this point, the grasper 1113 may be opened and retracted so that the jaw arms 1120 engage the inferior surface of the leaflets LF1, LF2. In this manner, the leaflets are secured between the stabilizers 1112 and the jaw arms 1120. This action allows for leaflets of many different shapes and orientations to be secured. Cardiomyopathic valves are often enlarged and distorted so that they coapt irregularly. Such irregularity creates difficulty in mechanically coapting such valves for tissue modification. The action of the grasper 1113 overcomes much of these difficulties.

Referring to FIG. 87B, the grasper 1113 will gradually close, drawing the leaflets LF1, LF2 together while maintaining a secure hold on the leaflets between the jaw arms 1120 and the stabilizers 1112. This may be accomplished by number of methods. For example, the stabilizers 1112 may be gradually collapsed by either extending the extenders 1116 or retracting the outer sheath 1110. As the stabilizers 1112 collapse, the jaw arms 1120 may collapse due to spring loading to gradually close the grasper 1113. Alternatively, the jaw arms 1120 may be actuated to close against the central shaft 1122 applying force to the stabilizers 1112 causing them to collapse. In either case, such action allows the stabilizers 1112 to simultaneously vertically retract and withdraw from the leaflets as the leaflets are clamped between the jaw arms 1120 and the central shaft 1122. In this manner, the leaflets are effectively "transferred" to the grasper 1113. Referring to FIG. 87C, once the collapsed stabilizers 1112 are completely withdrawn, the leaflets LF1, LF2 are held in vertical opposition by the grasper 1113 in a more natural coaptation geometry. At this point the leaflets may be adjusted and fixated. Fixation may be achieved with an external element or the grasper 1113 may be left in place as a fixation device.

The above described components may be manipulated and controlled by a handle 1126 connected to the proximal end 1106 of the catheter shaft 1102, as shown in FIG. 86. The handle 1026 permits independent control of the components described above.

C. Ventricular Device

Figure 88:
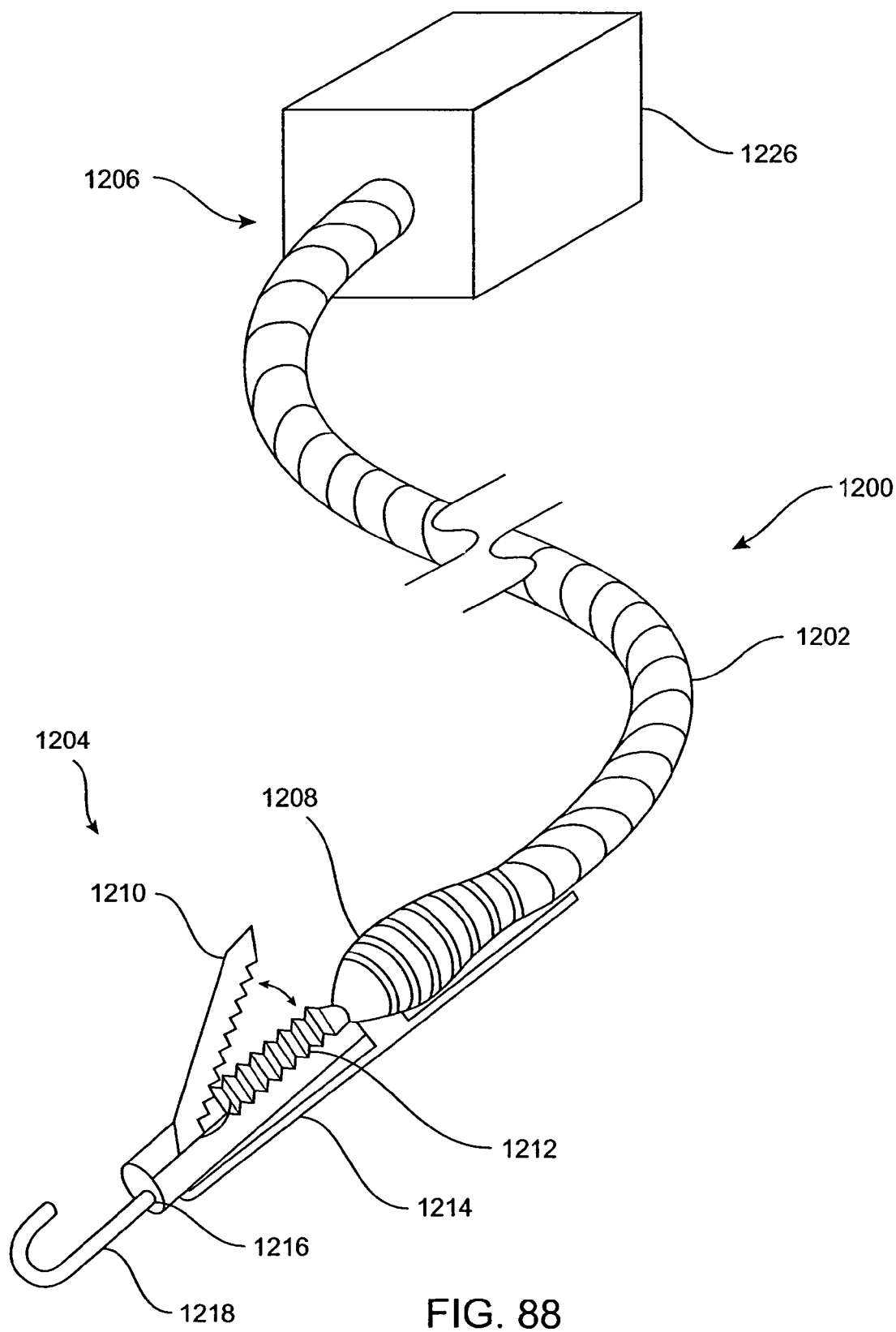
FIGS. 88-89, and FIGS. 90A-90B illustrate an embodiment of a ventricular device for valve tissue modification.

Referring to FIG. 88, the ventricular device 1200 is comprised of a catheter shaft 1202 having a distal end 1204 and a proximal end 1206. The distal end 1204 is comprised of a joining coil 1208, an upper jaw 1210, a lower jaw 1212, an actuator 1214 and a central lumen 1216 through which a guidewire 1218 or other wires may be inserted. The upper jaw 1210 may open and close (depicted by arrows) against the lower jaw 1212 by action of the actuator 1214. The upper jaw 1210 is shown in the open position. These components may be manipulated and controlled by a handle 1226 connected to the proximal end 1206 of the catheter shaft 1202 as shown.

Figure 89:
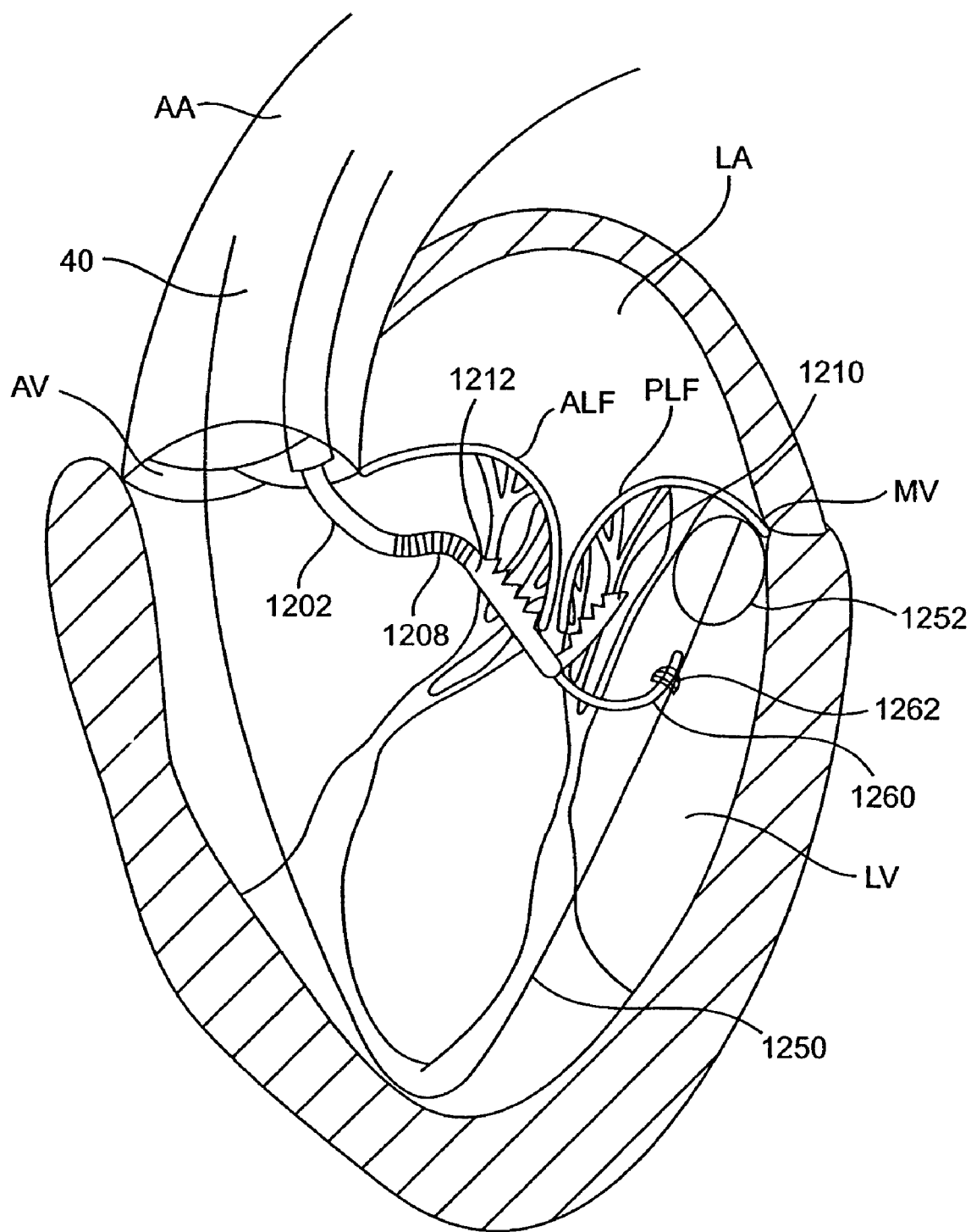

Referring to FIGS. 89, the ventricular device 1200 may be used with a typical retrograde approach to the mitral valve MV, as previously described and depicted in FIG. 9. Here the mitral valve MV may be accessed by an approach from the aortic arch AA across the aortic valve AV, and into the left ventricle LV below the mitral valve MV. Such access may be maintained with a guide catheter 40 through which the ventricular device 1200 may be introduced. The ventricular device 1200 may be inserted through the guide catheter 40 with the upper jaw 1210 in the closed position. After it exits the guide catheter 40 just below the aortic valve AV, the device 1200 may be advanced toward the mitral valve MV. The catheter shaft 1202 may be pre-shaped to provide favorable curvature in positioning the distal end 1204 beneath the valve leaflets ALF, PLF. Additionally, two mandrels with favorable shapes may be advanced into a lumen in the catheter shaft 1202. By changing the location of the mandrels with respect to each other and to the catheter shaft 1202, the general curvature of the shaft 1202 may be altered in-situ.

It is desired to position the distal end 1204 of the device 1200 beneath the mitral valve leaflets ALF, PLF with the upper jaw 1210 in the open configuration. The lower jaw 1212 is to be proximal to the anterior leaflet ALF and the upper jaw 1210 is to be distal of the posterior leaflet PLF, as shown in FIG. 89, such that the leaflets may be secured between the jaws 1210, 1212. To achieve such positioning, the device 1200 may be required to flex at an extreme angle in the region of the joining coil 1208. Therefore, the joining coil 1208 is designed to provide such flexibility.

To aid in positioning the device 1200, a balloon wire 1250 may be used. The balloon wire 1250 may first be inserted through the aortic valve AV, advanced down to the apex of the ventricle and then back upwards towards the mitral valve MV behind the posterior leaflet PLF. Once positioned, the balloon 1252 may be inflated to assist in holding the position stationary. A cuff wire 1260 may then be inserted through the aortic valve AV. The cuff wire 1260 may track along the balloon wire 1250 by means of a locking ring 1262. The cuff wire 1260 may track down to the apex of the ventricle and then back upwards toward the mitral valve MV. Once the cuff wire 1260 is advanced to a desirable position, the locking ring 1262 may be actuated to lock the cuff wire 1260 to the balloon wire 1250. A typical means of actuation is by inflation of the locking ring. 1262. The ventricular device 1200 may then be tracked over the cuff wire 1260 to the desired position, as shown in FIG. 89. The balloon, or balloon wire 1250, may also be used to walk or urge the posterior leaflet towards the center of the valve to facilitate grasping.

Figure 90A:
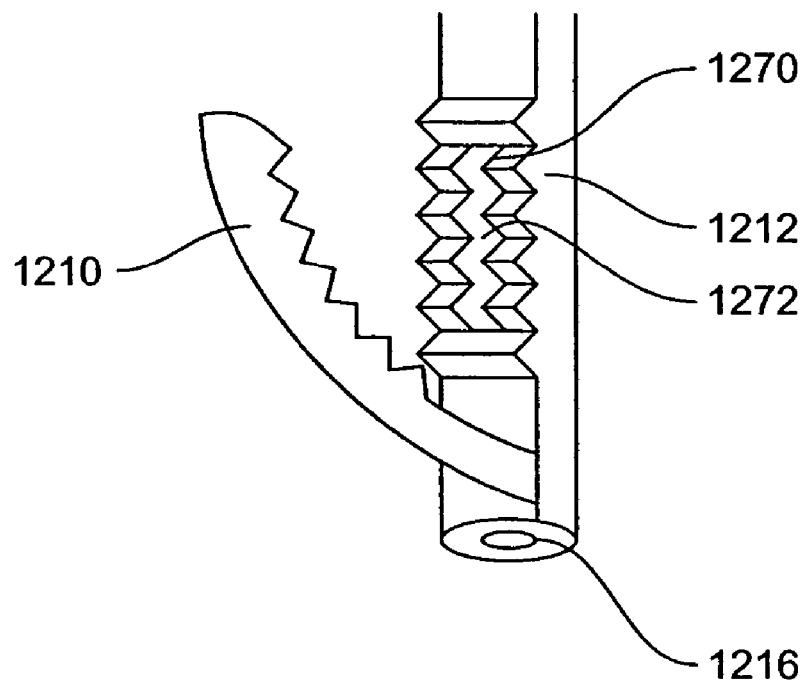
Figure 90B:
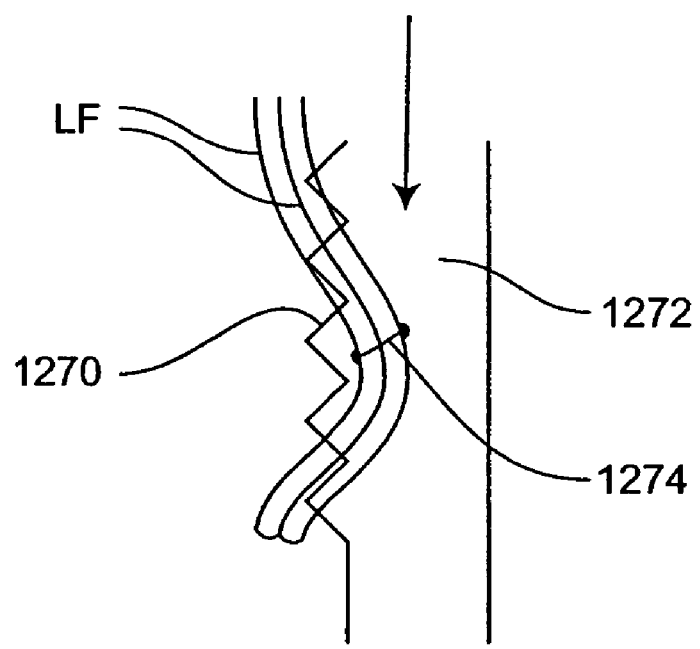

Once positioned, the upper jaw 1210 may be closed against the lower jaw 1212 such that the leaflets are grasped between them. It is often desirable to adjust or manipulate the leaflets once they are grasped. Manipulation should occur only in a superior/inferior (up/down) motion in order to bring the leaflets to a final position where regurgitation is minimized. The lower jaw 1212 may be fitted with a travel mechanism for extending or retracting the jaw 1212. This would move one leaflet up or down with respect to the other leaflet. Once the leaflets are sufficiently adjusted, fixation may occur in any manner previously described. In a preferred embodiment, fixation may be achieved through the lower jaw 1212, as depicted in FIGS. 90A and 90B. As shown in FIG. 90A, a cutout 1270 may be present in the lower jaw 1212 accessing a lumen 1272 which extends through the catheter shaft 1202 and lower jaw 1212; such a lumen may also serve as the guidewire lumen 1216. When the upper jaw 1210 is closed against the lower jaw 1212, the valve leaflets LF may be captured between the jaws. As shown a side-view, FIG. 90B, the captured leaflets LF may protrude into the cutout 1270 into the lumen 1272. A fixation device 1274 may then be inserted through the lumen 1272 (in the direction of the arrow) and may affix the leaflets LF together. It may be appreciated that such a method of fixation may be used in a number of devices involving jaw-type graspers, such as the atrial ventricular device 1100 depicted in FIG. 86.

Although the forgoing invention has been described in some detail by way of illustration and example, for purposes of clarity of understanding, it will be obvious that various alternatives, modifications and equivalents may be used and the above description should not be taken as limiting in scope of the invention which is defined by the appended claims.

What is claimed is:

1. A method of suturing heart valve leaflets of a patient, said method comprising:
    providing a suturing tool having an inner shaft, an outer shaft slidably disposed over the inner shaft and having a longitudinal axis, first and second needles removably coupled to the inner shaft, and a length of suture coupled to the first and second needles;
    advancing the inner and outer shafts through vasculature of the patient so that the needles are adjacent the valve leaflets;
    drawing the valve leaflets into first and second leaflet receptacles, the leaflet receptacles formed between the needles and an outer wall of the inner shaft;
    advancing the first and the second needles into first and second needle receptacles, the first and second needle receptacles comprising channels disposed in a sidewall of the outer shaft;
    releasably locking each one of the needles with a needle catch coupled to the outer shaft near a distal end thereof, wherein each of the needle catches comprise a detent mechanism cooperating with one of the needles;
    piercing the valve leaflets with the first and the second needles by linearly retracting the needles in a proximal direction substantially parallel to the longitudinal axis of the outer shaft;
    releasing the first and the second needles from the inner shaft;
    passing the first and second needles and the length of suture through the valve leaflets; and
    securing the suture so as to affix the valve leaflets to one another.

2. The method of claim 1, wherein the valve leaflets are pierced simultaneously.

3. The method of claim 1, wherein the securing comprises fastening the suture with a securing element selected from the group consisting of a knot, multiple knots, an anchor, an expandable anchor, a mechanical lock, and a fastener.

4. The method of claim 1, wherein the piercing comprises piercing the leaflets from an inferior side of the leaflets to a superior side of the leaflets.

5. The method of claim 1, wherein the locking comprises engaging a protuberance extending laterally from the outer shaft with a receptacle disposed on the first or the second needle.

6. The method of claim 1, wherein the heart valve leaflets are sutured while the patient's heart remains beating.

7. The method of claim 1, wherein the linear retraction of the needles comprises proximally retracting the outer shaft relative to the inner shaft.

8. The method of claim 1, wherein the releasing step comprises proximally retracting the outer shaft relative to the inner shaft so that the needles disengage from the inner shaft.

* * * * *